United States Patent
Bassler et al.

(10) Patent No.: US 7,208,612 B2
(45) Date of Patent: Apr. 24, 2007

(54) CRYSTALS OF LUXP AND COMPLEXES THEREOF

(75) Inventors: Bonnie L. Bassler, Princeton, NJ (US); Stephan Schauder, Lyons (FR); Xin Chen, Edison, NJ (US); Frederick M. Hughson, Princeton, NJ (US); Stephen R. Cooper, Carlsbad, CA (US)

(73) Assignee: Princeton University, Princeton, NJ (US)

( * ) Notice: Subject to any disclaimer, the term of this patent is extended or adjusted under 35 U.S.C. 154(b) by 577 days.

(21) Appl. No.: 10/227,400

(22) Filed: Aug. 22, 2002

(65) Prior Publication Data

US 2003/0175930 A1 Sep. 18, 2003

Related U.S. Application Data

(60) Provisional application No. 60/314,705, filed on Aug. 24, 2001.

(51) Int. Cl.
*C07D 307/94* (2006.01)
*A01N 43/30* (2006.01)

(52) U.S. Cl. ........................ 549/213; 514/462
(58) Field of Classification Search ............. None
See application file for complete search history.

(56) References Cited

U.S. PATENT DOCUMENTS

2003/0022932 A1* 1/2003 Surette et al. .............. 514/473

FOREIGN PATENT DOCUMENTS

WO W/O 0032152 6/2000

OTHER PUBLICATIONS

Xin Chen, Stephan Schauder, Noelle Potier, Alain Van Dorsselaer, Istvan Pelczer, Bonnie L. Bassler, & Frederick M. Hughson, Structural identification of a bacterial quorum-sensing signal containing boron, Nature, 415:545-549 (Jan. 31, 2002).*
Chen & Zhi, Ligand-Protein Inverse Docking and Its Potential Use in the Computer Search of Protein Targets of a Small Molecule, Proteins: Structure, Function, and Genetics, 43:217-226 (2001).*
Chen, Xin et al., "Structural identification of a bacterial quorum-sensing signal containing boron," Nature, vol. 415, pp. 545-549 (2002).
Klaus Benner, Peter Klufers, "A combined x-ray and NMR study of borate esters of furanoidic cis-1, 2-diols," Institute for Organic Chemistry University, Germany, Feb. 14, 2000.
Ron van den Berg, Joop A. Peters and Herman van Bekkum, "The structure and (local) stability constants of borate esters of mono- and di-saccharides as studied by 11B and 13C NMR spectroscopy," Laboratory of Organic Chemistry and Catalysts, Delft University of Technology, Netherlands, Jun. 29, 1993.

(Continued)

Primary Examiner—Rita Desai
(74) Attorney, Agent, or Firm—Mathews, Shepherd, McKay Bruneau, P.A.

(57) ABSTRACT

A crystal comprising LuxP is obtained, and a binding site for autoinducer-2 (AI-2) identified. The X-ray crystallographic data for LuxP and a LuxP-AI-2 complex is determined and used in a drug discovery method. Pharmaceutical compositions comprising ligands identified by such drug discovery methods are used to treat bacterial infections.

1 Claim, 4 Drawing Sheets

AI-2

OTHER PUBLICATIONS

Database Caplus, DN 121:247611. Bassler et al. Multiple signalling systems controlling expression of luminescence in *Vibrio harveyi*: sequence and function of genes encoding a second sensory pathway. Molecular Microbiology, 1994, vol. 13, No. 2, pp. 273-286.

Database Biosis, AN 2002:233419. Lo et al. Analysis of a quorum sensing system n Mannheimia (Pasteurella) haemolytica A1 and related pasteurellaceae species. Abstracts of the General Meeting of the American Society for Microbiology, (2001) vol. 101, pp. 741-742. Meeting Info: 101st General Meeting of the American Society for Microbiology, Orlando, FL, May 20-24, 2001.

International Preliminary Examination Report dated Dec. 23, 2003.

Crystal Screen User Guide, Hampton Research, 1991.

* cited by examiner

SEQUENCE LISTING

<160> NUMBER OF SEQ ID NOS: 1

<210> SEQ ID NO 1
<211> LENGTH: 342
<212> TYPE: PRT
<213> ORGANISM: Vibrio Harveyi

<400> SEQUENCE: 1

```
Val Leu Asn Gly Tyr Trp Gly Tyr Gln Glu Phe Leu Asp Glu Phe Pro
 1               5                  10                  15

Glu Gln Arg Asn Leu Thr Asn Ala Leu Ser Glu Ala Val Arg Ala Gln
            20                  25                  30

Pro Val Pro Leu Ser Lys Pro Thr Gln Arg Pro Ile Lys Ile Ser Val
        35                  40                  45

Val Tyr Pro Gly Gln Gln Val Ser Asp Tyr Trp Val Arg Asn Ile Ala
    50                  55                  60

Ser Phe Glu Lys Arg Leu Tyr Lys Leu Asn Ile Asn Tyr Gln Leu Asn
65                  70                  75                  80

Gln Val Phe Thr Arg Pro Asn Ala Asp Ile Lys Gln Gln Ser Leu Ser
                85                  90                  95

Leu Met Glu Ala Leu Lys Ser Lys Ser Asp Tyr Leu Ile Phe Thr Leu
            100                 105                 110

Asp Thr Thr Arg His Arg Lys Phe Val Glu His Val Leu Asp Ser Thr
        115                 120                 125

Asn Thr Lys Leu Ile Leu Gln Asn Ile Thr Thr Pro Val Arg Glu Trp
    130                 135                 140

Asp Lys His Gln Pro Phe Leu Tyr Val Gly Phe Asp His Ala Glu Gly
145                 150                 155                 160

Ser Arg Glu Leu Ala Thr Glu Phe Gly Lys Phe Phe Pro Lys His Thr
                165                 170                 175

Tyr Tyr Ser Val Leu Tyr Phe Ser Glu Gly Tyr Ile Ser Asp Val Arg
```

-continued

```
            180                 185                 190
Gly Asp Thr Phe Ile His Gln Val Asn Arg Asp Asn Asn Phe Glu Leu
        195                 200                 205
Gln Ser Ala Tyr Tyr Thr Lys Ala Thr Lys Gln Ser Gly Tyr Asp Ala
        210                 215                 220
Ala Lys Ala Ser Leu Ala Lys His Pro Asp Val Asp Phe Ile Tyr Ala
225                 230                 235                 240
Cys Ser Thr Asp Val Ala Leu Gly Ala Val Asp Ala Leu Ala Glu Leu
                245                 250                 255
Gly Arg Glu Asp Ile Met Ile Asn Gly Trp Gly Gly Ser Ala Glu
        260                 265                 270
Leu Asp Ala Ile Gln Lys Gly Asp Leu Asp Ile Thr Val Met Arg Met
        275                 280                 285
Asn Asp Asp Thr Gly Ile Ala Met Ala Glu Ala Ile Lys Trp Asp Leu
        290                 295                 300
Glu Asp Lys Pro Val Pro Thr Val Tyr Ser Gly Asp Phe Glu Ile Val
305                 310                 315                 320
Thr Lys Ala Asp Ser Pro Glu Arg Ile Glu Ala Leu Lys Lys Arg Ala
                325                 330                 335
Phe Arg Tyr Ser Asp Asn
                340
```

US 7,208,612 B2

CRYSTALS OF LUXP AND COMPLEXES THEREOF

RELATED APPLICATION INFORMATION

This application claims priority to U.S. Provisional Application Ser. No. 60/314,705, filed Aug. 24, 2001, which is hereby incorporated by reference in its entirety.

This application is related to U.S. patent application Ser. No. 10/227,327 filed Aug. 22, 2002, which is hereby incorporated by reference in its entirety.

FEDERAL FUNDING

This invention was funded in part through grants from the National Institutes of Health, the National Science Foundation, and the Office of Naval Research. Therefore, the federal government has certain rights in this invention.

BACKGROUND OF THE INVENTION

1. Field of the Invention

This invention relates to the LuxP protein, and more particularly to a crystalline form of the LuxP protein having sufficient crystal quality to allow crystallographic data to be obtained, as well as to methods of structure-based drug design based on the crystallographic data.

2. Description of the Related Art

Cell-cell communication in bacteria occurs through the exchange of extracellular signaling compounds called autoinducers. This process, termed quorum sensing, allows bacterial populations to coordinate gene expression. Community cooperation likely enhances the effectiveness of processes including bioluminescence, virulence factor expression, antibiotic production, and biofilm development. Unlike other autoinducers, which are specific to particular species of bacteria, a recently discovered autoinducer (AI-2) is produced by a large number of bacterial species. AI-2 has been proposed to serve as a universal signal for inter-species communication.

AI-2 was originally identified in the bioluminescent marine bacterium *Vibrio harveyi* as one of two autoinducers that regulate light production in response to cell density. The synthase required for AI-2 production, LuxS, is widely conserved among gram-negative and -positive bacteria. Bacteria produce AI-2 from S-adenosylmethionine in several enzymatic steps, as shown in FIG. 1. Consumption of S-adenosylmethionine as a methyl donor produces S-adenosylhomocysteine, which undergoes hydrolysis catalyzed by the nucleosidase Pfs to yield adenine and S-ribosylhomocysteine. Subsequently LuxS catalyzes cleavage of S-ribosylhomocysteine to homocysteine and 4,5-dihydroxy-2,3-pentanedione, which can then cyclize either by itself or in an enzyme-mediated process.

Detection of AI-2 by *V. harveyi* involves two proteins, LuxP and LuxQ. LuxP belongs to a large family of periplasmic binding proteins whose members bind diverse ligands, while LuxQ is a two-component hybrid sensor kinase embedded in the bacterial inner membrane. It is believed that LuxP is the primary AI-2 receptor, see X. Chen, S. Schauder, N. Potier, A. Van Dorsselaer, I. Pelczer, B. Bassler, and F. Hughson, "Structural Identification of a Bacterial Quorum-Sensing Signal Containing Boron," Nature, Vol. 415, pp. 545–549 (2002). In quorum sensing, the periplasmic LuxP-AI-2 complex likely interacts with LuxQ to transduce the autoinducer signal. However, heretofore LuxP has not been isolated in crystalline form suitable for structural determination by X-ray crystallography, and thus neither the crystal structure of LuxP nor the LuxP binding site for AI-2 were known prior to the instant invention.

SUMMARY OF THE INVENTION

A preferred embodiment provides a crystal comprising LuxP. The crystal may comprise a LuxP-ligand complex. Preferably, the ligand comprises boron and/or a furan moiety. AI-2 is an example of a preferred ligand.

Another preferred embodiment provides a method of using the crystal to identify whether a ligand binds to LuxP, comprising: obtaining the atomic coordinates in the crystal of at least a selected portion of LuxP; using the atomic coordinates to model the selected portion; identifying a potential ligand; and docking the potential ligand to the selected portion of LuxP. Preferably, the selected portion comprises an amino acid residue selected from the group consisting of Trp 82, Gln 77, Ser 79, Asp 267, Thr 266, Trp 289, Arg 310, Arg 215, and Asn 159 according to Table 1. Another preferred embodiment provides ligands identified by this method. A pharmaceutical composition comprising such a ligand is another preferred embodiment, and methods of treating bacterial infections by administering such pharmaceutical compositions to humans are another preferred embodiment.

These and other embodiments are described in greater detail below.

BRIEF DESCRIPTION OF THE DRAWINGS

Various aspects of the invention will be readily apparent from the following description and from the appended drawings, which are meant to illustrate and not to limit the invention, and wherein.

DETAILED DESCRIPTION OF THE PREFERRED EMBODIMENTS

Figure 1:
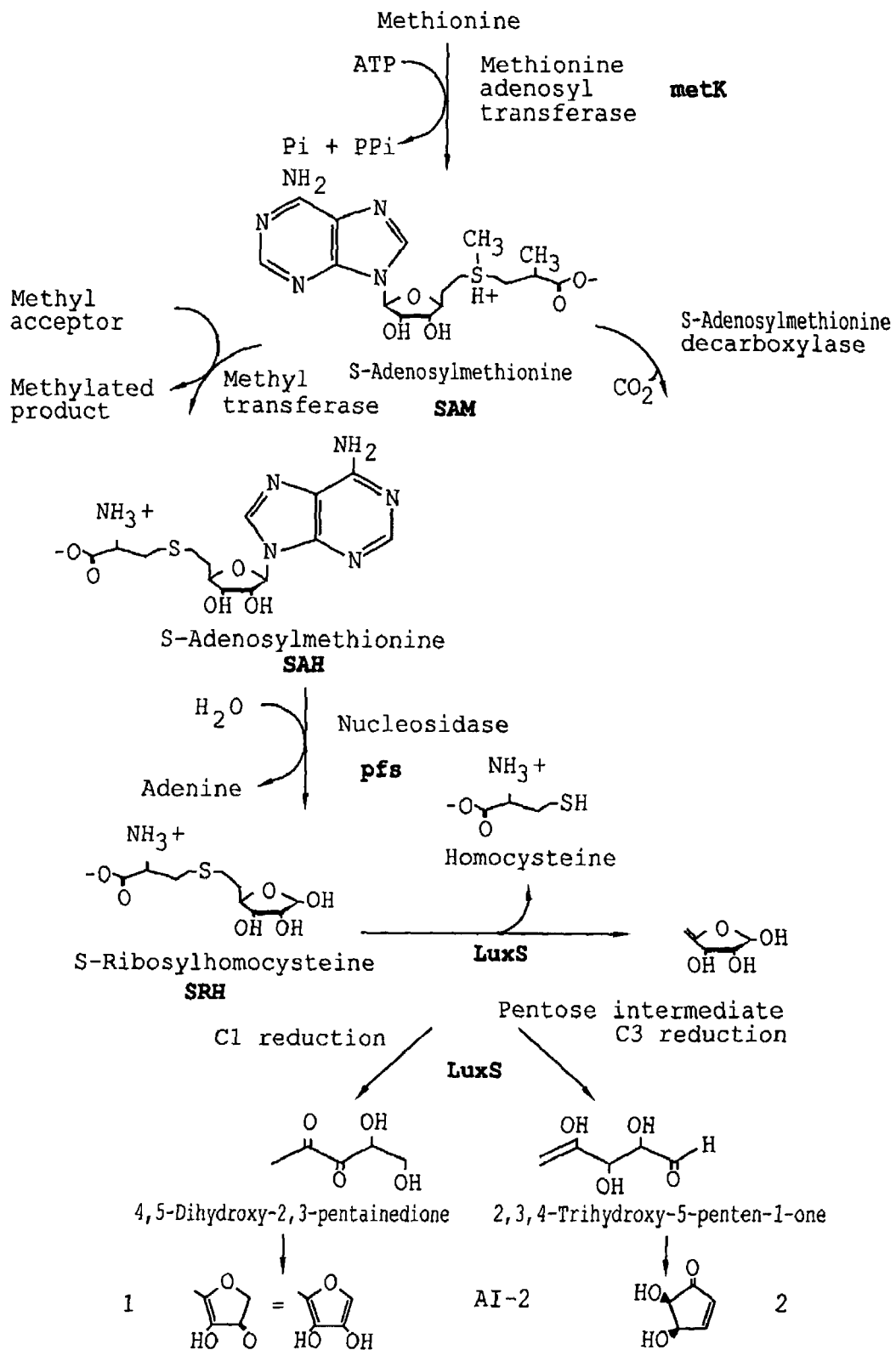
FIG. 1 illustrates several steps in the pathway of the production of AI-2 from S-adenosylmethionine.

A preferred embodiment provides a crystal comprising LuxP (SEQ ID NO: 1). In this context, those skilled in the art will understand that the term "crystal" refers to an ordered arrangement of atoms, the crystal having an overall size and quality sufficient for the elucidation of the atomic arrangement by X-ray crystallography. Preferably, the crystal diffracts X-rays to a resolution of greater than about 5.0 Angstroms (Å), more preferably greater than about 2.8 Å, even more preferably greater than about 1.5 Å. Those skilled in the art will understand that a resolution "greater than" a particular value means a resolution that numerically exceeds the recited value. For example, in the language of X-ray crystallography, a resolution of 2.8 Å is greater than a resolution of 5.0 Å. Crystals comprising LuxP are preferably prepared by the methods described in the Examples below. The atomic coordinates for LuxP are preferably determined by X-ray crystallography of a crystal comprising LuxP, preferably by the methods described in the Examples below. A set of atomic coordinates obtained by these methods for a crystal comprising LuxP appears in Table 1.

A preferred crystal comprises LuxP and a ligand. Preferably, the ligand comprises a furan moiety and/or a boron atom. In this context, those skilled in the art will understand that the term "ligand" refers to a molecule or ion that binds to LuxP. Preferably, binding between the ligand and LuxP occurs at a LuxP binding site. In this context, those skilled in the art will understand that the term "binding site" refers to a region of LuxP that favorably associates with a ligand, thus producing a LuxP-ligand complex in which the ligand binds relatively tightly to LuxP. Such strong binding may be produced, for example, when the shapes of the binding site and ligand are mutually compatible (e.g., "lock and key"), and/or when at least some of the ligand atoms are attracted to at least some of the LuxP atoms in the vicinity of the binding site by intermolecular forces, e.g., dipole-dipole interactions, Van der Waals attractions, hydrogen-bonding, etc.

Binding sites have significant utility in fields such as drug discovery. The association of natural ligands with the binding sites of their corresponding proteins, enzymes or receptors is the basis of many biological mechanisms of action. Similarly, many drugs exert their biological effects through association with the binding sites of proteins, enzymes, and receptors. Such associations may occur with all or any parts of the binding site. An understanding of such associations enables the design of drugs having more favorable associations with their target proteins, enzymes or receptors, and thus, improved biological effects. Therefore, this information is valuable in designing potential inhibitors of the binding sites of biologically important targets.

A preferred crystal comprises LuxP and AI-2, where the latter is an autoinducer that the bioluminescent marine bacterium *Vibrio harveyi* uses to regulate light production in response to cell density. It is believed that AI-2 has the following structure (I):

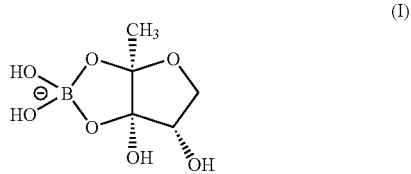

Figure 2:
FIG. 2 illustrates the structure of a LuxP-AI-2 complex.
Figure 3:
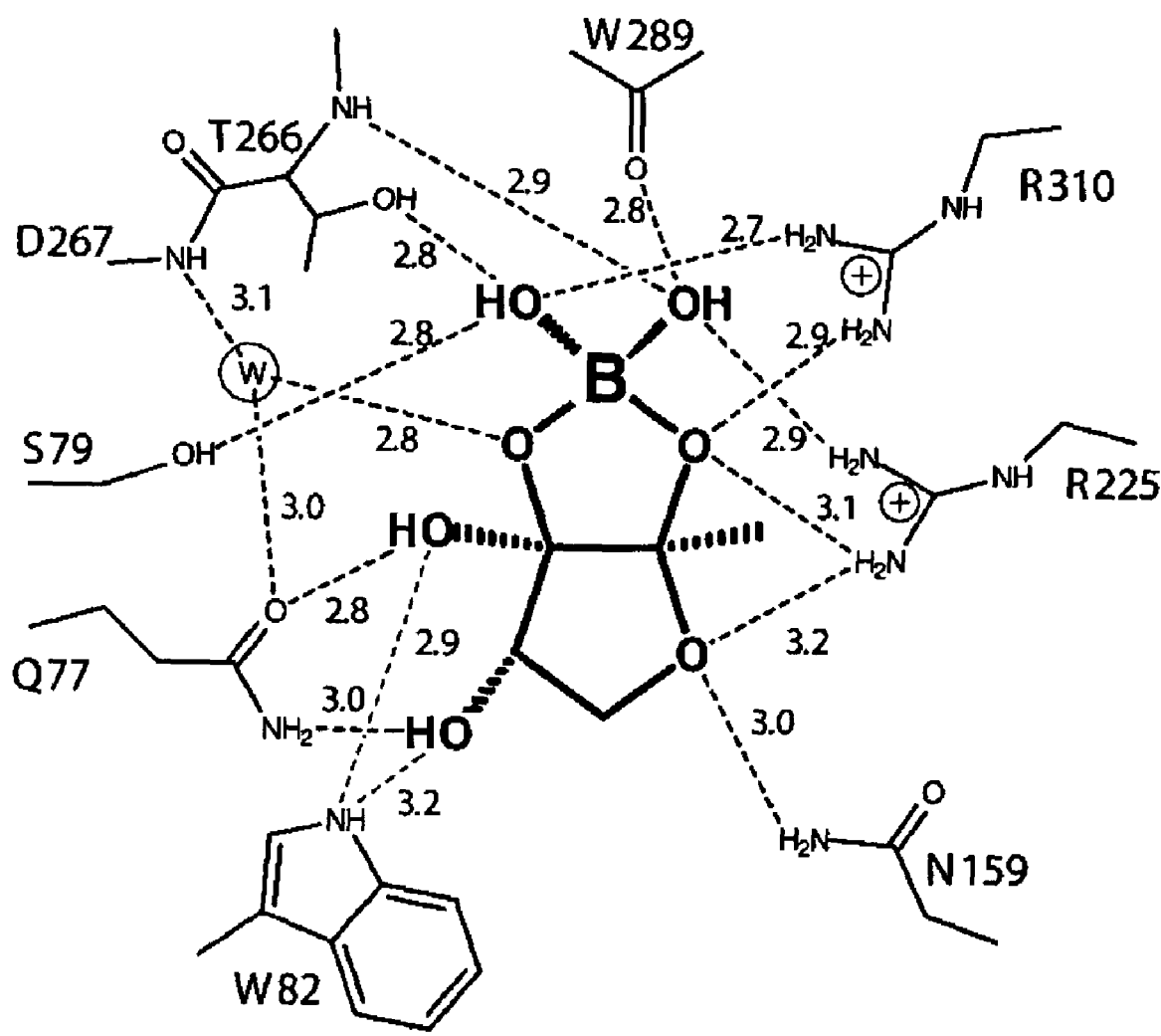
FIG. 3 shows the structure of LuxP and AI-2 at a binding site.

FIG. 2 shows a LuxP complex in which the compound represented by structure (I) (herein referred to as AI-2) occupies a LuxP binding site. FIG. 3 shows this binding site in greater detail. It is apparent from FIG. 3 that numerous polar interactions stabilize the two fused five-membered rings within the LuxP binding site. The positively charged side chains of Arg 215 and Arg 310 hydrogen-bond with three of the four borate oxygen atoms and likely stabilize the negative charge on the borate. As shown in FIG. 3, this binding site comprises at least one of the amino acid residues selected from the group consisting of Trp 82, Gln 77, Ser 79, Asp 267, Thr 266, Trp 289, Arg 310, Arg 215, and Asn 159, according to Table 1.

The LuxP X-ray crystallographic data shown in Table 1 may be used to identify whether a ligand binds to LuxP, and thus may be used for a variety of purposes, such as drug discovery. A preferred method comprises obtaining the atomic coordinates in the crystal of at least a selected portion of LuxP. Preferably, the selected portion comprises a binding site. More preferably, the selected portion comprises an amino acid residue selected from the group consisting of Trp 82, Gln 77, Ser 79, Asp 267, Thr 266, Trp 289, Arg 310, Arg 215, and Asn 159 according to Table 1. The atomic coordinates are preferably used to model the selected portion. Such modeling is preferably accomplished by storing crystallographic information about the selected portion on a computer and then using the computer to translate the atomic coordinates into the three-dimensional structure of the selected portion of LuxP. Computers and software suitable for carrying out these functions are commercially available. Preferred computer packages include Sybyl version 6.8 from Tripos, Inc. and MacroModel version 8.0 from Schrodinger Software. A potential ligand is then identified, and the likelihood of binding between the ligand and LuxP is determining by docking the potential ligand to the selected portion of LuxP. Such docking preferably involves computationally evaluating the ligand for its ability to bind with LuxP, preferably using the commercially available computational packages described above. Ligands that bind with LuxP are potential drug candidates. The LuxP structure encoded by the crystallographic data may be displayed in a graphical three-dimensional representation on a computer screen. This allows visual inspection of the structure, as well as visual inspection of the structure's association with the ligand. Preferably, a computer is used for the identifying of the potential ligand or the docking of the potential ligand to the binding site, or both.

The identification of ligands having the potential to bind to LuxP is preferably carried out by considering at least two factors. First, preferred ligands can bind to at least a portion of a LuxP binding site. Non-covalent molecular interactions important in this association include hydrogen bonding, van der Waals interactions, hydrophobic interactions and electrostatic interactions. Second, preferred ligands can assume a conformation that allows them to associate with the LuxP binding site directly. Although certain portions of the ligand may not directly participate in these associations, those portions of the ligand may still influence the overall conformation of the ligand. This, in turn, may have a significant impact on potency. Such conformational requirements include the overall three-dimensional structure and orientation of the ligand in relation to all or a portion of the binding site, and/or the spacing between functional groups of a ligand comprising several functional groups that directly interact with a LuxP binding site. Thus, a ligand identified by the method described above is a preferred embodiment.

After docking (preferably by the computational methods described above) indicates that a particular ligand has the potential to bind to LuxP, the interaction of the indicated ligand is preferably studied by obtaining a sample of the potential ligand and exposing a prokaryotic cell to the sample. Such exposure may be for various reasons, e.g., toxicity testing. Preferably, contacting is carried out with a group of quorum-sensing prokaryotic cells, e.g., bacteria, to determine whether and to what extent the ligand affects quorum sensing.

The ligands identified as having the potential to bind to LuxP ("binding ligands") are preferably administered to subjects in the form of pharmaceutical compositions comprising the binding ligand. The compound represented by structure (I) is an example of a binding ligand. A preferred mode of administration of the binding ligand is oral. Oral compositions preferably include an inert diluent and/or an edible carrier. The binding ligand can be enclosed in gelatin capsules or compressed into tablets. For the purpose of oral therapeutic administration, the binding ligand can be incorporated with excipients and used in the form of tablets, troches, or capsules. Pharmaceutically compatible binding agents and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; and/or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents. The ligand can be administered as a component of an elixir, suspension, syrup, wafer, chewing gum or the like. A syrup may contain, in addition to the ligand, sucrose as a sweetening agent and preservatives, dyes and colorings and flavors.

The binding ligand can also be mixed with other active materials that do not impair the desired action, or with materials that supplement the desired action, such as antibiotics. Preferred antibiotics for this purpose include aminoglycosides such as tobramycin, glycopeptides such as vancomycin, beta lactams such as amoxicillin, quinolones such as ciprofloxicin, macrolides such as azithromycin, tetracyclines, sulfonamides, trimethoprim-sulfamethoxazole, or chloramphenicol. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; chelating agents such as ethylenediaminetetraacetic acid (EDTA); buffers such as acetates, citrates or phosphates and agents for the adjustment of tonicity such as sodium chloride or dextrose. The parental preparation can be enclosed in ampoules, disposable syringes or multiple dose vials made of glass or plastic. If administered intravenously, preferred carriers are physiological saline or phosphate buffered saline (PBS).

In a preferred embodiment, the binding ligand is prepared with carriers that protect the ligand against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are known to those skilled in the art.

Pharmaceutical compositions are preferably administered to subjects, preferably humans, in an amount that is therapeutically effective to treat a bacterial infection. Therapeutically effective amounts can be determined by those skilled in the art by such methods as clinical trials. Dosage may be adjusted in individual cases as required to achieve the desired degree of target bacterial regulation. Sustained release dosages and infusions are specifically contemplated. Pharmaceutical compositions can be administered by any appropriate route for systemic, local or topical delivery, for example, orally, parenterally, intravenously, intradermally, subcutaneously, buccally, intranasally, by inhalation, vaginally, rectally or topically, in liquid or solid form. Methods of administering the compounds described herein may be by specific dose or by controlled release vehicles.

The pharmaceutical composition may be administered at once, or may be divided into a number of smaller doses to be administered at varying intervals of time. It is to be further understood that for any particular subject, specific dosage regimens should be adjusted over time according to the individual need and the professional judgment of the person administering or supervising the administration of the binding ligand, and that the concentration ranges set forth herein are exemplary only and are not intended to limit the scope or practice of the claimed methods.

The instant invention is not bound by any theory of operation. The following discussion is provided for the benefit of those skilled in the art, and does not limit the scope of the claims.

Figure 4:
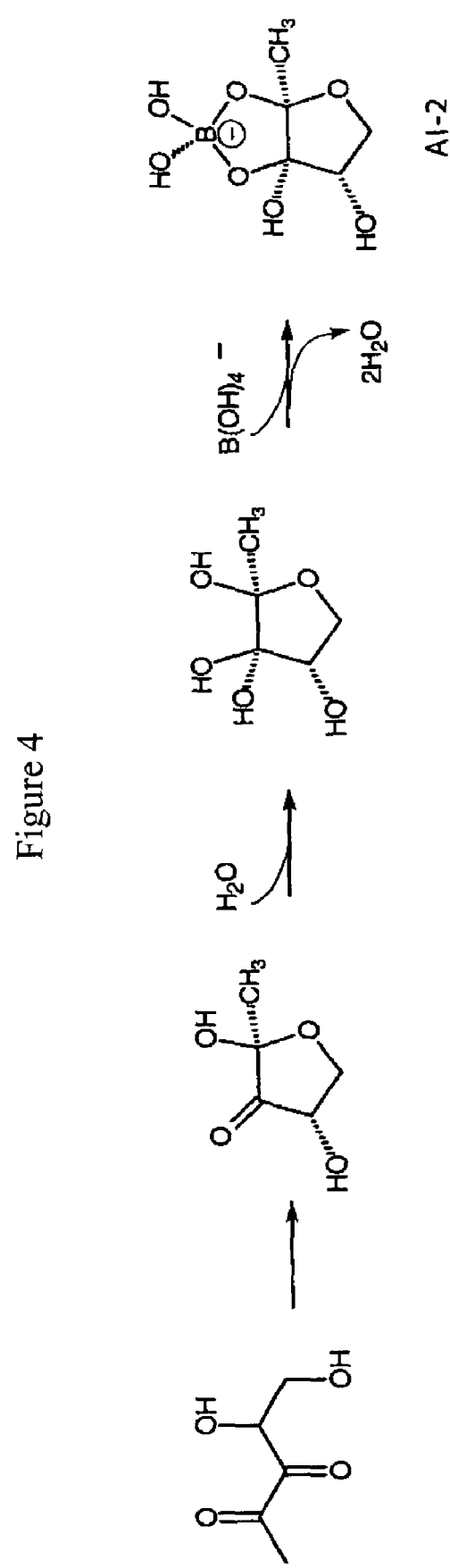
FIG. 4 illustrates a route for the conversion of 4,5-dihydroxy-2,3-pentanedione to AI-2.

FIG. 4 illustrates a chemically straightforward route connecting 4,5-dihydroxy-2,3-pentanedione, the product of the LuxS-catalyzed reaction, to AI-2. The cyclic form of 4,5-dihydroxy-2,3-pentanedione ("pro-AI-2"), can react with borate to form a cyclic borate diester. Boric acid is widely available in the biosphere; for example, the average boric acid concentration in seawater is approximately 0.4 mM. Borate, with a pKa of 9.2, is present largely as undissociated boric acid at neutral pH. Furthermore, furanosyl borate diesters similar in structure to AI-2 are relatively stable. Surprisingly, furanoid rings expected to form stable borate addition products are rare in nature with only two, ribose and apiose, known to have this configuration in their physiological derivatives. In addition to AI-2, other borate adducts may be produced from cyclic derivatives of 4,5-dihydroxy-2,3-pentanedione.

Boric acid has a dramatic effect on AI-2 signaling in *V. harveyi*, as shown through use of a LuxP$^+$, LuxS$^+$ reporter strain that produces its own AI-2. Endogenously produced AI-2 stimulates light production, but only after a delay during which the AI-2 concentration builds to a threshold level. During this delay period, the addition of the activity produced by the in vitro reaction of S-adenosylhomocysteine with Pfs and LuxS induces light production. It has been found that addition of 1 mM boric acid also results in substantial induction. Boric acid concentrations as low as 10 μM cause significant (10-fold) induction. It has also been found that boric acid has no effect on a LuxS$^-$ strain that cannot synthesize 4,5-dihydroxy-2,3-pentanedio latter strains show wild-type responses to the other *V. harveyi* autoinducer (AI-1) under these experimental conditions. Therefore, the induction of bioluminescence by boric acid is specific for the AI-2 detection system. The strong induction by boric acid in the bioassay is consistent with the proposed chemical structure for AI-2 shown in formula (1).

The structure shown in formula (I) is a novel furanosyl borate diester. By contrast, previously characterized autoinducers are acyl homoserine lactones, modified oligopeptides or quinolones. One of the most unexpected features of the proposed AI-2 structure is the presence of a boron atom. Boron has previously been found in a small number of polyketide antibiotics. It is also known to be essential for vascular plants and several other organisms including cyanobacteria; however, in no case is its functional role well understood. The results discussed herein provide evidence for a biochemically defined function for boron in bacterial quorum sensing.

Whereas acyl homoserine lactone and oligopeptide autoinducers are used for communication within a bacterial species, AI-2 is proposed to be a universal signal that facilitates inter-species communication. LuxS enzymes from a variety of bacteria produce AI-2 activity, presumably through the generation of a common intermediate, pro-AI-2. It is apparent that LuxP, the AI-2 sensor in *V. harveyi*, binds a borate diester of pro-AI-2. Since the biochemical machinery for synthesizing pro-AI-2 is broadly conserved, and borate is widely available, it is believed that AI-2 is produced and detected by diverse bacterial species.

EXAMPLES

LuxP (residues 24–365) from *Vibrio harveyi* was cloned into the pGEX-4T expression vector (Amersham Pharmacia) with an engineered thrombin cleavage site in between glutathione-S-transferase (GST) and the N-terminus of LuxP. The vector was transformed into *E. coli* strain BL21 for overexpression of GST-LuxP fusion protein upon induction with IPTG. After cell lysis, the GST-LuxP fusion protein was purified through use of a glutathione-agarose (Amersham Pharmacia) column. After elution, the fusion protein was digested with thrombin overnight on ice and further purified using an 8-ml MonoQ column (Amersham Pharmacia). The eluent was salt-adjusted and then concentrated through use of a pressure cell (Amicon) to yield a stock solution of 8 mg/mL LuxP in 0.05 M Tris-HCl, 0.15 M NaCl, pH 8.0.

The hanging drop vapor diffusion method was used for the crystallization. Crystals were grown by equilibrating a mixture of 1.0 µL of LuxP AI-2 solution and 1 µL of 0.1 M Tris-HCl, 16% PEG 4000, 18% glycerol (v/v), pH 8.5 at room temperature, against the same buffer/precipitant solution in the reservoir. The crystals are in space group $P2_1$, with cell parameters of a=42.3, b=77.5, c=52.0 Å and β=96.4°. X-ray diffraction data on the native protein were collected at beamline X12C of the National Synchrotron Light Source at the Brookhaven National Laboratories through use of a Brandeis CCD detector at 100 K. Data on heavy atom derivatives were collected through use of R-AXIS detectors at 100K. Diffraction data were all processed with the HKL program suite, see Otwinowski, Z. & Minor, W., Methods Enzymol., vol. 276, pp. 965–969 (1996). Heavy atom sites were located through use of the program Solve, see Terwilliger, T. C. & Berendzen, J., Acta Crystllogr. D, vol. 55, pp. 849–861 (1999). Multiple isomorphous phasing was done through use of MLPHARE and DM from the CCP4 suite. Model building and refinement were done through use of O, see Jones, T. A. et al., Acta Crystallogr. A, vol. 47, pp. 110–119 (1991), and CNS, see Brunger, A. T., et al. Acta Crystallogr. D, vol. 54, pp. 905–921 (1998), respectively.

The X-ray crystal structure of recombinant *V. harveyi* LuxP, overproduced in the LuxS[+] *E. coli* strain BL21, was determined by multiple isomorphous replacement at 2.8 Å resolution and refined to 1.5 Å resolution, see Table 1. The assignment of atom type at each position was dictated by both the valence and the local chemical environment within the protein. Thus, tetrahedrally substituted atoms were deemed to be carbon atoms, whereas atoms within hydrogen-bonding distance of at least one (but generally two or three) polar protein atoms or buried water molecules were deemed to be oxygen atoms. Weak bond length and bond angle restraints were applied to the ligand during subsequent refinement. The resulting structural model for the LuxP-AI-2 complex has an $R_{cryst}$ and $R_{free}$ of 0.21 and 0.24, respectively, and exhibits excellent geometry. No orientational or chemical heterogeneity of the buried ligand is evident in the crystallographic electron density.

Nuclear magnetic resonance (NMR) spectroscopy was used to confirm that the ligand contains boron. The $^{11}$B NMR spectrum of the LuxP-AI-2 complex shows a peak signifying the presence of boron. The chemical shift for this peak (6.2 ppm) is within the range (3.9–6.2 ppm) observed for borate esters of carbohydrate 1,2-diols. For comparison, borate esters of 1,3-diols and boric acid display chemical shifts of 0.3–0.9 and 18.8 ppm, respectively. The $^{11}$B NMR peak disappeared after ultrafiltration to remove protein. Furthermore, it was not observed in apo-LuxP overproduced in LuxS[−] BL21 *E. coli*.

The mass of the LuxP-AI-2 complex was determined through use of electrospray ionization mass spectrometry (ESI-MS). Under optimized conditions, peaks were observed for both LuxP and LuxP-AI-2 at molecular weights that differ by 194.2±3.0 Da. This mass increment agrees closely with the molecular weight of the AI-2 structure shown in formula (1) (192.9 Da).

It will be appreciated by those skilled in the art that various omissions, additions and modifications may be made to the processes described above without departing from the scope of the invention, and all such modifications and changes are intended to fall within the scope of the invention, as defined by the appended claims.

TABLE 1

Atomic structural coordinates for LuxP

| | ATOM TYPE | RESID | | NO | X | Y | Z | OCC | | |
|---|---|---|---|---|---|---|---|---|---|---|
| ATOM 1 | N | GLY | A | 27 | 1.162 | −8.03 | 2.941 | 1 | 29.45 | N |
| ATOM 2 | CA | GLY | A | 27 | 0.475 | −7.176 | 3.95 | 1 | 28.38 | C |
| ATOM 3 | C | GLY | A | 27 | 0.472 | −7.788 | 5.338 | 1 | 20.4 | C |
| ATOM 4 | O | GLY | A | 27 | 0.338 | −7.081 | 6.339 | 1 | 23.18 | O |
| ATOM 5 | N | TYR | A | 28 | 0.618 | −9.107 | 5.4 | 1 | 21.8 | N |
| ATOM 6 | CA | TYR | A | 28 | 0.628 | −9.807 | 6.679 | 1 | 20.8 | C |
| ATOM 7 | C | TYR | A | 28 | 1.858 | −10.672 | 6.881 | 1 | 21.68 | C |
| ATOM 8 | O | TYR | A | 28 | 2.453 | −11.172 | 5.923 | 1 | 23.26 | O |
| ATOM 9 | CB | TYR | A | 28 | −0.582 | −10.739 | 6.815 | 1 | 21.36 | C |
| ATOM 10 | CG | TYR | A | 28 | −1.935 | −10.089 | 6.71 | 1 | 15.4 | C |
| ATOM 11 | CD1 | TYR | A | 28 | −2.556 | −9.926 | 5.478 | 1 | 20.88 | C |
| ATOM 12 | CD2 | TYR | A | 28 | −2.615 | −9.676 | 7.853 | 1 | 18.36 | C |
| ATOM 13 | CE1 | TYR | A | 28 | −3.828 | −9.373 | 5.383 | 1 | 20.92 | C |
| ATOM 14 | CE2 | TYR | A | 28 | −3.882 | −9.124 | 7.769 | 1 | 15.1 | C |
| ATOM 15 | CZ | TYR | A | 28 | −4.484 | −8.976 | 6.536 | 1 | 21.78 | C |
| ATOM 16 | OH | TYR | A | 28 | −5.742 | −8.432 | 6.452 | 1 | 25.64 | O |
| ATOM 17 | N | TRP | A | 29 | 2.219 | −10.855 | 8.145 | 1 | 20.63 | N |
| ATOM 18 | CA | TRP | A | 29 | 3.327 | −11.72 | 8.516 | 1 | 20.65 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 19 | C | TRP | A | 29 | 2.747 | −13.121 | 8.628 | 1 | 26.86 | C |
| ATOM 20 | O | TRP | A | 29 | 1.628 | −13.291 | 9.11 | 1 | 23.58 | O |
| ATOM 21 | CB | TRP | A | 29 | 3.878 | −11.377 | 9.897 | 1 | 18.51 | C |
| ATOM 22 | CG | TRP | A | 29 | 4.745 | −10.177 | 9.976 | 1 | 20.78 | C |
| ATOM 23 | CD1 | TRP | A | 29 | 4.353 | −8.896 | 10.232 | 1 | 23.92 | C |
| ATOM 24 | CD2 | TRP | A | 29 | 6.168 | −10.142 | 9.827 | 1 | 25.35 | C |
| ATOM 25 | NE1 | TRP | A | 29 | 5.446 | −8.064 | 10.257 | 1 | 27.01 | N |
| ATOM 26 | CE2 | TRP | A | 29 | 6.573 | −8.803 | 10.01 | 1 | 28.52 | C |
| ATOM 27 | CE3 | TRP | A | 29 | 7.14 | −11.115 | 9.558 | 1 | 29.6 | C |
| ATOM 28 | CZ2 | TRP | A | 29 | 7.913 | −8.408 | 9.933 | 1 | 30.92 | C |
| ATOM 29 | CZ3 | TRP | A | 29 | 8.475 | −10.722 | 9.48 | 1 | 27.56 | C |
| ATOM 30 | CH2 | TRP | A | 29 | 8.845 | −9.378 | 9.668 | 1 | 29.9 | C |
| ATOM 31 | N | GLY | A | 30 | 3.495 | −14.121 | 8.184 | 1 | 22.93 | N |
| ATOM 32 | CA | GLY | A | 30 | 3.017 | −15.479 | 8.342 | 1 | 19.85 | C |
| ATOM 33 | C | GLY | A | 30 | 3.167 | −15.736 | 9.828 | 1 | 17.64 | C |
| ATOM 34 | O | GLY | A | 30 | 3.95 | −15.057 | 10.494 | 1 | 19.11 | O |
| ATOM 35 | N | TYR | A | 31 | 2.424 | −16.695 | 10.37 | 1 | 18.53 | N |
| ATOM 36 | CA | TYR | A | 31 | 2.522 | −16.99 | 11.796 | 1 | 14.51 | C |
| ATOM 37 | C | TYR | A | 31 | 3.933 | −17.437 | 12.19 | 1 | 19.56 | C |
| ATOM 38 | O | TYR | A | 31 | 4.554 | −16.849 | 13.079 | 1 | 18.61 | O |
| ATOM 39 | CB | TYR | A | 31 | 1.501 | −18.07 | 12.169 | 1 | 17.5 | C |
| ATOM 40 | CG | TYR | A | 31 | 1.495 | −18.451 | 13.632 | 1 | 15.52 | C |
| ATOM 41 | CD1 | TYR | A | 31 | 1.952 | −19.7 | 14.044 | 1 | 18.39 | C |
| ATOM 42 | CD2 | TYR | A | 31 | 1.034 | −17.566 | 14.606 | 1 | 14.9 | C |
| ATOM 43 | CE1 | TYR | A | 31 | 1.948 | −20.063 | 15.384 | 1 | 14.27 | C |
| ATOM 44 | CE2 | TYR | A | 31 | 1.027 | −17.916 | 15.957 | 1 | 14.18 | C |
| ATOM 45 | CZ | TYR | A | 31 | 1.484 | −19.171 | 16.338 | 1 | 16.72 | C |
| ATOM 46 | OH | TYR | A | 31 | 1.458 | −19.541 | 17.665 | 1 | 16.26 | O |
| ATOM 47 | N | GLN | A | 32 | 4.437 | −18.479 | 11.535 | 1 | 21.01 | N |
| ATOM 48 | CA | GLN | A | 32 | 5.779 | −18.96 | 11.833 | 1 | 23.08 | C |
| ATOM 49 | C | GLN | A | 32 | 6.815 | −17.943 | 11.372 | 1 | 20.05 | C |
| ATOM 50 | O | GLN | A | 32 | 7.864 | −17.802 | 11.993 | 1 | 20.08 | O |
| ATOM 51 | CB | GLN | A | 32 | 6.036 | −20.305 | 11.15 | 1 | 17.13 | C |
| ATOM 52 | CG | GLN | A | 32 | 5.224 | −21.465 | 11.728 | 1 | 22.16 | C |
| ATOM 53 | CD | GLN | A | 32 | 5.519 | −21.722 | 13.199 | 1 | 22.41 | C |
| ATOM 54 | OE1 | GLN | A | 32 | 6.646 | −21.532 | 13.657 | 1 | 28.21 | O |
| ATOM 55 | NE2 | GLN | A | 32 | 4.512 | −22.176 | 13.94 | 1 | 23.5 | N |
| ATOM 56 | N | GLU | A | 33 | 6.52 | −17.242 | 10.279 | 1 | 19.06 | N |
| ATOM 57 | CA | GLU | A | 33 | 7.435 | −16.229 | 9.758 | 1 | 17.66 | C |
| ATOM 58 | C | GLU | A | 33 | 7.67 | −15.152 | 10.811 | 1 | 22.74 | C |
| ATOM 59 | O | GLU | A | 33 | 8.793 | −14.686 | 11.003 | 1 | 22.54 | O |
| ATOM 60 | CB | GLU | A | 33 | 6.861 | −15.59 | 8.492 | 1 | 18.97 | C |
| ATOM 61 | CG | GLU | A | 33 | 7.665 | −14.393 | 7.999 | 1 | 22.99 | C |
| ATOM 62 | CD | GLU | A | 33 | 7.062 | −13.747 | 6.769 | 1 | 33.46 | C |
| ATOM 63 | OE1 | GLU | A | 33 | 5.824 | −13.814 | 6.603 | 1 | 26.18 | O |
| ATOM 64 | OE2 | GLU | A | 33 | 7.825 | −13.156 | 5.974 | 1 | 38.06 | O |
| ATOM 65 | N | PHE | A | 34 | 6.597 | −14.756 | 11.485 | 1 | 20.51 | N |
| ATOM 66 | CA | PHE | A | 34 | 6.663 | −13.74 | 12.53 | 1 | 15.44 | C |
| ATOM 67 | C | PHE | A | 34 | 7.476 | −14.251 | 13.713 | 1 | 17.03 | C |
| ATOM 68 | O | PHE | A | 34 | 8.348 | −13.553 | 14.23 | 1 | 19.46 | O |
| ATOM 69 | CB | PHE | A | 34 | 5.243 | −13.391 | 12.996 | 1 | 15.15 | C |
| ATOM 70 | CG | PHE | A | 34 | 5.19 | −12.367 | 14.104 | 1 | 15.59 | C |
| ATOM 71 | CD1 | PHE | A | 34 | 5.246 | −11.005 | 13.816 | 1 | 17.67 | C |
| ATOM 72 | CD2 | PHE | A | 34 | 5.07 | −12.766 | 15.434 | 1 | 17.88 | C |
| ATOM 73 | CE1 | PHE | A | 34 | 5.178 | −10.055 | 14.84 | 1 | 16.21 | C |
| ATOM 74 | CE2 | PHE | A | 34 | 5.003 | −11.823 | 16.468 | 1 | 16.44 | C |
| ATOM 75 | CZ | PHE | A | 34 | 5.056 | −10.462 | 16.166 | 1 | 14.7 | C |
| ATOM 76 | N | LEU | A | 35 | 7.185 | −15.476 | 14.14 | 1 | 17.21 | N |
| ATOM 77 | CA | LEU | A | 35 | 7.875 | −16.071 | 15.276 | 1 | 17.53 | C |
| ATOM 78 | C | LEU | A | 35 | 9.361 | −16.327 | 15.003 | 1 | 18.43 | C |
| ATOM 79 | O | LEU | A | 35 | 10.171 | −16.321 | 15.93 | 1 | 23.36 | O |
| ATOM 80 | CB | LEU | A | 35 | 7.164 | −17.363 | 15.695 | 1 | 18.99 | C |
| ATOM 81 | CG | LEU | A | 35 | 5.727 | −17.158 | 16.205 | 1 | 16.42 | C |
| ATOM 82 | CD1 | LEU | A | 35 | 5.121 | −18.499 | 16.617 | 1 | 17.82 | C |
| ATOM 83 | CD2 | LEU | A | 35 | 5.733 | −16.202 | 17.386 | 1 | 17.51 | C |
| ATOM 84 | N | ASP | A | 36 | 9.722 | −16.551 | 13.742 | 1 | 19.95 | N |
| ATOM 85 | CA | ASP | A | 36 | 11.127 | −16.773 | 13.407 | 1 | 23.07 | C |
| ATOM 86 | C | ASP | A | 36 | 11.85 | −15.435 | 13.306 | 1 | 26.54 | C |
| ATOM 87 | O | ASP | A | 36 | 13.038 | −15.328 | 13.624 | 1 | 24.96 | O |
| ATOM 88 | CB | ASP | A | 36 | 11.272 | −17.535 | 12.084 | 1 | 21.89 | C |
| ATOM 89 | CG | ASP | A | 36 | 10.973 | −19.015 | 12.226 | 1 | 22.8 | C |
| ATOM 90 | OD1 | ASP | A | 36 | 11.27 | −19.581 | 13.298 | 1 | 31.5 | O |
| ATOM 91 | OD2 | ASP | A | 36 | 10.453 | −19.616 | 11.262 | 1 | 41.76 | O |
| ATOM 92 | N | GLU | A | 37 | 11.127 | −14.411 | 12.867 | 1 | 24.64 | N |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 93 | CA | GLU | A | 37 | 11.706 | −13.081 | 12.729 | 1 | 23.71 | C |
| ATOM 94 | C | GLU | A | 37 | 12.01 | −12.476 | 14.097 | 1 | 24.63 | C |
| ATOM 95 | O | GLU | A | 37 | 13.006 | −11.766 | 14.267 | 1 | 24.74 | O |
| ATOM 96 | CB | GLU | A | 37 | 10.746 | −12.17 | 11.964 | 1 | 28.6 | C |
| ATOM 97 | CG | GLU | A | 37 | 11.372 | −10.87 | 11.499 | 1 | 39.23 | C |
| ATOM 98 | CD | GLU | A | 37 | 12.632 | −11.103 | 10.693 | 1 | 48.96 | C |
| ATOM 99 | OE1 | GLU | A | 37 | 13.701 | −11.31 | 11.306 | 1 | 54.15 | O |
| ATOM 100 | OE2 | GLU | A | 37 | 12.548 | −11.095 | 9.446 | 1 | 58.87 | O |
| ATOM 101 | N | PHE | A | 38 | 11.148 | −12.764 | 15.068 | 1 | 25.26 | N |
| ATOM 102 | CA | PHE | A | 38 | 11.302 | −12.252 | 16.425 | 1 | 22.67 | C |
| ATOM 103 | C | PHE | A | 38 | 11.382 | −13.411 | 17.415 | 1 | 22.23 | C |
| ATOM 104 | O | PHE | A | 38 | 10.374 | −13.831 | 17.986 | 1 | 20.26 | O |
| ATOM 105 | CB | PHE | A | 38 | 10.119 | −11.338 | 16.777 | 1 | 20.13 | C |
| ATOM 106 | CG | PHE | A | 38 | 9.855 | −10.267 | 15.755 | 1 | 20.74 | C |
| ATOM 107 | CD1 | PHE | A | 38 | 8.928 | −10.467 | 14.737 | 1 | 28.11 | C |
| ATOM 108 | CD2 | PHE | A | 38 | 10.552 | −9.063 | 15.799 | 1 | 26.96 | C |
| ATOM 109 | CE1 | PHE | A | 38 | 8.697 | −9.48 | 13.776 | 1 | 29.58 | C |
| ATOM 110 | CE2 | PHE | A | 38 | 10.329 | −8.07 | 14.843 | 1 | 27.85 | C |
| ATOM 111 | CZ | PHE | A | 38 | 9.401 | −8.279 | 13.832 | 1 | 29.82 | C |
| ATOM 112 | N | PRO | A | 39 | 12.594 | −13.944 | 17.641 | 1 | 22.82 | N |
| ATOM 113 | CA | PRO | A | 39 | 12.798 | −15.064 | 18.564 | 1 | 19.42 | C |
| ATOM 114 | C | PRO | A | 39 | 12.198 | −14.893 | 19.954 | 1 | 17.32 | C |
| ATOM 115 | O | PRO | A | 39 | 11.77 | −15.871 | 20.565 | 1 | 22.6 | O |
| ATOM 116 | CB | PRO | A | 39 | 14.324 | −15.218 | 18.595 | 1 | 23.31 | C |
| ATOM 117 | CG | PRO | A | 39 | 14.817 | −13.85 | 18.25 | 1 | 32.23 | C |
| ATOM 118 | CD | PRO | A | 39 | 13.886 | −13.445 | 17.14 | 1 | 29.65 | C |
| ATOM 119 | N | GLU | A | 40 | 12.172 | −13.663 | 20.461 | 1 | 21.53 | N |
| ATOM 120 | CA | GLU | A | 40 | 11.603 | −13.433 | 21.781 | 1 | 22.77 | C |
| ATOM 121 | C | GLU | A | 40 | 10.094 | −13.637 | 21.734 | 1 | 24.36 | C |
| ATOM 122 | O | GLU | A | 40 | 9.479 | −14.013 | 22.733 | 1 | 19.58 | O |
| ATOM 123 | CB | GLU | A | 40 | 11.917 | −12.022 | 22.282 | 1 | 27.51 | C |
| ATOM 124 | CG | GLU | A | 40 | 11.293 | −11.733 | 23.641 | 1 | 35.5 | C |
| ATOM 125 | CD | GLU | A | 40 | 11.69 | −12.755 | 24.699 | 1 | 44.86 | C |
| ATOM 126 | OE1 | GLU | A | 40 | 10.993 | −12.846 | 25.734 | 1 | 44.44 | O |
| ATOM 127 | OE2 | GLU | A | 40 | 12.703 | −13.463 | 24.503 | 1 | 44.74 | O |
| ATOM 128 | N | GLN | A | 41 | 9.5 | −13.385 | 20.572 | 1 | 20.19 | N |
| ATOM 129 | CA | GLN | A | 41 | 8.065 | −13.576 | 20.418 | 1 | 18.36 | C |
| ATOM 130 | C | GLN | A | 41 | 7.779 | −15.073 | 20.428 | 1 | 18.21 | C |
| ATOM 131 | O | GLN | A | 41 | 6.774 | −15.511 | 20.984 | 1 | 18.36 | O |
| ATOM 132 | CB | GLN | A | 41 | 7.569 | −12.929 | 19.123 | 1 | 22.56 | C |
| ATOM 133 | CG | GLN | A | 41 | 7.471 | −11.408 | 19.195 | 1 | 19.8 | C |
| ATOM 134 | CD | GLN | A | 41 | 6.596 | −10.94 | 20.347 | 1 | 24.82 | C |
| ATOM 135 | OE1 | GLN | A | 41 | 5.498 | −11.464 | 20.56 | 1 | 23.3 | O |
| ATOM 136 | NE2 | GLN | A | 41 | 7.069 | −9.945 | 21.088 | 1 | 28.69 | N |
| ATOM 137 | N | ARG | A | 42 | 8.665 | −15.869 | 19.834 | 1 | 20.57 | N |
| ATOM 138 | CA | ARG | A | 42 | 8.446 | −17.306 | 19.849 | 1 | 22.83 | C |
| ATOM 139 | C | ARG | A | 42 | 8.526 | −17.812 | 21.288 | 1 | 21.57 | C |
| ATOM 140 | O | ARG | A | 42 | 7.783 | −18.71 | 21.672 | 1 | 21.95 | O |
| ATOM 141 | CD | ARG | A | 42 | 9.464 | −18.05 | 18.975 | 1 | 20.98 | C |
| ATOM 142 | CG | ARG | A | 42 | 9.14 | −19.542 | 18.856 | 1 | 27.08 | C |
| ATOM 143 | CD | ARG | A | 42 | 10.126 | −20.289 | 17.975 | 1 | 18.51 | C |
| ATOM 144 | NE | ARG | A | 42 | 9.989 | −19.977 | 16.556 | 1 | 24.54 | N |
| ATOM 145 | CZ | ARG | A | 42 | 8.986 | −20.385 | 15.784 | 1 | 20.73 | C |
| ATOM 146 | NH1 | ARG | A | 42 | 8.01 | −21.127 | 16.29 | 1 | 25.96 | N |
| ATOM 147 | NH2 | ARG | A | 42 | 8.975 | −20.064 | 14.497 | 1 | 23.46 | N |
| ATOM 148 | N | ASN | A | 43 | 9.429 | −17.244 | 22.089 | 1 | 22.12 | N |
| ATOM 149 | CA | ASN | A | 43 | 9.541 | −17.669 | 23.481 | 1 | 20.58 | C |
| ATOM 150 | C | ASN | A | 43 | 8.271 | −17.321 | 24.246 | 1 | 20.85 | C |
| ATOM 151 | O | ASN | A | 43 | 7.783 | −18.119 | 25.044 | 1 | 19.6 | O |
| ATOM 152 | CD | ASN | A | 43 | 10.745 | −17.011 | 24.166 | 1 | 22.21 | C |
| ATOM 153 | CG | ASN | A | 43 | 12.067 | −17.591 | 23.705 | 1 | 32.88 | C |
| ATOM 154 | OD1 | ASN | A | 43 | 12.22 | −18.808 | 23.604 | 1 | 36 | O |
| ATOM 155 | ND2 | ASN | A | 43 | 13.036 | −16.723 | 23.436 | 1 | 36.08 | N |
| ATOM 156 | N | LEU | A | 44 | 7.733 | −16.13 | 23.994 | 1 | 17.99 | N |
| ATOM 157 | CA | LEU | A | 44 | 6.513 | −15.701 | 24.67 | 1 | 20.19 | C |
| ATOM 158 | C | LEU | A | 44 | 5.317 | −16.549 | 24.248 | 1 | 15.33 | C |
| ATOM 159 | O | LEU | A | 44 | 4.504 | −16.945 | 25.085 | 1 | 17.89 | O |
| ATOM 160 | CB | LEU | A | 44 | 6.238 | −14.22 | 24.388 | 1 | 19.56 | C |
| ATOM 161 | CG | LEU | A | 44 | 7.194 | −13.238 | 25.072 | 1 | 22.89 | C |
| ATOM 162 | CD1 | LEU | A | 44 | 6.926 | −11.823 | 24.588 | 1 | 18.96 | C |
| ATOM 163 | CD2 | LEU | A | 44 | 7.014 | −13.329 | 26.578 | 1 | 24.59 | C |
| ATOM 164 | N | THR | A | 45 | 5.22 | −16.839 | 22.955 | 1 | 17.94 | N |
| ATOM 165 | CA | THR | A | 45 | 4.119 | −17.652 | 22.452 | 1 | 16.32 | C |
| ATOM 166 | C | THR | A | 45 | 4.214 | −19.066 | 23.02 | 1 | 18.02 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 167 | O | THR | A | 45 | 3.209 | −19.647 | 23.431 | 1 | 18.28 | O |
| ATOM 168 | CB | THR | A | 45 | 4.126 | −17.706 | 20.906 | 1 | 17.76 | C |
| ATOM 169 | OG1 | THR | A | 45 | 3.87 | −16.394 | 20.383 | 1 | 17.62 | O |
| ATOM 170 | CG2 | THR | A | 45 | 3.052 | −18.663 | 20.395 | 1 | 14.35 | C |
| ATOM 171 | N | ASN | A | 46 | 5.419 | −19.624 | 23.065 | 1 | 17.53 | N |
| ATOM 172 | CA | ASN | A | 46 | 5.564 | −20.966 | 23.61 | 1 | 15.85 | C |
| ATOM 173 | C | ASN | A | 46 | 5.168 | −20.969 | 25.081 | 1 | 16.74 | C |
| ATOM 174 | O | ASN | A | 46 | 4.554 | −21.916 | 25.566 | 1 | 20.68 | O |
| ATOM 175 | CB | ASN | A | 46 | 7.005 | −21.477 | 23.474 | 1 | 19.44 | C |
| ATOM 176 | CG | ASN | A | 46 | 7.389 | −21.776 | 22.04 | 1 | 29.9 | C |
| ATOM 177 | OD1 | ASN | A | 46 | 6.531 | −22.051 | 21.201 | 1 | 29.41 | O |
| ATOM 178 | ND2 | ASN | A | 46 | 8.69 | −21.745 | 21.753 | 1 | 25.14 | N |
| ATOM 179 | N | ALA | A | 47 | 5.524 | −19.905 | 25.793 | 1 | 20.15 | N |
| ATOM 180 | CA | ALA | A | 47 | 5.197 | −19.805 | 27.211 | 1 | 17.95 | C |
| ATOM 181 | C | ALA | A | 47 | 3.688 | −19.749 | 27.443 | 1 | 24.56 | C |
| ATOM 182 | O | ALA | A | 47 | 3.178 | −20.31 | 28.413 | 1 | 21.65 | O |
| ATOM 183 | CB | ALA | A | 47 | 5.863 | −18.572 | 27.819 | 1 | 23.29 | C |
| ATOM 184 | N | LEU | A | 48 | 2.974 | −19.062 | 26.56 | 1 | 18.11 | N |
| ATOM 185 | CA | LEU | A | 48 | 1.527 | −18.962 | 26.693 | 1 | 20.32 | C |
| ATOM 186 | C | LEU | A | 48 | 0.929 | −20.333 | 26.391 | 1 | 16.61 | C |
| ATOM 187 | O | LEU | A | 48 | 0.022 | −20.784 | 27.083 | 1 | 19.1 | O |
| ATOM 188 | CB | LEU | A | 48 | 0.971 | −17.922 | 25.717 | 1 | 20.63 | C |
| ATOM 189 | CG | LEU | A | 48 | −0.283 | −17.136 | 26.116 | 1 | 28.38 | C |
| ATOM 190 | CD1 | LEU | A | 48 | −0.901 | −16.548 | 24.855 | 1 | 18.34 | C |
| ATOM 191 | CD2 | LEU | A | 48 | −1.281 | −18.019 | 26.836 | 1 | 35.91 | C |
| ATOM 192 | N | SER | A | 49 | 1.445 | −20.99 | 25.356 | 1 | 17.41 | N |
| ATOM 193 | CA | SER | A | 49 | 0.961 | −22.315 | 24.981 | 1 | 16.28 | C |
| ATOM 194 | C | SER | A | 49 | 1.067 | −23.27 | 26.165 | 1 | 18.03 | C |
| ATOM 195 | O | SER | A | 49 | 0.153 | −24.054 | 26.427 | 1 | 20.04 | O |
| ATOM 196 | CB | SER | A | 49 | 1.767 | −22.863 | 23.803 | 1 | 23.74 | C |
| ATOM 197 | OG | SER | A | 49 | 1.606 | −22.049 | 22.655 | 1 | 27.34 | O |
| ATOM 198 | N | GLU | A | 50 | 2.184 | −23.202 | 26.882 | 1 | 21.55 | N |
| ATOM 199 | CA | GLU | A | 50 | 2.382 | −24.066 | 28.036 | 1 | 22.38 | C |
| ATOM 200 | C | GLU | A | 50 | 1.402 | −23.706 | 29.148 | 1 | 18.52 | C |
| ATOM 201 | O | GLU | A | 50 | 0.862 | −24.589 | 29.813 | 1 | 21.1 | O |
| ATOM 202 | CB | GLU | A | 50 | 3.823 | −23.954 | 28.537 | 1 | 24.06 | C |
| ATOM 203 | CG | GLU | A | 50 | 4.848 | −24.33 | 27.479 | 1 | 35.54 | C |
| ATOM 204 | CD | GLU | A | 50 | 6.275 | −24.273 | 27.988 | 1 | 47.94 | C |
| ATOM 205 | OE1 | GLU | A | 50 | 7.201 | −24.524 | 27.186 | 1 | 47.59 | O |
| ATOM 206 | OE2 | GLU | A | 50 | 6.471 | −23.98 | 29.187 | 1 | 50.94 | O |
| ATOM 207 | N | ALA | A | 51 | 1.157 | −22.412 | 29.338 | 1 | 21.99 | N |
| ATOM 208 | CA | ALA | A | 51 | 0.228 | −21.964 | 30.371 | 1 | 19.46 | C |
| ATOM 209 | C | ALA | A | 51 | −1.201 | −22.425 | 30.054 | 1 | 21.37 | C |
| ATOM 210 | O | ALA | A | 51 | −1.971 | −22.765 | 30.955 | 1 | 20.17 | O |
| ATOM 211 | CB | ALA | A | 51 | 0.276 | −20.439 | 30.492 | 1 | 21.55 | C |
| ATOM 212 | N | VAL | A | 52 | −1.552 | −22.431 | 28.773 | 1 | 19.89 | N |
| ATOM 213 | CA | VAL | A | 52 | −2.884 | −22.856 | 28.345 | 1 | 20.49 | C |
| ATOM 214 | C | VAL | A | 52 | −3.148 | −24.328 | 28.683 | 1 | 21.19 | C |
| ATOM 215 | O | VAL | A | 52 | −4.239 | −24.683 | 29.129 | 1 | 21.63 | O |
| ATOM 216 | CB | VAL | A | 52 | −3.068 | −22.638 | 26.819 | 1 | 18.88 | C |
| ATOM 217 | CG1 | VAL | A | 52 | −4.31 | −23.372 | 26.321 | 1 | 19.99 | C |
| ATOM 218 | CG2 | VAL | A | 52 | −3.176 | −21.147 | 26.524 | 1 | 21.62 | C |
| ATOM 219 | N | ARG | A | 53 | −2.143 | −25.175 | 28.48 | 1 | 21.55 | N |
| ATOM 220 | CA | ARG | A | 53 | −2.269 | −26.607 | 28.746 | 1 | 20.49 | C |
| ATOM 221 | C | ARG | A | 53 | −2.106 | −26.963 | 30.223 | 1 | 27.11 | C |
| ATOM 222 | O | ARG | A | 53 | −2.699 | −27.93 | 30.703 | 1 | 27.25 | O |
| ATOM 223 | CB | ARG | A | 53 | −1.243 | −27.375 | 27.905 | 1 | 28.7 | C |
| ATOM 224 | CG | ARG | A | 53 | −1.497 | −27.261 | 26.405 | 1 | 34.9 | C |
| ATOM 225 | CD | ARG | A | 53 | −2.716 | −28.076 | 25.996 | 1 | 42.32 | C |
| ATOM 226 | NE | ARG | A | 53 | −2.353 | −29.451 | 25.659 | 1 | 46.73 | N |
| ATOM 227 | CZ | ARG | A | 53 | −3.15 | −30.502 | 25.825 | 1 | 45.26 | C |
| ATOM 228 | NH1 | ARG | A | 53 | −4.365 | −30.346 | 26.334 | 1 | 55.16 | N |
| ATOM 229 | NH2 | ARG | A | 53 | −2.733 | −31.71 | 25.471 | 1 | 40.55 | N |
| ATOM 230 | N | ALA | A | 54 | −1.311 | −26.178 | 30.941 | 1 | 22.82 | N |
| ATOM 231 | CA | ALA | A | 54 | −1.083 | −26.428 | 32.361 | 1 | 38.2 | C |
| ATOM 232 | C | ALA | A | 54 | −2.295 | −26.023 | 33.197 | 1 | 26.86 | C |
| ATOM 233 | O | ALA | A | 54 | −3.16 | −25.278 | 32.733 | 1 | 24.01 | O |
| ATOM 234 | CB | ALA | A | 54 | 0.152 | −25.665 | 32.829 | 1 | 28.64 | C |
| ATOM 235 | N | GLN | A | 55 | −2.353 | −26.523 | 34.429 | 1 | 29.9 | N |
| ATOM 236 | CA | GLN | A | 55 | −3.451 | −26.209 | 35.34 | 1 | 22.47 | C |
| ATOM 237 | C | GLN | A | 55 | −3.459 | −24.715 | 35.67 | 1 | 28.26 | C |
| ATOM 238 | O | GLN | A | 55 | −2.408 | −24.07 | 35.696 | 1 | 25.21 | O |
| ATOM 239 | CB | GLN | A | 55 | −3.317 | −27.021 | 36.635 | 1 | 29.59 | C |
| ATOM 240 | CG | GLN | A | 55 | −3.557 | −28.515 | 36.471 | 1 | 30.94 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 241 | CD | GLN | A | 55 | −4.968 | −28.825 | 36.004 | 1 | 35.33 | C |
| ATOM 242 | OE1 | GLN | A | 55 | −5.949 | −28.419 | 36.632 | 1 | 37.32 | O |
| ATOM 243 | NE2 | GLN | A | 55 | −5.078 | −29.547 | 34.897 | 1 | 40.37 | N |
| ATOM 244 | N | PRO | A | 56 | −4.651 | −24.148 | 35.926 | 1 | 24.7 | N |
| ATOM 245 | CA | PRO | A | 56 | −4.86 | −22.736 | 36.26 | 1 | 28.07 | C |
| ATOM 246 | C | PRO | A | 56 | −4.071 | −22.251 | 37.463 | 1 | 37.18 | C |
| ATOM 247 | O | PRO | A | 56 | −4.19 | −22.808 | 38.557 | 1 | 35.4 | O |
| ATOM 248 | CB | PRO | A | 56 | −6.352 | −22.66 | 36.552 | 1 | 33.2 | C |
| ATOM 249 | CG | PRO | A | 56 | −6.921 | −23.712 | 35.704 | 1 | 27.53 | C |
| ATOM 250 | CD | PRO | A | 56 | −5.944 | −24.85 | 35.849 | 1 | 28.62 | C |
| ATOM 251 | N | VAL | A | 57 | −3.285 | −21.202 | 37.255 | 1 | 32.87 | N |
| ATOM 252 | CA | VAL | A | 57 | −2.508 | −20.592 | 38.324 | 1 | 33.33 | C |
| ATOM 253 | C | VAL | A | 57 | −3.109 | −19.195 | 38.434 | 1 | 27.77 | C |
| ATOM 254 | O | VAL | A | 57 | −2.757 | −18.299 | 37.67 | 1 | 27.52 | O |
| ATOM 255 | CB | VAL | A | 57 | −1.027 | −20.474 | 37.945 | 1 | 31.9 | C |
| ATOM 256 | CG1 | VAL | A | 57 | −0.278 | −19.734 | 39.033 | 1 | 33.9 | C |
| ATOM 257 | CG2 | VAL | A | 57 | −0.431 | −21.851 | 37.719 | 1 | 31.68 | C |
| ATOM 258 | N | PRO | A | 58 | −4.035 | −18.999 | 39.383 | 1 | 24.3 | N |
| ATOM 259 | CA | PRO | A | 58 | −4.73 | −17.732 | 39.63 | 1 | 29.04 | C |
| ATOM 260 | C | PRO | A | 58 | −3.911 | −16.449 | 39.745 | 1 | 29.03 | C |
| ATOM 261 | O | PRO | A | 58 | −2.74 | −16.466 | 40.129 | 1 | 29.99 | O |
| ATOM 262 | CB | PRO | A | 58 | −5.533 | −18.025 | 40.898 | 1 | 31.96 | C |
| ATOM 263 | CG | PRO | A | 58 | −4.733 | −19.089 | 41.575 | 1 | 34.33 | C |
| ATOM 264 | CD | PRO | A | 58 | −4.378 | −19.98 | 40.425 | 1 | 32.58 | C |
| ATOM 265 | N | LEU | A | 59 | −4.564 | −15.339 | 39.41 | 1 | 29.62 | N |
| ATOM 266 | CA | LEU | A | 59 | −3.971 | −14.004 | 39.458 | 1 | 31.58 | C |
| ATOM 267 | C | LEU | A | 59 | −3.206 | −13.777 | 40.763 | 1 | 34.3 | C |
| ATOM 268 | O | LEU | A | 59 | −3.761 | −13.928 | 41.854 | 1 | 32.11 | O |
| ATOM 269 | CB | LEU | A | 59 | −5.077 | −12.953 | 39.318 | 1 | 30.88 | C |
| ATOM 270 | CG | LEU | A | 59 | −4.698 | −11.469 | 39.279 | 1 | 35.51 | C |
| ATOM 271 | CD1 | LEU | A | 59 | −3.841 | −11.187 | 38.055 | 1 | 33.71 | C |
| ATOM 272 | CD2 | LEU | A | 59 | −5.966 | −10.619 | 39.251 | 1 | 29.03 | C |
| ATOM 273 | N | SER | A | 60 | −1.933 | −13.412 | 40.643 | 1 | 33.96 | N |
| ATOM 274 | CA | SER | A | 60 | −1.087 | −13.172 | 41.808 | 1 | 43.71 | C |
| ATOM 275 | C | SER | A | 60 | −1.337 | −11.792 | 42.406 | 1 | 50.24 | C |
| ATOM 276 | O | SER | A | 60 | −1.147 | −11.582 | 43.605 | 1 | 52.86 | O |
| ATOM 277 | CB | SER | A | 60 | 0.389 | −13.297 | 41.426 | 1 | 35.46 | C |
| ATOM 278 | OG | SER | A | 60 | 0.766 | −12.292 | 40.5 | 1 | 46.53 | O |
| ATOM 279 | N | LYS | A | 61 | −1.764 | −10.853 | 41.567 | 1 | 51.04 | N |
| ATOM 280 | CA | LYS | A | 61 | −2.03 | −9.493 | 42.02 | 1 | 56.12 | C |
| ATOM 281 | C | LYS | A | 61 | −3.476 | −9.076 | 41.782 | 1 | 57.02 | C |
| ATOM 282 | O | LYS | A | 61 | −3.885 | −8.836 | 40.645 | 1 | 57.23 | O |
| ATOM 283 | CB | LYS | A | 61 | −1.097 | −8.512 | 41.312 | 1 | 55.29 | C |
| ATOM 284 | CG | LYS | A | 61 | 0.374 | −8.763 | 41.58 | 1 | 63.32 | C |
| ATOM 285 | CD | LYS | A | 61 | 1.233 | −7.662 | 40.986 | 1 | 64.79 | C |
| ATOM 286 | CE | LYS | A | 61 | 2.698 | −7.865 | 41.336 | 1 | 67.03 | C |
| ATOM 287 | NZ | LYS | A | 61 | 3.548 | −6.755 | 40.824 | 1 | 66.87 | N |
| ATOM 288 | N | PRO | A | 62 | −4.268 | −8.972 | 42.86 | 1 | 57.89 | N |
| ATOM 289 | CA | PRO | A | 62 | −5.674 | −8.579 | 42.755 | 1 | 57.68 | C |
| ATOM 290 | C | PRO | A | 62 | −5.852 | −7.132 | 42.297 | 1 | 58.77 | C |
| ATOM 291 | O | PRO | A | 62 | −5.2 | −6.22 | 42.81 | 1 | 55.1 | O |
| ATOM 292 | CB | PRO | A | 62 | −6.196 | −8.808 | 44.17 | 1 | 58.57 | C |
| ATOM 293 | CG | PRO | A | 62 | −5.002 | −8.487 | 45.012 | 1 | 56.62 | C |
| ATOM 294 | CD | PRO | A | 62 | −3.889 | −9.189 | 44.268 | 1 | 58.46 | C |
| ATOM 295 | N | THR | A | 63 | −6.73 | −6.935 | 41.319 | 1 | 55.42 | N |
| ATOM 296 | CA | THR | A | 63 | −7.015 | −5.604 | 40.796 | 1 | 59.69 | C |
| ATOM 297 | C | THR | A | 63 | −8.085 | −4.995 | 41.696 | 1 | 60.7 | C |
| ATOM 298 | O | THR | A | 63 | −9.065 | −5.657 | 42.032 | 1 | 64.21 | O |
| ATOM 299 | CB | THR | A | 63 | −7.551 | −5.672 | 39.353 | 1 | 57.25 | C |
| ATOM 300 | OG1 | THR | A | 63 | −8.833 | −6.312 | 39.348 | 1 | 56.26 | O |
| ATOM 301 | CG2 | THR | A | 63 | −6.594 | −6.464 | 38.469 | 1 | 58.42 | C |
| ATOM 302 | N | GLN | A | 64 | −7.898 | −3.738 | 42.084 | 1 | 60.57 | N |
| ATOM 303 | CA | GLN | A | 64 | −8.849 | −3.07 | 42.967 | 1 | 60.91 | C |
| ATOM 304 | C | GLN | A | 64 | −10.167 | −2.71 | 42.287 | 1 | 57.87 | C |
| ATOM 305 | O | GLN | A | 64 | −11.126 | −2.303 | 42.944 | 1 | 53.57 | O |
| ATOM 306 | CB | GLN | A | 64 | −8.207 | −1.818 | 43.567 | 1 | 66.1 | C |
| ATOM 307 | CG | GLN | A | 64 | −6.887 | −2.099 | 44.272 | 1 | 68.35 | C |
| ATOM 308 | CD | GLN | A | 64 | −6.433 | −0.943 | 45.136 | 1 | 70.28 | C |
| ATOM 309 | OE1 | GLN | A | 64 | −5.61 | −1.115 | 46.036 | 1 | 71.78 | O |
| ATOM 310 | NE2 | GLN | A | 64 | −6.969 | 0.244 | 44.872 | 1 | 70.8 | N |
| ATOM 311 | N | ARG | A | 65 | −10.204 | −2.859 | 40.969 | 1 | 52.04 | N |
| ATOM 312 | CA | ARG | A | 65 | −11.402 | −2.579 | 40.184 | 1 | 51.65 | C |
| ATOM 313 | C | ARG | A | 65 | −11.641 | −3.768 | 39.269 | 1 | 44.42 | C |
| ATOM 314 | O | ARG | A | 65 | −10.7 | −4.289 | 38.675 | 1 | 41.65 | O |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 315 | CB | ARG | A | 65 | −11.21 | −1.343 | 39.299 | 1 | 55.13 | C |
| ATOM 316 | CG | ARG | A | 65 | −11.698 | −0.02 | 39.861 | 1 | 63.02 | C |
| ATOM 317 | CD | ARG | A | 65 | −11.852 | 0.977 | 38.714 | 1 | 66.47 | C |
| ATOM 318 | NE | ARG | A | 65 | −12.158 | 2.336 | 39.154 | 1 | 70.01 | N |
| ATOM 319 | CZ | ARG | A | 65 | −12.466 | 3.332 | 38.328 | 1 | 70.17 | C |
| ATOM 320 | NH1 | ARG | A | 65 | −12.513 | 3.12 | 37.019 | 1 | 70.28 | N |
| ATOM 321 | NH2 | ARG | A | 65 | −12.721 | 4.543 | 38.807 | 1 | 71.13 | N |
| ATOM 322 | N | PRO | A | 66 | −12.893 | −4.235 | 39.157 | 1 | 43.09 | N |
| ATOM 323 | CA | PRO | A | 66 | −13.056 | −5.369 | 38.247 | 1 | 38.44 | C |
| ATOM 324 | C | PRO | A | 66 | −12.717 | −4.829 | 36.86 | 1 | 32.78 | C |
| ATOM 325 | O | PRO | A | 66 | −13.028 | −3.678 | 36.554 | 1 | 32.07 | O |
| ATOM 326 | CB | PRO | A | 66 | −14.533 | −5.722 | 38.398 | 1 | 43.16 | C |
| ATOM 327 | CG | PRO | A | 66 | −15.164 | −4.395 | 38.715 | 1 | 46.4 | C |
| ATOM 328 | CD | PRO | A | 66 | −14.189 | −3.804 | 39.709 | 1 | 39.37 | C |
| ATOM 329 | N | ILE | A | 67 | −12.057 | −5.632 | 36.035 | 1 | 27.26 | N |
| ATOM 330 | CA | ILE | A | 67 | −11.699 | −5.166 | 34.705 | 1 | 26.5 | C |
| ATOM 331 | C | ILE | A | 67 | −12.919 | −5.109 | 33.793 | 1 | 22.78 | C |
| ATOM 332 | O | ILE | A | 67 | −13.847 | −5.908 | 33.927 | 1 | 27.32 | O |
| ATOM 333 | CB | ILE | A | 67 | −10.611 | −6.057 | 34.065 | 1 | 21.16 | C |
| ATOM 334 | CG1 | ILE | A | 67 | −11.121 | −7.487 | 33.884 | 1 | 19.63 | C |
| ATOM 335 | CG2 | ILE | A | 67 | −9.363 | −6.05 | 34.944 | 1 | 27.03 | C |
| ATOM 336 | CD1 | ILE | A | 67 | −10.134 | −8.392 | 33.158 | 1 | 24.75 | C |
| ATOM 337 | N | LYS | A | 68 | −12.912 | −4.144 | 32.88 | 1 | 22.91 | N |
| ATOM 338 | CA | LYS | A | 68 | −14.007 | −3.951 | 31.938 | 1 | 20.61 | C |
| ATOM 339 | C | LYS | A | 68 | −13.619 | −4.536 | 30.591 | 1 | 18.14 | C |
| ATOM 340 | O | LYS | A | 68 | −12.618 | −4.134 | 29.994 | 1 | 22.59 | O |
| ATOM 341 | CB | LYS | A | 68 | −14.311 | −2.461 | 31.781 | 1 | 27.65 | C |
| ATOM 342 | CG | LYS | A | 68 | −14.867 | −1.802 | 33.034 | 1 | 31.62 | C |
| ATOM 343 | CD | LYS | A | 68 | −14.926 | −0.283 | 32.891 | 1 | 37.7 | C |
| ATOM 344 | CE | LYS | A | 68 | −13.528 | 0.319 | 32.784 | 1 | 42.83 | C |
| ATOM 345 | NZ | LYS | A | 68 | −13.55 | 1.808 | 32.739 | 1 | 47.26 | N |
| ATOM 346 | N | ILE | A | 69 | −14.42 | −5.481 | 30.118 | 1 | 17.67 | N |
| ATOM 347 | CA | ILE | A | 69 | −14.157 | −6.129 | 28.842 | 1 | 17.27 | C |
| ATOM 348 | C | ILE | A | 69 | −15.335 | −5.938 | 27.898 | 1 | 19.96 | C |
| ATOM 349 | O | ILE | A | 69 | −16.49 | −6.125 | 28.284 | 1 | 20.49 | O |
| ATOM 350 | CB | ILE | A | 69 | −13.934 | −7.647 | 29.014 | 1 | 14.79 | C |
| ATOM 351 | CG1 | ILE | A | 69 | −12.796 | −7.906 | 30.003 | 1 | 20.84 | C |
| ATOM 352 | CG2 | ILE | A | 69 | −13.627 | −8.288 | 27.658 | 1 | 17.06 | C |
| ATOM 353 | CD1 | ILE | A | 69 | −12.684 | −9.357 | 30.413 | 1 | 20.34 | C |
| ATOM 354 | N | SER | A | 70 | −15.043 | −5.55 | 26.662 | 1 | 17.79 | N |
| ATOM 355 | CA | SER | A | 70 | −16.085 | −5.387 | 25.657 | 1 | 14.85 | C |
| ATOM 356 | C | SER | A | 70 | −15.759 | −6.331 | 24.512 | 1 | 15.95 | C |
| ATOM 357 | O | SER | A | 70 | −14.617 | −6.397 | 24.071 | 1 | 16.89 | O |
| ATOM 358 | CB | SER | A | 70 | −16.128 | −3.956 | 25.12 | 1 | 15.73 | C |
| ATOM 359 | OG | SER | A | 70 | −16.596 | −3.049 | 26.101 | 1 | 21.15 | O |
| ATOM 360 | N | VAL | A | 71 | −16.766 | −7.058 | 24.045 | 1 | 16.14 | N |
| ATOM 361 | CA | VAL | A | 71 | −16.607 | −7.993 | 22.944 | 1 | 13.87 | C |
| ATOM 362 | C | VAL | A | 71 | −17.572 | −7.632 | 21.818 | 1 | 15.21 | C |
| ATOM 363 | O | VAL | A | 71 | −18.74 | −7.327 | 22.066 | 1 | 15.47 | O |
| ATOM 364 | CB | VAL | A | 71 | −16.919 | −9.437 | 23.395 | 1 | 13.04 | C |
| ATOM 365 | CG1 | VAL | A | 71 | −16.927 | −10.377 | 22.194 | 1 | 19.89 | C |
| ATOM 366 | CG2 | VAL | A | 71 | −15.898 | −9.893 | 24.424 | 1 | 18.38 | C |
| ATOM 367 | N | VAL | A | 72 | −17.066 | −7.642 | 20.586 | 1 | 13.98 | N |
| ATOM 368 | CA | VAL | A | 72 | −17.875 | −7.382 | 19.397 | 1 | 13.07 | C |
| ATOM 369 | C | VAL | A | 72 | −17.423 | −8.475 | 18.428 | 1 | 13.43 | C |
| ATOM 370 | O | VAL | A | 72 | −16.347 | −8.389 | 17.829 | 1 | 13.16 | O |
| ATOM 371 | CB | VAL | A | 72 | −17.603 | −5.996 | 18.783 | 1 | 13.87 | C |
| ATOM 372 | CG1 | VAL | A | 72 | −18.555 | −5.759 | 17.614 | 1 | 15.18 | C |
| ATOM 373 | CG2 | VAL | A | 72 | −17.79 | −4.909 | 19.833 | 1 | 16.54 | C |
| ATOM 374 | N | TYR | A | 73 | −18.252 | −9.505 | 18.297 | 1 | 13.92 | N |
| ATOM 375 | CA | TYR | A | 73 | −17.965 | −10.67 | 17.467 | 1 | 13.58 | C |
| ATOM 376 | C | TYR | A | 73 | −19.043 | −10.929 | 16.425 | 1 | 14.57 | C |
| ATOM 377 | O | TYR | A | 73 | −20.219 | −10.658 | 16.664 | 1 | 13.69 | O |
| ATOM 378 | CB | TYR | A | 73 | −17.93 | −11.933 | 18.339 | 1 | 11.78 | C |
| ATOM 379 | CG | TYR | A | 73 | −16.668 | −12.251 | 19.118 | 1 | 13.29 | C |
| ATOM 380 | CD1 | TYR | A | 73 | −16.666 | −13.314 | 20.022 | 1 | 11.55 | C |
| ATOM 381 | CD2 | TYR | A | 73 | −15.468 | −11.569 | 18.901 | 1 | 13.53 | C |
| ATOM 382 | CE1 | TYR | A | 73 | −15.518 | −13.698 | 20.677 | 1 | 11.37 | C |
| ATOM 383 | CE2 | TYR | A | 73 | −14.292 | −11.952 | 19.565 | 1 | 15.37 | C |
| ATOM 384 | CZ | TYR | A | 73 | −14.332 | −13.022 | 20.451 | 1 | 15.1 | C |
| ATOM 385 | OH | TYR | A | 73 | −13.195 | −13.431 | 21.115 | 1 | 15.6 | O |
| ATOM 386 | N | PRO | A | 74 | −18.663 | −11.48 | 15.259 | 1 | 13.32 | N |
| ATOM 387 | CA | PRO | A | 74 | −19.648 | −11.784 | 14.213 | 1 | 15.45 | C |
| ATOM 388 | C | PRO | A | 74 | −20.152 | −13.184 | 14.566 | 1 | 14.83 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 389 | O | PRO | A | 74 | −20.24 | −14.078 | 13.716 | 1 | 15.67 | O |
| ATOM 390 | CB | PRO | A | 74 | −18.805 | −11.783 | 12.946 | 1 | 16.2 | C |
| ATOM 391 | CG | PRO | A | 74 | −17.498 | −12.385 | 13.44 | 1 | 13.8 | C |
| ATOM 392 | CD | PRO | A | 74 | −17.285 | −11.646 | 14.756 | 1 | 17.69 | C |
| ATOM 393 | N | GLY | A | 75 | −20.479 | −13.345 | 15.844 | 1 | 14.16 | N |
| ATOM 394 | CA | GLY | A | 75 | −20.898 | −14.624 | 16.383 | 1 | 19.39 | C |
| ATOM 395 | C | GLY | A | 75 | −22.233 | −15.236 | 16.028 | 1 | 19.22 | C |
| ATOM 396 | O | GLY | A | 75 | −22.469 | −16.392 | 16.381 | 1 | 17.84 | O |
| ATOM 397 | N | GLN | A | 76 | −23.098 | −14.491 | 15.346 | 1 | 14.37 | N |
| ATOM 398 | CA | GLN | A | 76 | −24.407 | −15.015 | 14.966 | 1 | 16.75 | C |
| ATOM 399 | C | GLN | A | 76 | −24.255 | −15.847 | 13.697 | 1 | 15.94 | C |
| ATOM 400 | O | GLN | A | 76 | −24.381 | −15.333 | 12.579 | 1 | 17.3 | O |
| ATOM 401 | CB | GLN | A | 76 | −25.389 | −13.865 | 14.733 | 1 | 19.86 | C |
| ATOM 402 | CG | GLN | A | 76 | −26.836 | −14.312 | 14.671 | 1 | 23.48 | C |
| ATOM 403 | CD | GLN | A | 76 | −27.789 | −13.151 | 14.519 | 1 | 26.11 | C |
| ATOM 404 | OE1 | GLN | A | 76 | −27.623 | −12.111 | 15.159 | 1 | 21.28 | O |
| ATOM 405 | NE2 | GLN | A | 76 | −28.805 | −13.324 | 13.676 | 1 | 22.49 | N |
| ATOM 406 | N | GLN | A | 77 | −23.983 | −17.135 | 13.89 | 1 | 14.98 | N |
| ATOM 407 | CA | GLN | A | 77 | −23.772 | −18.093 | 12.801 | 1 | 12.04 | C |
| ATOM 408 | C | GLN | A | 77 | −24.133 | −19.5 | 13.267 | 1 | 12.55 | C |
| ATOM 409 | O | GLN | A | 77 | −24.386 | −19.736 | 14.45 | 1 | 16.92 | O |
| ATOM 410 | CB | GLN | A | 77 | −22.289 | −18.169 | 12.421 | 1 | 18.2 | C |
| ATOM 411 | CG | GLN | A | 77 | −21.573 | −16.88 | 12.144 | 1 | 16.21 | C |
| ATOM 412 | CD | GLN | A | 77 | −20.107 | −17.132 | 11.859 | 1 | 11.82 | C |
| ATOM 413 | OE1 | GLN | A | 77 | −19.723 | −18.233 | 11.437 | 1 | 14.4 | O |
| ATOM 414 | NE2 | GLN | A | 77 | −19.282 | −16.118 | 12.074 | 1 | 13.04 | N |
| ATOM 415 | N | VAL | A | 78 | −24.13 | −20.44 | 12.328 | 1 | 14.5 | N |
| ATOM 416 | CA | VAL | A | 78 | −24.368 | −21.832 | 12.675 | 1 | 12.8 | C |
| ATOM 417 | C | VAL | A | 78 | −23.1 | −22.28 | 13.407 | 1 | 16.59 | C |
| ATOM 418 | O | VAL | A | 78 | −23.166 | −23.044 | 14.372 | 1 | 16.75 | O |
| ATOM 419 | CB | VAL | A | 78 | −24.589 | −22.715 | 11.428 | 1 | 15.85 | C |
| ATOM 420 | CG1 | VAL | A | 78 | −24.66 | −24.182 | 11.836 | 1 | 17.01 | C |
| ATOM 421 | CG2 | VAL | A | 78 | −25.887 | −22.309 | 10.731 | 1 | 15.61 | C |
| ATOM 422 | N | SER | A | 79 | −21.944 | −21.797 | 12.951 | 1 | 13.83 | N |
| ATOM 423 | CA | SER | A | 79 | −20.678 | −22.131 | 13.594 | 1 | 12.18 | C |
| ATOM 424 | C | SER | A | 79 | −20.728 | −21.665 | 15.039 | 1 | 12.47 | C |
| ATOM 425 | O | SER | A | 79 | −21.136 | −20.535 | 15.316 | 1 | 12.91 | O |
| ATOM 426 | CB | SER | A | 79 | −19.504 | −21.436 | 12.898 | 1 | 11.35 | C |
| ATOM 427 | OG | SER | A | 79 | −18.293 | −21.722 | 13.59 | 1 | 13.48 | O |
| ATOM 428 | N | ASP | A | 80 | −20.289 | −22.527 | 15.955 | 1 | 13.24 | N |
| ATOM 429 | CA | ASP | A | 80 | −20.296 | −22.191 | 17.376 | 1 | 12.91 | C |
| ATOM 430 | C | ASP | A | 80 | −18.959 | −21.677 | 17.886 | 1 | 13.16 | C |
| ATOM 431 | O | ASP | A | 80 | −18.744 | −21.606 | 19.096 | 1 | 15.12 | O |
| ATOM 432 | CB | ASP | A | 80 | −20.703 | −23.427 | 18.196 | 1 | 15.8 | C |
| ATOM 433 | CG | ASP | A | 80 | −19.804 | −24.631 | 17.941 | 1 | 18.1 | C |
| ATOM 434 | OD1 | ASP | A | 80 | −20.098 | −25.723 | 18.482 | 1 | 15.35 | O |
| ATOM 435 | OD2 | ASP | A | 80 | −18.802 | −24.505 | 17.202 | 1 | 14.01 | O |
| ATOM 436 | N | TYR | A | 81 | −18.063 | −21.301 | 16.978 | 1 | 10.46 | N |
| ATOM 437 | CA | TYR | A | 81 | −16.748 | −20.831 | 17.395 | 1 | 11.8 | C |
| ATOM 438 | C | TYR | A | 81 | −16.761 | −19.665 | 18.37 | 1 | 12.12 | C |
| ATOM 439 | O | TYR | A | 81 | −16.097 | −19.694 | 19.409 | 1 | 14.87 | O |
| ATOM 440 | CB | TYR | A | 81 | −15.91 | −20.404 | 16.185 | 1 | 13.44 | C |
| ATOM 441 | CG | TYR | A | 81 | −14.521 | −19.959 | 16.581 | 1 | 12.93 | C |
| ATOM 442 | CD1 | TYR | A | 81 | −13.548 | −20.894 | 16.916 | 1 | 11.95 | C |
| ATOM 443 | CD2 | TYR | A | 81 | −14.206 | −18.606 | 16.709 | 1 | 12.04 | C |
| ATOM 444 | CE1 | TYR | A | 81 | −12.295 | −20.499 | 17.379 | 1 | 13.78 | C |
| ATOM 445 | CE2 | TYR | A | 81 | −12.953 | −18.197 | 17.172 | 1 | 14.71 | C |
| ATOM 446 | CZ | TYR | A | 81 | −12.005 | −19.156 | 17.507 | 1 | 14.05 | C |
| ATOM 447 | OH | TYR | A | 81 | −10.76 | −18.777 | 17.976 | 1 | 18.92 | O |
| ATOM 448 | N | TRP | A | 82 | −17.5 | −18.622 | 18.014 | 1 | 13.48 | N |
| ATOM 449 | CA | TRP | A | 82 | −17.534 | −17.414 | 18.811 | 1 | 9.63 | C |
| ATOM 450 | C | TRP | A | 82 | −18.23 | −17.591 | 20.151 | 1 | 12.54 | C |
| ATOM 451 | O | TRP | A | 82 | −17.767 | −17.062 | 21.16 | 1 | 14.4 | O |
| ATOM 452 | CB | TRP | A | 82 | −18.156 | −16.28 | 17.987 | 1 | 12.49 | C |
| ATOM 453 | CG | TRP | A | 82 | −17.524 | −16.165 | 16.605 | 1 | 12.45 | C |
| ATOM 454 | CD1 | TRP | A | 82 | −17.911 | −16.824 | 15.478 | 1 | 11.14 | C |
| ATOM 455 | CD2 | TRP | A | 82 | −16.372 | −15.386 | 16.236 | 1 | 11.21 | C |
| ATOM 456 | NE1 | TRP | A | 82 | −17.077 | −16.51 | 14.426 | 1 | 11.8 | N |
| ATOM 457 | CE2 | TRP | A | 82 | −16.126 | −15.631 | 14.864 | 1 | 11.6 | C |
| ATOM 458 | CE3 | TRP | A | 82 | −15.527 | −14.506 | 16.927 | 1 | 11.07 | C |
| ATOM 459 | CZ2 | TRP | A | 82 | −15.07 | −15.028 | 14.168 | 1 | 12.04 | C |
| ATOM 460 | CZ3 | TRP | A | 82 | −14.475 | −13.906 | 16.236 | 1 | 14.06 | C |
| ATOM 461 | CH2 | TRP | A | 82 | −14.26 | −14.174 | 14.87 | 1 | 11.17 | C |
| ATOM 462 | N | VAL | A | 83 | −19.331 | −18.338 | 20.158 | 1 | 13.62 | N |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 463 | CA | VAL | A | 83 | −20.056 | −18.596 | 21.396 | 1 | 17.63 | C |
| ATOM 464 | C | VAL | A | 83 | −19.178 | −19.415 | 22.343 | 1 | 13.39 | C |
| ATOM 465 | O | VAL | A | 83 | −19.064 | −19.085 | 23.526 | 1 | 16.28 | O |
| ATOM 466 | CB | VAL | A | 83 | −21.372 | −19.366 | 21.132 | 1 | 15.08 | C |
| ATOM 467 | CG1 | VAL | A | 83 | −22.064 | −19.67 | 22.457 | 1 | 20.75 | C |
| ATOM 468 | CG2 | VAL | A | 83 | −22.286 | −18.539 | 20.248 | 1 | 24.92 | C |
| ATOM 469 | N | ARG | A | 84 | −18.558 | −20.474 | 21.83 | 1 | 12.17 | N |
| ATOM 470 | CA | ARG | A | 84 | −17.686 | −21.314 | 22.657 | 1 | 13.19 | C |
| ATOM 471 | C | ARG | A | 84 | −16.446 | −20.548 | 23.103 | 1 | 17.39 | C |
| ATOM 472 | O | ARG | A | 84 | −15.918 | −20.783 | 24.188 | 1 | 19.01 | O |
| ATOM 473 | CB | ARG | A | 84 | −17.252 | −22.574 | 21.902 | 1 | 13.64 | C |
| ATOM 474 | CG | ARG | A | 84 | −18.323 | −23.668 | 21.771 | 1 | 15.57 | C |
| ATOM 475 | CD | ARG | A | 84 | −17.75 | −24.886 | 21.072 | 1 | 16.16 | C |
| ATOM 476 | NE | ARG | A | 84 | −18.698 | −25.997 | 20.963 | 1 | 20.65 | N |
| ATOM 477 | CZ | ARG | A | 84 | −19.079 | −26.77 | 21.977 | 1 | 19.78 | C |
| ATOM 478 | NH1 | ARG | A | 84 | −18.598 | −26.563 | 23.195 | 1 | 17.08 | N |
| ATOM 479 | NH2 | ARG | A | 84 | −19.939 | −27.761 | 21.766 | 1 | 16.02 | N |
| ATOM 480 | N | ASN | A | 85 | −15.965 | −19.635 | 22.266 | 1 | 15.2 | N |
| ATOM 481 | CA | ASN | A | 85 | −14.787 | −18.866 | 22.638 | 1 | 10.6 | C |
| ATOM 482 | C | ASN | A | 85 | −15.064 | −18.031 | 23.893 | 1 | 12.71 | C |
| ATOM 483 | O | ASN | A | 85 | −14.248 | −18.005 | 24.808 | 1 | 14.51 | O |
| ATOM 484 | CB | ASN | A | 85 | −14.346 | −17.973 | 21.465 | 1 | 13.46 | C |
| ATOM 485 | CG | ASN | A | 85 | −13.125 | −17.144 | 21.793 | 1 | 13.5 | C |
| ATOM 486 | OD1 | ASN | A | 85 | −13.237 | −15.974 | 22.151 | 1 | 15.89 | O |
| ATOM 487 | ND2 | ASN | A | 85 | −11.947 | −17.755 | 21.685 | 1 | 17.97 | N |
| ATOM 488 | N | ILE | A | 86 | −16.215 | −17.364 | 23.948 | 1 | 13.94 | N |
| ATOM 489 | CA | ILE | A | 86 | −16.545 | −16.549 | 25.111 | 1 | 13.86 | C |
| ATOM 490 | C | ILE | A | 86 | −16.779 | −17.434 | 26.329 | 1 | 14.7 | C |
| ATOM 491 | O | ILE | A | 86 | −16.366 | −17.091 | 27.439 | 1 | 18.49 | O |
| ATOM 492 | CB | ILE | A | 86 | −17.787 | −15.674 | 24.847 | 1 | 16.15 | C |
| ATOM 493 | CG1 | ILE | A | 86 | −17.474 | −14.683 | 23.722 | 1 | 22.28 | C |
| ATOM 494 | CG2 | ILE | A | 86 | −18.206 | −14.94 | 26.121 | 1 | 19.2 | C |
| ATOM 495 | CD1 | ILE | A | 86 | −16.237 | −13.833 | 23.977 | 1 | 20.12 | C |
| ATOM 496 | N | ALA | A | 87 | −17.42 | −18.578 | 26.118 | 1 | 15.62 | N |
| ATOM 497 | CA | ALA | A | 87 | −17.675 | −19.503 | 27.218 | 1 | 18.97 | C |
| ATOM 498 | C | ALA | A | 87 | −16.367 | −19.985 | 27.849 | 1 | 18.61 | C |
| ATOM 499 | O | ALA | A | 87 | −16.217 | −19.953 | 29.072 | 1 | 22.89 | O |
| ATOM 500 | CB | ALA | A | 87 | −18.488 | −20.696 | 26.734 | 1 | 16.56 | C |
| ATOM 501 | N | SER | A | 88 | −15.426 | −20.437 | 27.025 | 1 | 15.66 | N |
| ATOM 502 | CA | SER | A | 88 | −14.151 | −20.927 | 27.541 | 1 | 14.28 | C |
| ATOM 503 | C | SER | A | 88 | −13.366 | −19.776 | 28.174 | 1 | 18.98 | C |
| ATOM 504 | O | SER | A | 88 | −12.728 | −19.941 | 29.217 | 1 | 19 | O |
| ATOM 505 | CB | SER | A | 88 | −13.33 | −21.589 | 26.425 | 1 | 19.81 | C |
| ATOM 506 | OG | SER | A | 88 | −13.09 | −20.696 | 25.355 | 1 | 21.19 | O |
| ATOM 507 | N | PHE | A | 89 | −13.423 | −18.612 | 27.533 | 1 | 15.85 | N |
| ATOM 508 | CA | PHE | A | 89 | −12.754 | −17.407 | 28.009 | 1 | 18.18 | C |
| ATOM 509 | C | PHE | A | 89 | −13.244 | −17.04 | 29.4151 | 16.22 | | C |
| ATOM 510 | O | PHE | A | 89 | −12.441 | −16.877 | 30.336 | 1 | 17.17 | O |
| ATOM 511 | CB | PHE | A | 89 | −13.037 | −16.267 | 27.021 | 1 | 16.29 | C |
| ATOM 512 | CG | PHE | A | 89 | −12.483 | −14.928 | 27.433 | 1 | 13.26 | C |
| ATOM 513 | CD1 | PHE | A | 89 | −11.138 | −14.781 | 27.762 | 1 | 13.77 | C |
| ATOM 514 | CD2 | PHE | A | 89 | −13.298 | −13.797 | 27.43 | 1 | 16.83 | C |
| ATOM 515 | CE1 | PHE | A | 89 | −10.612 | −13.523 | 28.078 | 1 | 17.8 | C |
| ATOM 516 | CE2 | PHE | A | 89 | −12.783 | −12.537 | 27.743 | 1 | 16.66 | C |
| ATOM 517 | CZ | PHE | A | 89 | −11.433 | −12.402 | 28.067 | 1 | 13.73 | C |
| ATOM 518 | N | GLU | A | 90 | −14.559 | −16.936 | 29.584 | 1 | 17.47 | N |
| ATOM 519 | CA | GLU | A | 90 | −15.133 | −16.583 | 30.879 | 1 | 17.85 | C |
| ATOM 520 | C | GLU | A | 90 | −14.836 | −17.61 | 31.966 | 1 | 18.35 | C |
| ATOM 521 | O | GLU | A | 90 | −14.588 | −17.243 | 33.116 | 1 | 22.32 | O |
| ATOM 522 | CB | GLU | A | 90 | −16.649 | −16.387 | 30.76 | 1 | 20.22 | C |
| ATOM 523 | CG | GLU | A | 90 | −17.044 | −15.096 | 30.074 | 1 | 18.1 | C |
| ATOM 524 | CD | GLU | A | 90 | −18.521 | −14.79 | 30.221 | 1 | 29.21 | C |
| ATOM 525 | OE1 | GLU | A | 90 | −19.34 | −15.456 | 29.557 | 1 | 31.24 | O |
| ATOM 526 | OE2 | GLU | A | 90 | −18.864 | −13.887 | 31.014 | 1 | 37.67 | O |
| ATOM 527 | N | LYS | A | 91 | −14.85 | −18.888 | 31.607 | 1 | 18.25 | N |
| ATOM 528 | CA | LYS | A | 91 | −14.577 | −19.931 | 32.589 | 1 | 21.16 | C |
| ATOM 529 | C | LYS | A | 91 | −13.14 | −19.815 | 33.09 | 1 | 22.59 | C |
| ATOM 530 | O | LYS | A | 91 | −12.887 | −19.944 | 34.288 | 1 | 21.1 | O |
| ATOM 531 | CB | LYS | A | 91 | −14.814 | −21.317 | 31.984 | 1 | 20.11 | C |
| ATOM 532 | CG | LYS | A | 91 | −14.726 | −22.451 | 33.004 | 1 | 22.44 | C |
| ATOM 533 | CD | LYS | A | 91 | −15.194 | −23.776 | 32.412 | 1 | 28.63 | C |
| ATOM 534 | CE | LYS | A | 91 | −15.138 | −24.897 | 33.439 | 1 | 38.77 | C |
| ATOM 535 | NZ | LYS | A | 91 | −15.653 | −26.188 | 32.897 | 1 | 46.48 | N |
| ATOM 536 | N | ARG | A | 92 | −12.202 | −19.559 | 32.179 | 1 | 20.16 | N |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 537 | CA | ARG | A | 92 | −10.802 | −19.435 | 32.567 | 1 | 17.65 | C |
| ATOM 538 | C | ARG | A | 92 | −10.592 | −18.193 | 33.423 | 1 | 17.64 | C |
| ATOM 539 | O | ARG | A | 92 | −9.8 | −18.216 | 34.3681 | 20.29 | | O |
| ATOM 540 | CB | ARG | A | 92 | −9.892 | −19.382 | 31.335 | 1 | 18.99 | C |
| ATOM 541 | CG | ARG | A | 92 | −8.399 | −19.57 | 31.652 | 1 | 16.01 | C |
| ATOM 542 | CD | ARG | A | 92 | −8.101 | −20.988 | 32.15 | 1 | 19.26 | C |
| ATOM 543 | NE | ARG | A | 92 | −6.663 | −21.242 | 32.262 | 1 | 16.66 | N |
| ATOM 544 | CZ | ARG | A | 92 | −6.104 | −22.45 | 32.235 | 1 | 19.36 | C |
| ATOM 545 | NH1 | ARG | A | 92 | −6.854 | −23.539 | 32.105 | 1 | 19.23 | N |
| ATOM 546 | NH2 | ARG | A | 92 | −4.785 | −22.57 | 32.306 | 1 | 24.04 | N |
| ATOM 547 | N | LEU | A | 93 | −11.297 | −17.111 | 33.102 | 1 | 16.37 | N |
| ATOM 548 | CA | LEU | A | 93 | −11.179 | −15.884 | 33.886 | 1 | 19.44 | C |
| ATOM 549 | C | LEU | A | 93 | −11.631 | −16.198 | 35.311 | 1 | 21.18 | C |
| ATOM 550 | O | LEU | A | 93 | −11.049 | −15.717 | 36.281 | 1 | 27.96 | O |
| ATOM 551 | CB | LEU | A | 93 | −12.056 | −14.765 | 33.301 | 1 | 21.12 | C |
| ATOM 552 | CG | LEU | A | 93 | −11.582 | −14.041 | 32.032 | 1 | 18.3 | C |
| ATOM 553 | CD1 | LEU | A | 93 | −12.664 | −13.082 | 31.563 | 1 | 19.21 | C |
| ATOM 554 | CD2 | LEU | A | 93 | −10.292 | −13.279 | 32.309 | 1 | 18.98 | C |
| ATOM 555 | N | TYR | A | 94 | −12.671 | −17.019 | 35.417 | 1 | 20.72 | N |
| ATOM 556 | CA | TYR | A | 94 | −13.223 | −17.425 | 36.709 | 1 | 22.6 | C |
| ATOM 557 | C | TYR | A | 94 | −12.215 | −18.261 | 37.498 | 1 | 22.33 | C |
| ATOM 558 | O | TYR | A | 94 | −11.979 | −18.011 | 38.683 | 1 | 24.5 | O |
| ATOM 559 | CB | TYR | A | 94 | −14.498 | −18.24 | 36.483 | 1 | 20.56 | C |
| ATOM 560 | CG | TYR | A | 94 | −15.246 | −18.634 | 37.738 | 1 | 24.03 | C |
| ATOM 561 | CD1 | TYR | A | 94 | −15.964 | −17.688 | 38.468 | 1 | 25.9 | C |
| ATOM 562 | CD2 | TYR | A | 94 | −15.272 | −19.961 | 38.169 | 1 | 22.16 | C |
| ATOM 563 | CE1 | TYR | A | 94 | −16.701 | −18.055 | 39.598 | 1 | 28.08 | C |
| ATOM 564 | CE2 | TYR | A | 94 | −16.004 | −20.339 | 39.298 | 1 | 27.51 | C |
| ATOM 565 | CZ | TYR | A | 94 | −16.716 | −19.381 | 40.003 | 1 | 28.57 | C |
| ATOM 566 | OH | TYR | A | 94 | −17.455 | −19.749 | 41.105 | 1 | 30.87 | O |
| ATOM 567 | N | LYS | A | 95 | −11.617 | −19.248 | 36.836 | 1 | 23.2 | N |
| ATOM 568 | CA | LYS | A | 95 | −10.643 | −20.126 | 37.48 | 1 | 17.61 | C |
| ATOM 569 | C | LYS | A | 95 | −9.345 | −19.397 | 37.823 | 1 | 23.31 | C |
| ATOM 570 | O | LYS | A | 95 | −8.56 | −19.867 | 38.652 | 1 | 24.37 | O |
| ATOM 571 | CB | LYS | A | 95 | −10.345 | −21.332 | 36.587 | 1 | 24.14 | C |
| ATOM 572 | CG | LYS | A | 95 | −11.544 | −22.25 | 36.366 | 1 | 18.81 | C |
| ATOM 573 | CD | LYS | A | 95 | −11.142 | −23.502 | 35.61 | 1 | 23.58 | C |
| ATOM 574 | CE | LYS | A | 95 | −12.307 | −24.463 | 35.467 | 1 | 33.77 | C |
| ATOM 575 | NZ | LYS | A | 95 | −12.55 | −25.228 | 36.718 | 1 | 31.89 | N |
| ATOM 576 | N | LEU | A | 96 | −9.122 | −18.247 | 37.192 | 1 | 22.25 | N |
| ATOM 577 | CA | LEU | A | 96 | −7.918 | −17.466 | 37.452 | 1 | 23.23 | C |
| ATOM 578 | C | LEU | A | 96 | −8.181 | −16.397 | 38.5 | 1 | 21.71 | C |
| ATOM 579 | O | LEU | A | 96 | −7.287 | −15.621 | 38.852 | 1 | 25.01 | O |
| ATOM 580 | CB | LEU | A | 96 | −7.419 | −16.812 | 36.161 | 1 | 21.38 | C |
| ATOM 581 | CG | LEU | A | 96 | −6.896 | −17.783 | 35.102 | 1 | 20.61 | C |
| ATOM 582 | CD1 | LEU | A | 96 | −6.503 | −17.004 | 33.859 | 1 | 20.9 | C |
| ATOM 583 | CD2 | LEU | A | 96 | −5.704 | −18.567 | 35.657 | 1 | 20.54 | C |
| ATOM 584 | N | ASN | A | 97 | −9.419 | −16.363 | 38.988 | 1 | 21.93 | N |
| ATOM 585 | CA | ASN | A | 97 | −9.847 | −15.412 | 40.007 | 1 | 21.51 | C |
| ATOM 586 | C | ASN | A | 97 | −9.73 | −13.956 | 39.561 | 1 | 27.53 | C |
| ATOM 587 | O | ASN | A | 97 | −9.305 | −13.091 | 40.325 | 1 | 29.24 | O |
| ATOM 588 | CB | ASN | A | 97 | −9.042 | −15.627 | 41.295 | 1 | 30.65 | C |
| ATOM 589 | CG | ASN | A | 97 | −9.634 | −14.893 | 42.479 | 1 | 38.73 | C |
| ATOM 590 | OD1 | ASN | A | 97 | −8.987 | −14.033 | 43.076 | 1 | 49.46 | O |
| ATOM 591 | ND2 | ASN | A | 97 | −10.873 | −15.229 | 42.827 | 1 | 43.62 | N |
| ATOM 592 | N | ILE | A | 98 | −10.113 | −13.689 | 38.318 | 1 | 23.35 | N |
| ATOM 593 | CA | ILE | A | 98 | −10.064 | −12.34 | 37.778 | 1 | 26.56 | C |
| ATOM 594 | C | ILE | A | 98 | −11.472 | −11.756 | 37.799 | 1 | 29.03 | C |
| ATOM 595 | O | ILE | A | 98 | −12.379 | −12.292 | 37.163 | 1 | 27.76 | O |
| ATOM 596 | CB | ILE | A | 98 | −9.538 | −12.344 | 36.324 | 1 | 24.5 | C |
| ATOM 597 | CD1 | ILE | A | 98 | −8.086 | −12.829 | 36.3 | 1 | 27.25 | C |
| ATOM 598 | CG2 | ILE | A | 98 | −9.659 | −10.953 | 35.717 | 1 | 26.73 | C |
| ATOM 599 | CD1 | ILE | A | 98 | −7.509 | −13.005 | 34.907 | 1 | 24.97 | C |
| ATOM 600 | N | ASN | A | 99 | −11.659 | −10.674 | 38.55 | 1 | 26.95 | N |
| ATOM 601 | CA | ASN | A | 99 | −12.964 | −10.025 | 38.626 | 1 | 28.01 | C |
| ATOM 602 | C | ASN | A | 99 | −13.142 | −9.195 | 37.366 | 1 | 24.89 | C |
| ATOM 603 | O | ASN | A | 99 | −12.3 | −8.36 | 37.042 | 1 | 24.73 | O |
| ATOM 604 | CB | ASN | A | 99 | −13.054 | −9.126 | 39.861 | 1 | 32.66 | C |
| ATOM 605 | CG | ASN | A | 99 | −12.91 | −9.904 | 41.154 | 1 | 43.13 | C |
| ATOM 606 | OD1 | ASN | A | 99 | −13.529 | −10.954 | 41.332 | 1 | 40.93 | O |
| ATOM 607 | ND2 | ASN | A | 99 | −12.096 | −9.387 | 42.069 | 1 | 47 | N |
| ATOM 608 | N | TYR | A | 100 | −14.239 | −9.426 | 36.655 | 1 | 25.1 | N |
| ATOM 609 | CA | TYR | A | 100 | −14.476 | −8.706 | 35.415 | 1 | 25.31 | C |
| ATOM 610 | C | TYR | A | 100 | −15.941 | −8.404 | 35.146 | 1 | 24.08 | C |

TABLE 1-continued

Atomic structural coordinates for LuxP

| | ATOM TYPE | RESID | | NO | X | Y | Z | OCC | |
|---|---|---|---|---|---|---|---|---|---|
| ATOM 611 | O | TYR | A | 100 | −16.843 | −9.008 | 35.729 | 1 | 27.21 O |
| ATOM 612 | CB | TYR | A | 100 | −13.909 | −9.518 | 34.245 | 1 | 22.68 C |
| ATOM 613 | CG | TYR | A | 100 | −14.711 | −10.765 | 33.934 | 1 | 23.78 C |
| ATOM 614 | CD1 | TYR | A | 100 | −15.758 | −10.734 | 33.01 | 1 | 21.72 C |
| ATOM 615 | CD2 | TYR | A | 100 | −14.462 | −11.962 | 34.603 | 1 | 21.81 C |
| ATOM 616 | CE1 | TYR | A | 100 | −16.536 | −11.862 | 32.765 | 1 | 21.52 C |
| ATOM 617 | CE2 | TYR | A | 100 | −15.236 | −13.096 | 34.368 | 1 | 23.77 C |
| ATOM 618 | CZ | TYR | A | 100 | −16.272 | −13.039 | 33.45 | 1 | 21.96 C |
| ATOM 619 | OH | TYR | A | 100 | −17.059 | −14.149 | 33.238 | 1 | 25.08 O |
| ATOM 620 | N | GLN | A | 101 | −16.15 | −7.453 | 34.245 | 1 | 23.23 N |
| ATOM 621 | CA | GLN | A | 101 | −17.47 | −7.026 | 33.803 | 1 | 27.19 C |
| ATOM 622 | C | GLN | A | 101 | −17.359 | −7.155 | 32.29 | 1 | 25.84 C |
| ATOM 623 | O | GLN | A | 101 | −16.5 | −6.522 | 31.684 | 1 | 26.66 O |
| ATOM 624 | CB | GLN | A | 101 | −17.707 | −5.569 | 34.197 | 1 | 34.79 C |
| ATOM 625 | CG | GLN | A | 101 | −18.951 | −4.942 | 33.601 | 1 | 46.64 C |
| ATOM 626 | CD | GLN | A | 101 | −19.096 | −3.476 | 33.973 | 1 | 50.02 C |
| ATOM 627 | OE1 | GLN | A | 101 | −19.983 | −2.783 | 33.475 | 1 | 55.75 O |
| ATOM 628 | NE2 | GLN | A | 101 | −18.224 | −2.998 | 34.856 | 1 | 53.62 N |
| ATOM 629 | N | LEU | A | 102 | −18.205 | −7.978 | 31.683 | 1 | 23.39 N |
| ATOM 630 | CA | LEU | A | 102 | −18.136 | −8.183 | 30.243 | 1 | 20.49 C |
| ATOM 631 | C | LEU | A | 102 | −19.389 | −7.779 | 29.486 | 1 | 23.32 C |
| ATOM 632 | O | LEU | A | 102 | −20.494 | −8.223 | 29.81 | 1 | 22.69 O |
| ATOM 633 | CB | LEU | A | 102 | −17.811 | −9.653 | 29.95 | 1 | 19.63 C |
| ATOM 634 | CG | LEU | A | 102 | −17.648 | −10.144 | 28.504 | 1 | 28.05 C |
| ATOM 635 | CD1 | LEU | A | 102 | −19.001 | −10.285 | 27.835 | 1 | 32.9 C |
| ATOM 636 | CD2 | LEU | A | 102 | −16.76 | −9.192 | 27.737 | 1 | 31.41 C |
| ATOM 637 | N | ASN | A | 103 | −19.199 | −6.929 | 28.479 | 1 | 21.04 N |
| ATOM 638 | CA | ASN | A | 103 | −20.283 | −6.483 | 27.617 | 1 | 19.87 C |
| ATOM 639 | C | ASN | A | 103 | −20.072 | −7.217 | 26.299 | 1 | 20.98 C |
| ATOM 640 | O | ASN | A | 103 | −18.974 | −7.196 | 25.734 | 1 | 21.7 O |
| ATOM 641 | CB | ASN | A | 103 | −20.224 | −4.975 | 27.392 | 1 | 20.44 C |
| ATOM 642 | CG | ASN | A | 103 | −21.344 | −4.479 | 26.494 | 1 | 31.42 C |
| ATOM 643 | OD1 | ASN | A | 103 | −21.339 | −4.713 | 25.284 | 1 | 29.49 O |
| ATOM 644 | ND2 | ASN | A | 103 | −22.319 | −3.798 | 27.087 | 1 | 33.41 N |
| ATOM 645 | N | GLN | A | 104 | −21.123 | −7.863 | 25.813 | 1 | 19.18 N |
| ATOM 646 | CA | GLN | A | 104 | −21.03 | −8.637 | 24.587 | 1 | 21.63 C |
| ATOM 647 | C | GLN | A | 104 | −22.03 | −8.239 | 23.508 | 1 | 22.17 C |
| ATOM 648 | O | GLN | A | 104 | −23.213 | −8.034 | 23.78 | 1 | 22.15 O |
| ATOM 649 | CB | GLN | A | 104 | −21.22 | −10.113 | 24.925 | 1 | 24.92 C |
| ATOM 650 | CG | GLN | A | 104 | −21.082 | −11.067 | 23.758 | 1 | 34.45 C |
| ATOM 651 | CD | GLN | A | 104 | −21.392 | −12.494 | 24.159 | 1 | 35.02 C |
| ATOM 652 | OE1 | GLN | A | 104 | −22.228 | −13.152 | 23.544 | 1 | 43.05 O |
| ATOM 653 | NE2 | GLN | A | 104 | −20.719 | −12.979 | 25.195 | 1 | 33.41 N |
| ATOM 654 | N | VAL | A | 105 | −21.539 | −8.135 | 22.28 | 1 | 16.28 N |
| ATOM 655 | CA | VAL | A | 105 | −22.377 | −7.817 | 21.135 | 1 | 17.08 C |
| ATOM 656 | C | VAL | A | 105 | −22.021 | −8.816 | 20.035 | 1 | 16.56 C |
| ATOM 657 | O | VAL | A | 105 | −20.86 | −8.94 | 19.654 | 1 | 17.95 O |
| ATOM 658 | CB | VAL | A | 105 | −22.13 | −6.377 | 20.622 | 1 | 21.8 C |
| ATOM 659 | CG1 | VAL | A | 105 | −22.937 | −6.131 | 19.354 | 1 | 22.3 C |
| ATOM 660 | CG2 | VAL | A | 105 | −22.523 | −5.366 | 21.695 | 1 | 22.2 C |
| ATOM 661 | N | PHE | A | 106 | −23.018 | −9.553 | 19.559 | 1 | 16.97 N |
| ATOM 662 | CA | PHE | A | 106 | −22.819 | −10.523 | 18.493 | 1 | 13.5 C |
| ATOM 663 | C | PHE | A | 106 | −23.586 | −10.068 | 17.258 | 1 | 18.61 C |
| ATOM 664 | O | PHE | A | 106 | −24.767 | −9.717 | 17.341 | 1 | 19.47 O |
| ATOM 665 | CB | PHE | A | 106 | −23.321 | −11.905 | 18.914 | 1 | 16.23 C |
| ATOM 666 | CG | PHE | A | 106 | −22.277 | −12.772 | 19.556 | 1 | 15.98 C |
| ATOM 667 | CD1 | PHE | A | 106 | −21.235 | −12.217 | 20.293 | 1 | 15.25 C |
| ATOM 668 | CD2 | PHE | A | 106 | −22.373 | −14.157 | 19.473 | 1 | 20.46 C |
| ATOM 669 | CE1 | PHE | A | 106 | −20.308 | −13.034 | 20.942 | 1 | 17.8 C |
| ATOM 670 | CE2 | PHE | A | 106 | −21.451 | −14.979 | 20.118 | 1 | 18.33 C |
| ATOM 671 | CZ | PHE | A | 106 | −20.418 | −14.411 | 20.854 | 1 | 16.78 C |
| ATOM 672 | N | THR | A | 107 | −22.898 | −10.061 | 16.121 | 1 | 16.01 N |
| ATOM 673 | CA | THR | A | 107 | −23.488 | −9.669 | 14.85 | 1 | 18.37 C |
| ATOM 674 | C | THR | A | 107 | −23.327 | −10.827 | 13.872 | 1 | 20.11 C |
| ATOM 675 | O | THR | A | 107 | −22.713 | −11.843 | 14.198 | 1 | 16.95 O |
| ATOM 676 | CB | THR | A | 107 | −22.767 | −8.439 | 14.25 | 1 | 20.33 C |
| ATOM 677 | OG1 | THR | A | 107 | −21.403 | −8.774 | 13.972 | 1 | 23.29 O |
| ATOM 678 | CG2 | THR | A | 107 | −22.803 | −7.269 | 15.217 | 1 | 25.68 C |
| ATOM 679 | N | ARG | A | 108 | −23.89 | −10.674 | 12.677 | 1 | 20.06 N |
| ATOM 680 | CA | ARG | A | 108 | −23.765 | −11.694 | 11.64 | 1 | 17.35 C |
| ATOM 681 | C | ARG | A | 108 | −22.567 | −11.304 | 10.783 | 1 | 19.04 C |
| ATOM 682 | O | ARG | A | 108 | −22.314 | −10.118 | 10.56 | 1 | 20.18 O |
| ATOM 683 | CB | ARG | A | 108 | −25.012 | −11.728 | 10.755 | 1 | 21.04 C |
| ATOM 684 | CG | ARG | A | 108 | −26.254 | −12.277 | 11.43 | 1 | 21.29 C |

TABLE 1-continued

Atomic structural coordinates for LuxP

|  | ATOM TYPE | RESID |  | NO | X | Y | Z | OCC |  |  |
|---|---|---|---|---|---|---|---|---|---|---|
| ATOM 685 | CD | ARG | A | 108 | −27.479 | −11.957 | 10.595 | 1 | 31.38 | C |
| ATOM 686 | NE | ARG | A | 108 | −27.656 | −10.513 | 10.453 | 1 | 41.33 | N |
| ATOM 687 | CZ | ARG | A | 108 | −28.498 | −9.941 | 9.599 | 1 | 46.94 | C |
| ATOM 688 | NH1 | ARG | A | 108 | −29.246 | −10.69 | 8.801 | 1 | 49.7 | N |
| ATOM 689 | NH2 | ARG | A | 108 | −28.595 | −8.619 | 9.542 | 1 | 43.84 | N |
| ATOM 690 | N | PRO | A | 109 | −21.801 | −12.292 | 10.304 | 1 | 16.92 | N |
| ATOM 691 | CA | PRO | A | 109 | −20.649 | −11.939 | 9.472 | 1 | 17.72 | C |
| ATOM 692 | C | PRO | A | 109 | −21.113 | −11.343 | 8.144 | 1 | 18.31 | C |
| ATOM 693 | O | PRO | A | 109 | −22.188 | −11.681 | 7.648 | 1 | 22.02 | O |
| ATOM 694 | CB | PRO | A | 109 | −19.925 | −13.276 | 9.299 | 1 | 17.21 | C |
| ATOM 695 | CG | PRO | A | 109 | −21.043 | −14.281 | 9.366 | 1 | 17.4 | C |
| ATOM 696 | CD | PRO | A | 109 | −21.881 | −13.749 | 10.512 | 1 | 17.81 | C |
| ATOM 697 | N | ASN | A | 110 | −20.31 | −10.445 | 7.585 | 1 | 24.58 | N |
| ATOM 698 | CA | ASN | A | 110 | −20.638 | −9.818 | 6.304 | 1 | 24.62 | C |
| ATOM 699 | C | ASN | A | 110 | −21.929 | −9.002 | 6.377 | 1 | 28.46 | C |
| ATOM 700 | O | ASN | A | 110 | −22.593 | −8.789 | 5.365 | 1 | 31.27 | O |
| ATOM 701 | CB | ASN | A | 110 | −20.779 | −10.896 | 5.221 | 1 | 26.75 | C |
| ATOM 702 | CG | ASN | A | 110 | −20.777 | −10.323 | 3.813 | 1 | 27.93 | C |
| ATOM 703 | OD1 | ASN | A | 110 | −21.483 | −10.814 | 2.93 | 1 | 30.97 | O |
| ATOM 704 | ND2 | ASN | A | 110 | −19.969 | −9.294 | 3.593 | 1 | 21.74 | N |
| ATOM 705 | N | ALA | A | 111 | −22.286 | −8.547 | 7.573 | 1 | 25.63 | N |
| ATOM 706 | CA | ALA | A | 111 | −23.5 | −7.759 | 7.744 | 1 | 29.33 | C |
| ATOM 707 | C | ALA | A | 111 | −23.459 | −6.989 | 9.052 | 1 | 27.96 | C |
| ATOM 708 | O | ALA | A | 111 | −22.477 | −7.061 | 9.791 | 1 | 31.79 | O |
| ATOM 709 | CB | ALA | A | 111 | −24.722 | −8.667 | 7.71 | 1 | 30.67 | C |
| ATOM 710 | N | ASP | A | 112 | −24.526 | −6.246 | 9.328 | 1 | 26.55 | N |
| ATOM 711 | CA | ASP | A | 112 | −24.618 | −5.472 | 10.558 | 1 | 30.24 | C |
| ATOM 712 | C | ASP | A | 112 | −23.451 | −4.495 | 10.675 | 1 | 30.71 | C |
| ATOM 713 | O | ASP | A | 112 | −22.881 | −4.321 | 11.752 | 1 | 26.9 | O |
| ATOM 714 | CB | ASP | A | 112 | −24.633 | −6.427 | 11.759 | 1 | 32.69 | C |
| ATOM 715 | CG | ASP | A | 112 | −25.808 | −7.393 | 11.72 | 1 | 33.54 | C |
| ATOM 716 | OD1 | ASP | A | 112 | −25.701 | −8.505 | 12.283 | 1 | 27.86 | O |
| ATOM 717 | OD2 | ASP | A | 112 | −26.849 | −7.037 | 11.128 | 1 | 37.71 | O |
| ATOM 718 | N | ILE | A | 113 | −23.1 | −3.856 | 9.563 | 1 | 33.9 | N |
| ATOM 719 | CA | ILE | A | 113 | −21.998 | −2.902 | 9.556 | 1 | 28.33 | C |
| ATOM 720 | C | ILE | A | 113 | −22.242 | −1.754 | 10.527 | 1 | 28.82 | C |
| ATOM 721 | O | ILE | A | 113 | −21.324 | −1.323 | 11.223 | 1 | 28.18 | O |
| ATOM 722 | CB | ILE | A | 113 | −21.762 | −2.318 | 8.142 | 1 | 26.99 | C |
| ATOM 723 | CG1 | ILE | A | 113 | −21.272 | −3.419 | 7.202 | 1 | 36.77 | C |
| ATOM 724 | CG2 | ILE | A | 113 | −20.748 | −1.179 | 8.205 | 1 | 29.1 | C |
| ATOM 725 | CD1 | ILE | A | 113 | −21.012 | −2.946 | 5.785 | 1 | 37.69 | C |
| ATOM 726 | N | LYS | A | 114 | −23.473 | −1.255 | 10.575 | 1 | 26.53 | N |
| ATOM 727 | CA | LYS | A | 114 | −23.784 | −0.154 | 11.477 | 1 | 28.31 | C |
| ATOM 728 | C | LYS | A | 114 | −23.591 | −0.572 | 12.933 | 1 | 25.11 | C |
| ATOM 729 | O | LYS | A | 114 | −22.905 | 0.106 | 13.69 | 1 | 27.89 | O |
| ATOM 730 | CB | LYS | A | 114 | −25.222 | 0.334 | 11.274 | 1 | 26.67 | C |
| ATOM 731 | CG | LYS | A | 114 | −25.535 | 1.599 | 12.064 | 1 | 27.16 | C |
| ATOM 732 | CD | LYS | A | 114 | −26.972 | 2.058 | 11.881 | 1 | 33.61 | C |
| ATOM 733 | CE | LYS | A | 114 | −27.954 | 1.057 | 12.463 | 1 | 33.38 | C |
| ATOM 734 | NZ | LYS | A | 114 | −29.35 | 1.562 | 12.367 | 1 | 32.21 | N |
| ATOM 735 | N | GLN | A | 115 | −24.198 | −1.688 | 13.32 | 1 | 31.93 | N |
| ATOM 736 | CA | GLN | A | 115 | −24.081 | −2.178 | 14.691 | 1 | 28.72 | C |
| ATOM 737 | C | GLN | A | 115 | −22.617 | −2.366 | 15.079 | 1 | 27.28 | C |
| ATOM 738 | O | GLN | A | 115 | −22.19 | −1.958 | 16.16 | 1 | 23.57 | O |
| ATOM 739 | CB | GLN | A | 115 | −24.83 | −3.502 | 14.848 | 1 | 33.48 | C |
| ATOM 740 | CG | GLN | A | 115 | −24.913 | −3.979 | 16.285 | 1 | 38.79 | C |
| ATOM 741 | CD | GLN | A | 115 | −25.558 | −2.949 | 17.194 | 1 | 44.94 | C |
| ATOM 742 | OE1 | GLN | A | 115 | −24.937 | −2.461 | 18.138 | 1 | 48.09 | O |
| ATOM 743 | NE2 | GLN | A | 115 | −26.812 | −2.612 | 16.911 | 1 | 49.02 | N |
| ATOM 744 | N | GLN | A | 116 | −21.847 | −2.982 | 14.191 | 1 | 24.89 | N |
| ATOM 745 | CA | GLN | A | 116 | −20.433 | −3.214 | 14.455 | 1 | 31.48 | C |
| ATOM 746 | C | GLN | A | 116 | −19.75 | −1.88 | 14.759 | 1 | 22.97 | C |
| ATOM 747 | O | GLN | A | 116 | −19.024 | −1.746 | 15.744 | 1 | 26.39 | O |
| ATOM 748 | CB | GLN | A | 116 | −19.786 | −3.878 | 13.238 | 1 | 36.84 | C |
| ATOM 749 | CG | GLN | A | 116 | −18.472 | −4.58 | 13.525 | 1 | 45.85 | C |
| ATOM 750 | CD | GLN | A | 116 | −17.973 | −5.387 | 12.337 | 1 | 50.79 | C |
| ATOM 751 | OE1 | GLN | A | 116 | −16.973 | −6.099 | 12.432 | 1 | 55.68 | O |
| ATOM 752 | NE2 | GLN | A | 116 | −18.667 | −5.274 | 11.209 | 1 | 41.55 | N |
| ATOM 753 | N | SER | A | 117 | −20.004 | −0.892 | 13.907 | 1 | 26.95 | N |
| ATOM 754 | CA | SER | A | 117 | −19.425 | 0.433 | 14.061 | 1 | 25.86 | C |
| ATOM 755 | C | SER | A | 117 | −19.845 | 1.115 | 15.36 | 1 | 25.73 | C |
| ATOM 756 | O | SER | A | 117 | −19.008 | 1.645 | 16.092 | 1 | 25.5 | O |
| ATOM 757 | CB | SER | A | 117 | −19.826 | 1.308 | 12.868 | 1 | 28.9 | C |
| ATOM 758 | OG | SER | A | 117 | −19.342 | 2.632 | 13.013 | 1 | 33.75 | O |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 759 | N | LEU | A | 118 | −21.143 | 1.099 | 15.641 | 1 | 23.63 | N |
| ATOM 760 | CA | LEU | A | 118 | −21.671 | 1.731 | 16.844 | 1 | 27.5 | C |
| ATOM 761 | C | LEU | A | 118 | −21.198 | 1.029 | 18.117 | 1 | 20.15 | C |
| ATOM 762 | O | LEU | A | 118 | −20.909 | 1.679 | 19.119 | 1 | 24.85 | O |
| ATOM 763 | CB | LEU | A | 118 | −23.205 | 1.761 | 16.79 | 1 | 24.35 | C |
| ATOM 764 | CG | LEU | A | 118 | −23.807 | 2.437 | 15.55 | 1 | 32.46 | C |
| ATOM 765 | CD1 | LEU | A | 118 | −25.325 | 2.458 | 15.659 | 1 | 31.33 | C |
| ATOM 766 | CD2 | LEU | A | 118 | −23.268 | 3.853 | 15.415 | 1 | 33.6 | C |
| ATOM 767 | N | SER | A | 119 | −21.104 | −0.297 | 18.072 | 1 | 27.02 | N |
| ATOM 768 | CA | SER | A | 119 | −20.658 | −1.055 | 19.24 | 1 | 23.98 | C |
| ATOM 769 | C | SER | A | 119 | −19.173 | −0.839 | 19.533 | 1 | 18.61 | C |
| ATOM 770 | O | SER | A | 119 | −18.766 | −0.764 | 20.693 | 1 | 19.53 | O |
| ATOM 771 | CB | SER | A | 119 | −20.936 | −2.548 | 19.047 | 1 | 20.65 | C |
| ATOM 772 | OG | SER | A | 119 | −22.328 | −2.802 | 18.959 | 1 | 26.73 | O |
| ATOM 773 | N | LEU | A | 120 | −18.363 | −0.729 | 18.482 | 1 | 19.8 | N |
| ATOM 774 | CA | LEU | A | 120 | −16.934 | −0.511 | 18.663 | 1 | 22.18 | C |
| ATOM 775 | C | LEU | A | 120 | −16.681 | 0.852 | 19.292 | 1 | 20.63 | C |
| ATOM 776 | O | LEU | A | 120 | −15.856 | 0.984 | 20.195 | 1 | 25.03 | O |
| ATOM 777 | CB | LEU | A | 120 | −16.198 | −0.62 | 17.321 | 1 | 20.83 | C |
| ATOM 778 | CG | LEU | A | 120 | −16.063 | −2.032 | 16.74 | 1 | 23.39 | C |
| ATOM 779 | CD1 | LEU | A | 120 | −15.444 | −1.96 | 15.354 | 1 | 27.35 | C |
| ATOM 780 | CD2 | LEU | A | 120 | −15.204 | −2.89 | 17.664 | 1 | 20.28 | C |
| ATOM 781 | N | MET | A | 121 | −17.399 | 1.868 | 18.821 | 1 | 28.06 | N |
| ATOM 782 | CA | MET | A | 121 | −17.242 | 3.211 | 19.364 | 1 | 25.97 | C |
| ATOM 783 | C | MET | A | 121 | −17.694 | 3.256 | 20.819 | 1 | 27.9 | C |
| ATOM 784 | O | MET | A | 121 | −17.055 | 3.895 | 21.658 | 1 | 27.59 | O |
| ATOM 785 | CB | MET | A | 121 | −18.044 | 4.217 | 18.537 | 1 | 35.16 | C |
| ATOM 786 | CG | MET | A | 121 | −17.399 | 4.552 | 17.204 | 1 | 46.16 | C |
| ATOM 787 | SD | MET | A | 121 | −15.718 | 5.183 | 17.429 | 1 | 48.92 | S |
| ATOM 788 | CE | MET | A | 121 | −16.058 | 6.907 | 17.816 | 1 | 51.41 | C |
| ATOM 789 | N | GLU | A | 122 | −18.794 | 2.57 | 21.112 | 1 | 25.41 | N |
| ATOM 790 | CA | GLU | A | 122 | −19.317 | 2.528 | 22.473 | 1 | 28.77 | C |
| ATOM 791 | C | GLU | A | 122 | −18.301 | 1.873 | 23.403 | 1 | 30.19 | C |
| ATOM 792 | O | GLU | A | 122 | −18.189 | 2.239 | 24.574 | 1 | 31.1 | O |
| ATOM 793 | CB | GLU | A | 122 | −20.634 | 1.75 | 22.514 | 1 | 28.89 | C |
| ATOM 794 | CG | GLU | A | 122 | −21.258 | 1.675 | 23.9 | 1 | 40.77 | C |
| ATOM 795 | CD | GLU | A | 122 | −21.535 | 3.047 | 24.488 | 1 | 45.67 | C |
| ATOM 796 | OE1 | GLU | A | 122 | −22.323 | 3.807 | 23.885 | 1 | 50.83 | O |
| ATOM 797 | OE2 | GLU | A | 122 | −20.963 | 3.367 | 25.553 | 1 | 49.54 | O |
| ATOM 798 | N | ALA | A | 123 | −17.561 | 0.903 | 22.873 | 1 | 29.67 | N |
| ATOM 799 | CA | ALA | A | 123 | −16.549 | 0.201 | 23.652 | 1 | 35.03 | C |
| ATOM 800 | C | ALA | A | 123 | −15.479 | 1.174 | 24.141 | 1 | 30.1 | C |
| ATOM 801 | O | ALA | A | 123 | −15.016 | 1.083 | 25.279 | 1 | 29.04 | O |
| ATOM 802 | CB | ALA | A | 123 | −15.915 | −0.901 | 22.808 | 1 | 34.89 | C |
| ATOM 803 | N | LEU | A | 124 | −15.086 | 2.104 | 23.276 | 1 | 32.04 | N |
| ATOM 804 | CA | LEU | A | 124 | −14.076 | 3.093 | 23.634 | 1 | 34.19 | C |
| ATOM 805 | C | LEU | A | 124 | −14.669 | 4.165 | 24.535 | 1 | 31.52 | C |
| ATOM 806 | O | LEU | A | 124 | −13.991 | 4.689 | 25.419 | 1 | 34.72 | O |
| ATOM 807 | CB | LEU | A | 124 | −13.497 | 3.759 | 22.384 | 1 | 35.28 | C |
| ATOM 808 | CG | LEU | A | 124 | −12.734 | 2.894 | 21.383 | 1 | 38.85 | C |
| ATOM 809 | CD1 | LEU | A | 124 | −12.028 | 3.81 | 20.393 | 1 | 43.78 | C |
| ATOM 810 | CD2 | LEU | A | 124 | −11.72 | 2.016 | 22.104 | 1 | 39.89 | C |
| ATOM 811 | N | LYS | A | 125 | −15.936 | 4.492 | 24.299 | 1 | 33.85 | N |
| ATOM 812 | CA | LYS | A | 125 | −16.622 | 5.501 | 25.096 | 1 | 39.39 | C |
| ATOM 813 | C | LYS | A | 125 | −16.696 | 5.055 | 26.551 | 1 | 33.64 | C |
| ATOM 814 | O | LYS | A | 125 | −16.574 | 5.869 | 27.467 | 1 | 36.31 | O |
| ATOM 815 | CB | LYS | A | 125 | −18.037 | 5.733 | 24.558 | 1 | 41.62 | C |
| ATOM 816 | CG | LYS | A | 125 | −18.085 | 6.291 | 23.144 | 1 | 51.16 | C |
| ATOM 817 | CD | LYS | A | 125 | −19.517 | 6.409 | 22.637 | 1 | 51.79 | C |
| ATOM 818 | CE | LYS | A | 125 | −20.341 | 7.361 | 23.491 | 1 | 54.63 | C |
| ATOM 819 | NZ | LYS | A | 125 | −21.745 | 7.476 | 23 | 1 | 59.77 | N |
| ATOM 820 | N | SER | A | 126 | −16.891 | 3.756 | 26.756 | 1 | 37.65 | N |
| ATOM 821 | CA | SER | A | 126 | −16.987 | 3.197 | 28.1 | 1 | 35.04 | C |
| ATOM 822 | C | SER | A | 126 | −15.616 | 2.963 | 28.731 | 1 | 31.89 | C |
| ATOM 823 | O | SER | A | 126 | −15.521 | 2.453 | 29.847 | 1 | 31.14 | O |
| ATOM 824 | CB | SER | A | 126 | −17.767 | 1.881 | 28.064 | 1 | 35.47 | C |
| ATOM 825 | OG | SER | A | 126 | −17.14 | 0.939 | 27.21 | 1 | 34.05 | O |
| ATOM 826 | N | LYS | A | 127 | −14.56 | 3.339 | 28.014 | 1 | 27.67 | N |
| ATOM 827 | CA | LYS | A | 127 | −13.192 | 3.17 | 28.5 | 1 | 29.65 | C |
| ATOM 828 | C | LYS | A | 127 | −12.904 | 1.745 | 28.954 | 1 | 28.69 | C |
| ATOM 829 | O | LYS | A | 127 | −12.436 | 1.522 | 30.071 | 1 | 29.61 | O |
| ATOM 830 | CB | LYS | A | 127 | −12.899 | 4.12 | 29.667 | 1 | 34.04 | C |
| ATOM 831 | CG | LYS | A | 127 | −12.973 | 5.6 | 29.333 | 1 | 40.15 | C |
| ATOM 832 | CD | LYS | A | 127 | −14.368 | 6.148 | 29.559 | 1 | 50.74 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 833 | CE | LYS | A | 127 | −14.378 | 7.666 | 29.458 | 1 | 53.67 | C |
| ATOM 834 | NZ | LYS | A | 127 | −15.698 | 8.238 | 29.843 | 1 | 56.58 | N |
| ATOM 835 | N | SER | A | 128 | −13.181 | 0.781 | 28.085 | 1 | 25.8 | N |
| ATOM 836 | CA | SER | A | 128 | −12.93 | −0.615 | 28.406 | 1 | 23.03 | C |
| ATOM 837 | C | SER | A | 128 | −11.433 | −0.848 | 28.575 | 1 | 20.04 | C |
| ATOM 838 | O | SER | A | 128 | −10.619 | −0.151 | 27.972 | 1 | 26.91 | O |
| ATOM 839 | CB | SER | A | 128 | −13.458 | −1.513 | 27.286 | 1 | 26 | C |
| ATOM 840 | OG | SER | A | 128 | −14.864 | −1.395 | 27.154 | 1 | 33.17 | O |
| ATOM 841 | N | ASP | A | 129 | −11.076 | −1.827 | 29.403 | 1 | 21.3 | N |
| ATOM 842 | CA | ASP | A | 129 | −9.675 | −2.167 | 29.628 | 1 | 19.95 | C |
| ATOM 843 | C | ASP | A | 129 | −9.2 | −3.066 | 28.496 | 1 | 22.22 | C |
| ATOM 844 | O | ASP | A | 129 | −8.042 | −3.01 | 28.08 | 1 | 22.81 | O |
| ATOM 845 | CB | ASP | A | 129 | −9.513 | −2.891 | 30.961 | 1 | 24.17 | C |
| ATOM 846 | CG | ASP | A | 129 | −9.885 | −2.021 | 32.139 | 1 | 24.26 | C |
| ATOM 847 | OD1 | ASP | A | 129 | −9.196 | −1.004 | 32.37 | 1 | 29.48 | O |
| ATOM 848 | OD2 | ASP | A | 129 | −10.867 | −2.35 | 32.831 | 1 | 24.54 | O |
| ATOM 849 | N | TYR | A | 130 | −10.109 | −3.9 | 28.009 | 1 | 17.84 | N |
| ATOM 850 | CA | TYR | A | 130 | −9.815 | −4.805 | 26.907 | 1 | 15.84 | C |
| ATOM 851 | C | TYR | A | 130 | −10.989 | −4.796 | 25.946 | 1 | 18.89 | C |
| ATOM 852 | O | TYR | A | 130 | −12.151 | −4.894 | 26.361 | 1 | 16.89 | O |
| ATOM 853 | CB | TYR | A | 130 | −9.569 | −6.232 | 27.406 | 1 | 18.4 | C |
| ATOM 854 | CG | TYR | A | 130 | −8.459 | −6.324 | 28.421 | 1 | 17.71 | C |
| ATOM 855 | CD1 | TYR | A | 130 | −8.715 | −6.125 | 29.774 | 1 | 21.83 | C |
| ATOM 856 | CD2 | TYR | A | 130 | −7.14 | −6.54 | 28.023 | 1 | 19.74 | C |
| ATOM 857 | CE1 | TYR | A | 130 | −7.69 | −6.133 | 30.71 | 1 | 22.8 | C |
| ATOM 858 | CE2 | TYR | A | 130 | −6.102 | −6.549 | 28.953 | 1 | 19.7 | C |
| ATOM 859 | CZ | TYR | A | 130 | −6.388 | −6.341 | 30.296 | 1 | 21.91 | C |
| ATOM 860 | OH | TYR | A | 130 | −5.374 | −6.313 | 31.221 | 1 | 27.98 | O |
| ATOM 861 | N | LEU | A | 131 | −10.674 | −4.649 | 24.664 | 1 | 17.07 | N |
| ATOM 862 | CA | LEU | A | 131 | −11.666 | −4.631 | 23.598 | 1 | 16.58 | C |
| ATOM 863 | C | LEU | A | 131 | −11.311 | −5.814 | 22.706 | 1 | 16.98 | C |
| ATOM 864 | O | LEU | A | 131 | −10.194 | −5.9 | 22.175 | 1 | 17.96 | O |
| ATOM 865 | CB | LEU | A | 131 | −11.574 | −3.325 | 22.802 | 1 | 21.02 | C |
| ATOM 866 | CG | LEU | A | 131 | −12.796 | −2.868 | 21.994 | 1 | 33.62 | C |
| ATOM 867 | CD1 | LEU | A | 131 | −12.361 | −1.772 | 21.032 | 1 | 26.51 | C |
| ATOM 868 | CD2 | LEU | A | 131 | −13.415 | −4.024 | 21.226 | 1 | 34.39 | C |
| ATOM 869 | N | ILE | A | 132 | −12.264 | −6.721 | 22.543 | 1 | 16.8 | N |
| ATOM 870 | CA | ILE | A | 132 | −12.055 | −7.924 | 21.759 | 1 | 13.11 | C |
| ATOM 871 | C | ILE | A | 132 | −12.958 | −7.967 | 20.539 | 1 | 15.19 | C |
| ATOM 872 | O | ILE | A | 132 | −14.174 | −7.871 | 20.656 | 1 | 17.64 | O |
| ATOM 873 | CB | ILE | A | 132 | −12.331 | −9.178 | 22.614 | 1 | 15.25 | C |
| ATOM 874 | CG1 | ILE | A | 132 | −11.619 | −9.046 | 23.965 | 1 | 18.67 | C |
| ATOM 875 | CG2 | ILE | A | 132 | −11.866 | −10.419 | 21.882 | 1 | 17.91 | C |
| ATOM 876 | CD1 | ILE | A | 132 | −11.831 | −10.237 | 24.886 | 1 | 18.18 | C |
| ATOM 877 | N | PHE | A | 133 | −12.354 | −8.101 | 19.363 | 1 | 13 | N |
| ATOM 878 | CA | PHE | A | 133 | −13.121 | −8.178 | 18.133 | 1 | 11.34 | C |
| ATOM 879 | C | PHE | A | 133 | −12.294 | −8.804 | 17.027 | 1 | 13.11 | C |
| ATOM 880 | O | PHE | A | 133 | −11.202 | −9.31 | 17.274 | 1 | 19.08 | O |
| ATOM 881 | CB | PHE | A | 133 | −13.663 | −6.8 | 17.71 | 1 | 20.81 | C |
| ATOM 882 | CG | PHE | A | 133 | −12.607 | −5.763 | 17.456 | 1 | 19.1 | C |
| ATOM 883 | CD1 | PHE | A | 133 | −11.899 | −5.192 | 18.508 | 1 | 23.79 | C |
| ATOM 884 | CD2 | PHE | A | 133 | −12.36 | −5.315 | 16.161 | 1 | 25.87 | C |
| ATOM 885 | CE1 | PHE | A | 133 | −10.963 | −4.182 | 18.275 | 1 | 25.23 | C |
| ATOM 886 | CE2 | PHE | A | 133 | −11.427 | −4.307 | 15.918 | 1 | 24.98 | C |
| ATOM 887 | CZ | PHE | A | 133 | −10.729 | −3.741 | 16.977 | 1 | 23.68 | C |
| ATOM 888 | N | THR | A | 134 | −12.807 | −8.78 | 15.807 | 1 | 17.34 | N |
| ATOM 889 | CA | THR | A | 134 | −12.093 | −9.409 | 14.711 | 1 | 15.54 | C |
| ATOM 890 | C | THR | A | 134 | −11.984 | −8.486 | 13.51 | 1 | 20.86 | C |
| ATOM 891 | O | THR | A | 134 | −12.669 | −7.466 | 13.43 | 1 | 26.33 | O |
| ATOM 892 | CB | THR | A | 134 | −12.807 | −10.713 | 14.285 | 1 | 18.28 | C |
| ATOM 893 | OG1 | THR | A | 134 | −11.941 | −11.493 | 13.452 | 1 | 15.73 | O |
| ATOM 894 | CG2 | THR | A | 134 | −14.087 | −10.392 | 13.506 | 1 | 21.04 | C |
| ATOM 895 | N | LEU | A | 135 | −11.118 | −8.867 | 12.579 | 1 | 25.55 | N |
| ATOM 896 | CA | LEU | A | 135 | −10.908 | −8.097 | 11.365 | 1 | 28.99 | C |
| ATOM 897 | C | LEU | A | 135 | −10.823 | −9.017 | 10.158 | 1 | 20.16 | C |
| ATOM 898 | O | LEU | A | 135 | −10.016 | −9.947 | 10.131 | 1 | 24.15 | O |
| ATOM 899 | CB | LEU | A | 135 | −9.619 | −7.281 | 11.473 | 1 | 35.83 | C |
| ATOM 900 | CG | LEU | A | 135 | −9.609 | −6.145 | 12.498 | 1 | 36.62 | C |
| ATOM 901 | CD1 | LEU | A | 135 | −8.628 | −6.468 | 13.607 | 1 | 43.96 | C |
| ATOM 902 | CD2 | LEU | A | 135 | −9.227 | −4.846 | 11.808 | 1 | 37.81 | C |
| ATOM 903 | N | ASP | A | 136 | −11.664 | −8.756 | 9.166 | 1 | 23.09 | N |
| ATOM 904 | CA | ASP | A | 136 | −11.662 | −9.543 | 7.939 | 1 | 20.82 | C |
| ATOM 905 | C | ASP | A | 136 | −11.549 | −8.594 | 6.751 | 1 | 26.01 | C |
| ATOM 906 | O | ASP | A | 136 | −11.153 | −8.99 | 5.656 | 1 | 22.07 | O |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 907 | CB | ASP | A | 136 | −12.941 | −10.375 | 7.818 | 1 | 19.65 | C |
| ATOM 908 | CG | ASP | A | 136 | −12.878 | −11.352 | 6.659 | 1 | 20.23 | C |
| ATOM 909 | OD1 | ASP | A | 136 | −11.939 | −12.165 | 6.639 | 1 | 28.22 | O |
| ATOM 910 | OD2 | ASP | A | 136 | −13.756 | −11.307 | 5.775 | 1 | 40.11 | O |
| ATOM 911 | N | THR | A | 137 | −11.906 | −7.336 | 6.984 | 1 | 29.04 | N |
| ATOM 912 | CA | THR | A | 137 | −11.842 | −6.305 | 5.959 | 1 | 37.64 | C |
| ATOM 913 | C | THR | A | 137 | −10.933 | −5.191 | 6.473 | 1 | 36.95 | C |
| ATOM 914 | O | THR | A | 137 | −10.423 | −5.264 | 7.592 | 1 | 32.71 | O |
| ATOM 915 | CB | THR | A | 137 | −13.248 | −5.725 | 5.668 | 1 | 40.06 | C |
| ATOM 916 | OG1 | THR | A | 137 | −14.145 | −6.792 | 5.336 | 1 | 46.73 | O |
| ATOM 917 | CG2 | THR | A | 137 | −13.2 | −4.748 | 4.504 | 1 | 47.68 | C |
| ATOM 918 | N | THR | A | 138 | −10.727 | −4.17 | 5.65 | 1 | 37.03 | N |
| ATOM 919 | CA | THR | A | 138 | −9.892 | −3.03 | 6.011 | 1 | 33.74 | C |
| ATOM 920 | C | THR | A | 138 | −10.712 | −2.051 | 6.851 | 1 | 26.67 | C |
| ATOM 921 | O | THR | A | 138 | −10.177 | −1.118 | 7.445 | 1 | 29.65 | O |
| ATOM 922 | CB | THR | A | 138 | −9.398 | −2.293 | 4.744 | 1 | 43.15 | C |
| ATOM 923 | OG1 | THR | A | 138 | −10.449 | −2.264 | 3.767 | 1 | 46.68 | O |
| ATOM 924 | CG2 | THR | A | 138 | −8.184 | −2.987 | 4.154 | 1 | 45.96 | C |
| ATOM 925 | N | ARG | A | 139 | −12.016 | −2.293 | 6.901 | 1 | 27.09 | N |
| ATOM 926 | CA | ARG | A | 139 | −12.958 | −1.439 | 7.617 | 1 | 28.83 | C |
| ATOM 927 | C | ARG | A | 139 | −12.562 | −0.849 | 8.979 | 1 | 33.9 | C |
| ATOM 928 | O | ARG | A | 139 | −12.721 | 0.352 | 9.194 | 1 | 39.04 | O |
| ATOM 929 | CB | ARG | A | 139 | −14.303 | −2.165 | 7.747 | 1 | 29.24 | C |
| ATOM 930 | CG | ARG | A | 139 | −15.387 | −1.334 | 8.415 | 1 | 38.46 | C |
| ATOM 931 | CD | ARG | A | 139 | −16.774 | −1.967 | 8.32 | 1 | 44.16 | C |
| ATOM 932 | NE | ARG | A | 139 | −17.419 | −1.725 | 7.031 | 1 | 47.41 | N |
| ATOM 933 | CZ | ARG | A | 139 | −17.15 | −2.393 | 5.914 | 1 | 49.08 | C |
| ATOM 934 | NH1 | ARG | A | 139 | −16.243 | −3.359 | 5.916 | 1 | 52.59 | N |
| ATOM 935 | NH2 | ARG | A | 139 | −17.787 | −2.092 | 4.79 | 1 | 47.85 | N |
| ATOM 936 | N | HIS | A | 140 | −12.042 | −1.663 | 9.891 | 1 | 27.69 | N |
| ATOM 937 | CA | HIS | A | 140 | −11.693 | −1.154 | 11.219 | 1 | 31.31 | C |
| ATOM 938 | C | HIS | A | 140 | −10.211 | −0.923 | 11.512 | 1 | 29.45 | C |
| ATOM 939 | O | HIS | A | 140 | −9.823 | −0.794 | 12.676 | 1 | 25.65 | O |
| ATOM 940 | CD | HIS | A | 140 | −12.268 | −2.088 | 12.286 | 1 | 30.83 | C |
| ATOM 941 | CG | HIS | A | 140 | −13.702 | −2.447 | 12.058 | 1 | 30.87 | C |
| ATOM 942 | ND1 | HIS | A | 140 | −14.132 | −3.752 | 11.943 | 1 | 39.78 | N |
| ATOM 943 | CD2 | HIS | A | 140 | −14.806 | −1.674 | 11.931 | 1 | 28.22 | C |
| ATOM 944 | CE1 | HIS | A | 140 | −15.439 | −3.766 | 11.757 | 1 | 40.57 | C |
| ATOM 945 | NE2 | HIS | A | 140 | −15.874 | −2.519 | 11.746 | 1 | 35.94 | N |
| ATOM 946 | N | ARG | A | 141 | −9.387 | −0.857 | 10.471 | 1 | 23.61 | N |
| ATOM 947 | CA | ARG | A | 141 | −7.955 | −0.647 | 10.659 | 1 | 19.63 | C |
| ATOM 948 | C | ARG | A | 141 | −7.67 | 0.721 | 11.285 | 1 | 30.61 | C |
| ATOM 949 | O | ARG | A | 141 | −6.886 | 0.826 | 12.229 | 1 | 26.95 | O |
| ATOM 950 | CB | ARG | A | 141 | −7.23 | −0.767 | 9.315 | 1 | 29.57 | C |
| ATOM 951 | CG | ARG | A | 141 | −7.697 | −1.949 | 8.471 | 1 | 43.4 | C |
| ATOM 952 | CD | ARG | A | 141 | −6.804 | −3.172 | 8.592 | 1 | 47.35 | C |
| ATOM 953 | NE | ARG | A | 141 | −5.587 | −3.033 | 7.798 | 1 | 51.49 | N |
| ATOM 954 | CZ | ARG | A | 141 | −4.776 | −4.039 | 7.484 | 1 | 46.99 | C |
| ATOM 955 | NH1 | ARG | A | 141 | −5.047 | −5.269 | 7.895 | 1 | 55.28 | N |
| ATOM 956 | NH2 | ARG | A | 141 | −3.691 | −3.815 | 6.758 | 1 | 36.04 | N |
| ATOM 957 | N | LYS | A | 142 | −8.3 | 1.77 | 10.762 | 1 | 34.23 | N |
| ATOM 958 | CA | LYS | A | 142 | −8.079 | 3.106 | 11.307 | 1 | 33.11 | C |
| ATOM 959 | C | LYS | A | 142 | −8.581 | 3.181 | 12.739 | 1 | 30.14 | C |
| ATOM 960 | O | LYS | A | 142 | −8.026 | 3.909 | 13.565 | 1 | 33.03 | O |
| ATOM 961 | CD | LYS | A | 142 | −8.759 | 4.168 | 10.44 | 1 | 35.8 | C |
| ATOM 962 | CG | LYS | A | 142 | −8.032 | 4.413 | 9.124 | 1 | 43.3 | C |
| ATOM 963 | CD | LYS | A | 142 | −8.584 | 5.614 | 8.377 | 1 | 49.43 | C |
| ATOM 964 | CE | LYS | A | 142 | −7.766 | 5.895 | 7.123 | 1 | 52.47 | C |
| ATOM 965 | NZ | LYS | A | 142 | −8.249 | 7.098 | 6.393 | 1 | 58.42 | N |
| ATOM 966 | N | PHE | A | 143 | −9.634 | 2.423 | 13.029 | 1 | 28.39 | N |
| ATOM 967 | CA | PHE | A | 143 | −10.181 | 2.381 | 14.376 | 1 | 29.5 | C |
| ATOM 968 | C | PHE | A | 143 | −9.099 | 1.806 | 15.288 | 1 | 26.52 | C |
| ATOM 969 | O | PHE | A | 143 | −8.829 | 2.337 | 16.369 | 1 | 22.64 | O |
| ATOM 970 | CB | PHE | A | 143 | −11.423 | 1.484 | 14.423 | 1 | 30.18 | C |
| ATOM 971 | CG | PHE | A | 143 | −11.965 | 1.278 | 15.809 | 1 | 26.73 | C |
| ATOM 972 | CD1 | PHE | A | 143 | −12.619 | 2.309 | 16.476 | 1 | 29.05 | C |
| ATOM 973 | CD2 | PHE | A | 143 | −11.78 | 0.066 | 16.467 | 1 | 29.72 | C |
| ATOM 974 | CE1 | PHE | A | 143 | −13.081 | 2.137 | 17.777 | 1 | 26.46 | C |
| ATOM 975 | CE2 | PHE | A | 143 | −12.236 | −0.115 | 17.767 | 1 | 34.57 | C |
| ATOM 976 | CZ | PHE | A | 143 | −12.887 | 0.923 | 18.424 | 1 | 27.66 | C |
| ATOM 977 | N | VAL | A | 144 | −8.479 | 0.717 | 14.838 | 1 | 26.56 | N |
| ATOM 978 | CA | VAL | A | 144 | −7.42 | 0.06 | 15.598 | 1 | 21.08 | C |
| ATOM 979 | C | VAL | A | 144 | −6.291 | 1.044 | 15.859 | 1 | 20.24 | C |
| ATOM 980 | O | VAL | A | 144 | −5.818 | 1.182 | 16.987 | 1 | 22.27 | O |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 981 | CB | VAL | A | 144 | −6.85 | −1.158 | 14.833 | 1 | 26.95 | C |
| ATOM 982 | CG1 | VAL | A | 144 | −5.628 | −1.702 | 15.561 | 1 | 25.72 | C |
| ATOM 983 | CG2 | VAL | A | 144 | −7.917 | −2.239 | 14.703 | 1 | 25.69 | C |
| ATOM 984 | N | GLU | A | 145 | −5.868 | 1.737 | 14.807 | 1 | 26.16 | N |
| ATOM 985 | CA | GLU | A | 145 | −4.793 | 2.713 | 14.927 | 1 | 27.57 | C |
| ATOM 986 | C | GLU | A | 145 | −5.129 | 3.75 | 15.994 | 1 | 23 | C |
| ATOM 987 | O | GLU | A | 145 | −4.271 | 4.137 | 16.786 | 1 | 24.02 | O |
| ATOM 988 | CB | GLU | A | 145 | −4.554 | 3.4 | 13.578 | 1 | 32.73 | C |
| ATOM 989 | CG | GLU | A | 145 | −4.156 | 2.437 | 12.467 | 1 | 36.91 | C |
| ATOM 990 | CD | GLU | A | 145 | −4.012 | 3.113 | 11.118 | 1 | 47.48 | C |
| ATOM 991 | OE1 | GLU | A | 145 | −3.774 | 2.398 | 10.121 | 1 | 54.65 | O |
| ATOM 992 | OE2 | GLU | A | 145 | −4.134 | 4.356 | 11.053 | 1 | 50.54 | O |
| ATOM 993 | N | HIS | A | 146 | −6.38 | 4.195 | 16.016 | 1 | 27.53 | N |
| ATOM 994 | CA | HIS | A | 146 | −6.811 | 5.186 | 16.998 | 1 | 28.45 | C |
| ATOM 995 | C | HIS | A | 146 | −6.662 | 4.657 | 18.422 | 1 | 30.82 | C |
| ATOM 996 | O | HIS | A | 146 | −6.177 | 5.361 | 19.308 | 1 | 30.33 | O |
| ATOM 997 | CB | HIS | A | 146 | −8.269 | 5.581 | 16.746 | 1 | 26.97 | C |
| ATOM 998 | CG | HIS | A | 146 | −8.84 | 6.487 | 17.795 | 1 | 41.86 | C |
| ATOM 999 | ND1 | HIS | A | 146 | −9.943 | 6.149 | 18.55 | 1 | 46.26 | N |
| ATOM 1000 | CD2 | HIS | A | 146 | −8.463 | 7.719 | 18.21 | 1 | 41.59 | C |
| ATOM 1001 | CE1 | HIS | A | 146 | −10.221 | 7.135 | 19.385 | 1 | 44.81 | C |
| ATOM 1002 | NE2 | HIS | A | 146 | −9.338 | 8.099 | 19.199 | 1 | 44.64 | N |
| ATOM 1003 | N | VAL | A | 147 | −7.085 | 3.416 | 18.635 | 1 | 26.36 | N |
| ATOM 1004 | CA | VAL | A | 147 | −7 | 2.787 | 19.948 | 1 | 28.68 | C |
| ATOM 1005 | C | VAL | A | 147 | −5.547 | 2.681 | 20.392 | 1 | 25.63 | C |
| ATOM 1006 | O | VAL | A | 147 | −5.194 | 3.053 | 21.513 | 1 | 30.06 | O |
| ATOM 1007 | CB | VAL | A | 147 | −7.613 | 1.364 | 19.922 | 1 | 30.25 | C |
| ATOM 1008 | CG1 | VAL | A | 147 | −7.443 | 0.691 | 21.275 | 1 | 31.68 | C |
| ATOM 1009 | CG2 | VAL | A | 147 | −9.082 | 1.44 | 19.552 | 1 | 28.52 | C |
| ATOM 1010 | N | LEU | A | 148 | −4.706 | 2.176 | 19.496 | 1 | 24.96 | N |
| ATOM 1011 | CA | LEU | A | 148 | −3.291 | 1.996 | 19.785 | 1 | 22.36 | C |
| ATOM 1012 | C | LEU | A | 148 | −2.551 | 3.294 | 20.102 | 1 | 23.21 | C |
| ATOM 1013 | O | LEU | A | 148 | −1.785 | 3.359 | 21.065 | 1 | 25.14 | O |
| ATOM 1014 | CB | LEU | A | 148 | −2.607 | 1.294 | 18.604 | 1 | 24.61 | C |
| ATOM 1015 | CG | LEU | A | 148 | −3.067 | −0.136 | 18.299 | 1 | 25.84 | C |
| ATOM 1016 | CD1 | LEU | A | 148 | −2.392 | −0.653 | 17.031 | 1 | 32.25 | C |
| ATOM 1017 | CD2 | LEU | A | 148 | −2.743 | −1.028 | 19.485 | 1 | 32.5 | C |
| ATOM 1018 | N | ASP | A | 149 | −2.792 | 4.331 | 19.308 | 1 | 30.04 | N |
| ATOM 1019 | CA | ASP | A | 149 | −2.094 | 5.597 | 19.503 | 1 | 31.04 | C |
| ATOM 1020 | C | ASP | A | 149 | −2.607 | 6.55 | 20.577 | 1 | 32.64 | C |
| ATOM 1021 | O | ASP | A | 149 | −1.812 | 7.231 | 21.223 | 1 | 31.78 | O |
| ATOM 1022 | CB | ASP | A | 149 | −2.022 | 6.371 | 18.182 | 1 | 34.75 | C |
| ATOM 1023 | CG | ASP | A | 149 | −1.397 | 5.565 | 17.064 | 1 | 39.08 | C |
| ATOM 1024 | OD1 | ASP | A | 149 | −0.433 | 4.816 | 17.334 | 1 | 39.89 | O |
| ATOM 1025 | OD2 | ASP | A | 149 | −1.864 | 5.693 | 15.912 | 1 | 42.34 | O |
| ATOM 1026 | N | SER | A | 150 | −3.918 | 6.605 | 20.784 | 1 | 31.26 | N |
| ATOM 1027 | CA | SER | A | 150 | −4.448 | 7.559 | 21.753 | 1 | 32.41 | C |
| ATOM 1028 | C | SER | A | 150 | −5.255 | 7.053 | 22.947 | 1 | 29.72 | C |
| ATOM 1029 | O | SER | A | 150 | −5.834 | 7.86 | 23.675 | 1 | 28.94 | O |
| ATOM 1030 | CB | SER | A | 150 | −5.279 | 8.603 | 21.004 | 1 | 33.53 | C |
| ATOM 1031 | OG | SER | A | 150 | −4.943 | 8.615 | 19.628 | 1 | 44.93 | O |
| ATOM 1032 | N | THR | A | 151 | −5.304 | 5.745 | 23.171 | 1 | 27.55 | N |
| ATOM 1033 | CA | THR | A | 151 | −6.074 | 5.245 | 24.307 | 1 | 30.47 | C |
| ATOM 1034 | C | THR | A | 151 | −5.299 | 4.244 | 25.149 | 1 | 31.69 | C |
| ATOM 1035 | O | THR | A | 151 | −4.214 | 3.806 | 24.771 | 1 | 26.93 | O |
| ATOM 1036 | CB | THR | A | 151 | −7.382 | 4.565 | 23.855 | 1 | 32.24 | C |
| ATOM 1037 | OG1 | THR | A | 151 | −7.103 | 3.222 | 23.442 | 1 | 27.89 | O |
| ATOM 1038 | CG2 | THR | A | 151 | −8.007 | 5.327 | 22.693 | 1 | 25.93 | C |
| ATOM 1039 | N | ASN | A | 152 | −5.874 | 3.891 | 26.296 | 1 | 36.03 | N |
| ATOM 1040 | CA | ASN | A | 152 | −5.264 | 2.932 | 27.207 | 1 | 39.43 | C |
| ATOM 1041 | C | ASN | A | 152 | −5.965 | 1.579 | 27.085 | 1 | 38.56 | C |
| ATOM 1042 | O | ASN | A | 152 | −5.717 | 0.666 | 27.872 | 1 | 38.39 | O |
| ATOM 1043 | CB | ASN | A | 152 | −5.353 | 3.439 | 28.65 | 1 | 44.95 | C |
| ATOM 1044 | CG | ASN | A | 152 | −4.484 | 4.662 | 28.895 | 1 | 51.63 | C |
| ATOM 1045 | OD1 | ASN | A | 152 | −4.653 | 5.699 | 28.254 | 1 | 57.64 | O |
| ATOM 1046 | ND2 | ASN | A | 152 | −3.547 | 4.543 | 29.829 | 1 | 58.7 | N |
| ATOM 1047 | N | THR | A | 153 | −6.845 | 1.46 | 26.095 | 1 | 30.68 | N |
| ATOM 1048 | CA | THR | A | 153 | −7.579 | 0.221 | 25.865 | 1 | 27.53 | C |
| ATOM 1049 | C | THR | A | 153 | −6.727 | −0.769 | 25.076 | 1 | 28.36 | C |
| ATOM 1050 | O | THR | A | 153 | −6.225 | −0.447 | 24.001 | 1 | 29.97 | O |
| ATOM 1051 | CB | THR | A | 153 | −8.885 | 0.476 | 25.076 | 1 | 25.03 | C |
| ATOM 1052 | OG1 | THR | A | 153 | −9.727 | 1.372 | 25.812 | 1 | 28.71 | O |
| ATOM 1053 | CG2 | THR | A | 153 | −9.633 | −0.829 | 24.839 | 1 | 24.2 | C |
| ATOM 1054 | N | LYS | A | 154 | −6.562 | −1.972 | 25.615 | 1 | 24.4 | N |

TABLE 1-continued

Atomic structural coordinates for LuxP

| ATOM | ATOM TYPE | RESID | | NO | X | Y | Z | OCC | | |
|---|---|---|---|---|---|---|---|---|---|---|
| ATOM 1055 | CA | LYS | A | 154 | −5.778 | −2.997 | 24.938 | 1 | 23.02 | C |
| ATOM 1056 | C | LYS | A | 154 | −6.681 | −3.767 | 23.976 | 1 | 20.27 | C |
| ATOM 1057 | O | LYS | A | 154 | −7.858 | −3.996 | 24.264 | 1 | 23.07 | O |
| ATOM 1058 | CB | LYS | A | 154 | −5.138 | −3.927 | 25.967 | 1 | 23.06 | C |
| ATOM 1059 | CG | LYS | A | 154 | −4.199 | −3.188 | 26.928 | 1 | 23.56 | C |
| ATOM 1060 | CD | LYS | A | 154 | −3.211 | −4.137 | 27.579 | 1 | 31.59 | C |
| ATOM 1061 | CE | LYS | A | 154 | −2.228 | −3.395 | 28.478 | 1 | 36.59 | C |
| ATOM 1062 | NZ | LYS | A | 154 | −2.897 | −2.807 | 29.672 | 1 | 39.01 | N |
| ATOM 1063 | N | LEU | A | 155 | −6.127 | −4.163 | 22.834 | 1 | 18.01 | N |
| ATOM 1064 | CA | LEU | A | 155 | −6.896 | −4.855 | 21.804 | 1 | 17.01 | C |
| ATOM 1065 | C | LEU | A | 155 | −6.543 | −6.316 | 21.589 | 1 | 21.32 | C |
| ATOM 1066 | O | LEU | A | 155 | −5.371 | −6.667 | 21.458 | 1 | 19.44 | O |
| ATOM 1067 | CB | LEU | A | 155 | −6.726 | −4.138 | 20.464 | 1 | 23.04 | C |
| ATOM 1068 | CG | LEU | A | 155 | −7.133 | −2.669 | 20.361 | 1 | 28.13 | C |
| ATOM 1069 | CD1 | LEU | A | 155 | −6.743 | −2.131 | 18.994 | 1 | 33.07 | C |
| ATOM 1070 | CD2 | LEU | A | 155 | −8.625 | −2.535 | 20.58 | 1 | 32.14 | C |
| ATOM 1071 | N | ILE | A | 156 | −7.571 | −7.158 | 21.549 | 1 | 16.99 | N |
| ATOM 1072 | CA | ILE | A | 156 | −7.396 | −8.579 | 21.284 | 1 | 15.27 | C |
| ATOM 1073 | C | ILE | A | 156 | −8.145 | −8.843 | 19.983 | 1 | 14.39 | C |
| ATOM 1074 | O | ILE | A | 156 | −9.363 | −8.639 | 19.899 | 1 | 15.67 | O |
| ATOM 1075 | CB | ILE | A | 156 | −7.988 | −9.465 | 22.403 | 1 | 15.39 | C |
| ATOM 1076 | CG1 | ILE | A | 156 | −7.238 | −9.216 | 23.713 | 1 | 18.69 | C |
| ATOM 1077 | CG2 | ILE | A | 156 | −7.87 | −10.942 | 22.011 | 1 | 13.63 | C |
| ATOM 1078 | CD1 | ILE | A | 156 | −7.848 | −9.911 | 24.923 | 1 | 20.56 | C |
| ATOM 1079 | N | LEU | A | 157 | −7.416 | −9.267 | 18.959 | 1 | 14.22 | N |
| ATOM 1080 | CA | LEU | A | 157 | −8.03 | −9.548 | 17.673 | 1 | 13.11 | C |
| ATOM 1081 | C | LEU | A | 157 | −8.183 | −11.048 | 17.497 | 1 | 17.51 | C |
| ATOM 1082 | O | LEU | A | 157 | −7.215 | −11.78 | 17.295 | 1 | 17.11 | O |
| ATOM 1083 | CB | LEU | A | 157 | −7.193 | −8.946 | 16.539 | 1 | 14.57 | C |
| ATOM 1084 | CG | LEU | A | 157 | −6.995 | −7.43 | 16.635 | 1 | 18.97 | C |
| ATOM 1085 | CD1 | LEU | A | 157 | −6.214 | −6.952 | 15.413 | 1 | 18.42 | C |
| ATOM 1086 | CD2 | LEU | A | 157 | −8.343 | −6.726 | 16.715 | 1 | 21.58 | C |
| ATOM 1087 | N | GLN | A | 158 | −9.428 | −11.494 | 17.589 | 1 | 15.96 | N |
| ATOM 1088 | CA | GLN | A | 158 | −9.757 | −12.901 | 17.474 | 1 | 14.72 | C |
| ATOM 1089 | C | GLN | A | 158 | −9.865 | −13.371 | 16.025 | 1 | 14.75 | C |
| ATOM 1090 | O | GLN | A | 158 | −10.274 | −12.616 | 15.144 | 1 | 14.08 | O |
| ATOM 1091 | CB | GLN | A | 158 | −11.074 | −13.155 | 18.212 | 1 | 16.28 | C |
| ATOM 1092 | CG | GLN | A | 158 | −11.518 | −14.601 | 18.245 | 1 | 20.85 | C |
| ATOM 1093 | CD | GLN | A | 158 | −10.596 | −15.476 | 19.067 | 1 | 16.17 | C |
| ATOM 1094 | OE1 | GLN | A | 158 | −10.085 | −16.484 | 18.582 | 1 | 20.65 | O |
| ATOM 1095 | NE2 | GLN | A | 158 | −10.376 | −15.093 | 20.321 | 1 | 20.89 | N |
| ATOM 1096 | N | ASN | A | 159 | −9.492 | −14.63 | 15.8 | 1 | 12.59 | N |
| ATOM 1097 | CA | ASN | A | 159 | −9.548 | −15.279 | 14.489 | 1 | 13.19 | C |
| ATOM 1098 | C | ASN | A | 159 | −8.535 | −14.749 | 13.466 | 1 | 12.01 | C |
| ATOM 1099 | O | ASN | A | 159 | −8.771 | −14.803 | 12.262 | 1 | 13.88 | O |
| ATOM 1100 | CB | ASN | A | 159 | −10.98 | −15.195 | 13.934 | 1 | 12.91 | C |
| ATOM 1101 | CG | ASN | A | 159 | −11.325 | −16.353 | 13.008 | 1 | 14.54 | C |
| ATOM 1102 | OD1 | ASN | A | 159 | −10.82 | −17.469 | 13.172 | 1 | 16.41 | O |
| ATOM 1103 | ND2 | ASN | A | 159 | −12.212 | −16.102 | 12.045 | 1 | 11.08 | N |
| ATOM 1104 | N | ILE | A | 160 | −7.419 | −14.233 | 13.965 | 1 | 15.33 | N |
| ATOM 1105 | CA | ILE | A | 160 | −6.333 | −13.739 | 13.117 | 1 | 18.06 | C |
| ATOM 1106 | C | ILE | A | 160 | −5.032 | −14.045 | 13.853 | 1 | 13.96 | C |
| ATOM 1107 | O | ILE | A | 160 | −4.884 | −13.702 | 15.022 | 1 | 15.64 | O |
| ATOM 1108 | CB | ILE | A | 160 | −6.434 | −12.216 | 12.852 | 1 | 20.53 | C |
| ATOM 1109 | CG1 | ILE | A | 160 | −5.157 | −11.728 | 12.15 | 1 | 16.97 | C |
| ATOM 1110 | CG2 | ILE | A | 160 | −6.646 | −11.471 | 14.143 | 1 | 24.07 | C |
| ATOM 1111 | CD1 | ILE | A | 160 | −5.229 | −10.296 | 11.666 | 1 | 30.08 | C |
| ATOM 1112 | N | THR | A | 161 | −4.099 | −14.705 | 13.169 | 1 | 13.57 | N |
| ATOM 1113 | CA | THR | A | 161 | −2.821 | −15.076 | 13.77 | 1 | 13.62 | C |
| ATOM 1114 | C | THR | A | 161 | −1.664 | −14.609 | 12.898 | 1 | 17.43 | C |
| ATOM 1115 | O | THR | A | 161 | −0.536 | −15.098 | 13.02 | 1 | 18.31 | O |
| ATOM 1116 | CB | THR | A | 161 | −2.718 | −16.6 | 13.923 | 1 | 18.1 | C |
| ATOM 1117 | OG1 | THR | A | 161 | −2.994 | −17.213 | 12.66 | 1 | 19.62 | O |
| ATOM 1118 | CG2 | THR | A | 161 | −3.721 | −17.108 | 14.963 | 1 | 24.52 | C |
| ATOM 1119 | N | THR | A | 162 | −1.953 | −13.651 | 12.029 | 1 | 15.54 | N |
| ATOM 1120 | CA | THR | A | 162 | −0.963 | −13.121 | 11.097 | 1 | 13.43 | C |
| ATOM 1121 | C | THR | A | 162 | −0.843 | −11.607 | 11.286 | 1 | 16.72 | C |
| ATOM 1122 | O | THR | A | 162 | −1.614 | −10.839 | 10.715 | 1 | 15.06 | O |
| ATOM 1123 | CB | THR | A | 162 | −1.387 | −13.433 | 9.654 | 1 | 16.72 | C |
| ATOM 1124 | OG1 | THR | A | 162 | −2.676 | −12.861 | 9.404 | 1 | 16.24 | O |
| ATOM 1125 | CG2 | THR | A | 162 | −1.474 | −14.949 | 9.434 | 1 | 15.71 | C |
| ATOM 1126 | N | PRO | A | 163 | 0.133 | −11.163 | 12.097 | 1 | 16.45 | N |
| ATOM 1127 | CA | PRO | A | 163 | 0.321 | −9.729 | 12.35 | 1 | 15.92 | C |
| ATOM 1128 | C | PRO | A | 163 | 0.372 | −8.843 | 11.106 | 1 | 21.74 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 1129 | O | PRO | A | 163 | 1.001 | −9.182 | 10.102 | 1 | 19.48 | O |
| ATOM 1130 | CB | PRO | A | 163 | 1.617 | −9.693 | 13.15 | 1 | 16.96 | C |
| ATOM 1131 | CG | PRO | A | 163 | 1.539 | −10.979 | 13.945 | 1 | 19.94 | C |
| ATOM 1132 | CD | PRO | A | 163 | 1.083 | −11.965 | 12.891 | 1 | 18.53 | C |
| ATOM 1133 | N | VAL | A | 164 | −0.311 | −7.705 | 11.189 | 1 | 17.67 | N |
| ATOM 1134 | CA | VAL | A | 164 | −0.362 | −6.74 | 10.099 | 1 | 18.87 | C |
| ATOM 1135 | C | VAL | A | 164 | 0.971 | −5.992 | 10.064 | 1 | 22.07 | C |
| ATOM 1136 | O | VAL | A | 164 | 1.343 | −5.341 | 11.039 | 1 | 20.17 | O |
| ATOM 1137 | CB | VAL | A | 164 | −1.518 | −5.744 | 10.327 | 1 | 20.31 | C |
| ATOM 1138 | CG1 | VAL | A | 164 | −1.53 | −4.692 | 9.234 | 1 | 16.74 | C |
| ATOM 1139 | CG2 | VAL | A | 164 | −2.844 | −6.498 | 10.364 | 1 | 23.11 | C |
| ATOM 1140 | N | ARG | A | 165 | 1.685 | −6.094 | 8.945 | 1 | 22.66 | N |
| ATOM 1141 | CA | ARG | A | 165 | 2.988 | −5.446 | 8.801 | 1 | 21.67 | C |
| ATOM 1142 | C | ARG | A | 165 | 2.961 | −3.937 | 9.032 | 1 | 27.49 | C |
| ATOM 1143 | O | ARG | A | 165 | 3.841 | −3.398 | 9.702 | 1 | 24.62 | O |
| ATOM 1144 | CB | ARG | A | 165 | 3.582 | −5.743 | 7.416 | 1 | 23.08 | C |
| ATOM 1145 | CG | ARG | A | 165 | 3.994 | −7.204 | 7.193 | 1 | 26.66 | C |
| ATOM 1146 | CD | ARG | A | 165 | 4.44 | −7.451 | 5.752 | 1 | 26.89 | C |
| ATOM 1147 | NE | ARG | A | 165 | 4.715 | −8.863 | 5.484 | 1 | 26.88 | N |
| ATOM 1148 | CZ | ARG | A | 165 | 5.776 | −9.524 | 5.936 | 1 | 25.45 | C |
| ATOM 1149 | NH1 | ARG | A | 165 | 6.682 | −8.907 | 6.684 | 1 | 32.31 | N |
| ATOM 1150 | NH2 | ARG | A | 165 | 5.928 | −10.809 | 5.645 | 1 | 28.17 | N |
| ATOM 1151 | N | GLU | A | 166 | 1.957 | −3.252 | 8.497 | 1 | 23.06 | N |
| ATOM 1152 | CA | GLU | A | 166 | 1.896 | −1.805 | 8.677 | 1 | 29.19 | C |
| ATOM 1153 | C | GLU | A | 166 | 1.817 | −1.366 | 10.136 | 1 | 24.51 | C |
| ATOM 1154 | O | GLU | A | 166 | 1.972 | −0.184 | 10.434 | 1 | 23.78 | O |
| ATOM 1155 | CB | GLU | A | 166 | 0.735 | −1.205 | 7.877 | 1 | 28.74 | C |
| ATOM 1156 | CG | GLU | A | 166 | −0.587 | −1.917 | 8.03 | 1 | 43.37 | C |
| ATOM 1157 | CD | GLU | A | 166 | −1.686 | −1.271 | 7.208 | 1 | 50.05 | C |
| ATOM 1158 | OE1 | GLU | A | 166 | −2.133 | −0.165 | 7.576 | 1 | 52.22 | O |
| ATOM 1159 | OE2 | GLU | A | 166 | −2.095 | −1.865 | 6.186 | 1 | 60.61 | O |
| ATOM 1160 | N | TRP | A | 167 | 1.584 | −2.307 | 11.048 | 1 | 24.37 | N |
| ATOM 1161 | CA | TRP | A | 167 | 1.514 | −1.973 | 12.468 | 1 | 19.89 | C |
| ATOM 1162 | C | TRP | A | 167 | 2.741 | −2.458 | 13.246 | 1 | 18.79 | C |
| ATOM 1163 | O | TRP | A | 167 | 2.711 | −2.532 | 14.47 | 1 | 21 | O |
| ATOM 1164 | CB | TRP | A | 167 | 0.258 | −2.572 | 13.111 | 1 | 18.72 | C |
| ATOM 1165 | CG | TRP | A | 167 | −1.035 | −2.041 | 12.573 | 1 | 24.23 | C |
| ATOM 1166 | CD1 | TRP | A | 167 | −1.245 | −0.829 | 11.973 | 1 | 18.86 | C |
| ATOM 1167 | CD2 | TRP | A | 167 | −2.313 | −2.69 | 12.621 | 1 | 25.96 | C |
| ATOM 1168 | NE1 | TRP | A | 167 | −2.572 | −0.687 | 11.644 | 1 | 24.62 | N |
| ATOM 1169 | CE2 | TRP | A | 167 | −3.249 | −1.813 | 12.031 | 1 | 28.35 | C |
| ATOM 1170 | CE3 | TRP | A | 167 | −2.758 | −3.927 | 13.11 | 1 | 28.27 | C |
| ATOM 1171 | CZ2 | TRP | A | 167 | −4.605 | −2.134 | 11.912 | 1 | 26.08 | C |
| ATOM 1172 | CZ3 | TRP | A | 167 | −4.108 | −4.246 | 12.992 | 1 | 22.72 | C |
| ATOM 1173 | CH2 | TRP | A | 167 | −5.015 | −3.351 | 12.397 | 1 | 23.29 | C |
| ATOM 1174 | N | ASP | A | 168 | 3.82 | −2.778 | 12.536 | 1 | 21.78 | N |
| ATOM 1175 | CA | ASP | A | 168 | 5.037 | −3.268 | 13.18 | 1 | 21.94 | C |
| ATOM 1176 | C | ASP | A | 168 | 5.582 | −2.403 | 14.315 | 1 | 20.18 | C |
| ATOM 1177 | O | ASP | A | 168 | 6.191 | −2.92 | 15.249 | 1 | 25.98 | O |
| ATOM 1178 | CB | ASP | A | 168 | 6.15 | −3.477 | 12.146 | 1 | 26.61 | C |
| ATOM 1179 | CG | ASP | A | 168 | 5.949 | −4.726 | 11.311 | 1 | 32.95 | C |
| ATOM 1180 | OD1 | ASP | A | 168 | 5.375 | −5.707 | 11.832 | 1 | 30.02 | O |
| ATOM 1181 | OD2 | ASP | A | 168 | 6.383 | −4.736 | 10.138 | 1 | 34.77 | O |
| ATOM 1182 | N | LYS | A | 169 | 5.368 | −1.092 | 14.243 | 1 | 24 | N |
| ATOM 1183 | CA | LYS | A | 169 | 5.876 | −0.2 | 15.278 | 1 | 25.13 | C |
| ATOM 1184 | C | LYS | A | 169 | 5.035 | −0.228 | 16.546 | 1 | 26.05 | C |
| ATOM 1185 | O | LYS | A | 169 | 5.502 | 0.142 | 17.626 | 1 | 23.48 | O |
| ATOM 1186 | CB | LYS | A | 169 | 5.971 | 1.232 | 14.74 | 1 | 27.65 | C |
| ATOM 1187 | CG | LYS | A | 169 | 6.919 | 1.375 | 13.554 | 1 | 29.93 | C |
| ATOM 1188 | CD | LYS | A | 169 | 8.325 | 0.907 | 13.909 | 1 | 38.16 | C |
| ATOM 1189 | CE | LYS | A | 169 | 9.273 | 1.021 | 12.722 | 1 | 42.83 | C |
| ATOM 1190 | NZ | LYS | A | 169 | 10.636 | 0.511 | 13.05 | 1 | 42.3 | N |
| ATOM 1191 | N | HIS | A | 170 | 3.793 | −0.675 | 16.409 | 1 | 23.54 | N |
| ATOM 1192 | CA | HIS | A | 170 | 2.886 | −0.769 | 17.542 | 1 | 27.48 | C |
| ATOM 1193 | C | HIS | A | 170 | 1.788 | −1.767 | 17.2 | 1 | 23.5 | C |
| ATOM 1194 | O | HIS | A | 170 | 0.756 | −1.41 | 16.631 | 1 | 25.02 | O |
| ATOM 1195 | CB | HIS | A | 170 | 2.271 | 0.595 | 17.862 | 1 | 28.47 | C |
| ATOM 1196 | CG | HIS | A | 170 | 1.563 | 0.639 | 19.182 | 1 | 35.44 | C |
| ATOM 1197 | ND1 | HIS | A | 170 | 0.95 | 1.776 | 19.66 | 1 | 39.8 | N |
| ATOM 1198 | CD2 | HIS | A | 170 | 1.384 | −0.312 | 20.13 | 1 | 37.39 | C |
| ATOM 1199 | CE1 | HIS | A | 170 | 0.426 | 1.525 | 20.847 | 1 | 39.12 | C |
| ATOM 1200 | NE2 | HIS | A | 170 | 0.675 | 0.265 | 21.155 | 1 | 38.81 | N |
| ATOM 1201 | N | GLN | A | 171 | 2.039 | −3.025 | 17.543 | 1 | 23.46 | N |
| ATOM 1202 | CA | GLN | A | 171 | 1.1 | −4.106 | 17.284 | 1 | 20.96 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 1203 | C | GLN | A | 171 | 0.084 | −4.238 | 18.407 | 1 | 21.51 | C |
| ATOM 1204 | O | GLN | A | 171 | 0.353 | −3.87 | 19.553 | 1 | 24.89 | O |
| ATOM 1205 | CB | GLN | A | 171 | 1.853 | −5.436 | 17.152 | 1 | 22.08 | C |
| ATOM 1206 | CG | GLN | A | 171 | 2.705 | −5.569 | 15.9 | 1 | 21.95 | C |
| ATOM 1207 | CD | GLN | A | 171 | 1.875 | −5.761 | 14.649 | 1 | 23.21 | C |
| ATOM 1208 | OE1 | GLN | A | 171 | 0.644 | −5.72 | 14.693 | 1 | 20.38 | O |
| ATOM 1209 | NE2 | GLN | A | 171 | 2.545 | −5.974 | 13.52 | 1 | 18.1 | N |
| ATOM 1210 | N | PRO | A | 172 | −1.109 | −4.751 | 18.084 | 1 | 18.4 | N |
| ATOM 1211 | CA | PRO | A | 172 | −2.157 | −4.936 | 19.091 | 1 | 21.86 | C |
| ATOM 1212 | C | PRO | A | 172 | −1.66 | −5.818 | 20.239 | 1 | 24.75 | C |
| ATOM 1213 | O | PRO | A | 172 | −0.684 | −6.561 | 20.096 | 1 | 23.73 | O |
| ATOM 1214 | CB | PRO | A | 172 | −3.27 | −5.614 | 18.303 | 1 | 19.69 | C |
| ATOM 1215 | CG | PRO | A | 172 | −3.129 | −5.003 | 16.939 | 1 | 24.49 | C |
| ATOM 1216 | CD | PRO | A | 172 | −1.627 | −5.002 | 16.727 | 1 | 18.87 | C |
| ATOM 1217 | N | PHE | A | 173 | −2.342 | −5.727 | 21.374 | 1 | 17.97 | N |
| ATOM 1218 | CA | PHE | A | 173 | −2.013 | −6.506 | 22.56 | 1 | 17.62 | C |
| ATOM 1219 | C | PHE | A | 173 | −1.934 | −7.998 | 22.226 | 1 | 17.83 | C |
| ATOM 1220 | O | PHE | A | 173 | −1.015 | −8.695 | 22.663 | 1 | 18.9 | O |
| ATOM 1221 | CB | PHE | A | 173 | −3.084 | −6.252 | 23.629 | 1 | 18.51 | C |
| ATOM 1222 | CG | PHE | A | 173 | −2.941 | −7.095 | 24.87 | 1 | 19.39 | C |
| ATOM 1223 | CD1 | PHE | A | 173 | −1.852 | −6.939 | 25.723 | 1 | 17.98 | C |
| ATOM 1224 | CD2 | PHE | A | 173 | −3.928 | −8.018 | 25.209 | 1 | 17.61 | C |
| ATOM 1225 | CE1 | PHE | A | 173 | −1.751 | −7.688 | 26.901 | 1 | 19.9 | C |
| ATOM 1226 | CE2 | PHE | A | 173 | −3.838 | −8.77 | 26.38 | 1 | 17.32 | C |
| ATOM 1227 | CZ | PHE | A | 173 | −2.747 | −8.605 | 27.229 | 1 | 20.02 | C |
| ATOM 1228 | N | LEU | A | 174 | −2.892 | −8.495 | 21.448 | 1 | 16.34 | N |
| ATOM 1229 | CA | LEU | A | 174 | −2.876 | −9.912 | 21.1 | 1 | 18.23 | C |
| ATOM 1230 | C | LEU | A | 174 | −3.657 | −10.301 | 19.855 | 1 | 15.55 | C |
| ATOM 1231 | O | LEU | A | 174 | −4.789 | −9.855 | 19.659 | 1 | 15.36 | O |
| ATOM 1232 | CB | LEU | A | 174 | −3.411 | −10.738 | 22.277 | 1 | 15.31 | C |
| ATOM 1233 | CG | LEU | A | 174 | −3.516 | −12.254 | 22.069 | 1 | 16.43 | C |
| ATOM 1234 | CD1 | LEU | A | 174 | −2.12 | −12.864 | 21.994 | 1 | 17.64 | C |
| ATOM 1235 | CD2 | LEU | A | 174 | −4.306 | −12.878 | 23.219 | 1 | 15.97 | C |
| ATOM 1236 | N | TYR | A | 175 | −3.033 | −11.118 | 19.01 | 1 | 17.43 | N |
| ATOM 1237 | CA | TYR | A | 175 | −3.679 | −11.671 | 17.822 | 1 | 16.4 | C |
| ATOM 1238 | C | TYR | A | 175 | −3.852 | −13.117 | 18.271 | 1 | 14.21 | C |
| ATOM 1239 | O | TYR | A | 175 | −2.875 | −13.768 | 18.651 | 1 | 16.16 | O |
| ATOM 1240 | CB | TYR | A | 175 | −2.774 | −11.669 | 16.584 | 1 | 14.82 | C |
| ATOM 1241 | CG | TYR | A | 175 | −2.495 | −10.325 | 15.943 | 1 | 15.78 | C |
| ATOM 1242 | CD1 | TYR | A | 175 | −1.451 | −9.521 | 16.394 | 1 | 17.77 | C |
| ATOM 1243 | CD2 | TYR | A | 175 | −3.215 | −9.907 | 14.824 | 1 | 15.39 | C |
| ATOM 1244 | CE1 | TYR | A | 175 | −1.121 | −8.34 | 15.735 | 1 | 14.81 | C |
| ATOM 1245 | CE2 | TYR | A | 175 | −2.893 | −8.722 | 14.157 | 1 | 16.41 | C |
| ATOM 1246 | CZ | TYR | A | 175 | −1.84 | −7.953 | 14.619 | 1 | 16.83 | C |
| ATOM 1247 | OH | TYR | A | 175 | −1.475 | −6.825 | 13.918 | 1 | 21.48 | O |
| ATOM 1248 | N | VAL | A | 176 | −5.078 | −13.621 | 18.249 | 1 | 12.62 | N |
| ATOM 1249 | CA | VAL | A | 176 | −5.313 | −14.983 | 18.696 | 1 | 14.02 | C |
| ATOM 1250 | C | VAL | A | 176 | −6.3 | −15.732 | 17.809 | 1 | 13.57 | C |
| ATOM 1251 | O | VAL | A | 176 | −7.249 | −15.154 | 17.284 | 1 | 14.26 | O |
| ATOM 1252 | CB | VAL | A | 176 | −5.817 | −14.97 | 20.161 | 1 | 13.32 | C |
| ATOM 1253 | CG1 | VAL | A | 176 | −7.108 | −14.16 | 20.262 | 1 | 18.51 | C |
| ATOM 1254 | CG2 | VAL | A | 176 | −6.022 | −16.401 | 20.671 | 1 | 14.04 | C |
| ATOM 1255 | N | GLY | A | 177 | −6.053 | −17.024 | 17.627 | 1 | 12.53 | N |
| ATOM 1256 | CA | GLY | A | 177 | −6.943 | −17.839 | 16.821 | 1 | 15.6 | C |
| ATOM 1257 | C | GLY | A | 177 | −6.308 | −19.165 | 16.443 | 1 | 11.86 | C |
| ATOM 1258 | O | GLY | A | 177 | −5.385 | −19.633 | 17.108 | 1 | 13.58 | O |
| ATOM 1259 | N | PHE | A | 178 | −6.828 | −19.781 | 15.386 | 1 | 12.3 | N |
| ATOM 1260 | CA | PHE | A | 178 | −6.288 | −21.033 | 14.873 | 1 | 13.89 | C |
| ATOM 1261 | C | PHE | A | 178 | −5.879 | −20.686 | 13.448 | 1 | 14.22 | C |
| ATOM 1262 | O | PHE | A | 178 | −6.725 | −20.481 | 12.575 | 1 | 14.66 | O |
| ATOM 1263 | CB | PHE | A | 178 | −7.347 | −22.147 | 14.912 | 1 | 15.92 | C |
| ATOM 1264 | CG | PHE | A | 178 | −7.71 | −22.582 | 16.305 | 1 | 11.91 | C |
| ATOM 1265 | CD1 | PHE | A | 178 | −8.66 | −21.884 | 17.047 | 1 | 11.8 | C |
| ATOM 1266 | CD2 | PHE | A | 178 | −7.078 | −23.671 | 16.886 | 1 | 12.54 | C |
| ATOM 1267 | CE1 | PHE | A | 178 | −8.975 | −22.27 | 18.35 | 1 | 12.14 | C |
| ATOM 1268 | CE2 | PHE | A | 178 | −7.383 | −24.065 | 18.19 | 1 | 11.02 | C |
| ATOM 1269 | CZ | PHE | A | 178 | −8.328 | −23.369 | 18.922 | 1 | 11.71 | C |
| ATOM 1270 | N | ASP | A | 179 | −4.567 | −20.593 | 13.239 | 1 | 13.82 | N |
| ATOM 1271 | CA | ASP | A | 179 | −4.006 | −20.191 | 11.956 | 1 | 13.23 | C |
| ATOM 1272 | C | ASP | A | 179 | −4.668 | −20.76 | 10.715 | 1 | 13.52 | C |
| ATOM 1273 | O | ASP | A | 179 | −4.634 | −21.961 | 10.47 | 1 | 15.48 | O |
| ATOM 1274 | CB | ASP | A | 179 | −2.506 | −20.492 | 11.915 | 1 | 12.73 | C |
| ATOM 1275 | CG | ASP | A | 179 | −1.812 | −19.776 | 10.775 | 1 | 16.11 | C |
| ATOM 1276 | OD1 | ASP | A | 179 | −1.797 | −18.526 | 10.778 | 1 | 19.92 | O |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 1277 | OD2 | ASP | A | 179 | −1.301 | −20.46 | 9.87 | 1 | 18.19 | O |
| ATOM 1278 | N | HIS | A | 180 | −5.234 | −19.864 | 9.913 | 1 | 12.01 | N |
| ATOM 1279 | CA | HIS | A | 180 | −5.93 | −20.234 | 8.694 | 1 | 12.81 | C |
| ATOM 1280 | C | HIS | A | 180 | −5.049 | −20.936 | 7.665 | 1 | 15.18 | C |
| ATOM 1281 | O | HIS | A | 180 | −5.476 | −21.909 | 7.043 | 1 | 14.45 | O |
| ATOM 1282 | CB | HIS | A | 180 | −6.553 | −18.982 | 8.077 | 1 | 14.22 | C |
| ATOM 1283 | CG | HIS | A | 180 | −7.433 | −18.228 | 9.025 | 1 | 13.67 | C |
| ATOM 1284 | ND1 | HIS | A | 180 | −8.631 | −18.733 | 9.484 | 1 | 14.04 | N |
| ATOM 1285 | CD2 | HIS | A | 180 | −7.274 | −17.026 | 9.629 | 1 | 16.03 | C |
| ATOM 1286 | CE1 | HIS | A | 180 | −9.172 | −17.874 | 10.33 | 1 | 15.66 | C |
| ATOM 1287 | NE2 | HIS | A | 180 | −8.369 | −16.83 | 10.437 | 1 | 15.66 | N |
| ATOM 1288 | N | ALA | A | 181 | −3.828 | −20.441 | 7.479 | 1 | 15.09 | N |
| ATOM 1289 | CA | ALA | A | 181 | −2.919 | −21.042 | 6.506 | 1 | 16.49 | C |
| ATOM 1290 | C | ALA | A | 181 | −2.597 | −22.489 | 6.87 | 1 | 17.16 | C |
| ATOM 1291 | O | ALA | A | 181 | −2.598 | −23.364 | 6.008 | 1 | 16.93 | O |
| ATOM 1292 | CB | ALA | A | 181 | −1.628 | −20.225 | 6.413 | 1 | 18.69 | C |
| ATOM 1293 | N | GLU | A | 182 | −2.312 | −22.729 | 8.146 | 1 | 15.97 | N |
| ATOM 1294 | CA | GLU | A | 182 | −2.004 | −24.075 | 8.618 | 1 | 15.93 | C |
| ATOM 1295 | C | GLU | A | 182 | −3.19 | −25.01 | 8.406 | 1 | 18.1 | C |
| ATOM 1296 | O | GLU | A | 182 | −3.038 | −26.09 | 7.837 | 1 | 17.86 | O |
| ATOM 1297 | CB | GLU | A | 182 | −1.628 | −24.054 | 10.103 | 1 | 19.15 | C |
| ATOM 1298 | CG | GLU | A | 182 | −1.449 | −25.441 | 10.707 | 1 | 18.2 | C |
| ATOM 1299 | CD | GLU | A | 182 | −0.375 | −26.267 | 10.013 | 1 | 23.45 | C |
| ATOM 1300 | OE1 | GLU | A | 182 | −0.433 | −27.513 | 10.093 | 1 | 24.15 | O |
| ATOM 1301 | OE2 | GLU | A | 182 | 0.536 | −25.676 | 9.395 | 1 | 23.59 | O |
| ATOM 1302 | N | GLY | A | 183 | −4.372 | −24.594 | 8.855 | 1 | 16.43 | N |
| ATOM 1303 | CA | GLY | A | 183 | −5.547 | −25.434 | 8.688 | 1 | 14.07 | C |
| ATOM 1304 | C | GLY | A | 183 | −5.815 | −25.765 | 7.235 | 1 | 16.61 | C |
| ATOM 1305 | O | GLY | A | 183 | −6.153 | −26.899 | 6.894 | 1 | 18.5 | O |
| ATOM 1306 | N | SER | A | 184 | −5.661 | −24.767 | 6.37 | 1 | 12.86 | N |
| ATOM 1307 | CA | SER | A | 184 | −5.888 | −24.945 | 4.952 | 1 | 16.79 | C |
| ATOM 1308 | C | SER | A | 184 | −4.791 | −25.813 | 4.335 | 1 | 13.71 | C |
| ATOM 1309 | O | SER | A | 184 | −5.05 | −26.569 | 3.395 | 1 | 18.29 | O |
| ATOM 1310 | CB | SER | A | 184 | −5.961 | −23.575 | 4.271 | 1 | 17.31 | C |
| ATOM 1311 | OG | SER | A | 184 | −7.037 | −22.813 | 4.814 | 1 | 17.78 | O |
| ATOM 1312 | N | ARG | A | 185 | −3.569 | −25.719 | 4.854 | 1 | 17.01 | N |
| ATOM 1313 | CA | ARG | A | 185 | −2.497 | −26.553 | 4.314 | 1 | 21.78 | C |
| ATOM 1314 | C | ARG | A | 185 | −2.766 | −28.008 | 4.672 | 1 | 20.69 | C |
| ATOM 1315 | O | ARG | A | 185 | −2.527 | −28.914 | 3.869 | 1 | 17.12 | O |
| ATOM 1316 | CB | ARG | A | 185 | −1.134 | −26.134 | 4.869 | 1 | 17.61 | C |
| ATOM 1317 | CG | ARG | A | 185 | −0.532 | −24.916 | 4.178 | 1 | 26.97 | C |
| ATOM 1318 | CD | ARG | A | 185 | 0.956 | −24.823 | 4.478 | 1 | 29.24 | C |
| ATOM 1319 | NE | ARG | A | 185 | 1.202 | −24.64 | 5.902 | 1 | 29.35 | N |
| ATOM 1320 | CZ | ARG | A | 185 | 1.212 | −23.46 | 6.515 | 1 | 24.02 | C |
| ATOM 1321 | NH1 | ARG | A | 185 | 0.998 | −22.347 | 5.824 | 1 | 24.47 | N |
| ATOM 1322 | NH2 | ARG | A | 185 | 1.424 | −23.396 | 7.822 | 1 | 23.17 | N |
| ATOM 1323 | N | GLU | A | 186 | −3.274 | −28.232 | 5.879 | 1 | 15.58 | N |
| ATOM 1324 | CA | GLU | A | 186 | −3.572 | −29.588 | 6.319 | 1 | 17.12 | C |
| ATOM 1325 | C | GLU | A | 186 | −4.655 | −30.184 | 5.435 | 1 | 18.12 | C |
| ATOM 1326 | O | GLU | A | 186 | −4.562 | −31.34 | 5.024 | 1 | 19.52 | O |
| ATOM 1327 | CB | GLU | A | 186 | −4.002 | −29.598 | 7.794 | 1 | 18.77 | C |
| ATOM 1328 | CG | GLU | A | 186 | −2.829 | −29.366 | 8.752 | 1 | 20.64 | C |
| ATOM 1329 | CD | GLU | A | 186 | −3.213 | −29.438 | 10.222 | 1 | 22.25 | C |
| ATOM 1330 | OE1 | GLU | A | 186 | −4.122 | −30.221 | 10.576 | 1 | 27.02 | O |
| ATOM 1331 | OE2 | GLU | A | 186 | −2.586 | −28.718 | 11.033 | 1 | 24.42 | O |
| ATOM 1332 | N | LEU | A | 187 | −5.685 | −29.4 | 5.129 | 1 | 18.59 | N |
| ATOM 1333 | CA | LEU | A | 187 | −6.744 | −29.896 | 4.265 | 1 | 16.93 | C |
| ATOM 1334 | C | LEU | A | 187 | −6.22 | −30.168 | 2.861 | 1 | 18.44 | C |
| ATOM 1335 | O | LEU | A | 187 | −6.569 | −31.174 | 2.249 | 1 | 23.02 | O |
| ATOM 1336 | CB | LEU | A | 187 | −7.906 | −28.897 | 4.216 | 1 | 17.51 | C |
| ATOM 1337 | CG | LEU | A | 187 | −8.801 | −28.909 | 5.459 | 1 | 15.81 | C |
| ATOM 1338 | CD1 | LEU | A | 187 | −9.747 | −27.715 | 5.456 | 1 | 16.62 | C |
| ATOM 1339 | CD2 | LEU | A | 187 | −9.582 | −30.215 | 5.498 | 1 | 16.41 | C |
| ATOM 1340 | N | ALA | A | 188 | −5.374 | −29.274 | 2.359 | 1 | 15.89 | N |
| ATOM 1341 | CA | ALA | A | 188 | −4.807 | −29.424 | 1.023 | 1 | 17.53 | C |
| ATOM 1342 | C | ALA | A | 188 | −3.983 | −30.699 | 0.906 | 1 | 21.63 | C |
| ATOM 1343 | O | ALA | A | 188 | −4.021 | −31.383 | −0.113 | 1 | 21.83 | O |
| ATOM 1344 | CB | ALA | A | 188 | −3.949 | −28.207 | 0.675 | 1 | 19.13 | C |
| ATOM 1345 | N | THR | A | 189 | −3.236 | −31.012 | 1.955 | 1 | 18.41 | N |
| ATOM 1346 | CA | THR | A | 189 | −2.413 | −32.212 | 1.954 | 1 | 19.12 | C |
| ATOM 1347 | C | THR | A | 189 | −3.306 | −33.438 | 1.876 | 1 | 23.6 | C |
| ATOM 1348 | O | THR | A | 189 | −3.009 | −34.393 | 1.155 | 1 | 22.7 | O |
| ATOM 1349 | CB | THR | A | 189 | −1.558 | −32.297 | 3.225 | 1 | 21.31 | C |
| ATOM 1350 | OG1 | THR | A | 189 | −0.663 | −31.177 | 3.273 | 1 | 26.07 | O |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 1351 | CG2 | THR | A | 189 | −0.75 | −33.593 | 3.234 | 1 | 22.89 | C |
| ATOM 1352 | N | GLU | A | 190 | −4.414 | −33.397 | 2.607 | 1 | 19.53 | N |
| ATOM 1353 | CA | GLU | A | 190 | −5.346 | −34.517 | 2.622 | 1 | 17.9 | C |
| ATOM 1354 | C | GLU | A | 190 | −5.978 | −34.732 | 1.248 | 1 | 23.63 | C |
| ATOM 1355 | O | GLU | A | 190 | −5.945 | −35.841 | 0.721 | 1 | 22.32 | O |
| ATOM 1356 | CB | GLU | A | 190 | −6.426 | −34.281 | 3.68 | 1 | 21.99 | C |
| ATOM 1357 | CG | GLU | A | 190 | −6.612 | −35.436 | 4.647 | 1 | 40.03 | C |
| ATOM 1358 | CD | GLU | A | 190 | −5.301 | −35.934 | 5.234 | 1 | 43.16 | C |
| ATOM 1359 | OE1 | GLU | A | 190 | −4.52 | −35.111 | 5.753 | 1 | 46.91 | O |
| ATOM 1360 | OE2 | GLU | A | 190 | −5.052 | −37.155 | 5.178 | 1 | 40.58 | O |
| ATOM 1361 | N | PHE | A | 191 | −6.553 | −33.685 | 0.659 | 1 | 17.94 | N |
| ATOM 1362 | CA | PHE | A | 191 | −7.15 | −33.837 | −0.662 | 1 | 20.7 | C |
| ATOM 1363 | C | PHE | A | 191 | −6.091 | −34.282 | −1.668 | 1 | 20.08 | C |
| ATOM 1364 | O | PHE | A | 191 | −6.387 | −35.019 | −2.608 | 1 | 21.64 | O |
| ATOM 1365 | CB | PHE | A | 191 | −7.791 | −32.527 | −1.142 | 1 | 21.33 | C |
| ATOM 1366 | CG | PHE | A | 191 | −9.134 | −32.241 | −0.521 | 1 | 22.24 | C |
| ATOM 1367 | CD1 | PHE | A | 191 | −9.229 | −31.752 | 0.777 | 1 | 19.73 | C |
| ATOM 1368 | CD2 | PHE | A | 191 | −10.305 | −32.462 | −1.239 | 1 | 24.01 | C |
| ATOM 1369 | CE1 | PHE | A | 191 | −10.472 | −31.486 | 1.355 | 1 | 24.99 | C |
| ATOM 1370 | CE2 | PHE | A | 191 | −11.557 | −32.199 | −0.67 | 1 | 29.8 | C |
| ATOM 1371 | CZ | PHE | A | 191 | −11.64 | −31.709 | 0.629 | 1 | 23.39 | C |
| ATOM 1372 | N | GLY | A | 192 | −4.858 | −33.83 | −1.462 | 1 | 24.57 | N |
| ATOM 1373 | CA | GLY | A | 192 | −3.773 | −34.196 | −2.355 | 1 | 24.68 | C |
| ATOM 1374 | C | GLY | A | 192 | −3.523 | −35.693 | −2.352 | 1 | 29.36 | C |
| ATOM 1375 | O | GLY | A | 192 | −3.074 | −36.253 | −3.349 | 1 | 33.55 | O |
| ATOM 1376 | N | LYS | A | 193 | −3.814 | −36.342 | −1.23 | 1 | 23.03 | N |
| ATOM 1377 | CA | LYS | A | 193 | −3.618 | −37.783 | −1.108 | 1 | 32.95 | C |
| ATOM 1378 | C | LYS | A | 193 | −4.863 | −38.574 | −1.504 | 1 | 31.59 | C |
| ATOM 1379 | O | LYS | A | 193 | −4.783 | −39.768 | −1.8 | 1 | 32.2 | O |
| ATOM 1380 | CB | LYS | A | 193 | −3.214 | −38.137 | 0.325 | 1 | 32.47 | C |
| ATOM 1381 | CG | LYS | A | 193 | −1.835 | −37.616 | 0.712 | 1 | 39.23 | C |
| ATOM 1382 | CD | LYS | A | 193 | −1.414 | −38.054 | 2.11 | 1 | 42.31 | C |
| ATOM 1383 | CE | LYS | A | 193 | −2.306 | −37.454 | 3.183 | 1 | 48.81 | C |
| ATOM 1384 | NZ | LYS | A | 193 | −1.79 | −37.744 | 4.551 | 1 | 39.66 | N |
| ATOM 1385 | N | PHE | A | 194 | −6.009 | −37.904 | −1.52 | 1 | 27.22 | N |
| ATOM 1386 | CA | PHE | A | 194 | −7.272 | −38.548 | −1.87 | 1 | 25.28 | C |
| ATOM 1387 | C | PHE | A | 194 | −7.533 | −38.586 | −3.37 | 1 | 24.24 | C |
| ATOM 1388 | O | PHE | A | 194 | −8.205 | −39.493 | −3.86 | 1 | 28.73 | O |
| ATOM 1389 | CB | PHE | A | 194 | −8.446 | −37.824 | −1.199 | 1 | 30.82 | C |
| ATOM 1390 | CG | PHE | A | 194 | −8.407 | −37.844 | 0.304 | 1 | 37.96 | C |
| ATOM 1391 | CD1 | PHE | A | 194 | −9.183 | −36.95 | 1.034 | 1 | 38.24 | C |
| ATOM 1392 | CD2 | PHE | A | 194 | −7.616 | −38.759 | 0.991 | 1 | 40.72 | C |
| ATOM 1393 | CE1 | PHE | A | 194 | −9.173 | −36.964 | 2.427 | 1 | 37.32 | C |
| ATOM 1394 | CE2 | PHE | A | 194 | −7.598 | −38.783 | 2.383 | 1 | 42.12 | C |
| ATOM 1395 | CZ | PHE | A | 194 | −8.378 | −37.884 | 3.103 | 1 | 44.62 | C |
| ATOM 1396 | N | PHE | A | 195 | −7.016 | −37.598 | −4.096 | 1 | 22.39 | N |
| ATOM 1397 | CA | PHE | A | 195 | −7.237 | −37.526 | −5.536 | 1 | 23.55 | C |
| ATOM 1398 | C | PHE | A | 195 | −5.956 | −37.488 | −6.361 | 1 | 21.36 | C |
| ATOM 1399 | O | PHE | A | 195 | −4.914 | −37.043 | −5.889 | 1 | 23.64 | O |
| ATOM 1400 | CB | PHE | A | 195 | −8.092 | −36.297 | −5.875 | 1 | 21.36 | C |
| ATOM 1401 | CG | PHE | A | 195 | −9.435 | −36.29 | −5.198 | 1 | 22.13 | C |
| ATOM 1402 | CD1 | PHE | A | 195 | −9.618 | −35.624 | −3.989 | 1 | 17.34 | C |
| ATOM 1403 | CD2 | PHE | A | 195 | −10.51 | −36.972 | −5.757 | 1 | 18.98 | C |
| ATOM 1404 | CE1 | PHE | A | 195 | −10.852 | −35.638 | −3.345 | 1 | 16.77 | C |
| ATOM 1405 | CE2 | PHE | A | 195 | −11.751 | −36.994 | −5.12 | 1 | 22.92 | C |
| ATOM 1406 | CZ | PHE | A | 195 | −11.921 | −36.323 | −3.909 | 1 | 19.22 | C |
| ATOM 1407 | N | PRO | A | 196 | −6.028 | −37.959 | −7.616 | 1 | 23.11 | N |
| ATOM 1408 | CA | PRO | A | 196 | −4.886 | −37.992 | −8.536 | 1 | 23.9 | C |
| ATOM 1409 | C | PRO | A | 196 | −4.587 | −36.622 | −9.14 | 1 | 26.64 | C |
| ATOM 1410 | O | PRO | A | 196 | −5.4 | −35.704 | −9.041 | 1 | 24.83 | O |
| ATOM 1411 | CB | PRO | A | 196 | −5.338 | −38.992 | −9.591 | 1 | 25.08 | C |
| ATOM 1412 | CG | PRO | A | 196 | −6.801 | −38.698 | −9.689 | 1 | 27.07 | C |
| ATOM 1413 | CD | PRO | A | 196 | −7.209 | −38.591 | −8.231 | 1 | 25 | C |
| ATOM 1414 | N | LYS | A | 197 | −3.424 | −36.49 | −9.771 | 1 | 19.78 | N |
| ATOM 1415 | CA | LYS | A | 197 | −3.037 | −35.229 | −10.39 | 1 | 21.4 | C |
| ATOM 1416 | C | LYS | A | 197 | −4.097 | −34.778 | −11.397 | 1 | 21 | C |
| ATOM 1417 | O | LYS | A | 197 | −4.748 | −35.602 | −12.046 | 1 | 24.23 | O |
| ATOM 1418 | CB | LYS | A | 197 | −1.698 | −35.385 | −11.12 | 1 | 22.86 | C |
| ATOM 1419 | CG | LYS | A | 197 | −0.577 | −35.996 | −10.298 | 1 | 28.01 | C |
| ATOM 1420 | CD | LYS | A | 197 | −0.059 | −35.057 | −9.227 | 1 | 37.14 | C |
| ATOM 1421 | CE | LYS | A | 197 | 1.163 | −35.652 | −8.535 | 1 | 40.97 | C |
| ATOM 1422 | NZ | LYS | A | 197 | 1.773 | −34.725 | −7.539 | 1 | 37.96 | N |
| ATOM 1423 | N | HIS | A | 198 | −4.255 | −33.463 | −11.527 | 1 | 20.67 | N |
| ATOM 1424 | CA | HIS | A | 198 | −5.208 | −32.868 | −12.458 | 1 | 21.14 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 1425 | C | HIS | A | 198 | −6.684 | −33.068 | −12.115 | 1 | 19 | C |
| ATOM 1426 | O | HIS | A | 198 | −7.547 | −32.915 | −12.973 | 1 | 21.53 | O |
| ATOM 1427 | CB | HIS | A | 198 | −4.927 | −33.368 | −13.88 | 1 | 26.34 | C |
| ATOM 1428 | CG | HIS | A | 198 | −3.598 | −32.931 | −14.416 | 1 | 28.55 | C |
| ATOM 1429 | ND1 | HIS | A | 198 | −3.321 | −31.621 | −14.744 | 1 | 28.59 | N |
| ATOM 1430 | CD2 | HIS | A | 198 | −2.464 | −33.628 | −14.66 | 1 | 32.71 | C |
| ATOM 1431 | CE1 | HIS | A | 198 | −2.074 | −31.53 | −15.169 | 1 | 26.84 | C |
| ATOM 1432 | NE2 | HIS | A | 198 | −1.531 | −32.733 | −15.127 | 1 | 30.2 | N |
| ATOM 1433 | N | THR | A | 199 | −6.971 | −33.405 | −10.862 | 1 | 21.58 | N |
| ATOM 1434 | CA | THR | A | 199 | −8.354 | −33.588 | −10.426 | 1 | 22.81 | C |
| ATOM 1435 | C | THR | A | 199 | −9.088 | −32.248 | −10.515 | 1 | 22.54 | C |
| ATOM 1436 | O | THR | A | 199 | −8.533 | −31.205 | −10.153 | 1 | 21.75 | O |
| ATOM 1437 | CB | THR | A | 199 | −8.419 | −34.109 | −8.967 | 1 | 23.48 | C |
| ATOM 1438 | OG1 | THR | A | 199 | −8.054 | −35.495 | −8.942 | 1 | 22.06 | O |
| ATOM 1439 | CG2 | THR | A | 199 | −9.823 | −33.952 | −8.387 | 1 | 22.94 | C |
| ATOM 1440 | N | TYR | A | 200 | −10.322 | −32.285 | −11.015 | 1 | 22.11 | N |
| ATOM 1441 | CA | TYR | A | 200 | −11.151 | −31.082 | −11.154 | 1 | 18.46 | C |
| ATOM 1442 | C | TYR | A | 200 | −11.84 | −30.759 | −9.832 | 1 | 20.64 | C |
| ATOM 1443 | O | TYR | A | 200 | −12.371 | −31.65 | −9.163 | 1 | 21.77 | O |
| ATOM 1444 | CB | TYR | A | 200 | −12.224 | −31.295 | −12.221 | 1 | 21.25 | C |
| ATOM 1445 | CG | TYR | A | 200 | −11.761 | −31.126 | −13.651 | 1 | 24.42 | C |
| ATOM 1446 | CD1 | TYR | A | 200 | −10.46 | −31.447 | −14.033 | 1 | 30.44 | C |
| ATOM 1447 | CD2 | TYR | A | 200 | −12.646 | −30.684 | −14.634 | 1 | 31.04 | C |
| ATOM 1448 | CE1 | TYR | A | 200 | −10.052 | −31.332 | −15.361 | 1 | 32.72 | C |
| ATOM 1449 | CE2 | TYR | A | 200 | −12.251 | −30.569 | −15.961 | 1 | 37.53 | C |
| ATOM 1450 | CZ | TYR | A | 200 | −10.955 | −30.894 | −16.32 | 1 | 38.48 | C |
| ATOM 1451 | OH | TYR | A | 200 | −10.568 | −30.787 | −17.64 | 1 | 35.81 | O |
| ATOM 1452 | N | TYR | A | 201 | −11.836 | −29.485 | −9.458 | 1 | 17.19 | N |
| ATOM 1453 | CA | TYR | A | 201 | −12.485 | −29.072 | −8.217 | 1 | 15.94 | C |
| ATOM 1454 | C | TYR | A | 201 | −12.968 | −27.637 | −8.311 | 1 | 18.2 | C |
| ATOM 1455 | O | TYR | A | 201 | −12.602 | −26.905 | −9.225 | 1 | 22.01 | O |
| ATOM 1456 | CB | TYR | A | 201 | −11.525 | −29.206 | −7.027 | 1 | 18.25 | C |
| ATOM 1457 | CG | TYR | A | 201 | −10.439 | −28.152 | −6.952 | 1 | 16.28 | C |
| ATOM 1458 | CD1 | TYR | A | 201 | −10.496 | −27.128 | −6.005 | 1 | 18.38 | C |
| ATOM 1459 | CD2 | TYR | A | 201 | −9.345 | −28.18 | −7.822 | 1 | 19.6 | C |
| ATOM 1460 | CE1 | TYR | A | 201 | −9.489 | −26.159 | −5.922 | 1 | 19.25 | C |
| ATOM 1461 | CE2 | TYR | A | 201 | −8.332 | −27.213 | −7.751 | 1 | 19.09 | C |
| ATOM 1462 | CZ | TYR | A | 201 | −8.41 | −26.205 | −6.799 | 1 | 20.08 | C |
| ATOM 1463 | OH | TYR | A | 201 | −7.425 | −25.235 | −6.735 | 1 | 19.66 | O |
| ATOM 1464 | N | SER | A | 202 | −13.799 | −27.246 | −7.354 | 1 | 18.69 | N |
| ATOM 1465 | CA | SER | A | 202 | −14.323 | −25.89 | −7.29 | 1 | 18 | C |
| ATOM 1466 | C | SER | A | 202 | −14.211 | −25.426 | −5.85 | 1 | 17.48 | C |
| ATOM 1467 | O | SER | A | 202 | −14.15 | −26.239 | −4.928 | 1 | 18.4 | O |
| ATOM 1468 | CB | SER | A | 202 | −15.782 | −25.839 | −7.743 | 1 | 18.82 | C |
| ATOM 1469 | OG | SER | A | 202 | −15.885 | −25.946 | −9.153 | 1 | 19.96 | O |
| ATOM 1470 | N | VAL | A | 203 | −14.192 | −24.113 | −5.663 | 1 | 16.27 | N |
| ATOM 1471 | CA | VAL | A | 203 | −14.056 | −23.529 | −4.34 | 1 | 16.11 | C |
| ATOM 1472 | C | VAL | A | 203 | −15.202 | −22.595 | −3.972 | 1 | 15.85 | C |
| ATOM 1473 | O | VAL | A | 203 | −15.713 | −21.853 | −4.814 | 1 | 16.15 | O |
| ATOM 1474 | CB | VAL | A | 203 | −12.726 | −22.727 | −4.244 | 1 | 15.09 | C |
| ATOM 1475 | CG1 | VAL | A | 203 | −12.675 | −21.89 | −2.949 | 1 | 13.74 | C |
| ATOM 1476 | CG2 | VAL | A | 203 | −11.552 | −23.681 | −4.296 | 1 | 16.96 | C |
| ATOM 1477 | N | LEU | A | 204 | −15.614 | −22.66 | −2.708 | 1 | 15.2 | N |
| ATOM 1478 | CA | LEU | A | 204 | −16.641 | −21.765 | −2.192 | 1 | 14.55 | C |
| ATOM 1479 | C | LEU | A | 204 | −15.909 | −20.915 | −1.158 | 1 | 15.72 | C |
| ATOM 1480 | O | LEU | A | 204 | −15.519 | −21.401 | −0.094 | 1 | 14.19 | O |
| ATOM 1481 | CB | LEU | A | 204 | −17.784 | −22.542 | −1.532 | 1 | 15.37 | C |
| ATOM 1482 | CG | LEU | A | 204 | −18.554 | −23.473 | −2.474 | 1 | 14.39 | C |
| ATOM 1483 | CD1 | LEU | A | 204 | −19.679 | −24.171 | −1.724 | 1 | 17.12 | C |
| ATOM 1484 | CD2 | LEU | A | 204 | −19.11 | −22.664 | −3.654 | 1 | 18.15 | C |
| ATOM 1485 | N | TYR | A | 205 | −15.689 | −19.652 | −1.497 | 1 | 11.91 | N |
| ATOM 1486 | CA | TYR | A | 205 | −15.002 | −18.724 | −0.617 | 1 | 12.25 | C |
| ATOM 1487 | C | TYR | A | 205 | −15.945 | −18.231 | 0.477 | 1 | 14.45 | C |
| ATOM 1488 | O | TYR | A | 205 | −17.121 | −18.583 | 0.517 | 1 | 14.1 | O |
| ATOM 1489 | CB | TYR | A | 205 | −14.548 | −17.491 | −1.402 | 1 | 16.54 | C |
| ATOM 1490 | CG | TYR | A | 205 | −13.362 | −17.656 | −2.331 | 1 | 17.04 | C |
| ATOM 1491 | CD1 | TYR | A | 205 | −13.45 | −17.247 | −3.666 | 1 | 19.34 | C |
| ATOM 1492 | CD2 | TYR | A | 205 | −12.119 | −18.077 | −1.853 | 1 | 17.71 | C |
| ATOM 1493 | CE1 | TYR | A | 205 | −12.332 | −17.238 | −4.492 | 1 | 19.38 | C |
| ATOM 1494 | CE2 | TYR | A | 205 | −10.993 | −18.069 | −2.675 | 1 | 19.42 | C |
| ATOM 1495 | CZ | TYR | A | 205 | −11.108 | −17.642 | −3.992 | 1 | 17.94 | C |
| ATOM 1496 | OH | TYR | A | 205 | −9.991 | −17.567 | −4.794 | 1 | 22.41 | O |
| ATOM 1497 | N | PHE | A | 206 | −15.387 | −17.409 | 1.355 | 1 | 15.91 | N |
| ATOM 1498 | CA | PHE | A | 206 | −16.139 | −16.762 | 2.427 | 1 | 15.11 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 1499 | C | PHE | A | 206 | −16.567 | −15.495 | 1.678 | 1 | 17.76 | C |
| ATOM 1500 | O | PHE | A | 206 | −16.582 | −15.487 | 0.441 | 1 | 15.13 | O |
| ATOM 1501 | CB | PHE | A | 206 | −15.172 | −16.411 | 3.568 | 1 | 17.32 | C |
| ATOM 1502 | CG | PHE | A | 206 | −15.841 | −16.034 | 4.87 | 1 | 13.84 | C |
| ATOM 1503 | CD1 | PHE | A | 206 | −16.73 | −16.905 | 5.49 | 1 | 15.21 | C |
| ATOM 1504 | CD2 | PHE | A | 206 | −15.536 | −14.829 | 5.501 | 1 | 12.04 | C |
| ATOM 1505 | CE1 | PHE | A | 206 | −17.304 | −16.581 | 6.729 | 1 | 14.95 | C |
| ATOM 1506 | CE2 | PHE | A | 206 | −16.105 | −14.495 | 6.738 | 1 | 13.81 | C |
| ATOM 1507 | CZ | PHE | A | 206 | −16.986 | −15.371 | 7.351 | 1 | 14.54 | C |
| ATOM 1508 | N | SER | A | 207 | −16.935 | −14.44 | 2.392 | 1 | 17.68 | N |
| ATOM 1509 | CA | SER | A | 207 | −17.257 | −13.196 | 1.706 | 1 | 16.62 | C |
| ATOM 1510 | C | SER | A | 207 | −15.873 | −12.66 | 1.323 | 1 | 20.63 | C |
| ATOM 1511 | O | SER | A | 207 | −14.856 | −13.175 | 1.8 | 1 | 19.16 | O |
| ATOM 1512 | CB | SER | A | 207 | −17.992 | −12.244 | 2.653 | 1 | 17.18 | C |
| ATOM 1513 | OG | SER | A | 207 | −17.387 | −12.234 | 3.934 | 1 | 25.25 | O |
| ATOM 1514 | N | GLU | A | 208 | −15.806 | −11.655 | 0.456 | 1 | 18.7 | N |
| ATOM 1515 | CA | GLU | A | 208 | −14.508 | −11.127 | 0.059 | 1 | 18.24 | C |
| ATOM 1516 | C | GLU | A | 208 | −13.751 | −10.57 | 1.257 | 1 | 19.21 | C |
| ATOM 1517 | O | GLU | A | 208 | −14.309 | −9.83 | 2.072 | 1 | 26.49 | O |
| ATOM 1518 | CB | GLU | A | 208 | −14.669 | −10.038 | −1.004 | 1 | 24.19 | C |
| ATOM 1519 | CG | GLU | A | 208 | −15.241 | −10.544 | −2.31 | 1 | 29.67 | C |
| ATOM 1520 | CD | GLU | A | 208 | −15.208 | −9.496 | −3.405 | 1 | 37.5 | C |
| ATOM 1521 | OE1 | GLU | A | 208 | −14.099 | −9.056 | −3.774 | 1 | 44.76 | O |
| ATOM 1522 | OE2 | GLU | A | 208 | −16.292 | −9.115 | −3.894 | 1 | 40.92 | O |
| ATOM 1523 | N | GLY | A | 209 | −12.48 | −10.937 | 1.366 | 1 | 19.32 | N |
| ATOM 1524 | CA | GLY | A | 209 | −11.678 | −10.467 | 2.477 | 1 | 16.34 | C |
| ATOM 1525 | C | GLY | A | 209 | −10.553 | −11.393 | 2.907 | 1 | 17.85 | C |
| ATOM 1526 | O | GLY | A | 209 | −10.118 | −12.265 | 2.16 | 1 | 18.94 | O |
| ATOM 1527 | N | TYR | A | 210 | −10.098 | −11.193 | 4.14 | 1 | 13.51 | N |
| ATOM 1528 | CA | TYR | A | 210 | −8.997 | −11.947 | 4.73 | 1 | 13.39 | C |
| ATOM 1529 | C | TYR | A | 210 | −9.229 | −13.459 | 4.813 | 1 | 15.54 | C |
| ATOM 1530 | O | TYR | A | 210 | −8.38 | −14.244 | 4.396 | 1 | 15.4 | O |
| ATOM 1531 | CB | TYR | A | 210 | −8.714 | −11.377 | 6.125 | 1 | 18.02 | C |
| ATOM 1532 | CG | TYR | A | 210 | −7.718 | −12.144 | 6.964 | 1 | 16.31 | C |
| ATOM 1533 | CD1 | TYR | A | 210 | −6.346 | −12.071 | 6.709 | 1 | 17.16 | C |
| ATOM 1534 | CD2 | TYR | A | 210 | −8.147 | −12.92 | 8.038 | 1 | 15.91 | C |
| ATOM 1535 | CE1 | TYR | A | 210 | −5.425 | −12.752 | 7.512 | 1 | 16.7 | C |
| ATOM 1536 | CE2 | TYR | A | 210 | −7.239 | −13.604 | 8.844 | 1 | 17.17 | C |
| ATOM 1537 | CZ | TYR | A | 210 | −5.881 | −13.515 | 8.58 | 1 | 17.27 | C |
| ATOM 1538 | OH | TYR | A | 210 | −4.994 | −14.174 | 9.402 | 1 | 21.02 | O |
| ATOM 1539 | N | ILE | A | 211 | −10.368 | −13.869 | 5.36 | 1 | 14.85 | N |
| ATOM 1540 | CA | ILE | A | 211 | −10.666 | −15.295 | 5.489 | 1 | 13.83 | C |
| ATOM 1541 | C | ILE | A | 211 | −10.59 | −16 | 4.134 | 1 | 15.75 | C |
| ATOM 1542 | O | ILE | A | 211 | −9.992 | −17.072 | 4.007 | 1 | 16.02 | O |
| ATOM 1543 | CB | ILE | A | 211 | −12.069 | −15.523 | 6.108 | 1 | 15.81 | C |
| ATOM 1544 | CG1 | ILE | A | 211 | −12.105 | −14.987 | 7.542 | 1 | 22.29 | C |
| ATOM 1545 | CG2 | ILE | A | 211 | −12.413 | −17.011 | 6.101 | 1 | 18.97 | C |
| ATOM 1546 | CD1 | ILE | A | 211 | −11.188 | −15.719 | 8.51 | 1 | 19.69 | C |
| ATOM 1547 | N | SER | A | 212 | −11.195 | −15.398 | 3.118 | 1 | 14.2 | N |
| ATOM 1548 | CA | SER | A | 212 | −11.177 | −15.973 | 1.779 | 1 | 16.27 | C |
| ATOM 1549 | C | SER | A | 212 | −9.756 | −16.032 | 1.24 | 1 | 20.69 | C |
| ATOM 1550 | O | SER | A | 212 | −9.357 | −17.02 | 0.618 | 1 | 17.48 | O |
| ATOM 1551 | CB | SER | A | 212 | −12.046 | −15.15 | 0.824 | 1 | 18.05 | C |
| ATOM 1552 | OG | SER | A | 212 | −13.425 | −15.397 | 1.029 | 1 | 17.11 | O |
| ATOM 1553 | N | ASP | A | 213 | −8.991 | −14.973 | 1.477 | 1 | 17.18 | N |
| ATOM 1554 | CA | ASP | A | 213 | −7.615 | −14.931 | 1.001 | 1 | 17.05 | C |
| ATOM 1555 | C | ASP | A | 213 | −6.734 | −15.998 | 1.651 | 1 | 19.12 | C |
| ATOM 1556 | O | ASP | A | 213 | −6.08 | −16.771 | 0.951 | 1 | 24.38 | O |
| ATOM 1557 | CB | ASP | A | 213 | −6.992 | −13.549 | 1.248 | 1 | 20.58 | C |
| ATOM 1558 | CG | ASP | A | 213 | −7.622 | −12.448 | 0.4 | 1 | 22.19 | C |
| ATOM 1559 | OD1 | ASP | A | 213 | −8.399 | −12.748 | −0.532 | 1 | 21.27 | O |
| ATOM 1560 | OD2 | ASP | A | 213 | −7.33 | −11.263 | 0.67 | 1 | 25.39 | O |
| ATOM 1561 | N | VAL | A | 214 | −6.723 | −16.057 | 2.983 | 1 | 17.49 | N |
| ATOM 1562 | CA | VAL | A | 214 | −5.876 | −17.02 | 3.69 | 1 | 16.78 | C |
| ATOM 1563 | C | VAL | A | 214 | −6.373 | −18.461 | 3.791 | 1 | 18.1 | C |
| ATOM 1564 | O | VAL | A | 214 | −5.575 | −19.366 | 4.037 | 1 | 24.35 | O |
| ATOM 1565 | CB | VAL | A | 214 | −5.515 | −16.529 | 5.108 | 1 | 19.66 | C |
| ATOM 1566 | CG1 | VAL | A | 214 | −4.713 | −15.239 | 5.019 | 1 | 29.56 | C |
| ATOM 1567 | CG2 | VAL | A | 214 | −6.77 | −16.334 | 5.934 | 1 | 21.99 | C |
| ATOM 1568 | N | ARG | A | 215 | −7.672 | −18.688 | 3.633 | 1 | 13.99 | N |
| ATOM 1569 | CA | ARG | A | 215 | −8.173 | −20.065 | 3.667 | 1 | 12.82 | C |
| ATOM 1570 | C | ARG | A | 215 | −8.351 | −20.596 | 2.253 | 1 | 18.02 | C |
| ATOM 1571 | O | ARG | A | 215 | −8.043 | −21.759 | 1.97 | 1 | 16.88 | O |
| ATOM 1572 | CB | ARG | A | 215 | −9.514 | −20.157 | 4.409 | 1 | 12.31 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 1573 | CG | ARG | A | 215 | −9.407 | −20.069 | 5.917 | 1 | 12.9 | C |
| ATOM 1574 | CD | ARG | A | 215 | −10.755 | −20.367 | 6.569 | 1 | 11.35 | C |
| ATOM 1575 | NE | ARG | A | 215 | −10.748 | −20.158 | 8.012 | 1 | 12.79 | N |
| ATOM 1576 | CZ | ARG | A | 215 | −11.834 | −20.244 | 8.783 | 1 | 11.76 | C |
| ATOM 1577 | NH1 | ARG | A | 215 | −13.019 | −20.526 | 8.25 | 1 | 10.47 | N |
| ATOM 1578 | NH2 | ARG | A | 215 | −11.731 | −20.072 | 10.093 | 1 | 12.46 | N |
| ATOM 1579 | N | GLY | A | 216 | −8.828 | −19.735 | 1.361 | 1 | 16.84 | N |
| ATOM 1580 | CA | GLY | A | 216 | −9.074 | −20.152 | −0.004 | 1 | 16.24 | C |
| ATOM 1581 | C | GLY | A | 216 | −7.872 | −20.159 | −0.92 | 1 | 20.71 | C |
| ATOM 1582 | O | GLY | A | 216 | −7.558 | −21.185 | −1.529 | 1 | 18.26 | O |
| ATOM 1583 | N | ASP | A | 217 | −7.189 | −19.027 | −1.019 | 1 | 15.11 | N |
| ATOM 1584 | CA | ASP | A | 217 | −6.046 | −18.956 | −1.913 | 1 | 18.45 | C |
| ATOM 1585 | C | ASP | A | 217 | −4.865 | −19.809 | −1.467 | 1 | 22.11 | C |
| ATOM 1586 | O | ASP | A | 217 | −4.068 | −20.244 | −2.301 | 1 | 19.89 | O |
| ATOM 1587 | CB | ASP | A | 217 | −5.661 | −17.494 | −2.14 | 1 | 16.21 | C |
| ATOM 1588 | CG | ASP | A | 217 | −6.789 | −16.708 | −2.795 | 1 | 24.46 | C |
| ATOM 1589 | OD1 | ASP | A | 217 | −7.504 | −17.299 | −3.639 | 1 | 29.92 | O |
| ATOM 1590 | OD2 | ASP | A | 217 | −6.965 | −15.514 | −2.48 | 1 | 34.24 | O |
| ATOM 1591 | N | THR | A | 218 | −4.766 | −20.079 | −0.169 | 1 | 15.34 | N |
| ATOM 1592 | CA | THR | A | 218 | −3.686 | −20.922 | 0.344 | 1 | 18.75 | C |
| ATOM 1593 | C | THR | A | 218 | −3.917 | −22.341 | −0.17 | 1 | 19.52 | C |
| ATOM 1594 | O | THR | A | 218 | −2.995 | −23.003 | −0.652 | 1 | 18.56 | O |
| ATOM 1595 | CB | THR | A | 218 | −3.675 | −20.969 | 1.894 | 1 | 21.24 | C |
| ATOM 1596 | OG1 | THR | A | 218 | −3.32 | −19.683 | 2.415 | 1 | 23.49 | O |
| ATOM 1597 | CG2 | THR | A | 218 | −2.675 | −22.004 | 2.398 | 1 | 25.09 | C |
| ATOM 1598 | N | PHE | A | 219 | −5.16 | −22.799 | −0.067 | 1 | 17.19 | N |
| ATOM 1599 | CA | PHE | A | 219 | −5.523 | −24.141 | −0.505 | 1 | 17.58 | C |
| ATOM 1600 | C | PHE | A | 219 | −5.316 | −24.3 | −2.008 | 1 | 18.25 | C |
| ATOM 1601 | O | PHE | A | 219 | −4.697 | −25.261 | −2.458 | 1 | 17 | O |
| ATOM 1602 | CB | PHE | A | 219 | −6.988 | −24.423 | −0.149 | 1 | 15.8 | C |
| ATOM 1603 | CG | PHE | A | 219 | −7.456 | −25.797 | −0.533 | 1 | 12.8 | C |
| ATOM 1604 | CD1 | PHE | A | 219 | −7.326 | −26.863 | 0.352 | 1 | 18.51 | C |
| ATOM 1605 | CD2 | PHE | A | 219 | −8.02 | −26.026 | −1.788 | 1 | 13.71 | C |
| ATOM 1606 | CE1 | PHE | A | 219 | −7.755 | −28.145 | −0.008 | 1 | 14.53 | C |
| ATOM 1607 | CE2 | PHE | A | 219 | −8.447 | −27.294 | −2.159 | 1 | 12.72 | C |
| ATOM 1608 | CZ | PHE | A | 219 | −8.315 | −28.359 | −1.265 | 1 | 14.08 | C |
| ATOM 1609 | N | ILE | A | 220 | −5.849 | −23.355 | −2.774 | 1 | 15.59 | N |
| ATOM 1610 | CA | ILE | A | 220 | −5.734 | −23.366 | −4.227 | 1 | 16.56 | C |
| ATOM 1611 | C | ILE | A | 220 | −4.27 | −23.384 | −4.661 | 1 | 19.09 | C |
| ATOM 1612 | O | ILE | A | 220 | −3.881 | −24.171 | −5.525 | 1 | 20.67 | O |
| ATOM 1613 | CB | ILE | A | 220 | −6.433 | −22.121 | −4.83 | 1 | 19.13 | C |
| ATOM 1614 | CG1 | ILE | A | 220 | −7.945 | −22.231 | −4.609 | 1 | 14.55 | C |
| ATOM 1615 | CG2 | ILE | A | 220 | −6.094 | −21.981 | −6.314 | 1 | 19.66 | C |
| ATOM 1616 | CD1 | ILE | A | 220 | −8.703 | −20.948 | −4.922 | 1 | 20.52 | C |
| ATOM 1617 | N | HIS | A | 221 | −3.46 | −22.522 | −4.056 | 1 | 18.93 | N |
| ATOM 1618 | CA | HIS | A | 221 | −2.041 | −22.446 | −4.396 | 1 | 23.52 | C |
| ATOM 1619 | C | HIS | A | 221 | −1.315 | −23.776 | −4.199 | 1 | 27.23 | C |
| ATOM 1620 | O | HIS | A | 221 | −0.613 | −24.24 | −5.096 | 1 | 22.24 | O |
| ATOM 1621 | CB | HIS | A | 221 | −1.349 | −21.369 | −3.557 | 1 | 21.41 | C |
| ATOM 1622 | CG | HIS | A | 221 | 0.104 | −21.193 | −3.874 | 1 | 32.45 | C |
| ATOM 1623 | ND1 | HIS | A | 221 | 1.109 | −21.634 | −3.04 | 1 | 40.06 | N |
| ATOM 1624 | CD2 | HIS | A | 221 | 0.721 | −20.617 | −4.933 | 1 | 38.06 | C |
| ATOM 1625 | CE1 | HIS | A | 221 | 2.282 | −21.334 | −3.569 | 1 | 36.27 | C |
| ATOM 1626 | NE2 | HIS | A | 221 | 2.075 | −20.717 | −4.718 | 1 | 37 | N |
| ATOM 1627 | N | GLN | A | 222 | −1.486 | −24.388 | −3.03 | 1 | 22.59 | N |
| ATOM 1628 | CA | GLN | A | 222 | −0.812 | −25.649 | −2.735 | 1 | 21.93 | C |
| ATOM 1629 | C | GLN | A | 222 | −1.277 | −26.785 | −3.635 | 1 | 26.14 | C |
| ATOM 1630 | O | GLN | A | 222 | −0.472 | −27.519 | −4.202 | 1 | 22.6 | O |
| ATOM 1631 | CB | GLN | A | 222 | −1.029 | −26.046 | −1.275 | 1 | 26.35 | C |
| ATOM 1632 | CG | GLN | A | 222 | −0.216 | −27.266 | −0.868 | 1 | 28.26 | C |
| ATOM 1633 | CD | GLN | A | 222 | −0.395 | −27.64 | 0.587 | 1 | 20.59 | C |
| ATOM 1634 | OE1 | GLN | A | 222 | −0.238 | −26.805 | 1.477 | 1 | 33.62 | O |
| ATOM 1635 | NE2 | GLN | A | 222 | −0.718 | −28.903 | 0.839 | 1 | 31.66 | N |
| ATOM 1636 | N | VAL | A | 223 | −2.588 | −26.926 | −3.754 | 1 | 25.57 | N |
| ATOM 1637 | CA | VAL | A | 223 | −3.19 | −27.959 | −4.575 | 1 | 22.28 | C |
| ATOM 1638 | C | VAL | A | 223 | −2.778 | −27.866 | −6.049 | 1 | 26.12 | C |
| ATOM 1639 | O | VAL | A | 223 | −2.513 | −28.881 | −6.701 | 1 | 23.24 | O |
| ATOM 1640 | CB | VAL | A | 223 | −4.726 | −27.879 | −4.404 | 1 | 33.66 | C |
| ATOM 1641 | CG1 | VAL | A | 223 | −5.431 | −27.956 | −5.734 | 1 | 35.86 | C |
| ATOM 1642 | CG2 | VAL | A | 223 | −5.18 | −28.973 | −3.458 | 1 | 24.61 | C |
| ATOM 1643 | N | ASN | A | 224 | −2.715 | −26.648 | −6.573 | 1 | 24.06 | N |
| ATOM 1644 | CA | ASN | A | 224 | −2.329 | −26.438 | −7.965 | 1 | 26.77 | C |
| ATOM 1645 | C | ASN | A | 224 | −0.828 | −26.666 | −8.165 | 1 | 30.23 | C |
| ATOM 1646 | O | ASN | A | 224 | −0.402 | −27.224 | −9.177 | 1 | 30.96 | O |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 1647 | CB | ASN | A | 224 | −2.696 | −25.013 | −8.41 | 1 | 27.93 | C |
| ATOM 1648 | CG | ASN | A | 224 | −4.201 | −24.793 | −8.505 | 1 | 35.93 | C |
| ATOM 1649 | OD1 | ASN | A | 224 | −4.662 | −23.74 | −8.956 | 1 | 38.28 | O |
| ATOM 1650 | ND2 | ASN | A | 224 | −4.974 | −25.785 | −8.08 | 1 | 28.46 | N |
| ATOM 1651 | N | ARG | A | 225 | −0.036 | −26.245 | −7.185 | 1 | 24.99 | N |
| ATOM 1652 | CA | ARG | A | 225 | 1.416 | −26.373 | −7.241 | 1 | 30.13 | C |
| ATOM 1653 | C | ARG | A | 225 | 1.956 | −27.771 | −6.926 | 1 | 33.65 | C |
| ATOM 1654 | O | ARG | A | 225 | 2.968 | −28.188 | −7.494 | 1 | 35.75 | O |
| ATOM 1655 | CB | ARG | A | 225 | 2.047 | −25.34 | −6.297 | 1 | 34.33 | C |
| ATOM 1656 | CG | ARG | A | 225 | 3.567 | −25.371 | −6.214 | 1 | 45.02 | C |
| ATOM 1657 | CD | ARG | A | 225 | 4.035 | −26.043 | −4.933 | 1 | 48.55 | C |
| ATOM 1658 | NE | ARG | A | 225 | 3.513 | −25.373 | −3.743 | 1 | 54.69 | N |
| ATOM 1659 | CZ | ARG | A | 225 | 3.758 | −25.761 | −2.495 | 1 | 55.02 | C |
| ATOM 1660 | NH1 | ARG | A | 225 | 4.52 | −26.821 | −2.263 | 1 | 61.63 | N |
| ATOM 1661 | NH2 | ARG | A | 225 | 3.237 | −25.09 | −1.476 | 1 | 56.77 | N |
| ATOM 1662 | N | ASP | A | 226 | 1.287 | −28.5 | −6.038 | 1 | 22.15 | N |
| ATOM 1663 | CA | ASP | A | 226 | 1.755 | −29.835 | −5.665 | 1 | 26.67 | C |
| ATOM 1664 | C | ASP | A | 226 | 1.074 | −31.011 | −6.354 | 1 | 29.67 | C |
| ATOM 1665 | O | ASP | A | 226 | 1.674 | −32.078 | −6.483 | 1 | 31.37 | O |
| ATOM 1666 | CB | ASP | A | 226 | 1.642 | −30.047 | −4.153 | 1 | 24.83 | C |
| ATOM 1667 | CG | ASP | A | 226 | 2.536 | −29.117 | −3.361 | 1 | 36.65 | C |
| ATOM 1668 | OD1 | ASP | A | 226 | 3.549 | −28.651 | −3.92 | 1 | 33.56 | O |
| ATOM 1669 | OD2 | ASP | A | 226 | 2.233 | −28.867 | −2.174 | 1 | 33.14 | O |
| ATOM 1670 | N | ASN | A | 227 | −0.169 | −30.833 | −6.786 | 1 | 25.21 | N |
| ATOM 1671 | CA | ASN | A | 227 | −0.892 | −31.928 | −7.425 | 1 | 22.6 | C |
| ATOM 1672 | C | ASN | A | 227 | −1.495 | −31.534 | −8.764 | 1 | 19.12 | C |
| ATOM 1673 | O | ASN | A | 227 | −2.253 | −32.298 | −9.357 | 1 | 21.18 | O |
| ATOM 1674 | CB | ASN | A | 227 | −2.007 | −32.423 | −6.503 | 1 | 29.64 | C |
| ATOM 1675 | CG | ASN | A | 227 | −1.617 | −32.395 | −5.04 | 1 | 34.82 | C |
| ATOM 1676 | OD1 | ASN | A | 227 | −1.235 | −33.411 | −4.465 | 1 | 33.17 | O |
| ATOM 1677 | ND2 | ASN | A | 227 | −1.714 | −31.22 | −4.429 | 1 | 41.45 | N |
| ATOM 1678 | N | ASN | A | 228 | −1.155 | −30.34 | −9.242 | 1 | 17.63 | N |
| ATOM 1679 | CA | ASN | A | 228 | −1.681 | −29.854 | −10.507 | 1 | 20.48 | C |
| ATOM 1680 | C | ASN | A | 228 | −3.195 | −30.005 | −10.616 | 1 | 20.73 | C |
| ATOM 1681 | O | ASN | A | 228 | −3.714 | −30.279 | −11.696 | 1 | 23.6 | O |
| ATOM 1682 | CB | ASN | A | 228 | −1.019 | −30.575 | −11.689 | 1 | 21.55 | C |
| ATOM 1683 | CG | ASN | A | 228 | 0.472 | −30.313 | −11.774 | 1 | 32.02 | C |
| ATOM 1684 | OD1 | ASN | A | 228 | 0.928 | −29.185 | −11.59 | 1 | 28.46 | O |
| ATOM 1685 | ND2 | ASN | A | 228 | 1.238 | −31.355 | −12.068 | 1 | 37.38 | N |
| ATOM 1686 | N | PHE | A | 229 | −3.912 | −29.837 | −9.505 | 1 | 27.09 | N |
| ATOM 1687 | CA | PHE | A | 229 | −5.368 | −29.935 | −9.557 | 1 | 24.24 | C |
| ATOM 1688 | C | PHE | A | 229 | −5.85 | −28.796 | −10.45 | 1 | 20.7 | C |
| ATOM 1689 | O | PHE | A | 229 | −5.171 | −27.774 | −10.579 | 1 | 29.19 | O |
| ATOM 1690 | CB | PHE | A | 229 | −5.989 | −29.798 | −8.162 | 1 | 19.85 | C |
| ATOM 1691 | CG | PHE | A | 229 | −5.865 | −31.034 | −7.3 | 1 | 21.69 | C |
| ATOM 1692 | CD1 | PHE | A | 229 | −6.397 | −31.045 | −6.014 | 1 | 20.46 | C |
| ATOM 1693 | CD2 | PHE | A | 229 | −5.234 | −32.185 | −7.77 | 1 | 22.54 | C |
| ATOM 1694 | CE1 | PHE | A | 229 | −6.306 | −32.174 | −5.206 | 1 | 21.78 | C |
| ATOM 1695 | CE2 | PHE | A | 229 | −5.138 | −33.322 | −6.969 | 1 | 21.22 | C |
| ATOM 1696 | CZ | PHE | A | 229 | −5.675 | −33.317 | −5.685 | 1 | 20.84 | C |
| ATOM 1697 | N | GLU | A | 230 | −7.015 | −28.967 | −11.065 | 1 | 20.65 | N |
| ATOM 1698 | CA | GLU | A | 230 | −7.556 | −27.959 | −11.979 | 1 | 20.42 | C |
| ATOM 1699 | C | GLU | A | 230 | −8.785 | −27.258 | −11.414 | 1 | 19.12 | C |
| ATOM 1700 | O | GLU | A | 230 | −9.868 | −27.84 | −11.379 | 1 | 20.89 | O |
| ATOM 1701 | CB | GLU | A | 230 | −7.933 | −28.618 | −13.309 | 1 | 21.48 | C |
| ATOM 1702 | CG | GLU | A | 230 | −6.813 | −29.432 | −13.95 | 1 | 33.34 | C |
| ATOM 1703 | CD | GLU | A | 230 | −5.71 | −28.569 | −14.526 | 1 | 34.64 | C |
| ATOM 1704 | OE1 | GLU | A | 230 | −4.673 | −29.127 | −14.944 | 1 | 38.46 | O |
| ATOM 1705 | OE2 | GLU | A | 230 | −5.876 | −27.335 | −14.566 | 1 | 37.89 | O |
| ATOM 1706 | N | LEU | A | 231 | −8.616 | −26.008 | −10.989 | 1 | 20.54 | N |
| ATOM 1707 | CA | LEU | A | 231 | −9.719 | −25.227 | −10.428 | 1 | 20.94 | C |
| ATOM 1708 | C | LEU | A | 231 | −10.716 | −24.875 | −11.526 | 1 | 21.39 | C |
| ATOM 1709 | O | LEU | A | 231 | −10.362 | −24.245 | −12.521 | 1 | 22.72 | O |
| ATOM 1710 | CB | LEU | A | 231 | −9.177 | −23.95 | −9.774 | 1 | 19.08 | C |
| ATOM 1711 | CG | LEU | A | 231 | −10.192 | −22.984 | −9.154 | 1 | 20.28 | C |
| ATOM 1712 | CD1 | LEU | A | 231 | −10.943 | −23.676 | −8.028 | 1 | 21.78 | C |
| ATOM 1713 | CD2 | LEU | A | 231 | −9.462 | −21.762 | −8.623 | 1 | 18.11 | C |
| ATOM 1714 | N | GLN | A | 232 | −11.966 | −25.284 | −11.339 | 1 | 19.24 | N |
| ATOM 1715 | CA | GLN | A | 232 | −13.009 | −25.042 | −12.328 | 1 | 22.43 | C |
| ATOM 1716 | C | GLN | A | 232 | −13.812 | −23.774 | −12.08 | 1 | 23.25 | C |
| ATOM 1717 | O | GLN | A | 232 | −14.325 | −23.159 | −13.022 | 1 | 22.45 | O |
| ATOM 1718 | CB | GLN | A | 232 | −13.945 | −26.247 | −12.384 | 1 | 24.12 | C |
| ATOM 1719 | CG | GLN | A | 232 | −13.223 | −27.547 | −12.705 | 1 | 22.32 | C |
| ATOM 1720 | CD | GLN | A | 232 | −12.417 | −27.454 | −13.991 | 1 | 20.04 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 1721 | OE1 | GLN | A | 232 | −12.973 | −27.248 | −15.071 | 1 | 28.17 | O |
| ATOM 1722 | NE2 | GLN | A | 232 | −11.102 | −27.597 | −13.876 | 1 | 23.23 | N |
| ATOM 1723 | N | SER | A | 233 | −13.923 | −23.394 | −10.81 | 1 | 21.5 | N |
| ATOM 1724 | CA | SER | A | 233 | −14.654 | −22.194 | −10.423 | 1 | 18.46 | C |
| ATOM 1725 | C | SER | A | 233 | −14.376 | −21.883 | −8.957 | 1 | 23.65 | C |
| ATOM 1726 | O | SER | A | 233 | −14.029 | −22.777 | −8.186 | 1 | 17.93 | O |
| ATOM 1727 | CB | SER | A | 233 | −16.159 | −22.398 | −10.624 | 1 | 21.82 | C |
| ATOM 1728 | OG | SER | A | 233 | −16.678 | −23.361 | −9.713 | 1 | 18.97 | O |
| ATOM 1729 | N | ALA | A | 234 | −14.521 | −20.612 | −8.587 | 1 | 21.27 | N |
| ATOM 1730 | CA | ALA | A | 234 | −14.306 | −20.161 | −7.215 | 1 | 19.24 | C |
| ATOM 1731 | C | ALA | A | 234 | −15.3 | −19.034 | −6.957 | 1 | 21.39 | C |
| ATOM 1732 | O | ALA | A | 234 | −15.135 | −17.927 | −7.467 | 1 | 24.14 | O |
| ATOM 1733 | CB | ALA | A | 234 | −12.882 | −19.664 | −7.036 | 1 | 19.85 | C |
| ATOM 1734 | N | TYR | A | 235 | −16.326 | −19.325 | −6.162 | 1 | 19.07 | N |
| ATOM 1735 | CA | TYR | A | 235 | −17.382 | −18.36 | −5.866 | 1 | 18.33 | C |
| ATOM 1736 | C | TYR | A | 235 | −17.295 | −17.701 | −4.499 | 1 | 20.07 | C |
| ATOM 1737 | O | TYR | A | 235 | −17.119 | −18.384 | −3.493 | 1 | 16.02 | O |
| ATOM 1738 | CB | TYR | A | 235 | −18.753 | −19.04 | −5.94 | 1 | 19.24 | C |
| ATOM 1739 | CG | TYR | A | 235 | −19.229 | −19.432 | −7.32 | 1 | 23.46 | C |
| ATOM 1740 | CD1 | TYR | A | 235 | −18.536 | −20.368 | −8.085 | 1 | 27.99 | C |
| ATOM 1741 | CD2 | TYR | A | 235 | −20.392 | −18.876 | −7.854 | 1 | 31.96 | C |
| ATOM 1742 | CE1 | TYR | A | 235 | −18.991 | −20.741 | −9.349 | 1 | 33.26 | C |
| ATOM 1743 | CE2 | TYR | A | 235 | −20.854 | −19.241 | −9.114 | 1 | 31.89 | C |
| ATOM 1744 | CZ | TYR | A | 235 | −20.149 | −20.172 | −9.856 | 1 | 34.61 | C |
| ATOM 1745 | OH | TYR | A | 235 | −20.603 | −20.524 | −11.106 | 1 | 36.49 | O |
| ATOM 1746 | N | TYR | A | 236 | −17.426 | −16.379 | −4.455 | 1 | 18.52 | N |
| ATOM 1747 | CA | TYR | A | 236 | −17.451 | −15.692 | −3.17 | 1 | 16.5 | C |
| ATOM 1748 | C | TYR | A | 236 | −18.885 | −15.85 | −2.687 | 1 | 14.98 | C |
| ATOM 1749 | O | TYR | A | 236 | −19.811 | −15.973 | −3.492 | 1 | 19.61 | O |
| ATOM 1750 | CB | TYR | A | 236 | −17.092 | −14.208 | −3.309 | 1 | 16.13 | C |
| ATOM 1751 | CG | TYR | A | 236 | −15.605 | −13.983 | −3.473 | 1 | 17.08 | C |
| ATOM 1752 | CD1 | TYR | A | 236 | −15.043 | −13.762 | −4.731 | 1 | 19.78 | C |
| ATOM 1753 | CD2 | TYR | A | 236 | −14.745 | −14.063 | −2.374 | 1 | 16.51 | C |
| ATOM 1754 | CE1 | TYR | A | 236 | −13.663 | −13.631 | −4.89 | 1 | 22.05 | C |
| ATOM 1755 | CE2 | TYR | A | 236 | −13.368 | −13.936 | −2.521 | 1 | 21.69 | C |
| ATOM 1756 | CZ | TYR | A | 236 | −12.83 | −13.722 | −3.782 | 1 | 23.23 | C |
| ATOM 1757 | OH | TYR | A | 236 | −11.464 | −13.618 | −3.934 | 1 | 27.48 | O |
| ATOM 1758 | N | THR | A | 237 | −19.069 | −15.862 | −1.372 | 1 | 15.47 | N |
| ATOM 1759 | CA | THR | A | 237 | −20.394 | −16.033 | −0.792 | 1 | 15.3 | C |
| ATOM 1760 | C | THR | A | 237 | −20.708 | −14.899 | 0.174 | 1 | 13.93 | C |
| ATOM 1761 | O | THR | A | 237 | −19.92 | −13.968 | 0.334 | 1 | 17.49 | O |
| ATOM 1762 | CB | THR | A | 237 | −20.472 | −17.349 | −0.004 | 1 | 16.09 | C |
| ATOM 1763 | OG1 | THR | A | 237 | −19.528 | −17.306 | 1.073 | 1 | 15.63 | O |
| ATOM 1764 | CG2 | THR | A | 237 | −20.137 | −18.533 | −0.909 | 1 | 16.06 | C |
| ATOM 1765 | N | LYS | A | 238 | −21.867 | −14.994 | 0.814 | 1 | 16.56 | N |
| ATOM 1766 | CA | LYS | A | 238 | −22.279 | −14 | 1.797 | 1 | 16.79 | C |
| ATOM 1767 | C | LYS | A | 238 | −22.012 | −14.533 | 3.207 | 1 | 19.04 | C |
| ATOM 1768 | O | LYS | A | 238 | −22.559 | −14.03 | 4.194 | 1 | 21.08 | O |
| ATOM 1769 | CB | LYS | A | 238 | −23.761 | −13.661 | 1.617 | 1 | 17.82 | C |
| ATOM 1770 | CG | LYS | A | 238 | −24.062 | −13.002 | 0.28 | 1 | 26.13 | C |
| ATOM 1771 | CD | LYS | A | 238 | −25.529 | −12.646 | 0.142 | 1 | 33.16 | C |
| ATOM 1772 | CE | LYS | A | 238 | −25.773 | −11.876 | −1.148 | 1 | 39.64 | C |
| ATOM 1773 | NZ | LYS | A | 238 | −24.959 | −10.626 | −1.195 | 1 | 43.63 | N |
| ATOM 1774 | N | ALA | A | 239 | −21.175 | −15.567 | 3.28 | 1 | 15.73 | N |
| ATOM 1775 | CA | ALA | A | 239 | −20.768 | −16.192 | 4.541 | 1 | 14.78 | C |
| ATOM 1776 | C | ALA | A | 239 | −21.866 | −16.918 | 5.323 | 1 | 17.65 | C |
| ATOM 1777 | O | ALA | A | 239 | −21.67 | −17.265 | 6.491 | 1 | 18.08 | O |
| ATOM 1778 | CB | ALA | A | 239 | −20.104 | −15.144 | 5.435 | 1 | 15.7 | C |
| ATOM 1779 | N | THR | A | 240 | −23.002 | −17.164 | 4.679 | 1 | 17.41 | N |
| ATOM 1780 | CA | THR | A | 240 | −24.128 | −17.844 | 5.314 | 1 | 14.43 | C |
| ATOM 1781 | C | THR | A | 240 | −24.388 | −19.2 | 4.679 | 1 | 16.33 | C |
| ATOM 1782 | O | THR | A | 240 | −23.89 | −19.503 | 3.597 | 1 | 16.02 | O |
| ATOM 1783 | CB | THR | A | 240 | −25.428 | −17.047 | 5.167 | 1 | 16.81 | C |
| ATOM 1784 | OG1 | THR | A | 240 | −25.757 | −16.956 | 3.774 | 1 | 18.44 | O |
| ATOM 1785 | CG2 | THR | A | 240 | −25.279 | −15.65 | 5.757 | 1 | 19.91 | C |
| ATOM 1786 | N | LYS | A | 241 | −25.193 | −20.009 | 5.356 | 1 | 13.94 | N |
| ATOM 1787 | CA | LYS | A | 241 | −25.531 | −21.33 | 4.851 | 1 | 16.08 | C |
| ATOM 1788 | C | LYS | A | 241 | −26.34 | −21.224 | 3.559 | 1 | 15.6 | C |
| ATOM 1789 | O | LYS | A | 241 | −26.093 | −21.956 | 2.608 | 1 | 15.43 | O |
| ATOM 1790 | CB | LYS | A | 241 | −26.325 | −22.105 | 5.906 | 1 | 18.05 | C |
| ATOM 1791 | CG | LYS | A | 241 | −26.679 | −23.525 | 5.504 | 1 | 18.18 | C |
| ATOM 1792 | CD | LYS | A | 241 | −27.398 | −24.248 | 6.639 | 1 | 19.65 | C |
| ATOM 1793 | CE | LYS | A | 241 | −27.734 | −25.672 | 6.253 | 1 | 23.55 | C |
| ATOM 1794 | NZ | LYS | A | 241 | −28.512 | −26.356 | 7.321 | 1 | 25.13 | N |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 1795 | N | GLN | A | 242 | −27.3 | −20.306 | 3.528 | 1 | 17.58 | N |
| ATOM 1796 | CA | GLN | A | 242 | −28.128 | −20.132 | 2.344 | 1 | 17.51 | C |
| ATOM 1797 | C | GLN | A | 242 | −27.255 | −19.76 | 1.152 | 1 | 16.59 | C |
| ATOM 1798 | O | GLN | A | 242 | −27.461 | −20.26 | 0.043 | 1 | 16.96 | O |
| ATOM 1799 | CB | GLN | A | 242 | −29.181 | −19.045 | 2.582 | 1 | 15.63 | C |
| ATOM 1800 | CG | GLN | A | 242 | −30.133 | −18.828 | 1.4 | 1 | 23.08 | C |
| ATOM 1801 | CD | GLN | A | 242 | −30.898 | −20.084 | 1.022 | 1 | 26.2 | C |
| ATOM 1802 | OE1 | GLN | A | 242 | −31.54 | −20.714 | 1.864 | 1 | 29.84 | O |
| ATOM 1803 | NE2 | GLN | A | 242 | −30.836 | −20.453 | −0.254 | 1 | 30.81 | N |
| ATOM 1804 | N | SER | A | 243 | −26.281 | −18.884 | 1.385 | 1 | 15.55 | N |
| ATOM 1805 | CA | SER | A | 243 | −25.373 | −18.456 | 0.325 | 1 | 16.28 | C |
| ATOM 1806 | C | SER | A | 243 | −24.491 | −19.614 | −0.145 | 1 | 18.99 | C |
| ATOM 1807 | O | SER | A | 243 | −24.202 | −19.731 | −1.333 | 1 | 17.68 | O |
| ATOM 1808 | CB | SER | A | 243 | −24.507 | −17.288 | 0.808 | 1 | 21.34 | C |
| ATOM 1809 | OG | SER | A | 243 | −23.711 | −16.776 | −0.248 | 1 | 24.84 | O |
| ATOM 1810 | N | GLY | A | 244 | −24.059 | −20.468 | 0.782 | 1 | 15.13 | N |
| ATOM 1811 | CA | GLY | A | 244 | −23.236 | −21.605 | 0.389 | 1 | 15.21 | C |
| ATOM 1812 | C | GLY | A | 244 | −24.035 | −22.547 | −0.492 | 1 | 19.7 | C |
| ATOM 1813 | O | GLY | A | 244 | −23.53 | −23.107 | −1.465 | 1 | 18.76 | O |
| ATOM 1814 | N | TYR | A | 245 | −25.3 | −22.726 | −0.135 | 1 | 18.64 | N |
| ATOM 1815 | CA | TYR | A | 245 | −26.217 | −23.572 | −0.883 | 1 | 15.36 | C |
| ATOM 1816 | C | TYR | A | 245 | −26.393 | −22.984 | −2.288 | 1 | 18.93 | C |
| ATOM 1817 | O | TYR | A | 245 | −26.208 | −23.675 | −3.293 | 1 | 18.45 | O |
| ATOM 1818 | CB | TYR | A | 245 | −27.561 | −23.61 | −0.148 | 1 | 20.07 | C |
| ATOM 1819 | CG | TYR | A | 245 | −28.726 | −24.15 | −0.945 | 1 | 20.09 | C |
| ATOM 1820 | CD1 | TYR | A | 245 | −28.869 | −25.515 | −1.182 | 1 | 22.42 | C |
| ATOM 1821 | CD2 | TYR | A | 245 | −29.691 | −23.287 | −1.459 | 1 | 24.59 | C |
| ATOM 1822 | CE1 | TYR | A | 245 | −29.952 | −26.008 | −1.912 | 1 | 26.9 | C |
| ATOM 1823 | CE2 | TYR | A | 245 | −30.773 | −23.765 | −2.187 | 1 | 27.31 | C |
| ATOM 1824 | CZ | TYR | A | 245 | −30.897 | −25.125 | −2.411 | 1 | 27.74 | C |
| ATOM 1825 | OH | TYR | A | 245 | −31.968 | −25.592 | −3.137 | 1 | 28.12 | O |
| ATOM 1826 | N | ASP | A | 246 | −26.74 | −21.703 | −2.356 | 1 | 19.45 | N |
| ATOM 1827 | CA | ASP | A | 246 | −26.938 | −21.048 | −3.647 | 1 | 21.2 | C |
| ATOM 1828 | C | ASP | A | 246 | −25.693 | −21.119 | −4.53 | 1 | 23.49 | C |
| ATOM 1829 | O | ASP | A | 246 | −25.79 | −21.414 | −5.721 | 1 | 20.72 | O |
| ATOM 1830 | CB | ASP | A | 246 | −27.339 | −19.578 | −3.462 | 1 | 18.42 | C |
| ATOM 1831 | CG | ASP | A | 246 | −28.719 | −19.411 | −2.844 | 1 | 18.12 | C |
| ATOM 1832 | OD1 | ASP | A | 246 | −29.582 | −20.29 | −3.044 | 1 | 23.86 | O |
| ATOM 1833 | OD2 | ASP | A | 246 | −28.941 | −18.384 | −2.166 | 1 | 25.93 | O |
| ATOM 1834 | N | ALA | A | 247 | −24.528 | −20.853 | −3.944 | 1 | 17.77 | N |
| ATOM 1835 | CA | ALA | A | 247 | −23.269 | −20.868 | −4.684 | 1 | 17.2 | C |
| ATOM 1836 | C | ALA | A | 247 | −22.892 | −22.259 | −5.179 | 1 | 20.3 | C |
| ATOM 1837 | O | ALA | A | 247 | −22.375 | −22.408 | −6.289 | 1 | 19.2 | O |
| ATOM 1838 | CB | ALA | A | 247 | −22.15 | −20.299 | −3.814 | 1 | 18.5 | C |
| ATOM 1839 | N | ALA | A | 248 | −23.136 | −23.274 | −4.355 | 1 | 17.87 | N |
| ATOM 1840 | CA | ALA | A | 248 | −22.818 | −24.645 | −4.739 | 1 | 20.1 | C |
| ATOM 1841 | C | ALA | A | 248 | −23.661 | −25.06 | −5.939 | 1 | 22.85 | C |
| ATOM 1842 | O | ALA | A | 248 | −23.161 | −25.701 | −6.862 | 1 | 20.7 | O |
| ATOM 1843 | CB | ALA | A | 248 | −23.068 | −25.596 | −3.572 | 1 | 19.88 | C |
| ATOM 1844 | N | LYS | A | 249 | −24.941 | −24.694 | −5.92 | 1 | 17.73 | N |
| ATOM 1845 | CA | LYS | A | 249 | −25.847 | −25.03 | −7.015 | 1 | 18.02 | C |
| ATOM 1846 | C | LYS | A | 249 | −25.425 | −24.335 | −8.295 | 1 | 22.44 | C |
| ATOM 1847 | O | LYS | A | 249 | −25.437 | −24.934 | −9.372 | 1 | 22.66 | O |
| ATOM 1848 | CB | LYS | A | 249 | −27.28 | −24.623 | −6.672 | 1 | 21.97 | C |
| ATOM 1849 | CG | LYS | A | 249 | −27.925 | −25.488 | −5.611 | 1 | 23.17 | C |
| ATOM 1850 | CD | LYS | A | 249 | −29.371 | −25.088 | −5.369 | 1 | 36.08 | C |
| ATOM 1851 | CE | LYS | A | 249 | −30.233 | −25.32 | −6.603 | 1 | 40.98 | C |
| ATOM 1852 | NZ | LYS | A | 249 | −31.66 | −24.972 | −6.349 | 1 | 44.01 | N |
| ATOM 1853 | N | ALA | A | 250 | −25.057 | −23.066 | −8.177 | 1 | 18.6 | N |
| ATOM 1854 | CA | ALA | A | 250 | −24.636 | −22.301 | −9.342 | 1 | 21.92 | C |
| ATOM 1855 | C | ALA | A | 250 | −23.36 | −22.905 | −9.914 | 1 | 26.99 | C |
| ATOM 1856 | O | ALA | A | 250 | −23.24 | −23.115 | −11.123 | 1 | 27.31 | O |
| ATOM 1857 | CB | ALA | A | 250 | −24.4 | −20.848 | −8.952 | 1 | 21.55 | C |
| ATOM 1858 | N | SER | A | 251 | −22.412 | −23.196 | −9.033 | 1 | 20.13 | N |
| ATOM 1859 | CA | SER | A | 251 | −21.14 | −23.764 | −9.448 | 1 | 20.05 | C |
| ATOM 1860 | C | SER | A | 251 | −21.299 | −25.102 | −10.153 | 1 | 20.99 | C |
| ATOM 1861 | O | SER | A | 251 | −20.69 | −25.337 | −11.195 | 1 | 23.22 | O |
| ATOM 1862 | CB | SER | A | 251 | −20.218 | −23.939 | −8.242 | 1 | 22.59 | C |
| ATOM 1863 | OG | SER | A | 251 | −19.002 | −24.543 | −8.643 | 1 | 22 | O |
| ATOM 1864 | N | LEU | A | 252 | −22.12 | −25.975 | −9.584 | 1 | 22.67 | N |
| ATOM 1865 | CA | LEU | A | 252 | −22.341 | −27.294 | −10.164 | 1 | 19.88 | C |
| ATOM 1866 | C | LEU | A | 252 | −23.153 | −27.251 | −11.453 | 1 | 24.56 | C |
| ATOM 1867 | O | LEU | A | 252 | −23.055 | −28.155 | −12.281 | 1 | 24.24 | O |
| ATOM 1868 | CB | LEU | A | 252 | −23.013 | −28.206 | −9.135 | 1 | 23.48 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 1869 | CG | LEU | A | 252 | −22.077 | −28.549 | −7.971 | 1 | 24.2 | C |
| ATOM 1870 | CD1 | LEU | A | 252 | −22.857 | −29.19 | −6.842 | 1 | 25.68 | C |
| ATOM 1871 | CD2 | LEU | A | 252 | −20.969 | −29.476 | −8.468 | 1 | 21.66 | C |
| ATOM 1872 | N | ALA | A | 253 | −23.953 | −26.204 | −11.626 | 1 | 24.63 | N |
| ATOM 1873 | CA | ALA | A | 253 | −24.758 | −26.074 | −12.837 | 1 | 20.46 | C |
| ATOM 1874 | C | ALA | A | 253 | −23.846 | −25.799 | −14.028 | 1 | 26.77 | C |
| ATOM 1875 | O | ALA | A | 253 | −24.077 | −26.299 | −15.128 | 1 | 32.48 | O |
| ATOM 1876 | CB | ALA | A | 253 | −25.772 | −24.946 | −12.679 | 1 | 25.99 | C |
| ATOM 1877 | N | LYS | A | 254 | −22.801 | −25.012 | −13.797 | 1 | 25.67 | N |
| ATOM 1878 | CA | LYS | A | 254 | −21.856 | −24.663 | −14.849 | 1 | 23.54 | C |
| ATOM 1879 | C | LYS | A | 254 | −20.638 | −25.586 | −14.904 | 1 | 28.83 | C |
| ATOM 1880 | O | LYS | A | 254 | −19.981 | −25.686 | −15.939 | 1 | 26.92 | O |
| ATOM 1881 | CD | LYS | A | 254 | −21.399 | −23.21 | −14.675 | 1 | 28.32 | C |
| ATOM 1882 | CG | LYS | A | 254 | −22.376 | −22.177 | −15.234 | 1 | 43.54 | C |
| ATOM 1883 | CD | LYS | A | 254 | −23.783 | −22.351 | −14.676 | 1 | 48.51 | C |
| ATOM 1884 | CE | LYS | A | 254 | −24.777 | −21.441 | −15.388 | 1 | 45.62 | C |
| ATOM 1885 | NZ | LYS | A | 254 | −26.169 | −21.642 | −14.897 | 1 | 44.54 | N |
| ATOM 1886 | N | HIS | A | 255 | −20.347 | −26.265 | −13.798 | 1 | 23.15 | N |
| ATOM 1887 | CA | HIS | A | 255 | −19.194 | −27.167 | −13.73 | 1 | 23.69 | C |
| ATOM 1888 | C | HIS | A | 255 | −19.521 | −28.44 | −12.954 | 1 | 25.42 | C |
| ATOM 1889 | O | HIS | A | 255 | −19.017 | −28.649 | −11.849 | 1 | 25.23 | O |
| ATOM 1890 | CB | HIS | A | 255 | −18.017 | −26.468 | −13.044 | 1 | 21.64 | C |
| ATOM 1891 | CG | HIS | A | 255 | −17.585 | −25.203 | −13.717 | 1 | 27.2 | C |
| ATOM 1892 | ND1 | HIS | A | 255 | −16.911 | −25.193 | −14.918 | 1 | 31.93 | N |
| ATOM 1893 | CD2 | HIS | A | 255 | −17.733 | −23.906 | −13.356 | 1 | 30.72 | C |
| ATOM 1894 | CE1 | HIS | A | 255 | −16.661 | −23.944 | −15.269 | 1 | 32.6 | C |
| ATOM 1895 | NE2 | HIS | A | 255 | −17.15 | −23.144 | −14.339 | 1 | 30.64 | N |
| ATOM 1896 | N | PRO | A | 256 | −20.362 | −29.315 | −13.525 | 1 | 23.06 | N |
| ATOM 1897 | CA | PRO | A | 256 | −20.736 | −30.564 | −12.856 | 1 | 20.31 | C |
| ATOM 1898 | C | PRO | A | 256 | −19.625 | −31.613 | −12.791 | 1 | 24.27 | C |
| ATOM 1899 | O | PRO | A | 256 | −19.704 | −32.556 | −12.005 | 1 | 21.6 | O |
| ATOM 1900 | CB | PRO | A | 256 | −21.94 | −31.037 | −13.669 | 1 | 27.35 | C |
| ATOM 1901 | CG | PRO | A | 256 | −21.608 | −30.568 | −15.042 | 1 | 23.67 | C |
| ATOM 1902 | CD | PRO | A | 256 | −21.082 | −29.165 | −14.803 | 1 | 24.57 | C |
| ATOM 1903 | N | ASP | A | 257 | −18.588 | −31.442 | −13.606 | 1 | 22.47 | N |
| ATOM 1904 | CA | ASP | A | 257 | −17.482 | −32.391 | −13.637 | 1 | 24.55 | C |
| ATOM 1905 | C | ASP | A | 257 | −16.382 | −32.097 | −12.621 | 1 | 26.55 | C |
| ATOM 1906 | O | ASP | A | 257 | −15.222 | −31.906 | −12.986 | 1 | 32.87 | O |
| ATOM 1907 | CB | ASP | A | 257 | −16.872 | −32.443 | −15.041 | 1 | 26.6 | C |
| ATOM 1908 | CG | ASP | A | 257 | −16.376 | −31.088 | −15.511 | 1 | 42 | C |
| ATOM 1909 | OD1 | ASP | A | 257 | −15.706 | −31.032 | −16.564 | 1 | 50.11 | O |
| ATOM 1910 | OD2 | ASP | A | 257 | −16.66 | −30.078 | −14.831 | 1 | 45.91 | O |
| ATOM 1911 | N | VAL | A | 258 | −16.751 | −32.045 | −11.347 | 1 | 22.39 | N |
| ATOM 1912 | CA | VAL | A | 258 | −15.778 | −31.811 | −10.29 | 1 | 20.32 | C |
| ATOM 1913 | C | VAL | A | 258 | −15.835 | −33 | −9.343 | 1 | 18.99 | C |
| ATOM 1914 | O | VAL | A | 258 | −16.876 | −33.652 | −9.214 | 1 | 20.68 | O |
| ATOM 1915 | CB | VAL | A | 258 | −16.073 | −30.519 | −9.503 | 1 | 23.6 | C |
| ATOM 1916 | CG1 | VAL | A | 258 | −15.857 | −29.31 | −10.396 | 1 | 22.59 | C |
| ATOM 1917 | CG2 | VAL | A | 258 | −17.495 | −30.552 | −8.961 | 1 | 23.13 | C |
| ATOM 1918 | N | ASP | A | 259 | −14.715 | −33.297 | −8.696 | 1 | 17.58 | N |
| ATOM 1919 | CA | ASP | A | 259 | −14.676 | −34.424 | −7.778 | 1 | 22.44 | C |
| ATOM 1920 | C | ASP | A | 259 | −14.794 | −33.983 | −6.331 | 1 | 18.31 | C |
| ATOM 1921 | O | ASP | A | 259 | −15.098 | −34.79 | −5.45 | 1 | 18.32 | O |
| ATOM 1922 | CB | ASP | A | 259 | −13.403 | −35.243 | −7.992 | 1 | 18.89 | C |
| ATOM 1923 | CG | ASP | A | 259 | −13.373 | −35.916 | −9.351 | 1 | 24.05 | C |
| ATOM 1924 | OD1 | ASP | A | 259 | −14.459 | −36.244 | −9.872 | 1 | 30.29 | O |
| ATOM 1925 | OD2 | ASP | A | 259 | −12.269 | −36.124 | −9.89 | 1 | 32.89 | O |
| ATOM 1926 | N | PHE | A | 260 | −14.556 | −32.7 | −6.083 | 1 | 18.76 | N |
| ATOM 1927 | CA | PHE | A | 260 | −14.686 | −32.175 | −4.735 | 1 | 19.36 | C |
| ATOM 1928 | C | PHE | A | 260 | −14.851 | −30.67 | −4.749 | 1 | 16.27 | C |
| ATOM 1929 | O | PHE | A | 260 | −14.545 | −30.001 | −5.739 | 1 | 17.71 | O |
| ATOM 1930 | CB | PHE | A | 260 | −13.482 | −32.589 | −3.861 | 1 | 15.76 | C |
| ATOM 1931 | CG | PHE | A | 260 | −12.213 | −31.82 | −4.124 | 1 | 15.8 | C |
| ATOM 1932 | CD1 | PHE | A | 260 | −11.979 | −30.59 | −3.5 | 1 | 16.23 | C |
| ATOM 1933 | CD2 | PHE | A | 260 | −11.219 | −32.357 | −4.934 | 1 | 17.32 | C |
| ATOM 1934 | CE1 | PHE | A | 260 | −10.769 | −29.916 | −3.674 | 1 | 19.02 | C |
| ATOM 1935 | CE2 | PHE | A | 260 | −10.004 | −31.691 | −5.117 | 1 | 19.52 | C |
| ATOM 1936 | CZ | PHE | A | 260 | −9.778 | −30.469 | −4.482 | 1 | 19.39 | C |
| ATOM 1937 | N | ILE | A | 261 | −15.382 | −30.16 | −3.646 | 1 | 17.38 | N |
| ATOM 1938 | CA | ILE | A | 261 | −15.586 | −28.737 | −3.454 | 1 | 14.51 | C |
| ATOM 1939 | C | ILE | A | 261 | −14.916 | −28.384 | −2.137 | 1 | 16.16 | C |
| ATOM 1940 | O | ILE | A | 261 | −15.156 | −29.037 | −1.111 | 1 | 16.95 | O |
| ATOM 1941 | CB | ILE | A | 261 | −17.09 | −28.383 | −3.345 | 1 | 17.85 | C |
| ATOM 1942 | CG1 | ILE | A | 261 | −17.771 | −28.575 | −4.698 | 1 | 18.47 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 1943 | CG2 | ILE | A | 261 | −17.258 | −26.945 | −2.847 | 1 | 16.57 | C |
| ATOM 1944 | CD1 | ILE | A | 261 | −19.274 | −28.359 | −4.671 | 1 | 19.47 | C |
| ATOM 1945 | N | TYR | A | 262 | −14.061 | −27.368 | −2.172 | 1 | 16.12 | N |
| ATOM 1946 | CA | TYR | A | 262 | −13.372 | −26.895 | −0.98 | 1 | 12.03 | C |
| ATOM 1947 | C | TYR | A | 262 | −14.132 | −25.678 | −0.479 | 1 | 15.17 | C |
| ATOM 1948 | O | TYR | A | 262 | −14.29 | −24.69 | −1.208 | 1 | 15.03 | O |
| ATOM 1949 | CB | TYR | A | 262 | −11.927 | −26.5 | −1.306 | 1 | 14.1 | C |
| ATOM 1950 | CG | TYR | A | 262 | −11.204 | −25.852 | −0.141 | 1 | 13.6 | C |
| ATOM 1951 | CD1 | TYR | A | 262 | −10.837 | −26.597 | 0.98 | 1 | 12.65 | C |
| ATOM 1952 | CD2 | TYR | A | 262 | −10.893 | −24.491 | −0.159 | 1 | 17.31 | C |
| ATOM 1953 | CE1 | TYR | A | 262 | −10.178 | −26.011 | 2.054 | 1 | 15.07 | C |
| ATOM 1954 | CE2 | TYR | A | 262 | −10.234 | −23.893 | 0.91 | 1 | 15.67 | C |
| ATOM 1955 | CZ | TYR | A | 262 | −9.876 | −24.658 | 2.013 | 1 | 15.98 | C |
| ATOM 1956 | OH | TYR | A | 262 | −9.199 | −24.082 | 3.062 | 1 | 16.55 | O |
| ATOM 1957 | N | ALA | A | 263 | −14.617 | −25.765 | 0.757 | 1 | 13.19 | N |
| ATOM 1958 | CA | ALA | A | 263 | −15.358 | −24.672 | 1.382 | 1 | 14.32 | C |
| ATOM 1959 | C | ALA | A | 263 | −14.46 | −23.973 | 2.39 | 1 | 13.42 | C |
| ATOM 1960 | O | ALA | A | 263 | −13.688 | −24.617 | 3.102 | 1 | 15.5 | O |
| ATOM 1961 | CB | ALA | A | 263 | −16.605 | −25.206 | 2.073 | 1 | 12.67 | C |
| ATOM 1962 | N | CYS | A | 264 | −14.567 | −22.65 | 2.453 | 1 | 11.93 | N |
| ATOM 1963 | CA | CYS | A | 264 | −13.739 | −21.861 | 3.353 | 1 | 12.55 | C |
| ATOM 1964 | C | CYS | A | 264 | −14.318 | −21.574 | 4.736 | 1 | 11.89 | C |
| ATOM 1965 | O | CYS | A | 264 | −13.67 | −20.912 | 5.544 | 1 | 13.41 | O |
| ATOM 1966 | CB | CYS | A | 264 | −13.372 | −20.532 | 2.69 | 1 | 13.91 | C |
| ATOM 1967 | SG | CYS | A | 264 | −12.252 | −20.688 | 1.258 | 1 | 15.73 | S |
| ATOM 1968 | N | SER | A | 265 | −15.524 | −22.059 | 5.019 | 1 | 12.82 | N |
| ATOM 1969 | CA | SER | A | 265 | −16.121 | −21.803 | 6.325 | 1 | 11.64 | C |
| ATOM 1970 | C | SER | A | 265 | −17.256 | −22.766 | 6.643 | 1 | 11.07 | C |
| ATOM 1971 | O | SER | A | 265 | −17.86 | −23.36 | 5.749 | 1 | 12.39 | O |
| ATOM 1972 | CB | SER | A | 265 | −16.63 | −20.362 | 6.406 | 1 | 14.23 | C |
| ATOM 1973 | OG | SER | A | 265 | −17.696 | −20.152 | 5.497 | 1 | 15.66 | O |
| ATOM 1974 | N | THR | A | 266 | −17.547 | −22.888 | 7.934 | 1 | 13.84 | N |
| ATOM 1975 | CA | THR | A | 266 | −18.586 | −23.778 | 8.424 | 1 | 12.77 | C |
| ATOM 1976 | C | THR | A | 266 | −19.97 | −23.624 | 7.801 | 1 | 12.08 | C |
| ATOM 1977 | O | THR | A | 266 | −20.477 | −24.554 | 7.175 | 1 | 12.54 | O |
| ATOM 1978 | CB | THR | A | 266 | −18.729 | −23.638 | 9.951 | 1 | 13.01 | C |
| ATOM 1979 | OG1 | THR | A | 266 | −17.509 | −24.056 | 10.576 | 1 | 12.35 | O |
| ATOM 1980 | CG2 | THR | A | 266 | −19.874 | −24.492 | 10.472 | 1 | 12.67 | C |
| ATOM 1981 | N | ASP | A | 267 | −20.581 | −22.457 | 7.967 | 1 | 14.55 | N |
| ATOM 1982 | CA | ASP | A | 267 | −21.932 | −22.248 | 7.451 | 1 | 12.46 | C |
| ATOM 1983 | C | ASP | A | 267 | −22.018 | −22.505 | 5.957 | 1 | 12.08 | C |
| ATOM 1984 | O | ASP | A | 267 | −22.969 | −23.123 | 5.477 | 1 | 13.92 | O |
| ATOM 1985 | CB | ASP | A | 267 | −22.407 | −20.828 | 7.776 | 1 | 14.59 | C |
| ATOM 1986 | CG | ASP | A | 267 | −22.603 | −20.605 | 9.266 | 1 | 17.72 | C |
| ATOM 1987 | OD1 | ASP | A | 267 | −21.831 | −21.19 | 10.053 | 1 | 15.68 | O |
| ATOM 1988 | OD2 | ASP | A | 267 | −23.513 | −19.836 | 9.648 | 1 | 15.18 | O |
| ATOM 1989 | N | VAL | A | 268 | −21.014 | −22.037 | 5.226 | 1 | 13.49 | N |
| ATOM 1990 | CA | VAL | A | 268 | −20.99 | −22.218 | 3.785 | 1 | 15.16 | C |
| ATOM 1991 | C | VAL | A | 268 | −20.918 | −23.7 | 3.414 | 1 | 12.66 | C |
| ATOM 1992 | O | VAL | A | 268 | −21.652 | −24.16 | 2.535 | 1 | 14.4 | O |
| ATOM 1993 | CB | VAL | A | 268 | −19.813 | −21.43 | 3.17 | 1 | 14.33 | C |
| ATOM 1994 | CG1 | VAL | A | 268 | −19.57 | −21.862 | 1.721 | 1 | 15.08 | C |
| ATOM 1995 | CG2 | VAL | A | 268 | −20.12 | −19.939 | 3.243 | 1 | 15.9 | C |
| ATOM 1996 | N | ALA | A | 269 | −20.055 | −24.456 | 4.088 | 1 | 12.39 | N |
| ATOM 1997 | CA | ALA | A | 269 | −19.936 | −25.881 | 3.8 | 1 | 14.33 | C |
| ATOM 1998 | C | ALA | A | 269 | −21.24 | −26.627 | 4.081 | 1 | 14.48 | C |
| ATOM 1999 | O | ALA | A | 269 | −21.629 | −27.512 | 3.324 | 1 | 13.88 | O |
| ATOM 2000 | CB | ALA | A | 269 | −18.798 | −26.495 | 4.617 | 1 | 12.63 | C |
| ATOM 2001 | N | LEU | A | 270 | −21.919 | −26.275 | 5.169 | 1 | 15.58 | N |
| ATOM 2002 | CA | LEU | A | 270 | −23.171 | −26.949 | 5.502 | 1 | 14.04 | C |
| ATOM 2003 | C | LEU | A | 270 | −24.24 | −26.643 | 4.459 | 1 | 15.09 | C |
| ATOM 2004 | O | LEU | A | 270 | −25.11 | −27.468 | 4.199 | 1 | 15.98 | O |
| ATOM 2005 | CB | LEU | A | 270 | −23.643 | −26.539 | 6.897 | 1 | 14.14 | C |
| ATOM 2006 | CG | LEU | A | 270 | −22.682 | −27.006 | 7.998 | 1 | 15.91 | C |
| ATOM 2007 | CD1 | LEU | A | 270 | −23.131 | −26.435 | 9.334 | 1 | 18.11 | C |
| ATOM 2008 | CD2 | LEU | A | 270 | −22.619 | −28.538 | 8.027 | 1 | 17.44 | C |
| ATOM 2009 | N | GLY | A | 271 | −24.164 | −25.458 | 3.861 | 1 | 17.61 | N |
| ATOM 2010 | CA | GLY | A | 271 | −25.116 | −25.102 | 2.821 | 1 | 18.57 | C |
| ATOM 2011 | C | GLY | A | 271 | −24.807 | −25.933 | 1.585 | 1 | 17.14 | C |
| ATOM 2012 | O | GLY | A | 271 | −25.711 | −26.415 | 0.894 | 1 | 16.02 | O |
| ATOM 2013 | N | ALA | A | 272 | −23.52 | −26.102 | 1.301 | 1 | 16.25 | N |
| ATOM 2014 | CA | ALA | A | 272 | −23.098 | −26.895 | 0.151 | 1 | 17.87 | C |
| ATOM 2015 | C | ALA | A | 272 | −23.577 | −28.332 | 0.318 | 1 | 18.63 | C |
| ATOM 2016 | O | ALA | A | 272 | −23.987 | −28.967 | −0.651 | 1 | 19.06 | O |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 2017 | CB | ALA | A | 272 | −21.586 | −26.861 | 0.009 | 1 | 16.18 | C |
| ATOM 2018 | N | VAL | A | 273 | −23.521 | −28.844 | 1.547 | 1 | 15.69 | N |
| ATOM 2019 | CA | VAL | A | 273 | −23.982 | −30.205 | 1.823 | 1 | 18.89 | C |
| ATOM 2020 | C | VAL | A | 273 | −25.427 | −30.365 | 1.342 | 1 | 19.34 | C |
| ATOM 2021 | O | VAL | A | 273 | −25.752 | −31.323 | 0.641 | 1 | 19.61 | O |
| ATOM 2022 | CB | VAL | A | 273 | −23.916 | −30.53 | 3.339 | 1 | 17.8 | C |
| ATOM 2023 | CG1 | VAL | A | 273 | −24.706 | −31.793 | 3.642 | 1 | 16.77 | C |
| ATOM 2024 | CG2 | VAL | A | 273 | −22.462 | −30.709 | 3.775 | 1 | 16.64 | C |
| ATOM 2025 | N | ASP | A | 274 | −26.288 | −29.428 | 1.73 | 1 | 16.2 | N |
| ATOM 2026 | CA | ASP | A | 274 | −27.69 | −29.468 | 1.324 | 1 | 19.56 | C |
| ATOM 2027 | C | ASP | A | 274 | −27.825 | −29.458 | −0.199 | 1 | 19.92 | C |
| ATOM 2028 | O | ASP | A | 274 | −28.678 | −30.144 | −0.754 | 1 | 20.58 | O |
| ATOM 2029 | CB | ASP | A | 274 | −28.458 | −28.277 | 1.91 | 1 | 21.4 | C |
| ATOM 2030 | CG | ASP | A | 274 | −28.684 | −28.405 | 3.403 | 1 | 20.04 | C |
| ATOM 2031 | OD1 | ASP | A | 274 | −28.468 | −29.511 | 3.944 | 1 | 26.46 | O |
| ATOM 2032 | OD2 | ASP | A | 274 | −29.093 | −27.402 | 4.034 | 1 | 23.76 | O |
| ATOM 2033 | N | ALA | A | 275 | −26.984 | −28.674 | −0.868 | 1 | 21.12 | N |
| ATOM 2034 | CA | ALA | A | 275 | −27.022 | −28.588 | −2.324 | 1 | 20.03 | C |
| ATOM 2035 | C | ALA | A | 275 | −26.675 | −29.935 | −2.95 | 1 | 21.17 | C |
| ATOM 2036 | O | ALA | A | 275 | −27.365 | −30.405 | −3.857 | 1 | 21.89 | O |
| ATOM 2037 | CB | ALA | A | 275 | −26.054 | −27.517 | −2.815 | 1 | 15.02 | C |
| ATOM 2038 | N | LEU | A | 276 | −25.605 | −30.558 | −2.465 | 1 | 17.73 | N |
| ATOM 2039 | CA | LEU | A | 276 | −25.184 | −31.851 | −2.99 | 1 | 17.95 | C |
| ATOM 2040 | C | LEU | A | 276 | −26.281 | −32.895 | −2.82 | 1 | 21.59 | C |
| ATOM 2041 | O | LEU | A | 276 | −26.489 | −33.734 | −3.69 | 1 | 21.95 | O |
| ATOM 2042 | CB | LEU | A | 276 | −23.911 | −32.323 | −2.284 | 1 | 15.72 | C |
| ATOM 2043 | CG | LEU | A | 276 | −22.648 | −31.513 | −2.583 | 1 | 17.17 | C |
| ATOM 2044 | CD1 | LEU | A | 276 | −21.476 | −32.101 | −1.823 | 1 | 19.85 | C |
| ATOM 2045 | CD2 | LEU | A | 276 | −22.365 | −31.525 | −4.079 | 1 | 19.58 | C |
| ATOM 2046 | N | ALA | A | 277 | −26.98 | −32.836 | −1.693 | 1 | 19 | N |
| ATOM 2047 | CA | ALA | A | 277 | −28.059 | −33.777 | −1.414 | 1 | 22 | C |
| ATOM 2048 | C | ALA | A | 277 | −29.205 | −33.587 | −2.405 | 1 | 24 | C |
| ATOM 2049 | O | ALA | A | 277 | −29.739 | −34.552 | −2.951 | 1 | 28.72 | O |
| ATOM 2050 | CB | ALA | A | 277 | −28.561 | −33.577 | 0.008 | 1 | 22.94 | C |
| ATOM 2051 | N | GLU | A | 278 | −29.579 | −32.333 | −2.626 | 1 | 17.87 | N |
| ATOM 2052 | CA | GLU | A | 278 | −30.66 | −32.005 | −3.544 | 1 | 24.52 | C |
| ATOM 2053 | C | GLU | A | 278 | −30.332 | −32.439 | −4.972 | 1 | 27.05 | C |
| ATOM 2054 | O | GLU | A | 278 | −31.186 | −32.976 | −5.678 | 1 | 23.88 | O |
| ATOM 2055 | CB | GLU | A | 278 | −30.91 | −30.501 | −3.508 | 1 | 18.92 | C |
| ATOM 2056 | CG | GLU | A | 278 | −32.025 | −30.017 | −4.413 | 1 | 29.69 | C |
| ATOM 2057 | CD | GLU | A | 278 | −32.202 | −28.514 | −4.325 | 1 | 34.01 | C |
| ATOM 2058 | OE1 | GLU | A | 278 | −32.397 | −28.01 | −3.198 | 1 | 30.96 | O |
| ATOM 2059 | OE2 | GLU | A | 278 | −32.145 | −27.839 | −5.375 | 1 | 33.13 | O |
| ATOM 2060 | N | LEU | A | 279 | −29.092 | −32.203 | −5.388 | 1 | 25.91 | N |
| ATOM 2061 | CA | LEU | A | 279 | −28.654 | −32.553 | −6.735 | 1 | 21.83 | C |
| ATOM 2062 | C | LEU | A | 279 | −28.282 | −34.02 | −6.876 | 1 | 23.53 | C |
| ATOM 2063 | O | LEU | A | 279 | −27.961 | −34.48 | −7.971 | 1 | 24.17 | O |
| ATOM 2064 | CB | LEU | A | 279 | −27.452 | −31.699 | −7.137 | 1 | 23.78 | C |
| ATOM 2065 | CG | LEU | A | 279 | −27.676 | −30.195 | −7.264 | 1 | 25.04 | C |
| ATOM 2066 | CD1 | LEU | A | 279 | −26.371 | −29.522 | −7.649 | 1 | 25.13 | C |
| ATOM 2067 | CD2 | LEU | A | 279 | −28.748 | −29.926 | −8.306 | 1 | 26.56 | C |
| ATOM 2068 | N | GLY | A | 280 | −28.317 | −34.752 | −5.769 | 1 | 19.96 | N |
| ATOM 2069 | CA | GLY | A | 280 | −27.963 | −36.158 | −5.812 | 1 | 26.19 | C |
| ATOM 2070 | C | GLY | A | 280 | −26.511 | −36.363 | −6.2 | 1 | 25.19 | C |
| ATOM 2071 | O | GLY | A | 280 | −26.178 | −37.315 | −6.903 | 1 | 27.23 | O |
| ATOM 2072 | N | ARG | A | 281 | −25.641 | −35.463 | −5.748 | 1 | 23.08 | N |
| ATOM 2073 | CA | ARG | A | 281 | −24.218 | −35.562 | −6.052 | 1 | 24.8 | C |
| ATOM 2074 | C | ARG | A | 281 | −23.386 | −35.85 | −4.806 | 1 | 27.52 | C |
| ATOM 2075 | O | ARG | A | 281 | −22.375 | −35.188 | −4.555 | 1 | 25.95 | O |
| ATOM 2076 | CB | ARG | A | 281 | −23.719 | −34.276 | −6.725 | 1 | 23.78 | C |
| ATOM 2077 | CG | ARG | A | 281 | −24.221 | −34.066 | −8.152 | 1 | 28.9 | C |
| ATOM 2078 | CD | ARG | A | 281 | −23.882 | −35.255 | −9.049 | 1 | 25.69 | C |
| ATOM 2079 | NE | ARG | A | 281 | −22.445 | −35.512 | −9.129 | 1 | 27.28 | N |
| ATOM 2080 | CZ | ARG | A | 281 | −21.578 | −34.748 | −9.787 | 1 | 31.82 | C |
| ATOM 2081 | NH1 | ARG | A | 281 | −21.992 | −33.67 | −10.438 | 1 | 29.13 | N |
| ATOM 2082 | NH2 | ARG | A | 281 | −20.288 | −35.058 | −9.785 | 1 | 32.18 | N |
| ATOM 2083 | N | GLU | A | 282 | −23.809 | −36.847 | −4.034 | 1 | 26.79 | N |
| ATOM 2084 | CA | GLU | A | 282 | −23.098 | −37.229 | −2.819 | 1 | 28.65 | C |
| ATOM 2085 | C | GLU | A | 282 | −21.688 | −37.725 | −3.135 | 1 | 30.27 | C |
| ATOM 2086 | O | GLU | A | 282 | −20.863 | −37.876 | −2.235 | 1 | 32.37 | O |
| ATOM 2087 | CB | GLU | A | 282 | −23.854 | −38.332 | −2.072 | 1 | 35.26 | C |
| ATOM 2088 | CG | GLU | A | 282 | −25.2 | −37.931 | −1.484 | 1 | 35.32 | C |
| ATOM 2089 | CD | GLU | A | 282 | −26.282 | −37.746 | −2.531 | 1 | 41.31 | C |
| ATOM 2090 | OE1 | GLU | A | 282 | −26.14 | −38.286 | −3.648 | 1 | 34.68 | O |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 2091 | OE2 | GLU | A | 282 | −27.289 | −37.072 | −2.226 | 1 | 46.37 | O |
| ATOM 2092 | N | ASP | A | 283 | −21.418 | −37.988 | −4.41 | 1 | 26.81 | N |
| ATOM 2093 | CA | ASP | A | 283 | −20.105 | −38.467 | −4.832 | 1 | 26.7 | C |
| ATOM 2094 | C | ASP | A | 283 | −19.04 | −37.394 | −4.647 | 1 | 26.49 | C |
| ATOM 2095 | O | ASP | A | 283 | −17.862 | −37.698 | −4.455 | 1 | 25.26 | O |
| ATOM 2096 | CD | ASP | A | 283 | −20.137 | −38.888 | −6.305 | 1 | 30.53 | C |
| ATOM 2097 | CG | ASP | A | 283 | −20.531 | −37.75 | −7.229 | 1 | 26.7 | C |
| ATOM 2098 | OD1 | ASP | A | 283 | −21.672 | −37.257 | −7.113 | 1 | 30.7 | O |
| ATOM 2099 | OD2 | ASP | A | 283 | −19.701 | −37.343 | −8.069 | 1 | 31.73 | O |
| ATOM 2100 | N | ILE | A | 284 | −19.462 | −36.138 | −4.711 | 1 | 22.63 | N |
| ATOM 2101 | CA | ILE | A | 284 | −18.548 | −35.015 | −4.559 | 1 | 20.55 | C |
| ATOM 2102 | C | ILE | A | 284 | −18.153 | −34.826 | −3.099 | 1 | 18.99 | C |
| ATOM 2103 | O | ILE | A | 284 | −19.009 | −34.689 | −2.231 | 1 | 20.76 | O |
| ATOM 2104 | CB | ILE | A | 284 | −19.19 | −33.718 | −5.082 | 1 | 18.25 | C |
| ATOM 2105 | CG1 | ILE | A | 284 | −19.483 | −33.858 | −6.578 | 1 | 23.09 | C |
| ATOM 2106 | CG2 | ILE | A | 284 | −18.265 | −32.532 | −4.828 | 1 | 19.88 | C |
| ATOM 2107 | CD1 | ILE | A | 284 | −20.182 | −32.663 | −7.188 | 1 | 24.45 | C |
| ATOM 2108 | N | MET | A | 285 | −16.849 | −34.827 | −2.842 | 1 | 17.42 | N |
| ATOM 2109 | CA | MET | A | 285 | −16.326 | −34.657 | −1.497 | 1 | 18.46 | C |
| ATOM 2110 | C | MET | A | 285 | −16.438 | −33.187 | −1.107 | 1 | 16.71 | C |
| ATOM 2111 | O | MET | A | 285 | −16.248 | −32.299 | −1.946 | 1 | 18.03 | O |
| ATOM 2112 | CB | MET | A | 285 | −14.856 | −35.106 | −1.436 | 1 | 21.43 | C |
| ATOM 2113 | CG | MET | A | 285 | −14.28 | −35.198 | −0.025 | 1 | 23.38 | C |
| ATOM 2114 | SD | MET | A | 285 | −12.593 | −35.892 | 0.018 | 1 | 30.11 | S |
| ATOM 2115 | CE | MET | A | 285 | −11.83 | −34.887 | 1.262 | 1 | 40.63 | C |
| ATOM 2116 | N | ILE | A | 286 | −16.755 | −32.945 | 0.162 | 1 | 17.64 | N |
| ATOM 2117 | CA | ILE | A | 286 | −16.9 | −31.591 | 0.702 | 1 | 15.84 | C |
| ATOM 2118 | C | ILE | A | 286 | −16.284 | −31.554 | 2.103 | 1 | 15.37 | C |
| ATOM 2119 | O | ILE | A | 286 | −16.425 | −32.494 | 2.886 | 1 | 15.45 | O |
| ATOM 2120 | CB | ILE | A | 286 | −18.402 | −31.178 | 0.776 | 1 | 17.46 | C |
| ATOM 2121 | CG1 | ILE | A | 286 | −18.548 | −29.786 | 1.392 | 1 | 19.87 | C |
| ATOM 2122 | CG2 | ILE | A | 286 | −19.185 | −32.189 | 1.604 | 1 | 21.71 | C |
| ATOM 2123 | CD1 | ILE | A | 286 | −18.116 | −28.668 | 0.488 | 1 | 21.75 | C |
| ATOM 2124 | N | ASN | A | 287 | −15.594 | −30.465 | 2.417 | 1 | 13.66 | N |
| ATOM 2125 | CA | ASN | A | 287 | −14.958 | −30.309 | 3.717 | 1 | 12.69 | C |
| ATOM 2126 | C | ASN | A | 287 | −15.653 | −29.26 | 4.574 | 1 | 14.73 | C |
| ATOM 2127 | O | ASN | A | 287 | −16.383 | −28.406 | 4.073 | 1 | 14.38 | O |
| ATOM 2128 | CD | ASN | A | 287 | −13.519 | −29.831 | 3.545 | 1 | 13.83 | C |
| ATOM 2129 | CG | ASN | A | 287 | −13.454 | −28.434 | 2.944 | 1 | 14.03 | C |
| ATOM 2130 | OD1 | ASN | A | 287 | −13.784 | −28.249 | 1.774 | 1 | 14.61 | O |
| ATOM 2131 | ND2 | ASN | A | 287 | −13.053 | −27.445 | 3.749 | 1 | 12.29 | N |
| ATOM 2132 | N | GLY | A | 288 | −15.388 | −29.336 | 5.872 | 1 | 15.19 | N |
| ATOM 2133 | CA | GLY | A | 288 | −15.878 | −28.345 | 6.806 | 1 | 13.38 | C |
| ATOM 2134 | C | GLY | A | 288 | −14.601 | −27.564 | 7.119 | 1 | 12.94 | C |
| ATOM 2135 | O | GLY | A | 288 | −13.534 | −27.876 | 6.581 | 1 | 15.21 | O |
| ATOM 2136 | N | TRP | A | 289 | −14.696 | −26.535 | 7.953 | 1 | 10.62 | N |
| ATOM 2137 | CA | TRP | A | 289 | −13.52 | −25.761 | 8.318 | 1 | 10.96 | C |
| ATOM 2138 | C | TRP | A | 289 | −13.713 | −25.266 | 9.747 | 1 | 12.26 | C |
| ATOM 2139 | O | TRP | A | 289 | −14.395 | −24.27 | 9.99 | 1 | 13.99 | O |
| ATOM 2140 | CD | TRP | A | 289 | −13.325 | −24.57 | 7.351 | 1 | 13.07 | C |
| ATOM 2141 | CG | TRP | A | 289 | −11.868 | −24.219 | 7.121 | 1 | 11.42 | C |
| ATOM 2142 | CD1 | TRP | A | 289 | −11.175 | −24.299 | 5.935 | 1 | 13.14 | C |
| ATOM 2143 | CD2 | TRP | A | 289 | −10.919 | −23.778 | 8.106 | 1 | 11.88 | C |
| ATOM 2144 | NE1 | TRP | A | 289 | −9.864 | −23.938 | 6.129 | 1 | 14.65 | N |
| ATOM 2145 | CE2 | TRP | A | 289 | −9.676 | −23.616 | 7.449 | 1 | 12.37 | C |
| ATOM 2146 | CE3 | TRP | A | 289 | −10.997 | −23.505 | 9.48 | 1 | 11.62 | C |
| ATOM 2147 | CZ2 | TRP | A | 289 | −8.523 | −23.191 | 8.121 | 1 | 13.81 | C |
| ATOM 2148 | CZ3 | TRP | A | 289 | −9.842 | −23.08 | 10.15 | 1 | 10.35 | C |
| ATOM 2149 | CH2 | TRP | A | 289 | −8.624 | −22.93 | 9.464 | 1 | 13.72 | C |
| ATOM 2150 | N | GLY | A | 290 | −13.144 | −25.989 | 10.709 | 1 | 13.17 | N |
| ATOM 2151 | CA | GLY | A | 290 | −13.281 | −25.571 | 12.092 | 1 | 12.8 | C |
| ATOM 2152 | C | GLY | A | 290 | −13.601 | −26.698 | 13.058 | 1 | 12.77 | C |
| ATOM 2153 | O | GLY | A | 290 | −13.055 | −26.751 | 14.155 | 1 | 14.31 | O |
| ATOM 2154 | N | GLY | A | 291 | −14.51 | −27.584 | 12.67 | 1 | 13.89 | N |
| ATOM 2155 | CA | GLY | A | 291 | −14.847 | −28.702 | 13.537 | 1 | 13.81 | C |
| ATOM 2156 | C | GLY | A | 291 | −15.687 | −28.409 | 14.764 | 1 | 15.65 | C |
| ATOM 2157 | O | GLY | A | 291 | −15.443 | −28.987 | 15.83 | 1 | 15 | O |
| ATOM 2158 | N | GLY | A | 292 | −16.661 | −27.512 | 14.627 | 1 | 15.19 | N |
| ATOM 2159 | CA | GLY | A | 292 | −17.557 | −27.198 | 15.724 | 1 | 13.61 | C |
| ATOM 2160 | C | GLY | A | 292 | −18.619 | −28.286 | 15.812 | 1 | 12.33 | C |
| ATOM 2161 | O | GLY | A | 292 | −18.613 | −29.215 | 15.005 | 1 | 15.86 | O |
| ATOM 2162 | N | SER | A | 293 | −19.531 | −28.168 | 16.773 | 1 | 14.29 | N |
| ATOM 2163 | CA | SER | A | 293 | −20.565 | −29.18 | 16.97 | 1 | 15.42 | C |
| ATOM 2164 | C | SER | A | 293 | −21.408 | −29.518 | 15.747 | 1 | 15.81 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 2165 | O | SER | A | 293 | −21.66 | −30.697 | 15.484 | 1 | 18.39 | O |
| ATOM 2166 | CB | SER | A | 293 | −21.468 | −28.777 | 18.13 | 1 | 15.96 | C |
| ATOM 2167 | OG | SER | A | 293 | −20.735 | −28.794 | 19.342 | 1 | 19.35 | O |
| ATOM 2168 | N | ALA | A | 294 | −21.837 | −28.51 | 14.986 | 1 | 15.01 | N |
| ATOM 2169 | CA | ALA | A | 294 | −22.643 | −28.798 | 13.799 | 1 | 14.12 | C |
| ATOM 2170 | C | ALA | A | 294 | −21.82 | −29.58 | 12.781 | 1 | 14.94 | C |
| ATOM 2171 | O | ALA | A | 294 | −22.321 | −30.507 | 12.153 | 1 | 15.05 | O |
| ATOM 2172 | CB | ALA | A | 294 | −23.175 | −27.506 | 13.179 | 1 | 14.03 | C |
| ATOM 2173 | N | GLU | A | 295 | −20.551 | −29.215 | 12.609 | 1 | 13 | N |
| ATOM 2174 | CA | GLU | A | 295 | −19.705 | −29.94 | 11.668 | 1 | 13.11 | C |
| ATOM 2175 | C | GLU | A | 295 | −19.473 | −31.384 | 12.101 | 1 | 12.91 | C |
| ATOM 2176 | O | GLU | A | 295 | −19.53 | −32.295 | 11.282 | 1 | 16.62 | O |
| ATOM 2177 | CB | GLU | A | 295 | −18.349 | −29.251 | 11.501 | 1 | 13.81 | C |
| ATOM 2178 | CG | GLU | A | 295 | −18.422 | −27.963 | 10.698 | 1 | 12.15 | C |
| ATOM 2179 | CD | GLU | A | 295 | −17.069 | −27.518 | 10.196 | 1 | 13.93 | C |
| ATOM 2180 | OE1 | GLU | A | 295 | −17 | −26.426 | 9.598 | 1 | 14.13 | O |
| ATOM 2181 | OE2 | GLU | A | 295 | −16.075 | −28.255 | 10.385 | 1 | 13.75 | O |
| ATOM 2182 | N | LEU | A | 296 | −19.204 | −31.59 | 13.386 | 1 | 17.28 | N |
| ATOM 2183 | CA | LEU | A | 296 | −18.952 | −32.939 | 13.877 | 1 | 17.81 | C |
| ATOM 2184 | C | LEU | A | 296 | −20.183 | −33.825 | 13.711 | 1 | 16.46 | C |
| ATOM 2185 | O | LEU | A | 296 | −20.059 | −35.002 | 13.384 | 1 | 18.99 | O |
| ATOM 2186 | CB | LEU | A | 296 | −18.499 | −32.886 | 15.338 | 1 | 15.22 | C |
| ATOM 2187 | CG | LEU | A | 296 | −17.16 | −32.155 | 15.523 | 1 | 18.78 | C |
| ATOM 2188 | CD1 | LEU | A | 296 | −16.81 | −32.095 | 17.006 | 1 | 17.26 | C |
| ATOM 2189 | CD2 | LEU | A | 296 | −16.063 | −32.862 | 14.738 | 1 | 19.24 | C |
| ATOM 2190 | N | ASP | A | 297 | −21.365 | −33.259 | 13.926 | 1 | 16.82 | N |
| ATOM 2191 | CA | ASP | A | 297 | −22.589 | −34.032 | 13.744 | 1 | 18.32 | C |
| ATOM 2192 | C | ASP | A | 297 | −22.686 | −34.432 | 12.271 | 1 | 23.81 | C |
| ATOM 2193 | O | ASP | A | 297 | −23.038 | −35.567 | 11.946 | 1 | 21.5 | O |
| ATOM 2194 | CB | ASP | A | 297 | −23.823 | −33.212 | 14.133 | 1 | 19.92 | C |
| ATOM 2195 | CG | ASP | A | 297 | −23.988 | −33.066 | 15.639 | 1 | 24.81 | C |
| ATOM 2196 | OD1 | ASP | A | 297 | −23.258 | −33.741 | 16.399 | 1 | 26.16 | O |
| ATOM 2197 | OD2 | ASP | A | 297 | −24.859 | −32.282 | 16.064 | 1 | 24.74 | O |
| ATOM 2198 | N | ALA | A | 298 | −22.358 | −33.5 | 11.376 | 1 | 18.89 | N |
| ATOM 2199 | CA | ALA | A | 298 | −22.417 | −33.781 | 9.943 | 1 | 17.45 | C |
| ATOM 2200 | C | ALA | A | 298 | −21.382 | −34.836 | 9.555 | 1 | 16.12 | C |
| ATOM 2201 | O | ALA | A | 298 | −21.629 | −35.672 | 8.683 | 1 | 19.59 | O |
| ATOM 2202 | CB | ALA | A | 298 | −22.195 | −32.492 | 9.143 | 1 | 15.13 | C |
| ATOM 2203 | N | ILE | A | 299 | −20.219 | −34.788 | 10.201 | 1 | 17.92 | N |
| ATOM 2204 | CA | ILE | A | 299 | −19.151 | −35.753 | 9.946 | 1 | 18.88 | C |
| ATOM 2205 | C | ILE | A | 299 | −19.621 | −37.16 | 10.314 | 1 | 17.06 | C |
| ATOM 2206 | O | ILE | A | 299 | −19.482 | −38.101 | 9.528 | 1 | 21.72 | O |
| ATOM 2207 | CB | ILE | A | 299 | −17.9 | −35.441 | 10.798 | 1 | 19.24 | C |
| ATOM 2208 | CG1 | ILE | A | 299 | −17.208 | −34.177 | 10.275 | 1 | 22.12 | C |
| ATOM 2209 | CG2 | ILE | A | 299 | −16.942 | −36.639 | 10.779 | 1 | 20.43 | C |
| ATOM 2210 | CD1 | ILE | A | 299 | −16.475 | −34.369 | 8.972 | 1 | 21.95 | C |
| ATOM 2211 | N | GLN | A | 300 | −20.173 | −37.294 | 11.513 | 1 | 20.55 | N |
| ATOM 2212 | CA | GLN | A | 300 | −20.637 | −38.595 | 11.978 | 1 | 23.63 | C |
| ATOM 2213 | C | GLN | A | 300 | −21.832 | −39.096 | 11.174 | 1 | 26.31 | C |
| ATOM 2214 | O | GLN | A | 300 | −22.091 | −40.297 | 11.126 | 1 | 27.16 | O |
| ATOM 2215 | CB | GLN | A | 300 | −20.958 | −38.533 | 13.477 | 1 | 18.07 | C |
| ATOM 2216 | CG | GLN | A | 300 | −19.722 | −38.239 | 14.333 | 1 | 26.18 | C |
| ATOM 2217 | CD | GLN | A | 300 | −19.944 | −38.447 | 15.822 | 1 | 22.78 | C |
| ATOM 2218 | OE1 | GLN | A | 300 | −20.707 | −37.723 | 16.46 | 1 | 25.6 | O |
| ATOM 2219 | NE2 | GLN | A | 300 | −19.271 | −39.449 | 16.382 | 1 | 25.21 | N |
| ATOM 2220 | N | LYS | A | 301 | −22.542 | −38.169 | 10.537 | 1 | 22.21 | N |
| ATOM 2221 | CA | LYS | A | 301 | −23.695 | −38.495 | 9.698 | 1 | 30.89 | C |
| ATOM 2222 | C | LYS | A | 301 | −23.205 | −38.921 | 8.317 | 1 | 30.59 | C |
| ATOM 2223 | O | LYS | A | 301 | −23.893 | −39.645 | 7.597 | 1 | 32.5 | O |
| ATOM 2224 | CB | LYS | A | 301 | −24.599 | −37.267 | 9.537 | 1 | 37.88 | C |
| ATOM 2225 | CG | LYS | A | 301 | −25.62 | −37.052 | 10.639 | 1 | 44.11 | C |
| ATOM 2226 | CD | LYS | A | 301 | −26.964 | −37.646 | 10.251 | 1 | 51.31 | C |
| ATOM 2227 | CE | LYS | A | 301 | −28.052 | −37.259 | 11.244 | 1 | 56.1 | C |
| ATOM 2228 | NZ | LYS | A | 301 | −29.396 | −37.758 | 10.827 | 1 | 57.07 | N |
| ATOM 2229 | N | GLY | A | 302 | −22.011 | −38.458 | 7.953 | 1 | 23.28 | N |
| ATOM 2230 | CA | GLY | A | 302 | −21.447 | −38.78 | 6.654 | 1 | 25.4 | C |
| ATOM 2231 | C | GLY | A | 302 | −21.727 | −37.689 | 5.633 | 1 | 22.4 | C |
| ATOM 2232 | O | GLY | A | 302 | −21.362 | −37.816 | 4.462 | 1 | 26 | O |
| ATOM 2233 | N | ASP | A | 303 | −22.374 | −36.612 | 6.074 | 1 | 20.42 | N |
| ATOM 2234 | CA | ASP | A | 303 | −22.7 | −35.498 | 5.187 | 1 | 24.67 | C |
| ATOM 2235 | C | ASP | A | 303 | −21.472 | −34.653 | 4.876 | 1 | 22.9 | C |
| ATOM 2236 | O | ASP | A | 303 | −21.369 | −34.062 | 3.802 | 1 | 20.7 | O |
| ATOM 2237 | CB | ASP | A | 303 | −23.784 | −34.615 | 5.804 | 1 | 23.72 | C |
| ATOM 2238 | CG | ASP | A | 303 | −25.101 | −35.334 | 5.958 | 1 | 28.71 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 2239 | OD1 | ASP | A | 303 | −25.42 | −36.17 | 5.088 | 1 | 31.05 | O |
| ATOM 2240 | OD2 | ASP | A | 303 | −25.819 | −35.053 | 6.94 | 1 | 39 | O |
| ATOM 2241 | N | LEU | A | 304 | −20.558 | −34.571 | 5.837 | 1 | 20.04 | N |
| ATOM 2242 | CA | LEU | A | 304 | −19.318 | −33.827 | 5.656 | 1 | 19.99 | C |
| ATOM 2243 | C | LEU | A | 304 | −18.258 | −34.919 | 5.597 | 1 | 17.36 | C |
| ATOM 2244 | O | LEU | A | 304 | −18.265 | −35.831 | 6.413 | 1 | 21.06 | O |
| ATOM 2245 | CB | LEU | A | 304 | −19.087 | −32.895 | 6.845 | 1 | 23.78 | C |
| ATOM 2246 | CG | LEU | A | 304 | −18.618 | −31.457 | 6.593 | 1 | 31.59 | C |
| ATOM 2247 | CD1 | LEU | A | 304 | −19.298 | −30.841 | 5.373 | 1 | 19.08 | C |
| ATOM 2248 | CD2 | LEU | A | 304 | −18.927 | −30.639 | 7.835 | 1 | 17.98 | C |
| ATOM 2249 | N | ASP | A | 305 | −17.358 | −34.842 | 4.625 | 1 | 16.1 | N |
| ATOM 2250 | CA | ASP | A | 305 | −16.34 | −35.875 | 4.457 | 1 | 20.5 | C |
| ATOM 2251 | C | ASP | A | 305 | −15.116 | −35.705 | 5.321 | 1 | 22.96 | C |
| ATOM 2252 | O | ASP | A | 305 | −14.543 | −36.682 | 5.808 | 1 | 19.3 | O |
| ATOM 2253 | CB | ASP | A | 305 | −15.907 | −35.929 | 2.997 | 1 | 18.95 | C |
| ATOM 2254 | CG | ASP | A | 305 | −17.035 | −36.325 | 2.081 | 1 | 23.46 | C |
| ATOM 2255 | OD1 | ASP | A | 305 | −17.358 | −37.529 | 2.022 | 1 | 25.44 | O |
| ATOM 2256 | OD2 | ASP | A | 305 | −17.61 | −35.431 | 1.435 | 1 | 20.51 | O |
| ATOM 2257 | N | ILE | A | 306 | −14.718 | −34.458 | 5.513 | 1 | 17.58 | N |
| ATOM 2258 | CA | ILE | A | 306 | −13.535 | −34.165 | 6.29 | 1 | 21.34 | C |
| ATOM 2259 | C | ILE | A | 306 | −13.609 | −32.726 | 6.762 | 1 | 18.95 | C |
| ATOM 2260 | O | ILE | A | 306 | −14.375 | −31.919 | 6.23 | 1 | 16.53 | O |
| ATOM 2261 | CB | ILE | A | 306 | −12.27 | −34.348 | 5.405 | 1 | 18.2 | C |
| ATOM 2262 | CG1 | ILE | A | 306 | −10.998 | −34.08 | 6.212 | 1 | 17.65 | C |
| ATOM 2263 | CG2 | ILE | A | 306 | −12.349 | −33.414 | 4.204 | 1 | 19.15 | C |
| ATOM 2264 | CD1 | ILE | A | 306 | −9.713 | −34.253 | 5.406 | 1 | 26.23 | C |
| ATOM 2265 | N | THR | A | 307 | −12.832 | −32.418 | 7.786 | 1 | 17.98 | N |
| ATOM 2266 | CA | THR | A | 307 | −12.742 | −31.059 | 8.28 | 1 | 14.4 | C |
| ATOM 2267 | C | THR | A | 307 | −11.486 | −30.932 | 9.109 | 1 | 18.76 | C |
| ATOM 2268 | O | THR | A | 307 | −10.916 | −31.933 | 9.555 | 1 | 17.99 | O |
| ATOM 2269 | CB | THR | A | 307 | −13.942 | −30.64 | 9.155 | 1 | 15.38 | C |
| ATOM 2270 | OG1 | THR | A | 307 | −13.841 | −29.233 | 9.431 | 1 | 16.05 | O |
| ATOM 2271 | CG2 | THR | A | 307 | −13.956 | −31.404 | 10.474 | 1 | 20.1 | C |
| ATOM 2272 | N | VAL | A | 308 | −11.028 | −29.702 | 9.281 | 1 | 14.25 | N |
| ATOM 2273 | CA | VAL | A | 308 | −9.863 | −29.467 | 10.105 | 1 | 17.22 | C |
| ATOM 2274 | C | VAL | A | 308 | −10.496 | −28.976 | 11.398 | 1 | 15.57 | C |
| ATOM 2275 | O | VAL | A | 308 | −11.178 | −27.946 | 11.436 | 1 | 17.74 | O |
| ATOM 2276 | CB | VAL | A | 308 | −8.907 | −28.418 | 9.464 | 1 | 23.13 | C |
| ATOM 2277 | CG1 | VAL | A | 308 | −9.54 | −27.037 | 9.454 | 1 | 22.25 | C |
| ATOM 2278 | CG2 | VAL | A | 308 | −7.586 | −28.41 | 10.2 | 1 | 22.47 | C |
| ATOM 2279 | N | MET | A | 309 | −10.311 | −29.753 | 12.456 | 1 | 16.41 | N |
| ATOM 2280 | CA | MET | A | 309 | −10.912 | −29.436 | 13.734 | 1 | 13.28 | C |
| ATOM 2281 | C | MET | A | 309 | −9.962 | −28.712 | 14.664 | 1 | 18.26 | C |
| ATOM 2282 | O | MET | A | 309 | −8.888 | −29.225 | 14.986 | 1 | 19.36 | O |
| ATOM 2283 | CB | MET | A | 309 | −11.393 | −30.73 | 14.393 | 1 | 18.29 | C |
| ATOM 2284 | CG | MET | A | 309 | −11.977 | −30.548 | 15.758 | 1 | 15.2 | C |
| ATOM 2285 | SD | MET | A | 309 | −12.426 | −32.134 | 16.503 | 1 | 18.32 | S |
| ATOM 2286 | CE | MET | A | 309 | −13.19 | −31.644 | 17.896 | 1 | 16.87 | C |
| ATOM 2287 | N | ARG | A | 310 | −10.333 | −27.514 | 15.094 | 1 | 16.43 | N |
| ATOM 2288 | CA | ARG | A | 310 | −9.446 | −26.821 | 16.011 | 1 | 17.3 | C |
| ATOM 2289 | C | ARG | A | 310 | −9.734 | −27.239 | 17.457 | 1 | 20.83 | C |
| ATOM 2290 | O | ARG | A | 310 | −10.862 | −27.619 | 17.801 | 1 | 20.03 | O |
| ATOM 2291 | CB | ARG | A | 310 | −9.538 | −25.3 | 15.814 | 1 | 33.21 | C |
| ATOM 2292 | CG | ARG | A | 310 | −10.92 | −24.742 | 15.791 | 1 | 32.62 | C |
| ATOM 2293 | CD | ARG | A | 310 | −11.09 | −23.556 | 14.823 | 1 | 22.19 | C |
| ATOM 2294 | NE | ARG | A | 310 | −12.527 | −23.408 | 14.655 | 1 | 14.12 | N |
| ATOM 2295 | CZ | ARG | A | 310 | −13.166 | −22.661 | 13.76 | 1 | 13.48 | C |
| ATOM 2296 | NH1 | ARG | A | 310 | −12.52 | −21.916 | 12.867 | 1 | 13.71 | N |
| ATOM 2297 | NH2 | ARG | A | 310 | −14.491 | −22.692 | 13.758 | 1 | 12.47 | N |
| ATOM 2298 | N | MET | A | 311 | −8.695 | −27.235 | 18.29 | 1 | 18.23 | N |
| ATOM 2299 | CA | MET | A | 311 | −8.848 | −27.59 | 19.703 | 1 | 19.12 | C |
| ATOM 2300 | C | MET | A | 311 | −9.378 | −26.321 | 20.339 | 1 | 18.86 | C |
| ATOM 2301 | O | MET | A | 311 | −8.733 | −25.662 | 21.157 | 1 | 22.34 | O |
| ATOM 2302 | CB | MET | A | 311 | −7.499 | −28.005 | 20.29 | 1 | 21.97 | C |
| ATOM 2303 | CG | MET | A | 311 | −6.931 | −29.268 | 19.642 | 1 | 23.2 | C |
| ATOM 2304 | SD | MET | A | 311 | −8.025 | −30.718 | 19.788 | 1 | 24.12 | S |
| ATOM 2305 | CE | MET | A | 311 | −8.952 | −30.637 | 18.228 | 1 | 22.97 | C |
| ATOM 2306 | N | ASN | A | 312 | −10.596 | −26.021 | 19.911 | 1 | 18.43 | N |
| ATOM 2307 | CA | ASN | A | 312 | −11.368 | −24.839 | 20.243 | 1 | 19.7 | C |
| ATOM 2308 | C | ASN | A | 312 | −11.119 | −23.983 | 21.469 | 1 | 18.78 | C |
| ATOM 2309 | O | ASN | A | 312 | −10.745 | −22.814 | 21.35 | 1 | 16.82 | O |
| ATOM 2310 | CB | ASN | A | 312 | −12.856 | −25.182 | 20.219 | 1 | 17.92 | C |
| ATOM 2311 | CG | ASN | A | 312 | −13.714 | −23.946 | 20.161 | 1 | 16.75 | C |
| ATOM 2312 | OD1 | ASN | A | 312 | −14.003 | −23.429 | 19.077 | 1 | 20.16 | O |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 2313 | ND2 | ASN | A | 312 | −14.102 | −23.435 | 21.328 | 1 | 15.75 | N |
| ATOM 2314 | N | ASP | A | 313 | −11.356 | −24.542 | 22.648 | 1 | 17.02 | N |
| ATOM 2315 | CA | ASP | A | 313 | −11.228 | −23.77 | 23.867 | 1 | 14.9 | C |
| ATOM 2316 | C | ASP | A | 313 | −9.854 | −23.181 | 24.156 | 1 | 12.68 | C |
| ATOM 2317 | O | ASP | A | 313 | −9.756 | −22.239 | 24.93 | 1 | 15.15 | O |
| ATOM 2318 | CB | ASP | A | 313 | −11.712 | −24.596 | 25.066 | 1 | 18.9 | C |
| ATOM 2319 | CG | ASP | A | 313 | −13.218 | −24.854 | 25.031 | 1 | 21.53 | C |
| ATOM 2320 | OD1 | ASP | A | 313 | −13.918 | −24.324 | 24.136 | 1 | 18.19 | O |
| ATOM 2321 | OD2 | ASP | A | 313 | −13.713 | −25.588 | 25.91 | 1 | 19.99 | O |
| ATOM 2322 | N | ASP | A | 314 | −8.809 | −23.7 | 23.522 | 1 | 16.1 | N |
| ATOM 2323 | CA | ASP | A | 314 | −7.47 | −23.178 | 23.776 | 1 | 15.41 | C |
| ATOM 2324 | C | ASP | A | 314 | −7.343 | −21.674 | 23.527 | 1 | 16.31 | C |
| ATOM 2325 | O | ASP | A | 314 | −6.62 | −20.99 | 24.246 | 1 | 16.13 | O |
| ATOM 2326 | CB | ASP | A | 314 | −6.429 | −23.944 | 22.953 | 1 | 18.24 | C |
| ATOM 2327 | CG | ASP | A | 314 | −6.152 | −25.339 | 23.515 | 1 | 17.34 | C |
| ATOM 2328 | OD1 | ASP | A | 314 | −6.665 | −25.655 | 24.607 | 1 | 25.87 | O |
| ATOM 2329 | OD2 | ASP | A | 314 | −5.412 | −26.106 | 22.865 | 1 | 24.95 | O |
| ATOM 2330 | N | THR | A | 315 | −8.044 | −21.137 | 22.536 | 1 | 16.5 | N |
| ATOM 2331 | CA | THR | A | 315 | −7.918 | −19.702 | 22.306 | 1 | 14.09 | C |
| ATOM 2332 | C | THR | A | 315 | −8.637 | −18.887 | 23.377 | 1 | 22.81 | C |
| ATOM 2333 | O | THR | A | 315 | −8.121 | −17.858 | 23.82 | 1 | 25.53 | O |
| ATOM 2334 | CB | THR | A | 315 | −8.384 | −19.296 | 20.885 | 1 | 14.87 | C |
| ATOM 2335 | OG1 | THR | A | 315 | −9.658 | −19.881 | 20.598 | 1 | 17.94 | O |
| ATOM 2336 | CG2 | THR | A | 315 | −7.367 | −19.749 | 19.857 | 1 | 14.22 | C |
| ATOM 2337 | N | GLY | A | 316 | −9.808 | −19.344 | 23.815 | 1 | 14.73 | N |
| ATOM 2338 | CA | GLY | A | 316 | −10.51 | −18.619 | 24.859 | 1 | 16.85 | C |
| ATOM 2339 | C | GLY | A | 316 | −9.652 | −18.601 | 26.115 | 1 | 19.72 | C |
| ATOM 2340 | O | GLY | A | 316 | −9.525 | −17.58 | 26.796 | 1 | 21.03 | O |
| ATOM 2341 | N | ILE | A | 317 | −9.044 | −19.746 | 26.412 | 1 | 16.46 | N |
| ATOM 2342 | CA | ILE | A | 317 | −8.179 | −19.882 | 27.581 | 1 | 19.11 | C |
| ATOM 2343 | C | ILE | A | 317 | −6.929 | −19.006 | 27.439 | 1 | 15.92 | C |
| ATOM 2344 | O | ILE | A | 317 | −6.494 | −18.38 | 28.402 | 1 | 17.71 | O |
| ATOM 2345 | CB | ILE | A | 317 | −7.78 | −21.361 | 27.77 | 1 | 15.24 | C |
| ATOM 2346 | CG1 | ILE | A | 317 | −9.006 | −22.15 | 28.239 | 1 | 18.14 | C |
| ATOM 2347 | CG2 | ILE | A | 317 | −6.628 | −21.49 | 28.771 | 1 | 18.46 | C |
| ATOM 2348 | CD1 | ILE | A | 317 | −8.817 | −23.658 | 28.259 | 1 | 16.88 | C |
| ATOM 2349 | N | ALA | A | 318 | −6.363 | −18.957 | 26.237 | 1 | 18.13 | N |
| ATOM 2350 | CA | ALA | A | 318 | −5.174 | −18.144 | 26.004 | 1 | 16.84 | C |
| ATOM 2351 | C | ALA | A | 318 | −5.45 | −16.67 | 26.28 | 1 | 21.63 | C |
| ATOM 2352 | O | ALA | A | 318 | −4.586 | −15.951 | 26.776 | 1 | 18.5 | O |
| ATOM 2353 | CB | ALA | A | 318 | −4.688 | −18.313 | 24.564 | 1 | 16.87 | C |
| ATOM 2354 | N | MET | A | 319 | −6.654 | −16.217 | 25.955 | 1 | 17.9 | N |
| ATOM 2355 | CA | MET | A | 319 | −7.004 | −14.813 | 26.152 | 1 | 14.48 | C |
| ATOM 2356 | C | MET | A | 319 | −7.089 | −14.454 | 27.623 | 1 | 14.52 | C |
| ATOM 2357 | O | MET | A | 319 | −6.707 | −13.36 | 28.027 | 1 | 16.86 | O |
| ATOM 2358 | CB | MET | A | 319 | −8.327 | −14.518 | 25.466 | 1 | 17.8 | C |
| ATOM 2359 | CG | MET | A | 319 | −8.29 | −14.892 | 24.01 | 1 | 17.63 | C |
| ATOM 2360 | SD | MET | A | 319 | −9.93 | −14.959 | 23.39 | 1 | 28.86 | S |
| ATOM 2361 | CE | MET | A | 319 | −10.114 | −13.279 | 23.189 | 1 | 7.72 | C |
| ATOM 2362 | N | ALA | A | 320 | −7.598 | −15.383 | 28.422 | 1 | 15.21 | N |
| ATOM 2363 | CA | ALA | A | 320 | −7.705 | −15.158 | 29.855 | 1 | 16.04 | C |
| ATOM 2364 | C | ALA | A | 320 | −6.303 | −15.15 | 30.465 | 1 | 14.71 | C |
| ATOM 2365 | O | ALA | A | 320 | −6.017 | −14.361 | 31.364 | 1 | 21.86 | O |
| ATOM 2366 | CD | ALA | A | 320 | −8.55 | −16.25 | 30.491 | 1 | 17.02 | C |
| ATOM 2367 | N | GLU | A | 321 | −5.434 | −16.029 | 29.971 | 1 | 16.26 | N |
| ATOM 2368 | CA | GLU | A | 321 | −4.068 | −16.106 | 30.479 | 1 | 19.18 | C |
| ATOM 2369 | C | GLU | A | 321 | −3.282 | −14.857 | 30.098 | 1 | 20.52 | C |
| ATOM 2370 | O | GLU | A | 321 | −2.477 | −14.356 | 30.888 | 1 | 24.17 | O |
| ATOM 2371 | CB | GLU | A | 321 | −3.365 | −17.356 | 29.938 | 1 | 18.89 | C |
| ATOM 2372 | CG | GLU | A | 321 | −3.902 | −18.664 | 30.512 | 1 | 19.93 | C |
| ATOM 2373 | CD | GLU | A | 321 | −3.643 | −18.8 | 32.006 | 1 | 26.81 | C |
| ATOM 2374 | OE1 | GLU | A | 321 | −4.143 | −19.77 | 32.612 | 1 | 22.81 | O |
| ATOM 2375 | OE2 | GLU | A | 321 | −2.934 | −17.941 | 32.577 | 1 | 25.59 | O |
| ATOM 2376 | N | ALA | A | 322 | −3.517 | −14.351 | 28.89 | 1 | 17.9 | N |
| ATOM 2377 | CA | ALA | A | 322 | −2.823 | −13.151 | 28.429 | 1 | 19.69 | C |
| ATOM 2378 | C | ALA | A | 322 | −3.222 | −11.962 | 29.291 | 1 | 20.11 | C |
| ATOM 2379 | O | ALA | A | 322 | −2.381 | −11.146 | 29.666 | 1 | 19.54 | O |
| ATOM 2380 | CB | ALA | A | 322 | −3.157 | −12.873 | 26.971 | 1 | 19.08 | C |
| ATOM 2381 | N | ILE | A | 323 | −4.51 | −11.866 | 29.603 | 1 | 17.84 | N |
| ATOM 2382 | CA | ILE | A | 323 | −5 | −10.78 | 30.435 | 1 | 15.44 | C |
| ATOM 2383 | C | ILE | A | 323 | −4.398 | −10.915 | 31.83 | 1 | 22.34 | C |
| ATOM 2384 | O | ILE | A | 323 | −4.021 | −9.917 | 32.447 | 1 | 21.96 | O |
| ATOM 2385 | CD | ILE | A | 323 | −6.546 | −10.794 | 30.512 | 1 | 17.74 | C |
| ATOM 2386 | CG1 | ILE | A | 323 | −7.125 | −10.284 | 29.192 | 1 | 19.33 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 2387 | CG2 | ILE | A | 323 | −7.032 | −9.934 | 31.666 | 1 | 17.89 | C |
| ATOM 2388 | CD1 | ILE | A | 323 | −8.647 | −10.278 | 29.142 | 1 | 22.33 | C |
| ATOM 2389 | N | LYS | A | 324 | −4.293 | −12.148 | 32.318 | 1 | 20.37 | N |
| ATOM 2390 | CA | LYS | A | 324 | −3.714 | −12.388 | 33.633 | 1 | 21.75 | C |
| ATOM 2391 | C | LYS | A | 324 | −2.276 | −11.873 | 33.672 | 1 | 17.94 | C |
| ATOM 2392 | O | LYS | A | 324 | −1.898 | −11.155 | 34.594 | 1 | 24.29 | O |
| ATOM 2393 | CB | LYS | A | 324 | −3.712 | −13.878 | 33.971 | 1 | 16.78 | C |
| ATOM 2394 | CG | LYS | A | 324 | −3.334 | −14.158 | 35.426 | 1 | 23.05 | C |
| ATOM 2395 | CD | LYS | A | 324 | −3.133 | −15.641 | 35.693 | 1 | 21.25 | C |
| ATOM 2396 | CE | LYS | A | 324 | −1.812 | −16.134 | 35.114 | 1 | 22.88 | C |
| ATOM 2397 | NZ | LYS | A | 324 | −1.696 | −17.615 | 35.186 | 1 | 24.43 | N |
| ATOM 2398 | N | TRP | A | 325 | −1.475 | −12.247 | 32.676 | 1 | 21.03 | N |
| ATOM 2399 | CA | TRP | A | 325 | −0.087 | −11.798 | 32.621 | 1 | 15.72 | C |
| ATOM 2400 | C | TRP | A | 325 | −0.008 | −10.276 | 32.563 | 1 | 22.04 | C |
| ATOM 2401 | O | TRP | A | 325 | 0.864 | −9.665 | 33.185 | 1 | 21.55 | O |
| ATOM 2402 | CD | TRP | A | 325 | 0.633 | −12.389 | 31.401 | 1 | 22.16 | C |
| ATOM 2403 | CG | TRP | A | 325 | 0.989 | −13.841 | 31.548 | 1 | 22 | C |
| ATOM 2404 | CD1 | TRP | A | 325 | 0.8 | −14.624 | 32.651 | 1 | 23.23 | C |
| ATOM 2405 | CD2 | TRP | A | 325 | 1.6 | −14.682 | 30.56 | 1 | 19.87 | C |
| ATOM 2406 | NE1 | TRP | A | 325 | 1.254 | −15.899 | 32.413 | 1 | 26.06 | N |
| ATOM 2407 | CE2 | TRP | A | 325 | 1.75 | −15.963 | 31.137 | 1 | 28.16 | C |
| ATOM 2408 | CE3 | TRP | A | 325 | 2.036 | −14.477 | 29.245 | 1 | 28.68 | C |
| ATOM 2409 | CZ2 | TRP | A | 325 | 2.318 | −17.038 | 30.443 | 1 | 23.79 | C |
| ATOM 2410 | CZ3 | TRP | A | 325 | 2.601 | −15.545 | 28.554 | 1 | 26.91 | C |
| ATOM 2411 | CH2 | TRP | A | 325 | 2.736 | −16.809 | 29.157 | 1 | 24.58 | C |
| ATOM 2412 | N | ASP | A | 326 | −0.921 | −9.663 | 31.815 | 1 | 21.98 | N |
| ATOM 2413 | CA | ASP | A | 326 | −0.935 | −8.212 | 31.687 | 1 | 22.42 | C |
| ATOM 2414 | C | ASP | A | 326 | −1.204 | −7.574 | 33.046 | 1 | 20.9 | C |
| ATOM 2415 | O | ASP | A | 326 | −0.587 | −6.566 | 33.397 | 1 | 21.68 | O |
| ATOM 2416 | CB | ASP | A | 326 | −2.012 | −7.767 | 30.696 | 1 | 20.84 | C |
| ATOM 2417 | CG | ASP | A | 326 | −1.93 | −6.287 | 30.372 | 1 | 24.01 | C |
| ATOM 2418 | OD1 | ASP | A | 326 | −2.995 | −5.65 | 30.229 | 1 | 24.01 | O |
| ATOM 2419 | OD2 | ASP | A | 326 | −0.8 | −5.763 | 30.248 | 1 | 25.81 | O |
| ATOM 2420 | N | LEU | A | 327 | −2.131 | −8.157 | 33.801 | 1 | 22.57 | N |
| ATOM 2421 | CA | LEU | A | 327 | −2.472 | −7.638 | 35.119 | 1 | 17.48 | C |
| ATOM 2422 | C | LEU | A | 327 | −1.316 | −7.851 | 36.092 | 1 | 22.53 | C |
| ATOM 2423 | O | LEU | A | 327 | −1.219 | −7.169 | 37.112 | 1 | 24.63 | O |
| ATOM 2424 | CB | LEU | A | 327 | −3.742 | −8.316 | 35.639 | 1 | 24.96 | C |
| ATOM 2425 | CG | LEU | A | 327 | −5.012 | −8.018 | 34.832 | 1 | 24.04 | C |
| ATOM 2426 | CD1 | LEU | A | 327 | −6.151 | −8.897 | 35.325 | 1 | 25.54 | C |
| ATOM 2427 | CD2 | LEU | A | 327 | −5.375 | −6.544 | 34.954 | 1 | 28.36 | C |
| ATOM 2428 | N | GLU | A | 328 | −0.438 | −8.795 | 35.764 | 1 | 24.13 | N |
| ATOM 2429 | CA | GLU | A | 328 | 0.728 | −9.08 | 36.592 | 1 | 22.33 | C |
| ATOM 2430 | C | GLU | A | 328 | 1.958 | −8.377 | 36.012 | 1 | 22.48 | C |
| ATOM 2431 | O | GLU | A | 328 | 3.089 | −8.638 | 36.425 | 1 | 25.73 | O |
| ATOM 2432 | CB | GLU | A | 328 | 0.968 | −10.592 | 36.668 | 1 | 25.14 | C |
| ATOM 2433 | CG | GLU | A | 328 | −0.221 | −11.369 | 37.224 | 1 | 24.97 | C |
| ATOM 2434 | CD | GLU | A | 328 | 0.003 | −12.871 | 37.238 | 1 | 26.46 | C |
| ATOM 2435 | OE1 | GLU | A | 328 | 0.686 | −13.38 | 36.324 | 1 | 29.67 | O |
| ATOM 2436 | OE2 | GLU | A | 328 | −0.52 | −13.545 | 38.15 | 1 | 27.74 | O |
| ATOM 2437 | N | ASP | A | 329 | 1.724 | −7.485 | 35.052 | 1 | 24.38 | N |
| ATOM 2438 | CA | ASP | A | 329 | 2.789 | −6.721 | 34.401 | 1 | 23.21 | C |
| ATOM 2439 | C | ASP | A | 329 | 3.883 | −7.593 | 33.781 | 1 | 26.1 | C |
| ATOM 2440 | O | ASP | A | 329 | 5.07 | −7.253 | 33.81 | 1 | 26.61 | O |
| ATOM 2441 | CB | ASP | A | 329 | 3.395 | −5.727 | 35.398 | 1 | 30.2 | C |
| ATOM 2442 | CG | ASP | A | 329 | 2.442 | −4.588 | 35.732 | 1 | 32.53 | C |
| ATOM 2443 | OD1 | ASP | A | 329 | 2.656 | −3.904 | 36.754 | 1 | 39.92 | O |
| ATOM 2444 | OD2 | ASP | A | 329 | 1.481 | −4.369 | 34.964 | 1 | 31.99 | O |
| ATOM 2445 | N | LYS | A | 330 | 3.466 | −8.72 | 33.213 | 1 | 24.44 | N |
| ATOM 2446 | CA | LYS | A | 330 | 4.378 | −9.649 | 32.553 | 1 | 26.77 | C |
| ATOM 2447 | C | LYS | A | 330 | 4.243 | −9.453 | 31.052 | 1 | 29.98 | C |
| ATOM 2448 | O | LYS | A | 330 | 3.197 | −9.02 | 30.57 | 1 | 26.9 | O |
| ATOM 2449 | CB | LYS | A | 330 | 4.023 | −11.095 | 32.906 | 1 | 28.35 | C |
| ATOM 2450 | CG | LYS | A | 330 | 4.238 | −11.451 | 34.365 | 1 | 33.36 | C |
| ATOM 2451 | CD | LYS | A | 330 | 3.877 | −12.901 | 34.645 | 1 | 38.4 | C |
| ATOM 2452 | CE | LYS | A | 330 | 4.116 | −13.247 | 36.105 | 1 | 37.54 | C |
| ATOM 2453 | NZ | LYS | A | 330 | 3.733 | −14.648 | 36.429 | 1 | 44.84 | N |
| ATOM 2454 | N | PRO | A | 331 | 5.302 | −9.757 | 30.29 | 1 | 25.27 | N |
| ATOM 2455 | CA | PRO | A | 331 | 5.216 | −9.588 | 28.839 | 1 | 26 | C |
| ATOM 2456 | C | PRO | A | 331 | 4.238 | −10.59 | 28.227 | 1 | 16.46 | C |
| ATOM 2457 | O | PRO | A | 331 | 4.168 | −11.741 | 28.654 | 1 | 20.69 | O |
| ATOM 2458 | CB | PRO | A | 331 | 6.657 | −9.813 | 28.383 | 1 | 28.32 | C |
| ATOM 2459 | CG | PRO | A | 331 | 7.176 | −10.787 | 29.388 | 1 | 32.63 | C |
| ATOM 2460 | CD | PRO | A | 331 | 6.639 | −10.234 | 30.688 | 1 | 29.35 | C |

TABLE 1-continued

Atomic structural coordinates for LuxP

| | ATOM TYPE | RESID | | NO | X | Y | Z | OCC | |
|---|---|---|---|---|---|---|---|---|---|
| ATOM 2461 | N | VAL | A | 332 | 3.493 | −10.139 | 27.225 | 1 | 22.56 N |
| ATOM 2462 | CA | VAL | A | 332 | 2.514 | −10.986 | 26.553 | 1 | 19.35 C |
| ATOM 2463 | C | VAL | A | 332 | 2.856 | −11.107 | 25.071 | 1 | 19.95 C |
| ATOM 2464 | O | VAL | A | 332 | 3.146 | −10.112 | 24.414 | 1 | 19.33 O |
| ATOM 2465 | CB | VAL | A | 332 | 1.091 | −10.392 | 26.701 | 1 | 22.7 C |
| ATOM 2466 | CG1 | VAL | A | 332 | 0.085 | −11.224 | 25.912 | 1 | 22.2 C |
| ATOM 2467 | CG2 | VAL | A | 332 | 0.706 | −10.34 | 28.171 | 1 | 20.62 C |
| ATOM 2468 | N | PRO | A | 333 | 2.828 | −12.336 | 24.521 | 1 | 15.23 N |
| ATOM 2469 | CA | PRO | A | 333 | 3.147 | −12.51 | 23.102 | 1 | 16.9 C |
| ATOM 2470 | C | PRO | A | 333 | 2.175 | −11.765 | 22.203 | 1 | 16.52 C |
| ATOM 2471 | O | PRO | A | 333 | 0.993 | −11.618 | 22.532 | 1 | 19.97 O |
| ATOM 2472 | CB | PRO | A | 333 | 3.058 | −14.022 | 22.91 | 1 | 15.91 C |
| ATOM 2473 | CG | PRO | A | 333 | 2.006 | −14.426 | 23.919 | 1 | 17.23 C |
| ATOM 2474 | CD | PRO | A | 333 | 2.409 | −13.612 | 25.128 | 1 | 19.34 C |
| ATOM 2475 | N | THR | A | 334 | 2.672 | −11.289 | 21.069 | 1 | 18.7 N |
| ATOM 2476 | CA | THR | A | 334 | 1.832 | −10.579 | 20.124 | 1 | 19.05 C |
| ATOM 2477 | C | THR | A | 334 | 0.87 | −11.549 | 19.441 | 1 | 18.65 C |
| ATOM 2478 | O | THR | A | 334 | −0.224 | −11.164 | 19.032 | 1 | 18.25 O |
| ATOM 2479 | CB | THR | A | 334 | 2.682 | −9.866 | 19.043 | 1 | 19.04 C |
| ATOM 2480 | OG1 | THR | A | 334 | 3.459 | −8.834 | 19.661 | 1 | 21.77 O |
| ATOM 2481 | CG2 | THR | A | 334 | 1.795 | −9.248 | 17.967 | 1 | 21.88 C |
| ATOM 2482 | N | VAL | A | 335 | 1.27 | −12.811 | 19.317 | 1 | 16.28 N |
| ATOM 2483 | CA | VAL | A | 335 | 0.402 | −13.773 | 18.657 | 1 | 17.39 C |
| ATOM 2484 | C | VAL | A | 335 | 0.342 | −15.146 | 19.315 | 1 | 13.24 C |
| ATOM 2485 | O | VAL | A | 335 | 1.259 | −15.56 | 20.026 | 1 | 17.88 O |
| ATOM 2486 | CB | VAL | A | 335 | 0.807 | −13.946 | 17.166 | 1 | 22.58 C |
| ATOM 2487 | CG1 | VAL | A | 335 | 2.129 | −14.705 | 17.063 | 1 | 20.58 C |
| ATOM 2488 | CG2 | VAL | A | 335 | −0.302 | −14.654 | 16.402 | 1 | 28.01 C |
| ATOM 2489 | N | TYR | A | 336 | −0.778 | −15.832 | 19.095 | 1 | 14.71 N |
| ATOM 2490 | CA | TYR | A | 336 | −0.984 | −17.185 | 19.608 | 1 | 16.06 C |
| ATOM 2491 | C | TYR | A | 336 | −1.949 | −17.951 | 18.716 | 1 | 14.29 C |
| ATOM 2492 | O | TYR | A | 336 | −3.06 | −17.494 | 18.469 | 1 | 16.39 O |
| ATOM 2493 | CB | TYR | A | 336 | −1.573 | −17.184 | 21.022 | 1 | 18.34 C |
| ATOM 2494 | CG | TYR | A | 336 | −1.998 | −18.57 | 21.479 | 1 | 18.81 C |
| ATOM 2495 | CD1 | TYR | A | 336 | −1.072 | −19.469 | 22.005 | 1 | 19.56 C |
| ATOM 2496 | CD2 | TYR | A | 336 | −3.32 | −18.999 | 21.343 | 1 | 18.86 C |
| ATOM 2497 | CE1 | TYR | A | 336 | −1.449 | −20.761 | 22.384 | 1 | 22.04 C |
| ATOM 2498 | CE2 | TYR | A | 336 | −3.709 | −20.292 | 21.72 | 1 | 19.67 C |
| ATOM 2499 | CZ | TYR | A | 336 | −2.77 | −21.164 | 22.239 | 1 | 19.58 C |
| ATOM 2500 | OH | TYR | A | 336 | −3.154 | −22.435 | 22.619 | 1 | 19.69 O |
| ATOM 2501 | N | SER | A | 337 | −1.517 | −19.113 | 18.235 | 1 | 17.55 N |
| ATOM 2502 | CA | SER | A | 337 | −2.372 | −19.963 | 17.415 | 1 | 13.86 C |
| ATOM 2503 | C | SER | A | 337 | −2.543 | −21.311 | 18.091 | 1 | 17.89 C |
| ATOM 2504 | O | SER | A | 337 | −1.561 | −21.915 | 18.542 | 1 | 17.52 O |
| ATOM 2505 | CB | SER | A | 337 | −1.78 | −20.206 | 16.033 | 1 | 15.11 C |
| ATOM 2506 | OG | SER | A | 337 | −2.591 | −21.144 | 15.326 | 1 | 16.31 O |
| ATOM 2507 | N | GLY | A | 338 | −3.786 | −21.78 | 18.15 | 1 | 13.98 N |
| ATOM 2508 | CA | GLY | A | 338 | −4.067 | −23.072 | 18.749 | 1 | 14.28 C |
| ATOM 2509 | C | GLY | A | 338 | −3.785 | −24.122 | 17.695 | 1 | 14.97 C |
| ATOM 2510 | O | GLY | A | 338 | −3.432 | −23.78 | 16.564 | 1 | 17.62 O |
| ATOM 2511 | N | ASP | A | 339 | −3.942 | −25.394 | 18.048 | 1 | 18.19 N |
| ATOM 2512 | CA | ASP | A | 339 | −3.682 | −26.464 | 17.097 | 1 | 21.09 C |
| ATOM 2513 | C | ASP | A | 339 | −4.929 | −27.114 | 16.52 | 1 | 13.8 C |
| ATOM 2514 | O | ASP | A | 339 | −6.047 | −26.916 | 17.027 | 1 | 16.42 O |
| ATOM 2515 | CB | ASP | A | 339 | −2.796 | −27.531 | 17.734 | 1 | 28.38 C |
| ATOM 2516 | CG | ASP | A | 339 | −1.432 | −26.993 | 18.115 | 1 | 34.82 C |
| ATOM 2517 | OD1 | ASP | A | 339 | −0.775 | −26.373 | 17.249 | 1 | 36.87 O |
| ATOM 2518 | OD2 | ASP | A | 339 | −1.019 | −27.194 | 19.275 | 1 | 33.01 O |
| ATOM 2519 | N | PHE | A | 340 | −4.704 | −27.881 | 15.451 | 1 | 17.85 N |
| ATOM 2520 | CA | PHE | A | 340 | −5.755 | −28.592 | 14.724 | 1 | 17.19 C |
| ATOM 2521 | C | PHE | A | 340 | −5.561 | −30.097 | 14.707 | 1 | 20.73 C |
| ATOM 2522 | O | PHE | A | 340 | −4.471 | −30.614 | 14.96 | 1 | 21.84 O |
| ATOM 2523 | CB | PHE | A | 340 | −5.795 | −28.203 | 13.245 | 1 | 17.83 C |
| ATOM 2524 | CG | PHE | A | 340 | −5.973 | −26.743 | 12.977 | 1 | 15.76 C |
| ATOM 2525 | CD1 | PHE | A | 340 | −4.871 | −25.905 | 12.835 | 1 | 18.8 C |
| ATOM 2526 | CD2 | PHE | A | 340 | −7.25 | −26.222 | 12.778 | 1 | 14.43 C |
| ATOM 2527 | CE1 | PHE | A | 340 | −5.039 | −24.562 | 12.487 | 1 | 20.03 C |
| ATOM 2528 | CE2 | PHE | A | 340 | −7.429 | −24.886 | 12.431 | 1 | 16.22 C |
| ATOM 2529 | CZ | PHE | A | 340 | −6.324 | −24.057 | 12.284 | 1 | 17.43 C |
| ATOM 2530 | N | GLU | A | 341 | −6.634 | −30.778 | 14.322 | 1 | 19.75 N |
| ATOM 2531 | CA | GLU | A | 341 | −6.654 | −32.222 | 14.169 | 1 | 20.31 C |
| ATOM 2532 | C | GLU | A | 341 | −7.556 | −32.485 | 12.968 | 1 | 19.31 C |
| ATOM 2533 | O | GLU | A | 341 | −8.671 | −31.951 | 12.899 | 1 | 21.46 O |
| ATOM 2534 | CB | GLU | A | 341 | −7.24 | −32.894 | 15.41 | 1 | 26.22 C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 2535 | CG | GLU | A | 341 | −6.332 | −32.86 | 16.623 | 1 | 28.13 | C |
| ATOM 2536 | CD | GLU | A | 341 | −5.212 | −33.881 | 16.545 | 1 | 36.79 | C |
| ATOM 2537 | OE1 | GLU | A | 341 | −4.506 | −33.921 | 15.516 | 1 | 43.25 | O |
| ATOM 2538 | OE2 | GLU | A | 341 | −5.034 | −34.64 | 17.52 | 1 | 46.25 | O |
| ATOM 2539 | N | ILE | A | 342 | −7.07 | −33.266 | 12.008 | 1 | 21.27 | N |
| ATOM 2540 | CA | ILE | A | 342 | −7.874 | −33.597 | 10.837 | 1 | 18.31 | C |
| ATOM 2541 | C | ILE | A | 342 | −8.894 | −34.644 | 11.266 | 1 | 22.04 | C |
| ATOM 2542 | O | ILE | A | 342 | −8.564 | −35.588 | 11.984 | 1 | 24.41 | O |
| ATOM 2543 | CB | ILE | A | 342 | −7.009 | −34.166 | 9.677 | 1 | 20.03 | C |
| ATOM 2544 | CG1 | ILE | A | 342 | −6.227 | −33.036 | 9 | 1 | 21.49 | C |
| ATOM 2545 | CG2 | ILE | A | 342 | −7.89 | −34.892 | 8.665 | 1 | 23 | C |
| ATOM 2546 | CD1 | ILE | A | 342 | −7.094 | −32.043 | 8.234 | 1 | 25.41 | C |
| ATOM 2547 | N | VAL | A | 343 | −10.137 | −34.465 | 10.835 | 1 | 17.79 | N |
| ATOM 2548 | CA | VAL | A | 343 | −11.215 | −35.386 | 11.175 | 1 | 17.92 | C |
| ATOM 2549 | C | VAL | A | 343 | −11.938 | −35.786 | 9.896 | 1 | 23.17 | C |
| ATOM 2550 | O | VAL | A | 343 | −12.212 | −34.944 | 9.039 | 1 | 19.54 | O |
| ATOM 2551 | CB | VAL | A | 343 | −12.221 | −34.725 | 12.149 | 1 | 19.61 | C |
| ATOM 2552 | CG1 | VAL | A | 343 | −13.436 | −35.615 | 12.339 | 1 | 26.53 | C |
| ATOM 2553 | CG2 | VAL | A | 343 | −11.547 | −34.463 | 13.49 | 1 | 22.28 | C |
| ATOM 2554 | N | THR | A | 344 | −12.234 | −37.075 | 9.757 | 1 | 21.25 | N |
| ATOM 2555 | CA | THR | A | 344 | −12.928 | −37.554 | 8.567 | 1 | 19.51 | C |
| ATOM 2556 | C | THR | A | 344 | −14.135 | −38.379 | 8.973 | 1 | 21.29 | C |
| ATOM 2557 | O | THR | A | 344 | −14.287 | −38.737 | 10.144 | 1 | 22.6 | O |
| ATOM 2558 | CB | THR | A | 344 | −12.023 | −38.431 | 7.689 | 1 | 25.78 | C |
| ATOM 2559 | OG1 | THR | A | 344 | −11.885 | −39.724 | 8.294 | 1 | 28.71 | O |
| ATOM 2560 | CG2 | THR | A | 344 | −10.65 | −37.792 | 7.534 | 1 | 25.55 | C |
| ATOM 2561 | N | LYS | A | 345 | −14.992 | −38.684 | 8.005 | 1 | 20.94 | N |
| ATOM 2562 | CA | LYS | A | 345 | −16.186 | −39.467 | 8.292 | 1 | 23.86 | C |
| ATOM 2563 | C | LYS | A | 345 | −15.833 | −40.917 | 8.605 | 1 | 25.35 | C |
| ATOM 2564 | O | LYS | A | 345 | −16.673 | −41.671 | 9.097 | 1 | 27.3 | O |
| ATOM 2565 | CB | LYS | A | 345 | −17.16 | −39.413 | 7.109 | 1 | 22.57 | C |
| ATOM 2566 | CG | LYS | A | 345 | −16.572 | −39.874 | 5.786 | 1 | 21.72 | C |
| ATOM 2567 | CD | LYS | A | 345 | −17.628 | −39.883 | 4.683 | 1 | 30.4 | C |
| ATOM 2568 | CE | LYS | A | 345 | −17.035 | −40.322 | 3.352 | 1 | 30.26 | C |
| ATOM 2569 | NZ | LYS | A | 345 | −18.028 | −40.272 | 2.241 | 1 | 43.9 | N |
| ATOM 2570 | N | ALA | A | 346 | −14.588 | −41.295 | 8.326 | 1 | 24.86 | N |
| ATOM 2571 | CA | ALA | A | 346 | −14.119 | −42.657 | 8.577 | 1 | 22.39 | C |
| ATOM 2572 | C | ALA | A | 346 | −13.614 | −42.813 | 10.003 | 1 | 33.23 | C |
| ATOM 2573 | O | ALA | A | 346 | −13.333 | −43.927 | 10.45 | 1 | 29.28 | O |
| ATOM 2574 | CB | ALA | A | 346 | −13.013 | −43.022 | 7.592 | 1 | 27.32 | C |
| ATOM 2575 | N | ASP | A | 347 | −13.492 | −41.701 | 10.722 | 1 | 22.79 | N |
| ATOM 2576 | CA | ASP | A | 347 | −13.014 | −41.762 | 12.096 | 1 | 27.28 | C |
| ATOM 2577 | C | ASP | A | 347 | −14.015 | −42.454 | 13.008 | 1 | 33.28 | C |
| ATOM 2578 | O | ASP | A | 347 | −15.229 | −42.323 | 12.838 | 1 | 26.16 | O |
| ATOM 2579 | CB | ASP | A | 347 | −12.698 | −40.36 | 12.627 | 1 | 28.54 | C |
| ATOM 2580 | CG | ASP | A | 347 | −11.397 | −39.813 | 12.078 | 1 | 28.83 | C |
| ATOM 2581 | OD1 | ASP | A | 347 | −10.395 | −40.559 | 12.077 | 1 | 38.41 | O |
| ATOM 2582 | OD2 | ASP | A | 347 | −11.366 | −38.64 | 11.656 | 1 | 35.54 | O |
| ATOM 2583 | N | SER | A | 348 | −13.493 | −43.202 | 13.973 | 1 | 30.34 | N |
| ATOM 2584 | CA | SER | A | 348 | −14.334 | −43.925 | 14.914 | 1 | 28.82 | C |
| ATOM 2585 | C | SER | A | 348 | −14.961 | −42.958 | 15.904 | 1 | 27.91 | C |
| ATOM 2586 | O | SER | A | 348 | −14.44 | −41.864 | 16.13 | 1 | 34.24 | O |
| ATOM 2587 | CB | SER | A | 348 | −13.499 | −44.956 | 15.672 | 1 | 22.18 | C |
| ATOM 2588 | OG | SER | A | 348 | −12.518 | −44.31 | 16.463 | 1 | 24.48 | O |
| ATOM 2589 | N | PRO | A | 349 | −16.096 | −43.342 | 16.509 | 1 | 29.75 | N |
| ATOM 2590 | CA | PRO | A | 349 | −16.753 | −42.465 | 17.478 | 1 | 30.1 | C |
| ATOM 2591 | C | PRO | A | 349 | −15.868 | −42.199 | 18.692 | 1 | 35.85 | C |
| ATOM 2592 | O | PRO | A | 349 | −16.029 | −41.188 | 19.374 | 1 | 33.3 | O |
| ATOM 2593 | CB | PRO | A | 349 | −18.028 | −43.23 | 17.83 | 1 | 38.73 | C |
| ATOM 2594 | CG | PRO | A | 349 | −17.628 | −44.655 | 17.642 | 1 | 39.38 | C |
| ATOM 2595 | CD | PRO | A | 349 | −16.845 | −44.601 | 16.354 | 1 | 33.27 | C |
| ATOM 2596 | N | GLU | A | 350 | −14.933 | −43.107 | 18.964 | 1 | 32.02 | N |
| ATOM 2597 | CA | GLU | A | 350 | −14.03 | −42.916 | 20.09 | 1 | 36.25 | C |
| ATOM 2598 | C | GLU | A | 350 | −13.046 | −41.802 | 19.762 | 1 | 25.63 | C |
| ATOM 2599 | O | GLU | A | 350 | −12.701 | −41.002 | 20.63 | 1 | 34.68 | O |
| ATOM 2600 | CB | GLU | A | 350 | −13.269 | −44.205 | 20.42 | 1 | 34.34 | C |
| ATOM 2601 | CG | GLU | A | 350 | −14.07 | −45.204 | 21.242 | 1 | 42.41 | C |
| ATOM 2602 | CD | GLU | A | 350 | −15.148 | −45.897 | 20.437 | 1 | 44.07 | C |
| ATOM 2603 | OE1 | GLU | A | 350 | −16.024 | −46.545 | 21.048 | 1 | 43.29 | O |
| ATOM 2604 | OE2 | GLU | A | 350 | −15.113 | −45.805 | 19.193 | 1 | 46.46 | O |
| ATOM 2605 | N | ARG | A | 351 | −12.596 | −41.751 | 18.511 | 1 | 27.66 | N |
| ATOM 2606 | CA | ARG | A | 351 | −11.664 | −40.707 | 18.096 | 1 | 19.2 | C |
| ATOM 2607 | C | ARG | A | 351 | −12.357 | −39.35 | 18.165 | 1 | 26.27 | C |
| ATOM 2608 | O | ARG | A | 351 | −11.752 | −38.367 | 18.581 | 1 | 23.92 | O |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 2609 | CB | ARG | A | 351 | −11.152 | −40.963 | 16.675 | 1 | 28.4 | C |
| ATOM 2610 | CG | ARG | A | 351 | −10.293 | −39.833 | 16.113 | 1 | 31.87 | C |
| ATOM 2611 | CD | ARG | A | 351 | −9.13 | −39.5 | 17.037 | 1 | 42.42 | C |
| ATOM 2612 | NE | ARG | A | 351 | −8.38 | −38.333 | 16.579 | 1 | 43.93 | N |
| ATOM 2613 | CZ | ARG | A | 351 | −7.712 | −38.276 | 15.432 | 1 | 44.56 | C |
| ATOM 2614 | NH1 | ARG | A | 351 | −7.693 | −39.323 | 14.619 | 1 | 54.96 | N |
| ATOM 2615 | NH2 | ARG | A | 351 | −7.067 | −37.169 | 15.091 | 1 | 49.45 | N |
| ATOM 2616 | N | ILE | A | 352 | −13.629 | −39.308 | 17.772 | 1 | 24.83 | N |
| ATOM 2617 | CA | ILE | A | 352 | −14.401 | −38.067 | 17.792 | 1 | 22.54 | C |
| ATOM 2618 | C | ILE | A | 352 | −14.653 | −37.616 | 19.221 | 1 | 24.31 | C |
| ATOM 2619 | O | ILE | A | 352 | −14.504 | −36.436 | 19.551 | 1 | 25.64 | O |
| ATOM 2620 | CB | ILE | A | 352 | −15.775 | −38.232 | 17.088 | 1 | 22.74 | C |
| ATOM 2621 | CG1 | ILE | A | 352 | −15.576 | −38.642 | 15.626 | 1 | 30.42 | C |
| ATOM 2622 | CG2 | ILE | A | 352 | −16.572 | −36.931 | 17.179 | 1 | 23.14 | C |
| ATOM 2623 | CD1 | ILE | A | 352 | −14.832 | −37.624 | 14.787 | 1 | 27.22 | C |
| ATOM 2624 | N | GLU | A | 353 | −15.043 | −38.557 | 20.074 | 1 | 26.88 | N |
| ATOM 2625 | CA | GLU | A | 353 | −15.316 | −38.236 | 21.465 | 1 | 22.82 | C |
| ATOM 2626 | C | GLU | A | 353 | −14.041 | −37.758 | 22.16 | 1 | 21.89 | C |
| ATOM 2627 | O | GLU | A | 353 | −14.075 | −36.825 | 22.963 | 1 | 24.79 | O |
| ATOM 2628 | CB | GLU | A | 353 | −15.883 | −39.457 | 22.188 | 1 | 31.83 | C |
| ATOM 2629 | CG | GLU | A | 353 | −16.31 | −39.186 | 23.621 | 1 | 33.4 | C |
| ATOM 2630 | CD | GLU | A | 353 | −17.276 | −38.019 | 23.735 | 1 | 47.73 | C |
| ATOM 2631 | OE1 | GLU | A | 353 | −18.25 | −37.965 | 22.953 | 1 | 46.82 | O |
| ATOM 2632 | OE2 | GLU | A | 353 | −17.067 | −37.157 | 24.615 | 1 | 50.19 | O |
| ATOM 2633 | N | ALA | A | 354 | −12.919 | −38.394 | 21.837 | 1 | 23.53 | N |
| ATOM 2634 | CA | ALA | A | 354 | −11.642 | −38.02 | 22.427 | 1 | 28.77 | C |
| ATOM 2635 | C | ALA | A | 354 | −11.293 | −36.585 | 22.033 | 1 | 24.63 | C |
| ATOM 2636 | O | ALA | A | 354 | −10.808 | −35.809 | 22.856 | 1 | 25.43 | O |
| ATOM 2637 | CB | ALA | A | 354 | −10.547 | −38.975 | 21.962 | 1 | 32.14 | C |
| ATOM 2638 | N | LEU | A | 355 | −11.546 | −36.233 | 20.775 | 1 | 22.99 | N |
| ATOM 2639 | CA | LEU | A | 355 | −11.25 | −34.884 | 20.302 | 1 | 19.64 | C |
| ATOM 2640 | C | LEU | A | 355 | −12.164 | −33.847 | 20.954 | 1 | 21.12 | C |
| ATOM 2641 | O | LEU | A | 355 | −11.722 | −32.746 | 21.291 | 1 | 21.15 | O |
| ATOM 2642 | CB | LEU | A | 355 | −11.359 | −34.825 | 18.774 | 1 | 22.21 | C |
| ATOM 2643 | CG | LEU | A | 355 | −10.259 | −35.597 | 18.036 | 1 | 21.93 | C |
| ATOM 2644 | CD1 | LEU | A | 355 | −10.514 | −35.592 | 16.537 | 1 | 29.24 | C |
| ATOM 2645 | CD2 | LEU | A | 355 | −8.905 | −34.971 | 18.353 | 1 | 29.69 | C |
| ATOM 2646 | N | LYS | A | 356 | −13.433 | −34.189 | 21.147 | 1 | 21.08 | N |
| ATOM 2647 | CA | LYS | A | 356 | −14.369 | −33.262 | 21.78 | 1 | 17.35 | C |
| ATOM 2648 | C | LYS | A | 356 | −13.961 | −33.01 | 23.226 | 1 | 24.94 | C |
| ATOM 2649 | O | LYS | A | 356 | −14.16 | −31.918 | 23.768 | 1 | 21.19 | O |
| ATOM 2650 | CD | LYS | A | 356 | −15.791 | −33.823 | 21.758 | 1 | 21.09 | C |
| ATOM 2651 | CG | LYS | A | 356 | −16.464 | −33.824 | 20.399 | 1 | 20.97 | C |
| ATOM 2652 | CD | LYS | A | 356 | −17.873 | −34.376 | 20.538 | 1 | 26.46 | C |
| ATOM 2653 | CE | LYS | A | 356 | −18.611 | −34.455 | 19.211 | 1 | 24.1 | C |
| ATOM 2654 | NZ | LYS | A | 356 | −19.936 | −35.121 | 19.404 | 1 | 23.45 | N |
| ATOM 2655 | N | LYS | A | 357 | −13.389 | −34.032 | 23.852 | 1 | 24.65 | N |
| ATOM 2656 | CA | LYS | A | 357 | −12.963 | −33.908 | 25.234 | 1 | 30.51 | C |
| ATOM 2657 | C | LYS | A | 357 | −11.846 | −32.878 | 25.335 | 1 | 20.54 | C |
| ATOM 2658 | O | LYS | A | 357 | −11.781 | −32.116 | 26.297 | 1 | 27.16 | O |
| ATOM 2659 | CD | LYS | A | 357 | −12.488 | −35.264 | 25.762 | 1 | 33.52 | C |
| ATOM 2660 | CG | LYS | A | 357 | −13.071 | −35.614 | 27.118 | 1 | 45.63 | C |
| ATOM 2661 | CD | LYS | A | 357 | −14.593 | −35.616 | 27.067 | 1 | 42.28 | C |
| ATOM 2662 | CE | LYS | A | 357 | −15.196 | −35.87 | 28.437 | 1 | 52.76 | C |
| ATOM 2663 | NZ | LYS | A | 357 | −16.686 | −35.815 | 28.402 | 1 | 51.1 | N |
| ATOM 2664 | N | ARG | A | 358 | −10.977 | −32.863 | 24.33 | 1 | 20.99 | N |
| ATOM 2665 | CA | ARG | A | 358 | −9.863 | −31.921 | 24.281 | 1 | 23.3 | C |
| ATOM 2666 | C | ARG | A | 358 | −10.332 | −30.526 | 23.854 | 1 | 28.01 | C |
| ATOM 2667 | O | ARG | A | 358 | −10.058 | −29.535 | 24.527 | 1 | 19.37 | O |
| ATOM 2668 | CD | ARG | A | 358 | −8.804 | −32.421 | 23.296 | 1 | 30.22 | C |
| ATOM 2669 | CC | ARG | A | 358 | −7.526 | −32.956 | 23.93 | 1 | 46.04 | C |
| ATOM 2670 | CD | ARG | A | 358 | −6.361 | −32.006 | 23.665 | 1 | 47.89 | C |
| ATOM 2671 | NE | ARG | A | 358 | −6.486 | −30.757 | 24.412 | 1 | 53.03 | N |
| ATOM 2672 | CZ | ARG | A | 358 | −6.041 | −29.58 | 23.982 | 1 | 53.78 | C |
| ATOM 2673 | NH1 | ARG | A | 358 | −5.443 | −29.486 | 22.802 | 1 | 50.08 | N |
| ATOM 2674 | NH2 | ARG | A | 358 | −6.191 | −28.496 | 24.734 | 1 | 41.44 | N |
| ATOM 2675 | N | ALA | A | 359 | −11.058 | −30.464 | 22.74 | 1 | 21.36 | N |
| ATOM 2676 | CA | ALA | A | 359 | −11.538 | −29.198 | 22.182 | 1 | 19.29 | C |
| ATOM 2677 | C | ALA | A | 359 | −12.552 | −28.401 | 22.997 | 1 | 17.81 | C |
| ATOM 2678 | O | ALA | A | 359 | −12.47 | −27.18 | 23.062 | 1 | 19.12 | O |
| ATOM 2679 | CB | ALA | A | 359 | −12.096 | −29.445 | 20.777 | 1 | 18.72 | C |
| ATOM 2680 | N | PHE | A | 360 | −13.52 | −29.075 | 23.613 | 1 | 19.35 | N |
| ATOM 2681 | CA | PHE | A | 360 | −14.539 | −28.365 | 24.382 | 1 | 17.52 | C |
| ATOM 2682 | C | PHE | A | 360 | −14.465 | −28.633 | 25.882 | 1 | 23.4 | C |

TABLE 1-continued

Atomic structural coordinates for LuxP

| | ATOM TYPE | RESID | | NO | X | Y | Z | OCC | | |
|---|---|---|---|---|---|---|---|---|---|---|
| ATOM 2683 | O | PHE | A | 360 | −15.485 | −28.65 | 26.568 | 1 | 18.82 | O |
| ATOM 2684 | CB | PHE | A | 360 | −15.941 | −28.74 | 23.881 | 1 | 21.28 | C |
| ATOM 2685 | CG | PHE | A | 360 | −16.066 | −28.796 | 22.381 | 1 | 20.12 | C |
| ATOM 2686 | CD1 | PHE | A | 360 | −15.51 | −27.802 | 21.58 | 1 | 22.9 | C |
| ATOM 2687 | CD2 | PHE | A | 360 | −16.757 | −29.837 | 21.769 | 1 | 20.57 | C |
| ATOM 2688 | CE1 | PHE | A | 360 | −15.64 | −27.846 | 20.191 | 1 | 16.44 | C |
| ATOM 2689 | CE2 | PHE | A | 360 | −16.893 | −29.886 | 20.381 | 1 | 20.06 | C |
| ATOM 2690 | CZ | PHE | A | 360 | −16.329 | −28.884 | 19.592 | 1 | 18.58 | C |
| ATOM 2691 | N | ARG | A | 361 | −13.258 | −28.833 | 26.394 | 1 | 19.92 | N |
| ATOM 2692 | CA | ARG | A | 361 | −13.09 | −29.097 | 27.822 | 1 | 20.13 | C |
| ATOM 2693 | C | ARG | A | 361 | −13.792 | −28.075 | 28.72 | 1 | 22.77 | C |
| ATOM 2694 | O | ARG | A | 361 | −14.269 | −28.413 | 29.808 | 1 | 26.04 | O |
| ATOM 2695 | CB | ARG | A | 361 | −11.601 | −29.159 | 28.167 | 1 | 25.3 | C |
| ATOM 2696 | CG | ARG | A | 361 | −10.772 | −28.007 | 27.616 | 1 | 28.29 | C |
| ATOM 2697 | CD | ARG | A | 361 | −9.385 | −28.027 | 28.218 | 1 | 29.59 | C |
| ATOM 2698 | NE | ARG | A | 361 | −8.456 | −27.131 | 27.539 | 1 | 30.51 | N |
| ATOM 2699 | CZ | ARG | A | 361 | −7.33 | −26.689 | 28.088 | 1 | 37.53 | C |
| ATOM 2700 | NH1 | ARG | A | 361 | −7.011 | −27.061 | 29.321 | 1 | 27.67 | N |
| ATOM 2701 | NH2 | ARG | A | 361 | −6.523 | −25.887 | 27.408 | 1 | 28.47 | N |
| ATOM 2702 | N | TYR | A | 362 | −13.861 | −26.827 | 28.264 | 1 | 24.18 | N |
| ATOM 2703 | CA | TYR | A | 362 | −14.493 | −25.752 | 29.029 | 1 | 17.05 | C |
| ATOM 2704 | C | TYR | A | 362 | −15.882 | −25.347 | 28.534 | 1 | 23.46 | C |
| ATOM 2705 | O | TYR | A | 362 | −16.789 | −25.095 | 29.334 | 1 | 21.48 | O |
| ATOM 2706 | CB | TYR | A | 362 | −13.607 | −24.504 | 29.003 | 1 | 20.57 | C |
| ATOM 2707 | CG | TYR | A | 362 | −12.529 | −24.438 | 30.066 | 1 | 23.89 | C |
| ATOM 2708 | CD1 | TYR | A | 362 | −11.913 | −25.59 | 30.545 | 1 | 22.14 | C |
| ATOM 2709 | CD2 | TYR | A | 362 | −12.097 | −23.207 | 30.556 | 1 | 23.91 | C |
| ATOM 2710 | CE1 | TYR | A | 362 | −10.89 | −25.518 | 31.488 | 1 | 27.1 | C |
| ATOM 2711 | CE2 | TYR | A | 362 | −11.074 | −23.121 | 31.495 | 1 | 23.92 | C |
| ATOM 2712 | CZ | TYR | A | 362 | −10.476 | −24.281 | 31.955 | 1 | 20.01 | C |
| ATOM 2713 | OH | TYR | A | 362 | −9.45 | −24.2 | 32.865 | 1 | 18.84 | O |
| ATOM 2714 | N | SER | A | 363 | −16.037 | −25.263 | 27.215 | 1 | 21.26 | N |
| ATOM 2715 | CA | SER | A | 363 | −17.298 | −24.842 | 26.618 | 1 | 20.33 | C |
| ATOM 2716 | C | SER | A | 363 | −18.393 | −25.908 | 26.63 | 1 | 16.94 | C |
| ATOM 2717 | O | SER | A | 363 | −19.564 | −25.589 | 26.43 | 1 | 21.73 | O |
| ATOM 2718 | CB | SER | A | 363 | −17.057 | −24.325 | 25.181 | 1 | 13.91 | C |
| ATOM 2719 | OG | SER | A | 363 | −16.41 | −25.283 | 24.364 | 1 | 17.11 | O |
| ATOM 2720 | N | ASP | A | 364 | −17.997 | −27.158 | 26.873 | 1 | 22.18 | N |
| ATOM 2721 | CA | ASP | A | 364 | −18.913 | −28.304 | 26.941 | 1 | 25 | C |
| ATOM 2722 | C | ASP | A | 364 | −19.24 | −28.942 | 25.593 | 1 | 40.26 | C |
| ATOM 2723 | O | ASP | A | 364 | −19.988 | −28.39 | 24.787 | 1 | 30.26 | O |
| ATOM 2724 | CB | ASP | A | 364 | −20.208 | −27.906 | 27.662 | 1 | 44.3 | C |
| ATOM 2725 | CG | ASP | A | 364 | −20.287 | −28.465 | 29.072 | 1 | 48.83 | C |
| ATOM 2726 | OD1 | ASP | A | 364 | −21.052 | −27.916 | 29.893 | 1 | 57.71 | O |
| ATOM 2727 | OD2 | ASP | A | 364 | −19.591 | −29.464 | 29.353 | 1 | 58.06 | O |
| TER 2728 | | ASP | A | 364 | | | | | | |
| HETATM 2729 | CA | CA | A | 401 | −0.216 | 4.628 | 14.948 | 1 | 50.08 | CA |
| HETATM 2730 | O1 | AI2 | | 400 | −16.596 | −19.949 | 10.433 | 1 | 11.97 | O |
| HETATM 2731 | B2 | AI2 | | 400 | −15.677 | −20.978 | 10.735 | 1 | 13.76 | B |
| HETATM 2732 | O9 | AI2 | | 400 | −16.204 | −21.932 | 11.778 | 1 | 12.65 | O |
| HETATM 2733 | O10 | AI2 | | 400 | −15.374 | −21.705 | 9.501 | 1 | 9.59 | O |
| HETATM 2734 | O3 | AI2 | | 400 | −14.482 | −20.302 | 11.367 | 1 | 10.8 | O |
| HETATM 273S | C4 | AI2 | | 400 | −14.786 | −18.893 | 11.645 | 1 | 14.48 | C |
| HETATM 2736 | C11 | AI2 | | 400 | −14.418 | −18.731 | 13.082 | 1 | 12.08 | C |
| HETATM 2737 | O5 | AI2 | | 400 | −14.011 | −18.038 | 10.755 | 1 | 11.2 | O |
| HETATM 2738 | C6 | AI2 | | 400 | −14.926 | −17.522 | 9.797 | 1 | 11.2 | C |
| HETATM 2739 | C7 | AI2 | | 400 | −16.282 | −17.481 | 10.471 | 1 | 10.92 | C |
| HETATM 2740 | O12 | AI2 | | 400 | −16.438 | −16.337 | 11.246 | 1 | 11.56 | O |
| HETATM 2741 | C8 | AI2 | | 400 | −16.346 | −18.875 | 11.178 | 1 | 10.38 | C |
| HETATM 2742 | O13 | AI2 | | 400 | −17.16 | −18.716 | 12.351 | 1 | 11.74 | O |
| HETATM 2743 | O | HOH | | 402 | −9.814 | −20.544 | 12.498 | 1 | 13.3 | O |
| HETATM 2744 | O | HOH | | 403 | −16.501 | −23.933 | 15.768 | 1 | 14.71 | O |
| HETATM 2745 | O | HOH | | 404 | 4.144 | −13.672 | 19.667 | 1 | 16.73 | O |
| HETATM 2746 | O | HOH | | 405 | −20.505 | −18.611 | 17.196 | 1 | 14.46 | O |
| HETATM 2747 | O | HOH | | 406 | −13.969 | −24.701 | 16.66 | 1 | 13.83 | O |
| HETATM 2748 | O | HOH | | 407 | −19.645 | −19.116 | 6.923 | 1 | 17.5 | O |
| HETATM 2749 | O | HOH | | 408 | −19.849 | −26.386 | 13.543 | 1 | 13.33 | O |
| HETATM 2750 | O | HOH | | 409 | −12.853 | −13.288 | 11.514 | 1 | 13.85 | O |
| HETATM 2751 | O | HOH | | 410 | −13.571 | −27.341 | 17.295 | 1 | 16.09 | O |
| HETATM 2752 | O | HOH | | 411 | −21.764 | −25.204 | 15.311 | 1 | 16.95 | O |
| HETATM 2753 | O | HOH | | 412 | −17.411 | −25.068 | 13.193 | 1 | 12.88 | O |
| HETATM 2754 | O | HOH | | 413 | −25.698 | −19.285 | 8.136 | 1 | 18.04 | O |
| HETATM 2755 | O | HOH | | 414 | −3.033 | −17.807 | 8.414 | 1 | 16.09 | O |
| HETATM 2756 | O | HOH | | 415 | −12.955 | −13.167 | 3.839 | 1 | 17.91 | O |

TABLE 1-continued

Atomic structural coordinates for LuxP

| | ATOM TYPE | RESID | NO | X | Y | Z | OCC | | |
|---|---|---|---|---|---|---|---|---|---|
| HETATM 2757 | O | HOH | 416 | −20.989 | −35.118 | 16.782 | 1 | 25.63 | O |
| HETATM 2758 | O | HOH | 417 | −19.085 | −20.184 | 9.345 | 1 | 13.39 | O |
| HETATM 2759 | O | HOH | 418 | −2.682 | −20.351 | 34.72 | 1 | 28.14 | O |
| HETATM 2760 | O | HOH | 419 | 3.633 | 0.627 | 12.696 | 1 | 24.97 | O |
| HETATM 2761 | O | HOH | 420 | 1.401 | −8.25 | 23.683 | 1 | 20.21 | O |
| HETATM 2762 | O | HOH | 421 | −25.107 | −30.671 | 11.731 | 1 | 21.65 | O |
| HETATM 2763 | O | HOH | 422 | −22.367 | −25.889 | 19.709 | 1 | 22.68 | O |
| HETATM 2764 | O | HOH | 423 | −24.932 | −34.053 | 0.865 | 1 | 20.29 | O |
| HETATM 2765 | O | HOH | 424 | −3.45 | −3.033 | 22.243 | 1 | 21.88 | O |
| HETATM 2766 | O | HOH | 425 | −23.013 | −17.143 | 8.943 | 1 | 21.02 | O |
| HETATM 2767 | O | HOH | 426 | 1.769 | −7.0882 | 1.063 | 1 | 19.92 | O |
| HETATM 2768 | O | HOH | 427 | −28.518 | −18.918 | 5.905 | 1 | 18.59 | O |
| HETATM 2769 | O | HOH | 428 | 1.826 | −22.825 | 12.507 | 1 | 22.04 | O |
| HETATM 2770 | O | HOH | 429 | −9.62 | −18.874 | 15.022 | 1 | 20.7 | O |
| HETATM 2771 | O | HOH | 430 | −19.329 | −4.893 | 23.368 | 1 | 22.77 | O |
| HETATM 2772 | O | HOH | 431 | −27.59 | −15.22 | 13.077 | 1 | 25.28 | O |
| HETATM 2773 | O | HOH | 432 | −9.975 | −14.644 | −2.108 | 1 | 22.17 | O |
| HETATM 2774 | O | HOH | 433 | 3.193 | −20.021 | 9.499 | 1 | 29.3 | O |
| HETATM 2775 | O | HOH | 434 | −23.511 | −20.45 | 17.267 | 1 | 25.05 | O |
| HETATM 2776 | O | HOH | 435 | −25.724 | −9.592 | 20.977 | 1 | 25.09 | O |
| HETATM 2777 | O | HOH | 436 | −19.247 | −40.903 | 9.684 | 1 | 30.29 | O |
| HETATM 2778 | O | HOH | 437 | −16.57 | −20.392 | 2.785 | 1 | 20.9 | O |
| HETATM 2779 | O | HOH | 438 | 0.432 | −18.04 | 8.566 | 1 | 21.18 | O |
| HETATM 2780 | O | HOH | 439 | 1.833 | −19.648 | 6.839 | 1 | 29.97 | O |
| HETATM 2781 | O | HOH | 440 | −17.911 | −14.848 | −6.906 | 1 | 22.88 | O |
| HETATM 2782 | O | HOH | 441 | −11.171 | −11.947 | −0.836 | 1 | 25.08 | O |
| HETATM 2783 | O | HOH | 442 | −6.546 | −22.024 | −11.237 | 1 | 29.28 | O |
| HETATM 2784 | O | HOH | 443 | −7.733 | −8.865 | 8.783 | 1 | 23.93 | O |
| HETATM 2785 | O | HOH | 444 | 1.11 | −21.534 | 9.956 | 1 | 28.62 | O |
| HETATM 2786 | O | HOH | 445 | −24.979 | −15.597 | 9.942 | 1 | 21.89 | O |
| HETATM 2787 | O | HOH | 446 | −1.894 | −30.987 | −1.877 | 1 | 29.44 | O |
| HETATM 2788 | O | HOH | 447 | −2.897 | −33.13 | 6.419 | 1 | 30.76 | O |
| HETATM 2789 | O | HOH | 448 | −9.13 | −26.787 | 24.65 | 1 | 25.71 | O |
| HETATM 2790 | O | HOH | 449 | −20.307 | −8.543 | 11.624 | 1 | 26.45 | O |
| HETATM 2791 | O | HOH | 450 | 7.012 | −22.486 | 18.656 | 1 | 33.91 | O |
| HETATM 2792 | O | HOH | 451 | −10.106 | −37.423 | −9.432 | 1 | 28.78 | O |
| HETATM 2793 | O | HOH | 452 | −18.46 | −20.423 | 30.697 | 1 | 26.81 | O |
| HETATM 2794 | O | HOH | 453 | −18.34 | −27.14 | −9.513 | 1 | 23.19 | O |
| HETATM 2795 | O | HOH | 454 | −2.746 | −35.775 | −6.294 | 1 | 33.48 | O |
| HETATM 2796 | O | HOH | 455 | −9.906 | 1.65 | 8.173 | 1 | 32.35 | O |
| HETATM 2797 | O | HOH | 456 | −5.669 | −25.976 | 31.578 | 1 | 26.3 | O |
| HETATM 2798 | O | HOH | 457 | −19.147 | −37.613 | 20.403 | 1 | 29.09 | O |
| HETATM 2799 | O | HOH | 458 | −21.078 | −34.133 | 22.006 | 1 | 28.88 | O |
| HETATM 2800 | O | HOH | 459 | −6.03 | −18.139 | −6.043 | 1 | 26 | O |
| HETATM 2801 | O | HOH | 460 | 0.111 | −30.019 | 5.856 | 1 | 39.02 | O |
| HETATM 2802 | O | HOH | 461 | −4.632 | −16.642 | 10.845 | 1 | 31 | O |
| HETATM 2803 | O | HOH | 462 | 4.756 | −22.916 | 16.902 | 1 | 30.63 | O |
| HETATM 2804 | O | HOH | 463 | −26.883 | −11.734 | 17.537 | 1 | 30.55 | O |
| HETATM 2805 | O | HOH | 464 | −23.561 | −27.944 | 21.028 | 1 | 30.07 | O |
| HETATM 2806 | O | HOH | 465 | −15.669 | −27.461 | −15.668 | 1 | 36.01 | O |
| HETATM 2807 | O | HOH | 466 | −16.334 | −11.242 | 38.127 | 1 | 33.99 | O |
| HETATM 2808 | O | HOH | 467 | 11.01 | −14.509 | 9.401 | 1 | 31.14 | O |
| HETATM 2809 | O | HOH | 468 | 0.192 | −4.309 | 6.367 | 1 | 29.62 | O |
| HETATM 2810 | O | HOH | 469 | −31.032 | −30.699 | 0.363 | 1 | 29.1 | O |
| HETATM 2811 | O | HOH | 470 | 15.499 | −15.62 | 11.545 | 1 | 37.41 | O |
| HETATM 2812 | O | HOH | 471 | −25.584 | −1.889 | 8.908 | 1 | 35.2 | O |
| HETATM 2813 | O | HOH | 472 | −25.8 | −32.576 | 8.186 | 1 | 37.39 | O |
| HETATM 2814 | O | HOH | 473 | 2.627 | −21.986 | 18.351 | 1 | 22.54 | O |
| HETATM 2815 | O | HOH | 474 | −26.924 | −26.375 | 9.66 | 1 | 29.85 | O |
| HETATM 2816 | O | HOH | 475 | 5.345 | −8.871 | 23.462 | 1 | 28.39 | O |
| HETATM 2817 | O | HOH | 476 | −23.544 | −7.901 | 27.282 | 1 | 26.96 | O |
| HETATM 2818 | O | HOH | 477 | −20.808 | −17.909 | 25.351 | 1 | 27.71 | O |
| HETATM 2819 | O | HOH | 478 | −0.266 | −22.369 | −0.194 | 1 | 24.37 | O |
| HETATM 2820 | O | HOH | 479 | −15.401 | −13.987 | 10.43 | 1 | 15.55 | O |
| HETATM 2821 | O | HOH | 480 | −23.584 | −25.976 | 17.112 | 1 | 21.93 | O |
| HETATM 2822 | O | HOH | 481 | −0.951 | −16.89 | 6.507 | 1 | 23.45 | O |
| HETATM 2823 | O | HOH | 482 | −19.984 | −31.474 | 19.727 | 1 | 23.36 | O |
| HETATM 2824 | O | HOH | 483 | −20.734 | −37.975 | 0.191 | 1 | 22.57 | O |
| HETATM 2825 | O | HOH | 484 | −1.305 | −22.783 | 3.533 | 1 | 24 | O |
| HETATM 2826 | O | HOH | 485 | −14.126 | −6.686 | 9.391 | 1 | 29.31 | O |
| HETATM 2827 | O | HOH | 486 | 12.18 | −18.065 | 16.553 | 1 | 28.27 | O |
| HETATM 2828 | O | HOH | 487 | −8.865 | −26.351 | 34.301 | 1 | 27.06 | O |
| HETATM 2829 | O | HOH | 488 | −22.341 | −34.547 | 1.461 | 1 | 22.94 | O |
| HETATM 2830 | O | HOH | 489 | −27.266 | −33.359 | −10.502 | 1 | 29.83 | O |

TABLE 1-continued

Atomic structural coordinates for LuxP

| | ATOM TYPE | RESID | NO | X | Y | Z | OCC | | | |
|---|---|---|---|---|---|---|---|---|---|---|
| HETATM 2831 | O | HOH | 490 | 4.824 | −18.32 | 8.069 | 1 | 28.27 | O |
| HETATM 2832 | O | HOH | 491 | 3.811 | −22.324 | 20.788 | 1 | 27.91 | O |
| HETATM 2833 | O | HOH | 492 | −11.364 | −34.776 | −12.089 | 1 | 29.47 | O |
| HETATM 2834 | O | HOH | 493 | −24.935 | −3.884 | 7.089 | 1 | 31.43 | O |
| HETATM 2835 | O | HOH | 494 | 12.295 | −10.786 | 19.365 | 1 | 33.09 | O |
| HETATM 2836 | O | HOH | 495 | −18.846 | −1.624 | 25.337 | 1 | 25.99 | O |
| HETATM 2837 | O | HOH | 496 | −15.819 | −8.134 | 15.323 | 1 | 21.36 | O |
| HETATM 2838 | O | HOH | 497 | −0.337 | −16.252 | 38.205 | 1 | 30 | O |
| HETATM 2839 | O | HOH | 498 | −5.96 | −10.676 | 2.704 | 1 | 25.13 | O |
| HETATM 2840 | O | HOH | 499 | −18.004 | −9.266 | 10.116 | 1 | 30.32 | O |
| HETATM 2841 | O | HOH | 500 | −20.514 | −22.84 | 24.849 | 1 | 29.26 | O |
| HETATM 2842 | O | HOH | 501 | −18.556 | −8.149 | 15.05 | 1 | 31.79 | O |
| HETATM 2843 | O | HOH | 502 | −6.99 | −8.755 | 4.093 | 1 | 28.65 | O |
| HETATM 2844 | O | HOH | 503 | −9.249 | −26.719 | −15.867 | 1 | 29.95 | O |
| HETATM 2845 | O | HOH | 504 | −6.748 | −17.352 | 13.053 | 1 | 26.27 | O |
| HETATM 2846 | O | HOH | 505 | 9.247 | −20.224 | 26.396 | 1 | 30.66 | O |
| HETATM 2847 | O | HOH | 506 | −19.884 | −2.388 | 22.65 | 1 | 24.58 | O |
| HETATM 2848 | O | HOH | 507 | −20.027 | −35.626 | 0.036 | 1 | 25.22 | O |
| HETATM 2849 | O | HOH | 508 | −13.344 | −41.437 | 24.034 | 1 | 32.75 | O |
| HETATM 2850 | O | HOH | 509 | −17.974 | −10.11 | −0.442 | 1 | 28.83 | O |
| HETATM 2851 | O | HOH | 510 | −18.836 | −39.877 | 19.419 | 1 | 33.9 | O |
| HETATM 2852 | O | HOH | 511 | 6.945 | −6.343 | 7.751 | 1 | 33.86 | O |
| HETATM 2853 | O | HOH | 512 | −27.965 | −20.966 | −7.241 | 1 | 28.36 | O |
| HETATM 2854 | O | HOH | 513 | −24.393 | −37.167 | 13.644 | 1 | 29.05 | O |
| HETATM 2855 | O | HOH | 514 | −0.181 | −25.149 | 36.99 | 1 | 34.99 | O |
| HETATM 2856 | O | HOH | 515 | −0.078 | −22.541 | −7.647 | 1 | 30.01 | O |
| HETATM 2857 | O | HOH | 516 | −27.456 | −26.745 | −9.906 | 1 | 28.84 | O |
| HETATM 2858 | O | HOH | 517 | −14.717 | −18.657 | −10.796 | 1 | 30.11 | O |
| HETATM 2859 | O | HOH | 518 | −17.64 | −41.459 | 14.178 | 1 | 30.5 | O |
| HETATM 2860 | O | HOH | 519 | −22.594 | −26.691 | 24.838 | 1 | 39.92 | O |
| HETATM 2861 | O | HOH | 520 | 1.977 | −6.842 | 29.51 | 1 | 39.31 | O |
| HETATM 2862 | O | HOH | 521 | −25.821 | −14.418 | 18.474 | 1 | 32.17 | O |
| HETATM 2863 | O | HOH | 522 | 0.538 | −11.051 | 3.362 | 1 | 33.91 | O |
| HETATM 2864 | O | HOH | 523 | −17.263 | −16.586 | 34.715 | 1 | 33.47 | O |
| HETATM 2865 | O | HOH | 524 | −7.567 | −37.763 | 6.215 | 1 | 42.81 | O |
| HETATM 2866 | O | HOH | 525 | −21.751 | −15.787 | 23.984 | 1 | 33.41 | O |
| HETATM 2867 | O | HOH | 526 | 4.566 | −3.593 | 19.218 | 1 | 34.46 | O |
| HETATM 2868 | O | HOH | 527 | 4.248 | −20.667 | 30.819 | 1 | 29.38 | O |
| HETATM 2869 | O | HOH | 528 | 0.43 | −30.621 | −0.898 | 1 | 35.93 | O |
| HETATM 2870 | O | HOH | 529 | −22.839 | −19.709 | 25.914 | 1 | 31.75 | O |
| HETATM 2871 | O | HOH | 530 | −24.685 | −32.67 | −11.303 | 1 | 30.9 | O |
| HETATM 2872 | O | HOH | 531 | 0.137 | −17.827 | 4.186 | 1 | 34.32 | O |
| HETATM 2873 | O | HOH | 532 | −5.289 | 9.141 | 17.085 | 1 | 40.95 | O |
| HETATM 2874 | O | HOH | 533 | −20.454 | −11.091 | −0.034 | 1 | 40.44 | O |
| HETATM 2875 | O | HOH | 534 | −24.193 | −15.392 | 22.888 | 1 | 35.02 | O |
| HETATM 2876 | O | HOH | 535 | −22.28 | −32.776 | 18.97 | 1 | 37.43 | O |
| HETATM 2877 | O | HOH | 536 | 1.217 | −27.509 | 6.993 | 1 | 33.62 | O |
| HETATM 2878 | O | HOH | 537 | −20.428 | −17.27 | 27.97 | 1 | 29.57 | O |
| HETATM 2879 | O | HOH | 538 | −29.198 | −33.158 | 9.243 | 1 | 46.11 | O |
| HETATM 2880 | O | HOH | 539 | −14.311 | −14.091 | 37.921 | 1 | 29.85 | O |
| HETATM 2881 | O | HOH | 540 | −27.108 | −37.999 | −9.496 | 1 | 39.54 | O |
| HETATM 2882 | O | HOH | 541 | −11.971 | 2.282 | 11.15 | 1 | 30.38 | O |
| HETATM 2883 | O | HOH | 542 | 5.265 | −13.557 | 30.59 | 1 | 38.5 | O |
| HETATM 2884 | O | HOH | 543 | −26.405 | −35.696 | 2.344 | 1 | 33.37 | O |
| HETATM 2885 | O | HOH | 544 | −11.782 | −45.762 | 11.432 | 1 | 60.31 | O |
| HETATM 2886 | O | HOH | 545 | 10.468 | −12.588 | 6.42 | 1 | 44.73 | O |
| HETATM 2887 | O | HOH | 546 | −30.199 | −21.148 | −5.617 | 1 | 40.24 | O |
| HETATM 2888 | O | HOH | 547 | 12.866 | 0.264 | 11.617 | 1 | 35 | O |
| HETATM 2889 | O | HOH | 548 | −27.384 | −34.321 | 4.22 | 1 | 41.78 | O |
| HETATM 2890 | O | HOH | 549 | −3.482 | −28.381 | 21.788 | 1 | 64.58 | O |
| HETATM 2891 | O | HOH | 550 | −25.292 | −23.792 | 15.901 | 1 | 29.14 | O |
| HETATM 2892 | O | HOH | 551 | −31.404 | −32.014 | 2.601 | 1 | 40.99 | O |
| HETATM 2893 | O | HOH | 552 | −8.57 | −11.178 | 42.419 | 1 | 43.79 | O |
| HETATM 2894 | O | HOH | 553 | −4.519 | −34.388 | 12.878 | 1 | 33.84 | O |
| HETATM 2895 | O | HOH | 554 | −10.105 | 3.951 | 25.962 | 1 | 37.19 | O |
| HETATM 2896 | O | HOH | 555 | −17.975 | −19.361 | 33.552 | 1 | 36.89 | O |
| HETATM 2897 | O | HOH | 556 | −16.612 | −37.194 | −8.579 | 1 | 36.06 | O |
| HETATM 2898 | O | HOH | 557 | 3.188 | −4.81 | 21.255 | 1 | 44.84 | O |
| HETATM 2899 | O | HOH | 558 | −20.11 | −10.053 | 33.086 | 1 | 40.81 | O |
| HETATM 2900 | O | HOH | 559 | 5.409 | −6.523 | 22.223 | 1 | 47.69 | O |
| HETATM 2901 | O | HOH | 560 | −24.237 | −17.933 | 17.729 | 1 | 35.12 | O |
| HETATM 2902 | O | HOH | 561 | −2.367 | −6.405 | 5.728 | 1 | 37.19 | O |
| HETATM 2903 | O | HOH | 562 | −9.56 | 11.7 | 19.78 | 1 | 48.74 | O |
| HETATM 2904 | O | HOH | 563 | −22.909 | −23.549 | 21.049 | 1 | 41.34 | O |

TABLE 1-continued

Atomic structural coordinates for LuxP

| | ATOM TYPE | RESID | NO | X | Y | Z | OCC | | |
|---|---|---|---|---|---|---|---|---|---|
| HETATM 2905 | O | HOH | 564 | −24.531 | −11.657 | 22.681 | 1 | 45.87 | O |
| HETATM 2906 | O | HOH | 565 | −2.107 | −27.982 | 14.209 | 1 | 29.68 | O |
| HETATM 2907 | O | HOH | 566 | −0.559 | −34.89 | −0.164 | 1 | 33.83 | O |
| HETATM 2908 | O | HOH | 567 | −25.757 | −33.207 | 10.82 | 1 | 34.04 | O |
| HETATM 2909 | O | HOH | 568 | −0.383 | −23.827 | 20.018 | 1 | 45.9 | O |
| HETATM 2910 | O | HOH | 569 | 2.644 | −27.241 | −11.112 | 1 | 42.23 | O |
| HETATM 2911 | O | HOH | 570 | −3.97 | 7.299 | 15.436 | 1 | 45.9 | O |
| HETATM 2912 | O | HOH | 571 | −25.879 | −30.613 | 14.356 | 1 | 35.74 | O |
| HETATM 2913 | O | HOH | 572 | −8.007 | −18.135 | −8.427 | 1 | 50.34 | O |
| HETATM 2914 | O | HOH | 573 | −15.88 | −48.081 | 23.199 | 1 | 42.08 | O |
| HETATM 2915 | O | HOH | 574 | 8.911 | −3.443 | 10.086 | 1 | 40.88 | O |
| HETATM 2916 | O | HOH | 575 | −30.542 | −25.025 | 2.412 | 1 | 42.58 | O |
| HETATM 2917 | O | HOH | 576 | −2.96 | −38.508 | −4.681 | 1 | 45.94 | O |
| HETATM 2918 | O | HOH | 577 | −7.771 | −11.834 | −3.379 | 1 | 42.7 | O |
| HETATM 2919 | O | HOH | 578 | 2.978 | −30.576 | −9.585 | 1 | 49.04 | O |
| HETATM 2920 | O | HOH | 579 | 14.432 | −17.36 | 14.854 | 1 | 41.9 | O |
| HETATM 2921 | O | HOH | 580 | −2.598 | −21.342 | −8.623 | 1 | 30.95 | O |
| HETATM 2922 | O | HOH | 581 | −31.593 | −17.188 | −2.395 | 1 | 41.61 | O |
| HETATM 2923 | O | HOH | 582 | −1.57 | −40.391 | −2.138 | 1 | 46.37 | O |
| HETATM 2924 | O | HOH | 583 | 5.861 | −4.15 | 24.04 | 1 | 51.73 | O |
| HETATM 2925 | O | HOH | 584 | −29.929 | −37.188 | −2.587 | 1 | 47.72 | O |
| HETATM 2926 | O | HOH | 585 | −27.533 | −16.367 | −1.503 | 1 | 40.5 | O |
| HETATM 2927 | O | HOH | 586 | −32.555 | −28.795 | −7.914 | 1 | 50.34 | O |
| HETATM 2928 | O | HOH | 587 | −8.81 | −8.98 | 0.063 | 1 | 37.26 | O |
| HETATM 2929 | O | HOH | 588 | −29.335 | −16.296 | 5.172 | 1 | 33.79 | O |
| HETATM 2930 | O | HOH | 589 | −16.631 | −11.749 | 9.34 | 1 | 27.17 | O |
| HETATM 2931 | O | HOH | 590 | −12.772 | −20.531 | 20.625 | 1 | 24.81 | O |
| HETATM 2932 | O | HOH | 591 | −26.211 | −29.492 | 6.086 | 1 | 27.94 | O |
| HETATM 2933 | O | HOH | 592 | 0.537 | −23.376 | 16.992 | 1 | 31 | O |
| HETATM 2934 | O | HOH | 593 | −22.603 | −1.587 | 22.227 | 1 | 31.67 | O |
| HETATM 2935 | O | HOH | 594 | −0.052 | −14.336 | 6.488 | 1 | 25.99 | O |
| HETATM 2936 | O | HOH | 595 | −10.49 | −12.81 | 10.299 | 1 | 35.63 | O |
| HETATM 2937 | O | HOH | 596 | 4.581 | −4.426 | 38.337 | 1 | 30.99 | O |
| HETATM 2938 | O | HOH | 597 | −11.204 | −1.146 | 35.411 | 1 | 34.8 | O |
| HETATM 2939 | O | HOH | 598 | −26.846 | −12.491 | 3.753 | 1 | 33.36 | O |
| HETATM 2940 | O | HOH | 599 | −15.614 | −10.401 | 4.311 | 1 | 39.07 | O |
| HETATM 2941 | O | HOH | 600 | −28.127 | −22.235 | −9.8 | 1 | 32.28 | O |
| HETATM 2942 | O | HOH | 601 | −25.16 | −28.203 | 16.71 | 1 | 36.31 | O |
| HETATM 2943 | O | HOH | 602 | −24.234 | −12.404 | 5.561 | 1 | 42.06 | O |
| HETATM 2944 | O | HOH | 603 | −0.656 | −23.56 | −10.026 | 1 | 45.93 | O |
| HETATM 2945 | O | HOH | 604 | −29.259 | −24.805 | −10.452 | 1 | 37.42 | O |
| HETATM 2946 | O | HOH | 605 | −15.287 | −37.53 | −5.482 | 1 | 36.29 | O |
| HETATM 2947 | O | HOH | 606 | −22.887 | −37.26 | 1.253 | 1 | 42.31 | O |
| HETATM 2948 | O | HOH | 607 | −18.24 | −38.612 | −0.598 | 1 | 36.59 | O |
| HETATM 2949 | O | HOH | 608 | −25.023 | −29.916 | −12.36 | 1 | 29.35 | O |
| HETATM 2950 | O | HOH | 609 | −1.652 | −24.538 | 23.841 | 1 | 33.65 | O |
| HETATM 2951 | O | HOH | 610 | 0.152 | −4.248 | 32.144 | 1 | 45.52 | O |
| HETATM 2952 | O | HOH | 611 | −0.746 | −2.816 | 21.838 | 1 | 39.69 | O |
| HETATM 2953 | O | HOH | 612 | 0.093 | −19.493 | −0.123 | 1 | 44.37 | O |
| HETATM 2954 | O | HOH | 613 | −21.348 | −40.416 | 0.449 | 1 | 37.66 | O |
| HETATM 2955 | O | HOH | 614 | 9.935 | −9.122 | 20.852 | 1 | 35.68 | O |
| HETATM 2956 | O | HOH | 615 | −9.451 | −9.237 | 39.133 | 1 | 32.82 | O |
| HETATM 2957 | O | HOH | 616 | −6.081 | −2.271 | 29.649 | 1 | 36.85 | O |
| HETATM 2958 | O | HOH | 617 | −26.115 | −3.071 | 11.79 | 1 | 34.96 | O |
| HETATM 2959 | O | HOH | 618 | 1.061 | −18.062 | 34.513 | 1 | 37.13 | O |
| HETATM 2960 | O | HOH | 619 | −3.36 | −6.057 | 38.878 | 1 | 30.87 | O |
| HETATM 2961 | O | HOH | 620 | −28.99 | −32.278 | 3.75 | 1 | 45.31 | O |
| HETATM 2962 | O | HOH | 621 | −0.682 | −19.446 | 2.372 | 1 | 29.21 | O |
| HETATM 2963 | O | HOH | 622 | −10.43 | −23.454 | −15.329 | 1 | 46.6 | O |
| HETATM 2964 | O | HOH | 623 | −26.508 | −16.824 | 18.219 | 1 | 42.03 | O |
| HETATM 2965 | O | HOH | 624 | −25.02 | −15.949 | −2.434 | 1 | 38.51 | O |
| HETATM 2966 | O | HOH | 625 | −28.61 | −14.764 | 7.347 | 1 | 41.16 | O |
| HETATM 2967 | O | HOH | 626 | 10.862 | −17.281 | 8.37 | 1 | 41.15 | O |
| HETATM 2968 | O | HOH | 627 | 5.685 | −7.256 | 18.393 | 1 | 44.42 | O |
| HETATM 2969 | O | HOH | 628 | −22.867 | −19.186 | −12.162 | 1 | 38.61 | O |
| HETATM 2970 | O | HOH | 629 | −3.111 | −31.695 | 12.737 | 1 | 36.89 | O |
| HETATM 2971 | O | HOH | 630 | −30.03 | −22.722 | 3.7 | 1 | 40.75 | O |
| HETATM 2972 | O | HOH | 631 | −3.984 | −25.807 | 20.752 | 1 | 35.86 | O |
| HETATM 2973 | O | HOH | 632 | −2.621 | −26.891 | −11.016 | 1 | 45.77 | O |
| HETATM 2974 | O | HOH | 633 | −3.704 | −0.27 | 29.333 | 1 | 40.68 | O |
| HETATM 2975 | O | HOH | 634 | −0.477 | −23.108 | 13.92 | 1 | 48.58 | O |
| HETATM 2976 | O | HOH | 635 | 2.261 | −24.011 | 36.113 | 1 | 39 | O |
| HETATM 2977 | O | HOH | 636 | −7.258 | 0.369 | 30.999 | 1 | 32.49 | O |
| HETATM 2978 | O | HOH | 637 | 1.793 | −5.628 | 24.565 | 1 | 41.09 | O |

TABLE 1-continued

Atomic structural coordinates for LuxP

| | ATOM TYPE | RESID | NO | X | Y | Z | OCC | | |
|---|---|---|---|---|---|---|---|---|---|
| HETATM 2979 | O | HOH | 638 | −9.184 | −36.77 | 24.865 | 1 | 33.79 | O |
| HETATM 2980 | O | HOH | 639 | −28.895 | −30.857 | −11.271 | 1 | 37.13 | O |
| HETATM 2981 | O | HOH | 640 | −27.809 | −37.347 | 0.76 | 1 | 35.8 | O |
| HETATM 2982 | O | HOH | 641 | −21.798 | 4.232 | 19.72 | 1 | 39.57 | O |
| HETATM 2983 | O | HOH | 642 | −9.3 | −7.67 | 4.188 | 1 | 40.43 | O |
| HETATM 2984 | O | HOH | 643 | −11.14 | −10.192 | −3.156 | 1 | 41.84 | O |
| HETATM 2985 | O | HOH | 644 | 9.521 | −22.454 | 11.542 | 1 | 48.13 | O |
| HETATM 2986 | O | HOH | 645 | −19.459 | −34.845 | 24.2 | 1 | 47.28 | O |
| HETATM 2987 | O | HOH | 646 | −5.996 | −25.202 | −11.174 | 1 | 41.31 | O |
| HETATM 2988 | O | HOH | 647 | −25.515 | 0.079 | 20.078 | 1 | 40.31 | O |
| HETATM 2989 | O | HOH | 648 | −17.053 | −40.643 | −4.693 | 1 | 39.47 | O |
| HETATM 2990 | O | HOH | 649 | −5.075 | −13.727 | −1.977 | 1 | 37.71 | O |
| HETATM 2991 | O | HOH | 650 | −18.252 | −20.032 | 36.469 | 1 | 52.94 | O |
| HETATM 2992 | O | HOH | 651 | −10.525 | −16.713 | −7.787 | 1 | 50.42 | O |
| HETATM 2993 | O | HOH | 652 | −26.603 | −20.55 | 16.045 | 1 | 47.72 | O |
| HETATM 2994 | O | HOH | 653 | 9.795 | −9.836 | 6.305 | 1 | 44.25 | O |
| HETATM 2995 | O | HOH | 654 | −26.963 | −38.396 | 5.309 | 1 | 44 | O |
| HETATM 2996 | O | HOH | 655 | 4.84 | −22.335 | 8.374 | 1 | 35.47 | O |
| HETATM 2997 | O | HOH | 656 | 7.985 | −8.058 | 24.606 | 1 | 54.06 | O |
| HETATM 2998 | O | HOH | 657 | −7.895 | −14.032 | −5.182 | 1 | 50.86 | O |
| HETATM 2999 | O | HOH | 658 | −15.82 | −7.607 | 1.831 | 1 | 40.59 | O |
| HETATM 3000 | O | HOH | 659 | −30.032 | −39.265 | −4.097 | 1 | 42.45 | O |
| HETATM 3001 | O | HOH | 660 | −13.064 | −23.295 | −15.487 | 1 | 39.35 | O |
| HETATM 3002 | O | HOH | 661 | −9.468 | −42.825 | 10.925 | 1 | 49.04 | O |
| HETATM 3003 | O | HOH | 662 | −25.025 | −20.47 | 24.37 | 1 | 37.74 | O |
| HETATM 3004 | O | HOH | 663 | 14.429 | −9.579 | 17.245 | 1 | 37.99 | O |
| HETATM 3005 | O | HOH | 664 | 3.068 | −4.212 | 32.466 | 1 | 41.96 | O |
| HETATM 3006 | O | HOH | 665 | 7.052 | −21.585 | 29.996 | 1 | 49.37 | O |
| HETATM 3007 | O | HOH | 666 | 1.464 | −22.459 | 33.93 | 1 | 43.97 | O |
| HETATM 3008 | O | HOH | 667 | 11.211 | −22.844 | 20.278 | 1 | 49.17 | O |
| HETATM 3009 | O | HOH | 668 | 14.08 | −8.828 | 14.04 | 1 | 41.13 | O |
| HETATM 3010 | O | HOH | 669 | 7.729 | −5.421 | 15.019 | 1 | 47.75 | O |
| HETATM 3011 | O | HOH | 670 | −27.524 | −28.658 | −11.786 | 1 | 33.78 | O |
| HETATM 3012 | O | HOH | 671 | 1.093 | 0.584 | 14.808 | 1 | 45.14 | O |
| HETATM 3013 | O | HOH | 672 | −28.602 | −28.987 | 6.608 | 1 | 36.94 | O |
| HETATM 3014 | O | HOH | 673 | −1.707 | −18.179 | −2.651 | 1 | 51.3 | O |
| HETATM 3015 | O | HOH | 674 | −28.516 | −26.965 | −13.989 | 1 | 30.56 | O |
| HETATM 3016 | O | HOH | 675 | −18.54 | −0.92 | 11.011 | 1 | 42.85 | O |
| HETATM 3017 | O | HOH | 676 | −9.423 | −37.628 | 13.434 | 1 | 35.34 | O |
| HETATM 3018 | O | HOH | 677 | −0.6 | 2.482 | 14.999 | 1 | 34.45 | O |
| HETATM 3019 | O | HOH | 678 | 7.51 | −9.424 | 34.74 | 1 | 32.82 | O |
| HETATM 3020 | O | HOH | 679 | −5.675 | −2.458 | 39.724 | 1 | 36.27 | O |
| HETATM 3021 | O | HOH | 680 | −28.281 | −20.413 | 8.785 | 1 | 38.88 | O |
| HETATM 3022 | O | HOH | 681 | −7.479 | −6.143 | 8.182 | 1 | 33.35 | O |
| HETATM 3023 | O | HOH | 682 | −8.663 | −28.617 | 31.054 | 1 | 42.06 | O |
| HETATM 3024 | O | HOH | 683 | −20.361 | −19.697 | 38.36 | 1 | 46.41 | O |
| HETATM 3025 | O | HOH | 684 | −1.281 | 4.49 | 12.993 | 1 | 38.62 | O |
| HETATM 3026 | O | HOH | 685 | 3.157 | −7.398 | 27.107 | 1 | 42.79 | O |
| HETATM 3027 | O | HOH | 686 | −3.957 | −40.357 | −6.228 | 1 | 42.11 | O |
| HETATM 3028 | O | HOH | 687 | −12.984 | −40.757 | 5.444 | 1 | 43.87 | O |
| HETATM 3029 | O | HOH | 688 | 5.496 | −6.591 | 14.351 | 1 | 40.95 | O |
| HETATM 3030 | O | HOH | 689 | −8.389 | −34.589 | −15.09 | 1 | 44.94 | O |
| HETATM 3031 | O | HOH | 690 | −13.693 | −23.277 | 38.418 | 1 | 37.9 | O |
| HETATM 3032 | O | HOH | 691 | −24.58 | −22.039 | 19.006 | 1 | 42.55 | O |
| HETATM 3033 | O | HOH | 692 | −32.378 | −33.164 | −0.652 | 1 | 35.17 | O |
| HETATM 3034 | O | HOH | 693 | 7.74 | −7.592 | 16.899 | 1 | 45.17 | O |
| HETATM 3035 | O | HOH | 694 | −3.078 | −15.934 | 0.801 | 1 | 32.55 | O |
| HETATM 3036 | O | HOH | 695 | 1.545 | −32.331 | 1.679 | 1 | 38.68 | O |
| HETATM 3037 | O | HOH | 696 | −13.291 | −39.415 | 25.93 | 1 | 38.96 | O |
| HETATM 3038 | O | HOH | 697 | −10.871 | 6.311 | 25.436 | 1 | 43.63 | O |
| HETATM 3039 | O | HOH | 698 | 2.111 | −28.771 | 3.625 | 1 | 47.5 | O |
| HETATM 3040 | O | HOH | 699 | −25.058 | −17.44 | 20.303 | 1 | 41.65 | O |
| HETATM 3041 | O | HOH | 700 | −26.881 | −20.967 | −11.816 | 1 | 43.72 | O |
| HETATM 3042 | O | HOH | 701 | −18.579 | −29.941 | 31.735 | 1 | 47.55 | O |
| HETATM 3043 | O | HOH | 702 | −12.931 | −32.713 | 28.639 | 1 | 42.82 | O |
| HETATM 3044 | O | HOH | 703 | 9.727 | −4.271 | 13.634 | 1 | 37.42 | O |
| HETATM 3045 | O | HOH | 704 | −27.58 | −9.379 | 14.292 | 1 | 38.1 | O |
| HETATM 3046 | O | HOH | 705 | −20.978 | −15.421 | −5.923 | 1 | 47.01 | O |
| HETATM 3047 | O | HOH | 706 | −8.667 | 2.095 | 29.458 | 1 | 42.59 | O |
| HETATM 3048 | O | HOH | 707 | −1.418 | 0.133 | 23.496 | 1 | 48.61 | O |
| HETATM 3049 | O | HOH | 708 | −13.603 | −10.702 | −6.571 | 1 | 45 | O |
| HETATM 3050 | O | HOH | 709 | 4.41 | −13.251 | 4.468 | 1 | 43.85 | O |
| HETATM 3051 | O | HOH | 710 | −23.922 | −3.45 | 24.197 | 1 | 38.06 | O |
| HETATM 3052 | O | HOH | 711 | 0.226 | −35.566 | −2.582 | 1 | 43.2 | O |

TABLE 1-continued

Atomic structural coordinates for LuxP

| | ATOM TYPE | RESID | NO | X | Y | Z | OCC | | |
|---|---|---|---|---|---|---|---|---|---|
| HETATM 3053 | O | HOH | 712 | −20.222 | −31.592 | 22.479 | 1 | 27.77 | O |
| HETATM 3054 | O | HOH | 713 | −22.635 | −30.126 | 22.425 | 1 | 31.56 | O |
| HETATM 3055 | O | HOH | 714 | −17.559 | −5.685 | 8.831 | 1 | 45.79 | O |
| HETATM 3056 | O | HOH | 715 | 8.19 | −11.688 | 33.399 | 1 | 43.54 | O |
| HETATM 3057 | O | HOH | 716 | 10.533 | −21.61 | 24.327 | 1 | 39.34 | O |
| HETATM 3058 | O | HOH | 717 | −24.657 | −30.228 | 19.001 | 1 | 43 | O |
| HETATM 3059 | O | HOH | 718 | −26.946 | −22.666 | 17.665 | 1 | 47.2 | O |
| HETATM 3060 | O | HOH | 719 | 9.128 | −7.202 | 19.12 | 1 | 47 | O |
| HETATM 3061 | O | HOH | 720 | −11.86 | −4.72 | 9.98 | 1 | 38.65 | O |
| HETATM 3062 | O | HOH | 721 | −12.774 | −6.861 | 0.956 | 1 | 47.14 | O |
| HETATM 3063 | O | HOH | 722 | −5.571 | −3.93 | 32.406 | 1 | 45.17 | O |
| HETATM 3064 | O | HOH | 723 | −20.186 | −32.195 | 29.15 | 1 | 45.57 | O |
| HETATM 3065 | O | HOH | 724 | −3.551 | −25.129 | −13.339 | 1 | 47.19 | O |
| HETATM 3066 | O | HOH | 725 | −10.386 | −4.742 | 2.482 | 1 | 46.15 | O |
| HETATM 3067 | O | HOH | 726 | −7.038 | −27.167 | −17.385 | 1 | 42.26 | O |
| HETATM 3068 | O | HOH | 727 | 15.868 | −16.793 | 22.193 | 1 | 40.5 | O |
| HETATM 3069 | O | HOH | 728 | −14.832 | −5.697 | 14.299 | 1 | 48.99 | O |
| HETATM 3070 | O | HOH | 729 | −28.684 | −15.039 | 0.609 | 1 | 43.79 | O |
| HETATM 3071 | O | HOH | 730 | −2.557 | −30.903 | 16.875 | 1 | 43.03 | O |
| HETATM 3072 | O | HOH | 731 | −14.657 | 2.174 | 9.541 | 1 | 48.86 | O |
| HETATM 3073 | O | HOH | 732 | −11.561 | −6.706 | 41.726 | 1 | 44.28 | O |
| HETATM 3074 | O | HOH | 733 | −27.931 | −31.049 | 7.921 | 1 | 40.28 | O |

What is claimed is:

1. The isolated ligand having the chemical formula:

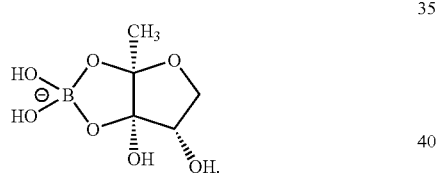

* * * * *